US011214785B2

(12) United States Patent
Gamboa et al.

(10) Patent No.: US 11,214,785 B2
(45) **Date of Patent: *Jan. 4, 2022**

(54) MODIFIED STRAINS FOR THE PRODUCTION OF RECOMBINANT SILK

(71) Applicant: Bolt Threads, Inc., Emeryville, CA (US)

(72) Inventors: Matthew Scott Gamboa, Richmond, CA (US); Joshua Tyler Kittleson, Pleasant Hill, CA (US)

(73) Assignee: Bolt Threads, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,498

(22) Filed: Apr. 7, 2020

(65) Prior Publication Data

US 2020/0283750 A1 Sep. 10, 2020

Related U.S. Application Data

(63) Continuation of application No. 15/724,196, filed on Oct. 3, 2017, now Pat. No. 10,647,975.

(51) Int. Cl.

*C12N 9/60* (2006.01)
*C07K 14/435* (2006.01)

(52) U.S. Cl.

CPC .......... *C12N 9/60* (2013.01); *C07K 14/43518* (2013.01); *C12Y 304/23041* (2013.01)

(58) Field of Classification Search

CPC .............................................. C12Y 304/23041
USPC ........................................................... 435/224
See application file for complete search history.

(56) References Cited

U.S. PATENT DOCUMENTS

| | | | |
|---|---|---|---|
| 7,262,287 | B2 | 8/2007 | Kang et al. |
| 8,440,456 | B2 | 5/2013 | Callewaert et al. |
| 2011/0021378 | A1 | 1/2011 | Callewaert et al. |
| 2012/0142895 | A1 | 6/2012 | Jin et al. |
| 2016/0222174 | A1 | 8/2016 | Widmaier et al. |

FOREIGN PATENT DOCUMENTS

| | | | |
|---|---|---|---|
| CN | 102676563 | A | 9/2012 |
| WO | WO 2010/135678 | A1 | 11/2010 |
| WO | WO 2015/004241 | A2 | 1/2015 |
| WO | WO 2015/042164 | A2 | 3/2015 |

OTHER PUBLICATIONS

Cho, E.Y. et al., "Multiple-Yapsin-Deficient Mutant Strains for High-Level Production of Intact Recombinant Proteins in *Saccharomyces cerevisiae*," Journal of Biotechnology, 2010, pp. 1-7, vol. 149.

Guan, B. et al., "Absence of Yps7p, a Putative Glycosylphophatidylinositol-Linked Aspartyl Protease in Pichia pastoris, Results in Aberrant Cell Wall Composition and Increased Osmotic Stress Resistance," FEMS Yeast Res, 2012, pp. 969-979, vol. 12.

PCT International Search Report and Written Opinion, PCT Application No. PCT/US2017/054997, dated Feb. 20, 2018, 15 pages.

Sazonova, E.A. et al., "Effect of Disruption of Pichia pastoris YPS1 Gene on Viability and Production of Recombinant Proteins," Russian Journal of Genetics, 2013, pp. 602-608, vol. 49, No. 6.

Silva, C.I.F. et al., "Secreted Production of Collagen-Inspired Gel-Forming Polymers with High Thermal Stability in Pichia pastoris," Biotechnology and Bioengineering, Nov. 2011, pp. 2517-2525, vol. 108, No. 11.

Wu et al., "Disruption of YPS1 and PEP4 Genes Reduces Proteolytic Degradation of Secreted HAS/PTH in Pichia pastoris GS115," J. Ind. Microbiol. Biotechnol., Mar. 26, 2013, pp. 589-599, vol. 40.

Yao et al., "Degradation of HAS-AX15(R13K) When Expressed in Pichia pastoris Can Be Reduced Via the Disruption of YPS1 Gene in this Yeast," Journal of Biotechnology, Jan. 15, 2009, pp. 131-136, vol. 139, Iss. 2.

Cregg, J., et al., "Recombinant Protein Expression in Pichia pastoris", Molecular Biotechnology, vol. 16, Jan. 1, 2000, 30 pages.

Extended European Search Report for Application No. 17928005.2, 11 pages.

*Primary Examiner* — Sheridan Swope
(74) *Attorney, Agent, or Firm* — Goodwin Procter LLP

(57) ABSTRACT

Disclosed herein are modified strains for reducing degradation of recombinantly expressed products secreted from a host organism and methods of using the modified strains. In some embodiments, to attenuate a protease activity in *Pichia pastoris*, the genes encoding enzymes the degrade proteases are inactivated or mutated to reduce or eliminate activity. In preferred strains, the protease activity of proteases encoded by PAS_chr4_0584 (YPS1-1) and PAS_chr3_1157 (YPS1-2) (e.g., polypeptides comprising SEQ ID NO: 66 and 67) is attenuated.

17 Claims, 6 Drawing Sheets

Specification includes a Sequence Listing.

Nourseothricin Marker Plasmid

Homology Arm Insertion into Nourseothricin Marker Plasmid

2X KO Western

SEQUENCE LISTING

<160> NUMBER OF SEQ ID NOS: 522

<210> SEQ ID NO 1
<211> LENGTH: 1800
<212> TYPE: DNA
<213> ORGANISM: Pichia pastoris

<400> SEQUENCE: 1
atgttgaagg atcagttctt gttatgggtt gctttgatag cgagcgtacc ggtttccggc 60
gtgatggcag ctcctagcga gtccgggcat aacacggttg aaaaacgaga tgccaaaaac 120
gttgttggcg ttcaacagtt ggacttcagc gttctgaggg gtgattcctt cgaaagtgcc 180
tcttcagaga acgtgcctcg gcttgtgagg agagatgaca cgctagaagc tgagctaatc 240
aaccagcaat cattctactt gtcacgactg aaagttggat cacatcaagc ggatattgga 300
atcctagtgg acacaggatc ctctgattta tgggtaatgg actcggtaaa cccatactgc 360
agtagccgtt cccgcgtgaa gagagatata cacgatgaga agatcgccga atgggatccc 420
atcaatctca agaaaaatga aacttctcag aataaaaatt tttgggattg gctcgttgga 480
actagcacta gttctccttc caccgccacg gcaactggta gtggtagtgg tagtggtagt 540

-continued

```
ggtagtggta gtggtagtgc tgccacagcc gtatcggtaa gttctgcaca ggcaacattg    600

gattgctcta cgtatggaac gtttgatcac gctgattcct cgacgttcca tgacaataat    660

acagactttt tcatctcata cgctgatacc acttttgctt caggaatctg ggttatgac     720

gacgtcatta tcgacggcat agaggtgaaa gaactttcct tcgccgttgc agacatgacc    780

aattcctcta ttggtgtgtt aggtattgga ctgaaaggcc tagaatccac atatgctagt    840

gcatcttcgg tcagtgaaat gtatcagtat gacaatttgc cagccaagat ggtcaccgat    900

gggttgatca acaaaaatgc atactccttg tacttgaact ccaaggacgc ctcaagtggt    960

tccatcctct ttggaggtgt ggatcatgaa aaatattcgg gacaattgtt gacagttcca   1020

gtcatcaaca cactcgcttc cagtggttac agagaggcaa ttcgtttaca aattacttta   1080

aatggaatag atgtgaaaaa gggttctgac cagggaactc ttttacaagg gagatttgct   1140

gcattattgg actctggagc tacgctaacg tatgctcctt cttctgtttt aaattcaatt   1200

ggccggaacc tgggcggctc ctatgattcg tcaagacaag cttataccat tcgttgtgtt   1260

tctgcatcag ataccacttc tctggtattc aattttgggg gtgctacagt ggaagtttcc   1320

ctgtacgatc tacagattgc aacatattac accgggggaa gtgccacgca atgtcttatt   1380

ggaatattca gctctggaag tgatgagttt gtgctcggtg ataccttctt gaggtcagcc   1440

tacgtggttt acgatcttga tgggcttgaa gtgtcgcttg cccaagccaa cttcaacgaa   1500

accgattctg atgttgaggc tattacctcc agtgtacctt ccgctactcg tgcatccgga   1560

tacagttcta catggtctgg ttctgccagc ggtacagttt acacttcggt tcagatggaa   1620

tccggtgctg cttccagctc caactcttct ggatcgaata tgggttcctc ttcctcatcg   1680

tcctcttcat cgtcctcgac ttccagtgga gacgaagaag gagggagctc cgccaacagg   1740

gtccccttca gctacctttc tctctgtttg gtagttattc tcggcgtgtg tatagtatag   1800
```

<210> SEQ ID NO 2
<211> LENGTH: 1781
<212> TYPE: DNA
<213> ORGANISM: Pichia pastoris

<400> SEQUENCE: 2

```
atgatcatca accacttggt attgacagcc ctcagcattg cactagcaag tgcgcaactc     60

caatcgcctt tcaaggctaa caagttgcca ttcaaaaagt ttatcattcc aacgacccaa    120

aggaccgttt aattaagaga gatgactacg agtccctcga cttgagacac atcggagtct    180

tgtacactgc agagatccaa attggatctg acgaaactga aattgaggtc attgtcgaca    240

ctggttctgc cgacttgtgg gtcatcgatt ccgacgctgc cgtctgtgag ttatcctacg    300

atgagattga ggccaatagc ttttcctcgg cttctgccaa attcatggac aagatagctc    360

ctccatcaca agagctcctg gatgggctga gtgagtttgg atttgctctc gatggtgaaa    420

tttctcaata cctagccgat aaatctggac gtgtttcgaa aagagaggaa aatcaacaag    480

atttcaacat taaccgtgac gagcctgtgt gtgaacagtt tggttccttc gattctagtt    540

cttccgacac tttccaaagc aacaattcag cttttggtat tgcttacctt gatggaacca    600

ctgctaacgg aacttgggtc agggacacag tccgcatcgg cgactttgcc atcagccaac    660

agagttttgc cttagtcaac atcacagata actacatggg aatcttgggt ctcggtcctg    720

ctacccaaca aaccaccaat agtaacccaa ttgcagcaaa cagatttact tatgatggtg    780

ttgtggattc attgcggtcc caaggattta tcaattcagc atcgttttct gtttacttgt    840

ctccagatga agataacgag cacgacgaat tcagcgacgg agaaatttta tttggtgcta    900
```

```
ttgatagggc caagatagac gggccattta gacttttccc atatgtcaat ccttacaaac    960

cagtttaccc cgatcaatat acttcctacg ttacagtgtc cacaattgcg gtgtcttcgt   1020

cagatgaaac tctcattatt gaaagacgtc ctcgtttggc attaatcgat acaggtgcca   1080

ccttctccta tttgccaacc tacccattga ttcgtttagc gttttccatc catggaggct   1140

ttgaatatgt ttctcaattg ggactatttg tcattcgtac aagttctctg tctgttgcta   1200

gaaataaggt gattgagttc aagtttggtg aagacgttgt gatccaatcc ccagtttctg   1260

atcatctatt ggacgtctca ggccttttta ctgatggcca acaatactcc gcattaactg   1320

tacgtgaaag tcttgacgga ctttccattc taggtgatac attcatcaaa tcggcctact   1380

tattctttga caatgaaaac agccagctgg gtattggtca gatcaacgtc actgatgacg   1440

aggatattga ggtggtcggt gatttcacta ttgaacgaga cccagcctac tcctctactt   1500

ggtctagcga tttacctcat gaaacaccca ctagggcttt gagtactgct tcagggggag   1560

gccttggtac cggaataaac acggccacaa gtcgtgcaag ttctcgttcc acatctggct   1620

ctacttcacg aacttcttct acatctggct ctgcttctgg tacttcttca ggtgcatctt   1680

ctgctactca aaatgacgaa acatccactg atcttggagc tccagctgca tctttaagtg   1740

caacgccatg tctttttgcc atcttgctgc tcatgttgta g                       1781
```

<210> SEQ ID NO 3
<211> LENGTH: 1584
<212> TYPE: DNA
<213> ORGANISM: Pichia pastoris

<400> SEQUENCE: 3

```
atgaacccta gcagcttaat tctacttgca ctcagcattg gctactccat tgctgagtca     60

aatttctctt tcaaacccag caagttacct ctcaaaaaac atcgtgattc ttcttccccg    120

catgaacgat ttcttaaacg agatggaccc tatcatccgc tagaagccga cgcttacttt    180

tactacacta cgtctatatt ggttggatca gaagaagaaa aagttgaagt aacagttgat    240

ttaggaacct ctgatttatg ggtcgtcgat tacaacaccg gtttatgtga tagatccttt    300

gacgaaacct atcttaaacg tagtctggat acttctgagg aagattattc tgctggagat    360

cttggctcct cagtcggtgt acgcagcgct agaaaattct tgcgcaaaag ggacaccaat    420

caaactgagg ttaatgaagc taactatggt gcttgtccaa attcgattac cttcaatcca    480

gaaaactcgt cttctttcca gagtaatgat actgctttca atatcagcta ctttgatgga    540

accagtgcta gtggtttttg ggctactgat acaatttact ttggtgacct tgaggtcagc    600

gagcaatttt ttgggctggc aaacttaaca ataagttatg gaggagtctt aggtcttggc    660

ccttccaacc tacaaacaac caatgctaac cccaacggtg aggaattcat ttacagcgga    720

gtcttagatt ccatgcgtga tcaagggctt atcaactcgg cttctttctc aatctatctc    780

aatccagaga atttcagaga tgaagataac tattctaatg aaggagcgat tttgttcgga    840

gcaattgata atgcgaagat tgacgggtca ttgaagctgt taccatacgt gacttcaggt    900

ggacactctc agattgatgc taatttcact tacatcacct tgaataatat tgccgtggct    960

gacaatgata cagccctgat cgttgagacc aacccccaat tggcaatgtt gaatccaaag   1020

tttatataca cctattttcc aaacgaagta ttgacccggc tggtaaactc tattgacaat   1080

ctagaatatg atcctgttga ggggttatat aggataagga gaacaaacat tagggatatt   1140

aacaaaaaaa tcatagagtt tcaatttggt gacgagattg tgatacattc tcccttatca   1200
```

aattatctgt ctgatacatg ggttccaagc acaaactaca cctatttgga gattcaggat 1260
agcagagagg atttctttat ccttggtaat gcatttttca agtctgcgta tttgtttttt 1320
gacaatgata acagtgaagt cggtattggc caactaaagg ttaccgataa ggaggacatc 1380
gttccagttg gtgaattttc tttggatcaa gattcagggt actcgtcaac ctggtcaacg 1440
ttctcctatg aaactggttc agctcccttg ggtacgtcaa ctttcgaaac gagtacaaaa 1500
actagttcag atggagctgc cccgtcggtg tctcacatta acactagttc ctacttattt 1560
gcgtttgtac tacttttcct ttag 1584

<210> SEQ ID NO 4
<211> LENGTH: 1422
<212> TYPE: DNA
<213> ORGANISM: Pichia pastoris

<400> SEQUENCE: 4
atgttgccca tccgcttatc caaacttctg cttttgctct ccttaaagtt gaaattgggt 60
acagctgaag aaaaatacca aaagttggat ttaaaaagaa ttgacaaaga ctattatgcc 120
gtcgatgtca aagtcggctc cgatgagcag gagatcaaag aggtactaat agatacgggt 180
tcatctgatt tctggatctt ggacaaatcg ttctgtaatt ctccaacatc agaggaagaa 240
gagaacagta acgggcgtag caacaaggaa agctgtggag tctatggctc gttcgactcc 300
aacaagtcag agacatttca ggcaactggc caagtatttg acgctgctta cggtgacacc 360
acagccgagt cgacaggatc ttcaggagtt cgaggaattg atcagctacg ggtaggagat 420
attcatatag aagaactcta ttttggacta gtgacaaaca ctacaagttt accacccgtt 480
ttaggaattg cccagctttc cgaagagttc agcaacaact cttatcctaa ctttccatac 540
cagatgaaag aggaaggtct gattgatgtt gttgcatact ctctctcctt gggccaaagt 600
aaaggtgaac tactgttcgg ggctatggac cactcaaaat ataatggaac actattgaaa 660
gcccctatat tgcaggcggg cacaccagga atgcaagttc ttttaactgg agtggccctt 720
acaaatggtt catcaagcgt cttcaatgag acagacaata aaggttttat ctactttgac 780
agtgggacta ctgcttccac tctgccatca gagcactttg atgatctttt caaccatcac 840
ggatgggcgt acgatggtga tacattgaca tattcgattc aatgcgatag tgagggagaa 900
aaatctttac ttgacttcac tttagaatat accattgctg gtaatattgt catcaaagta 960
ccatttgaag acattattat gaagaatgaa aatgatggag aatgcctctc aaccgtaatg 1020
gtgtcgaacc agacttcttt ttcatattcc gatgacacac cctttttcgt tgctggagac 1080
gaagttctgt tgaacgctta tgttgtttac aacctagaaa cacaagagct ggccattgct 1140
ccagcagtgg ataatccaga agatactgaa gaagatattg agattatctc cgcagacttt 1200
gatatttcag aagccagaga ttatagcgtt ggattagagt tcagaaatac cacaattcca 1260
gctacaactg attacttgcc ttcctcgatg tcgtcaggtt cagtcagcga agagactggt 1320
tccaagtctg agagctctac ttctgaggac tttgctgcag ccacgttgaa accatttaca 1380
ttttggggtt tcgtcctttt tttctttcac tttttgattt ga 1422

<210> SEQ ID NO 5
<211> LENGTH: 1839
<212> TYPE: DNA
<213> ORGANISM: Pichia pastoris

<400> SEQUENCE: 5
atgttagttg ctgttgccct agtgttgtta ctgtctacag gctatgctgg aatcgtcgcc 60

-continued

```
attgataccg aatatgagtt caccattggt tttcttagta cgatagaaat agggtttccc    120
ccacaaagca taacggctca atgggataca ggatcgtctg acctcttggt caattccgtg    180
acaaattcac agtgtgctca ggacggatgt agctttggtg cgttcgcctt caacaaatcc    240
accacttatt ccaatataac aaaccctaac aaccttcatg ttcagttctc ctttgcaagc    300
ggcagcgtgg ttgatgacaa acttgtgagt gacactattt ttgtagattc caaggtaatc    360
ccacggttca actttgcact ggtatcgaag ggagacctgt atggtgataa tatttttggt    420
attggaccga gagggaacca gggaacattc gattccaatg gaactccagc tttctatgat    480
agctttcctt atcacttgaa ggccctcggt ttaatcaaac gactggctta ctcattttac    540
actgggccca cccagggaaa ggtagtattt ggaggggtgg atcatggaaa gtacgatggg    600
tgcctggaga aactcgagat tgtccatgac agtgcttttt acacactgct tgaggcaatt    660
gatgctgatg atacttccgt cttggatgag caaattcatg ttttgtttga tactggtacc    720
gccttgacac tttttcccag ctttattgct gaacaactgg ctgatttttt gaaagctaca    780
tattcggacg aatacaatac gtttgtagtt ccctgcgacc aagattttga ttttgaatac    840
cttcattttg gttttcgaaa cattaagttg tcggtgcgct ttaaggatct gtttttagtc    900
attgacgata gtgtttgtgc tgtggggttt gatcaagggg cagatgcaaa caagataacc    960
tttgggtctt cacttttaag aaactactac acgctttatg atctagattc caaagaaatt   1020
ttgattgctg acgtcaagcc tgatggtcca gacgatattg aaatattatc gggtccagtt   1080
caacgaattt gtgatgaaaa gggtgtcagt agcacttcat tatggagtag tctgagtata   1140
gagtccacga tagaaccaga cacttttacc actaagcctt ctatttccca gacacggtat   1200
tcgactagct ccattggacc tcaaaacatt tctaactctt taggtgaata tccttcagtt   1260
tccgtcactc tttctgaaca ccataacact acttccatag cctcaaattc ctcattagaa   1320
gggaaaccag caactccaac tgttacagac cagtcgtacc agaataataa gactacctct   1380
accgtaattg ctgtgaattt gattacccat tcaaccactc attcaaccac tcattcaccc   1440
acctattcaa ccactcattc tagtaatgga tcacgctcaa ctttagagta cacttcaacc   1500
aaggaatcct cggtgaaaat gccctgtgcg ttgatcatct ccgacacaat tccgtacaat   1560
gcttccggtg ggaatagtag ttatggatcg ttaatttcaa catctacggt taacaatgtt   1620
gaagagaata attcaaacac tgttagacca agaaaaagac agaccttcgt ttcgggaacc   1680
acttccacga tactactcta ttcctcaact acgacccaag catatcagat gttgtcctca   1740
acttcaatcc cccgaccatc cataaaagcc agttcaaatg ctggtagccg caaaacttca   1800
aagacattat taacatttat catattgtat attttttag                          1839
```

<210> SEQ ID NO 6
<211> LENGTH: 1749
<212> TYPE: DNA
<213> ORGANISM: Pichia pastoris

<400> SEQUENCE: 6

```
atgtaccagg cgttgttggt tttgtctctg atatgctttt cgtcggctaa ttttgttaag     60
ctgcgaagca acgctggtat gttttatgat actatggctg gagttccacg ttcagatgaa    120
gagttctggt tgcgtttgga tattaaccaa ggtctctctt ggactctgga tagtagctac    180
tactcctgta atggctcaaa tgtttcgtct tccctgtgtt tcaattctgc tcaaaacgtt    240
tacgatgctt ccaatagtcc aactgcagat ttcgttgatg tctacgcaaa cacaactgta    300
```

-continued

```
aacaatacag atgaggcatc ggccgagaga gtaaatctta caaacaactt atttgctgat    360
ggcgtttata tggaagacaa tttttacgtc acattgaata atggagcaag aatgactgct    420
acagatctga aatttttgaa tgcccacaat agtagcgccg ctgtggggtc tttggcgttg    480
gggagttaca cctcacagga cgtgccaact ttcttacaaa gactccaaag cggtggtctt    540
attgaatcca actcgttttc attggcatta aacgaaatcg attcttcata tggagagctc    600
tatttgggga caataaactc taccaagtat gtcgagcctc tggtagaatt cgattttatt    660
ccggtgtcag atcccaatgg agtttttgga ttcgattggg aagatacatt ccctacagtt    720
ccgatcagcg gattaagcat gtcttcgaat gacaaacaga gaactgtctt tttccccaat    780
gagtggaaca acacggtctt aacgggaaca tacccacttc caatgatgtt agattcaaga    840
aacatcttta tccatcttcc attctcttca atcatacata tagcagtgca gcttaatgca    900
ctgtatcttg atacacttca taaatgggcc gtgaactgtt ctgttggtca actggacgca    960
actttaaact ttcacatggg taaccttacc gttcatgctc ctatcaagga gttgatttat   1020
ccagcatacc aaggagacaa aaggctgagc tttgctaatg gagaagatgt ttgtattctt   1080
gccatggctc ctgatgttta cattggttat ccactgctag gaaccccctt tttaaggaat   1140
gcagtggttg ccgttaatca tgattcaaaa aaggtcgccg ttgccaatct taatagagat   1200
agcattcctc ccgcttcgaa cgtttctgtt tcggaatcaa tgggagttta tgttcctcca   1260
cctgtttcaa cttcaagaac atcggagaga ccgtccacac tagatgagac tagtacagcc   1320
aattttgaca aaagggaaga gtctgcaata tcatcaagtt cagtcactaa cagctcgtct   1380
agaaattctt caaccataac ttcttcagga actcaaaccg agcaaacatc aggcatagct   1440
accatcgaaa cagatagcat accaggagct ctagggaata atttaactga ttattcaacg   1500
ctgactctaa caatatacac caattccgaa gtggacgaac tcaatcctaa catagcaaca   1560
gcattcattt ccaatggttc tatttattca gagccttacc ccttttccgg aactgcagtt   1620
gctgaatcat tcagtgcatc accttcacag gctgaaggat cgaactcatc gtcctcagga   1680
tcttctttag ttttgtgttt ctttacatca ttggccagtc tgttgactgt gagctgtcta   1740
ctactgtaa                                                           1749
```

<210> SEQ ID NO 7
<211> LENGTH: 1895
<212> TYPE: DNA
<213> ORGANISM: Pichia pastoris

<400> SEQUENCE: 7

```
atgtttgtga tccagctggc attcctatgt ctaggcgtca gcctaaccac tgcacaacct     60
agttcacctt tcaaggcaaa taagtttcct tttaaaaagg ttcactactc atcaaaccct    120
agcgatcgcc ttattaagcg agacaactat aagaagcttg acttgagaca tcttggcgtc    180
ttgtatactg cggaaattga aattggttca ggcaaaactg aaatcgaagt tattgttgac    240
accggatctg cagatttgtg ggtaattgac tcaaatgcag ccgtatgcga ttgtcctatc    300
ttgagataca aggtacaagt gtttccaccc ttagtcaaac tgccaacgta acacccctat    360
caggtaaact tttgaatgga cttcaagaaa ttggcattgt aactgatggc aaaatttcca    420
aaaagtttca ggaaaaccat cttttgaaga gaaacgaggc cttgaatttt gatgtcgatc    480
tgaataagcc catttgtgat caatttggat ccttcaatcc acagtcatca agaacttttc    540
aaagcaacga cacagcattt agtatcagat atctggacaa ctcttttgcc aatggatcgt    600
gggtgaggga tacggtttat gttggtgatt ttgaaattga ccagcaaagt tttgcattgg    660
```

```
ttgatatcac aaataactac atgggaattc tgggccttgg tccttctagt cagcagacaa    720
ccaatagtga tcctacagat aacagtttca cttatcttgg tattctggat tctttgcggg    780
cccaaggatt cattaattca gcctcgtact cggtttatct ggccccagat ggtaagactg    840
atgatactga tcacgatgat ggtgagatcc tgtttggtgc tatcgacgag gctaaaatta    900
atggacagtt gaagttgttt ccatatgtca atccttataa atcggtatac cctgaccaat    960
acgcttcata catcaccgtt tccagtatta ctgtagccag ttattttagt agccgcttgg   1020
ttgaaagaat ccctcaatta gctcttttag acactggtgc cacattttct tacttgccaa   1080
cttatacgct gatacgtctc gcctatgcca tccatcctgg ttttgagtat gtccgacaac   1140
tgggtttatt tattatagag tcaaacgtac tctccagtgc gagacaaagt accattgact   1200
tccggtttgg caaagacgta gtaattcgat ccaatgtttc agaccatcta ctcgacgtat   1260
cacaatactt cacatctgga cattatcttg cacttaccat ccatgaaagt gtcgatgggc   1320
ttctcatttt gggtgacacg tttatcaagt ccacctactt atttttcgac aatgataaca   1380
gtgaattggg tattggtcag atcaaaatta ccaatgacga ggatattcaa gaagttggtg   1440
aattcacctt agaacgcgat tcagactatt cttctacatg gtccatttac tcttatgaaa   1500
cttctttgga tcccttaagc actggcactg gtacggggtc aacctattct cctactcgca   1560
gtactacagc tagaagcgaa ccgactacgt ctcgacgctc caccaccctt caacccagaa   1620
caactgtgat tccttctatt gacaggcttt cattgaacag cataactagt catggttcct   1680
ctactaacgg aacctcccca actaatgaga cttcttttgc tgaggatgga ggaactttga   1740
cacccgaaga agcttctttg acaacttcac taaattctgc tactatttct gagactactt   1800
ttgtcgatgt tgaaacttct actaccaatg gtgcttcagt tgtatctttg agtgttggtc   1860
cctgcattat tgccttccta ctactcatct cttaa                              1895
```

<210> SEQ ID NO 8
<211> LENGTH: 3201
<212> TYPE: DNA
<213> ORGANISM: Pichia pastoris

<400> SEQUENCE: 8

```
atgagcatgg gagctactgt ttcaaaggag tccactgtag acctaacact gccgctgttg     60
cagctgagtc caagactgtt gttcctgcct ggagttgtct acaagacgac tttcaagttc    120
caggaggggg tcaacatctt gctacgtttt agagacctgt tcgatgagtc tttttctgaa    180
agaaatgacg ttctaggtga tattgcccgc tcgcagaagg aacaacagga aaacgattat    240
gaccatatcc ctttttttgag cagcaatgct aagaagagca taggtgtcct gaaagaccaa    300
cttgaacttg gtgggtctga tgacaagtca cttccctggg ttattgcctg tctccctggg    360
ttcgaccagt cagaccagga ctccattgcc actacaattt gtcagataac tgaggtgtcc    420
gtcgttaacc aggatattgt actatccttc gaagcattaa ccagaggatc tttaaaatcc    480
aaaaagacca tctccatgaa tgaatcaacc atatctgtgg aagtggatat accatttact    540
gaggttgacc agaccatcag taacaagctc atcttgacaa atattgataa gggtctgcaa    600
ctactggaga atatcaaaca gtttctagtc acctatcaaa atgacatgat gaaccttgaa    660
gatactacca tggaaaagaa ctcccgtcta aagtctgcaa tgatgatttt ggctccgttg    720
tctcacttga tctacgccac tgtctcatct caagaatcca ctcatgctta tactagacta    780
tccaaccagt acaagtccgc taagaaggaa ttagattcaa ccaaaaacag aaagtcttta    840
```

-continued

```
ctcaagaaga ttttgaaaac taatgatatt ctcacttcag tgttcccctt cagtatggtt    900
caaaaggtgg atgtcttggg agctatttca agttctacag acaggatcca aacaactatc    960
gacgcgttgg actttgccaa tccacttttc gaaacatatt tgaacgttga ttatgttctg   1020
gagacatgga aagattttga cactaagaac ggcaaaattg ctgccaattt gaccaggtct   1080
caattagtat ctaaccactt gaagggcctc agagtactga ttgaagacat ccaaggaact   1140
tcaagaaggc gggtcagtcc ttctcagaga actcgtttgg cgccttcgcc caatacaaat   1200
tctgcaaatc aggcaccgaa agctggagaa tcagacgacg aaaataaaga attgcgtgat   1260
tttatcaaca acctctccaa attgaagatc tcagaggatg gaaagaggct cgttaccaaa   1320
gatttcaaca gaatgactca aatgcaacca agttcatcgg agtaccaact gctcagaact   1380
tatttagaga ttattatgga tatcccatgg gaaacaaaaa atattgtaaa acaacaaatt   1440
tttgatctag acaaggccaa agaaacacta gatcaggacc attacggaat ggactccgtc   1500
aaagatagga tcttagagta tttagcagtt cttaaactcc acgatcacat taaaacgtcc   1560
aaccccaagc aagaagacga ggaaatcaaa gccagagcac ccattctctt actaacaggt   1620
ccacctggtg ttggtaaaac ttcgttagga aaatctattg caaaggctct gaacaaaaag   1680
ttccagcgag taagtcttgg aggattgaag gatgagtccg aaattaaggg acatcgcaga   1740
acttacgttg gagcaatgcc aggactattg acccaagcac tgaggaaatc tcaatctttt   1800
gatccagtga tacttttgga tgaaattgac aaggttgtcg atggatccca aggccctggt   1860
agtcgtgtaa acggtgatcc agctgctgct ttgcttgaag tgttagaccc agagcaaaat   1920
tctaacttct ctgaccatta tatcgggttc ccacttgact tgtctcgtgt tgtttttatc   1980
tgtacgtcca acgatatgag catgatcagt gccccattaa gggatagaat ggaggttatt   2040
gaactgaatg gctacaatta tttcgaaaaa gtggagattg ttaaacaatt cttattacca   2100
aagcagatca aaagaaacgg actgcctacg aatgccgaat caccatcggt ggttattcct   2160
gacgaagtga ttatgtacat cgctgtcaat tatactcggg agccaggtat tcgtaatttg   2220
gaacggttaa tagggagtat ctgtcggggt aaggctattg aatactctag cttgatgagt   2280
agtactcaag ctccaggcga aattccaaag ggatacgttt ccaaggtcac ggtagataat   2340
ctttcaaagt acattggaat acccccggaa ttgtctacag gcaagaatat gaggaatgat   2400
tcagctatct ctaaaaagta cggaatcgtg aacggcctca gttacaatag tagcggacat   2460
ggaagtaccc tagtctttga aatgaccggt atacctaata gtactaacac taacatgatt   2520
acgaccggca gattgggtga tgttcttaca gaaagtgtca agatcgcaag aacaattata   2580
agatcgatgt ttagtcacaa cttactacaa ttaaaggatg acgaaacttc aacttctggg   2640
gatcttttga agaggtttga cactactcag gttcacatgc atgtgcccgc tggtgctatt   2700
caaaaagacg gacccagtgc tggaatcacc attacgctgt gccttctgtc ggtgatgcta   2760
gagaaacctg taccaaggga tttggccatg actggagaga ttactttgag agggatggta   2820
ctgccaattg gaggtgttca tgagaagcta ctaggagcac atttaactgg aaccgttaaa   2880
agggtgatcc ttccaagaag taatcgaaga gatgtcattc aagactttat ctctaacttg   2940
gaagccaata acagaagttc tagggataag ctactggtag atcttatcaa agaggaggag   3000
tcattactgt ccaactcaaa taaatccgaa cgaattggag tgttcgggct tcctgaaaaa   3060
tgggttcaag agaagttggg acttcaagtg agctacgtgg aagaattttg ggatgttatc   3120
cagattgtct ggaacgatca ggttgaaatt gacagcacca aattacacga gctagctact   3180
aaagagttcg caaggctatg a                                             3201
```

<210> SEQ ID NO 9
<211> LENGTH: 1680
<212> TYPE: DNA
<213> ORGANISM: Pichia pastoris

<400> SEQUENCE: 9
atgcaattgc gtcattccgt tggattggct atcttatctg ccatagcagt ccaaggattg 60
ctaattccta acattgagtc attacccagc cagtttggtg ctaatggtga cagtgaacaa 120
ggtgtattag cccaccatgg taaacatcct aaagttgata tggctcacca tggaaagcat 180
cctaaaatcg ctaaggattc caagggacac cctaagcttt gccctgaagc tttgaagaag 240
atgaaagaag gccacccttc ggctccagtc attactaccc attccgcttc taaaaactta 300
atcccttact cttatattat agtcttcaag aagggtgtca cttcagagga tatcgacttc 360
caccgtgacc ttatctccac tcttcatgaa gagtctgtga gcaaattaag agagtcagat 420
ccaaatcact catttttcgt ttctaatgag aatggcgaaa caggttacac cggtgacttc 480
tccgttggtg acttgctcaa gggttacacc ggatacttca cggatgacac tttagagctt 540
atcagtaagc atccagcagt tgctttcatt gaaagggatt cgagagtatt tgccaccgat 600
tttgaaactc aaaacggtgc tccttggggt ttggccagag tctctcacag aaagcctctt 660
tccctaggca gcttcaacaa gtacttatat gatggagctg gtggtgaagg tgttacttcc 720
tatgttatcg atacaggtat ccacgtcact cacaaagaat tccagggtag agcatcttgg 780
ggtaagacca ttccagctgg agacgttgat gacgatggaa acggtcacgg aactcactgt 840
gctggtacca ttgcttctga aagctacggt gttgccaaga aggctaatgt tgttgccatc 900
aaggtcttga gatctaatgg ttctggttcg atgtcagatg ttctgaaggg tgttgagtat 960
gccacccaat cccacttgga tgctgttaaa aagggcaaca agaaatttaa gggctctacc 1020
gctaacatgt cactgggtgg tggtaaatct cctgctttgg accttgcagt caatgctgct 1080
gttaagaatg gtattcactt tgccgttgca gcaggtaacg aaaaccaaga tgcttgtaac 1140
acctcgccag cagctgctga gaatgccatc accgtcggtg catcaacctt atcagacgct 1200
agagcttact tttctaacta cggtaaatgt gttgacattt tcgctccagg tttaaacatt 1260
ctttctacct acactggttc ggatgacgca actgctacct tgtctggtac ttcaatggcc 1320
tctcctcaca ttgctggtct gttgacttac ttcctatcat tgcagcctgc tgctggatct 1380
ctgtactcta acggaggatc tgagggtgtc acacctgctc aattgaaaaa gaacctcctc 1440
aagtatgcat ctgtcggagt attagaggat gttccagaag acactccaaa cctcttggtt 1500
tacaatggtg gtggacaaaa cctttcttct ttctggggaa aggagacaga agacaatgtt 1560
gcttcctccg acgatactgg tgagtttcac tcttttgtga acaagcttga atcagctgtt 1620
gaaaacttgg cccaagagtt tgcacattca gtgaaggagc tggcttctga acttatttag 1680

<210> SEQ ID NO 10
<211> LENGTH: 1233
<212> TYPE: DNA
<213> ORGANISM: Pichia pastoris

<400> SEQUENCE: 10
atgatatttg acggtactac gatgtcaatt gccattggtt tgctctctac tctaggtatt 60
ggtgctgaag ccaaagttca ttctgctaag atacacaagc atccagtctc agaaacttta 120
aaagaggcca attttgggca gtatgtctct gctctggaac ataaatatgt ttctctgttc 180

-continued

```
aacgaacaaa atgctttgtc caagtcgaat tttatgtctc agcaagatgg ttttgccgtt    240
gaagcttcgc atgatgctcc acttacaaac tatcttaacg ctcagtattt tactgaggta    300
tcattaggta cccctccaca atcgttcaag gtgattcttg acacaggatc ctccaattta    360
tgggttccta gcaaagattg tggatcatta gcttgcttct tgcatgctaa gtatgaccat    420
gatgagtctt ctacttataa gaagaatggt agtagctttg aaattaggta tggatccggt    480
tccatggaag ggtatgtttc tcaggatgtg ttgcaaattg ggatttgac cattcccaaa     540
gttgattttg ctgaggccac atcggagccg gggttggcct tcgcttttgg caaatttgac    600
ggaattttgg ggcttgctta tgattcaata tcagtaaata agattgttcc tccaatttac    660
aaggctttgg aattagatct ccttgacgaa ccaaaatttg ccttctactt gggggatacg    720
gacaaagatg aatccgatgg cggtttggcc acatttggtg gtgtggacaa atctaagtat    780
gaaggaaaga tcacctggtt gcctgtcaga agaaaggctt actgggaggt ctcttttgat    840
ggtgtaggtt tgggatccga atatgctgaa ttgcaaaaaa ctggtgcagc catcgacact    900
ggaacctcat tgattgcttt gcccagtggc ctagctgaaa ttctcaatgc agaaattggt    960
gctaccaagg gttggtctgg tcaatacgct gtggactgtg acactagaga ctctttgcca   1020
gacttaactt taaccttcgc cggttacaac tttaccatta ctccatatga ctatactttg   1080
gaggtttctg ggtcatgtat tagtgctttc acccccatgg actttcctga accaataggt   1140
cctttggcaa tcattggtga ctcgttcttg agaaaatatt actcagttta tgacctaggc   1200
aaagatgcag taggtttagc caagtctatt tag                                1233
```

<210> SEQ ID NO 11
<211> LENGTH: 942
<212> TYPE: DNA
<213> ORGANISM: Pichia pastoris

<400> SEQUENCE: 11

```
atgaagctct ccaccaattt gattctagct attgcagcag cttccgccgt tgtctcagct     60
gctccagttg ctccagccga agaggcagca aaccacttgc acaagcgtgc ttactacacc    120
gacacaacca agactcacac tttcactgag gttgttactg tctaccgaac tttgaaaccg    180
ggcgaaagta tcccaactga ctctccaagc cacggtggta aaagtactaa aaagggtaag    240
ggtagtacca ctcactctgg tgctccagga gctacctctg gtgctccaac tgacgacacc    300
acttcgacta gtggctcagt agggttacca actagcgcaa cttcagttac ctcttctacc    360
tcctctgcaa gtacaacaag cagtggaact tcagccacta gcactggtac cggtactagc    420
actagcacta gcactggtac tggtactggt actacaggca caggaaccac tagttccagc    480
actagctctt ctgctacttc gactccaacc ggttctatcg acgctatcag ccagacactt    540
ctggatactc acaatgataa gcgtgctttg cacggcgtcc cagaccttac ttggtctacc    600
gaactcgctg actacgccca aggttacgcc gattcataca cttgtggctc ttcattagaa    660
cacacaggtg gaccatacgg tgaaaatttg gcctctggat actctcctgc tggcagtgta    720
gaagcatggt acaacgagat cagcgactac gatttctcta acccaggtta ttctgctggt    780
accggtcact tcacccaagt tgtctggaaa tcaactacac agctgggctg tggatacaag    840
gagtgcagta ccgacagata ctacatcatc tgcgaatacg cacctcgtgg aaatattgtt    900
tctgccggct acttcgaaga caacgtcctg cctcctgttt ga                       942
```

<210> SEQ ID NO 12
<211> LENGTH: 690

<212> TYPE: DNA
<213> ORGANISM: Pichia pastoris

<400> SEQUENCE: 12
atgactgtgc aaattttgat tgtagttacc agtgttgcta agtatgaaag cggaaagctg 60
ccaacaggct tgtggttaag tgagttgaca catatgtatc atagtgcaaa agagaacggc 120
tatgatgtga cgattgcgag tccgcaaggc ggaaacattc cgcttgaccc tgaaagcttg 180
aaatcaatgc tgattgacaa gctttcaaag gattatgaga caaaccaaga ctttatgaag 240
ttgttgcaaa acacaaaaag tttgggtgaa gtcacaggac aacagtttga cgttgtttat 300
ttggcaggtg gacacggaac aatgtatgac tttccgaaca acactgtttt acaaaacatc 360
atcaaagaac actatgaggc gggcaaaatt gttgccgctg tatgtcacgg agtttgtggg 420
cttttgaacg taaaactgtc tgatggcgag tatctaatca aagacaaggc cattacagga 480
tttaattggt ttgaagaagc tatagcagga cgcagaaaag aagtaccgtt caaccttgaa 540
gcagaattga ataaaaaaac ttcaaaatac gagaaagctt ttatcccaat gacgtcaaaa 600
gtggtcgtgg acgggaactt aatcacagga cagaacccat tcagttcaaa agaaattgcg 660
aaagtggtaa tggaacaact gaagcaataa 690

<210> SEQ ID NO 13
<211> LENGTH: 2517
<212> TYPE: DNA
<213> ORGANISM: Pichia pastoris

<400> SEQUENCE: 13
atgattgatg agaagcaatt gaatcaaccc aaaaggagcg tcttaagacg tctccatatg 60
ctgtttctgc cattactagc tatctccttt ttcctgatat atttaagtga tatcacacag 120
cctctcttcc gtgcccgaaa ggaagacgaa aacccgttgg aaatttactt gaaggcattg 180
gaaacgaatg aagctcacaa atggtcaaag gtgtacactt cgcagcctca tttggccgga 240
accaactacg gattggttga gtttactaag tccaaatttg aagaatatgg atttgaggcc 300
agtgtcgatg actacgatgt gtacctgagt taccctattg atcatagttt ggaattgtat 360
gagcattctg aggataaaaa tgacaagctc ttgtataagg cttcgctgca agaggacgtt 420
ctctctgaag acccaactac ttcaggcgac gacctgatcc ctaccttcct tggttacggt 480
gctaacggca atgtatctgc agaatacatc tacgctaact atggaaccaa agaggacttt 540
gaggatttgg tggcccgtgg tgttccaatc aaggggaaga tcgcagtcat tagatatggt 600
caaatattta gaggcttaaa ggtgaaattt gcccaagaat atggcgcaat cggtgctgtc 660
atatacagtg acccaggcga cgattatggt atcacccctg aaaatggtta caagccttac 720
cctcatggta aagccagaaa cccaagctct gtgcaaagag gttctgccca atttttgtct 780
gtttatcccg gtgacccaac cacgccagga gttggatcga agaagggagt agaaagagtt 840
gatcctcatg ctacaacccc ttccattcca gtcttgcctt tgagtttcaa agatgccttg 900
ccaattttga agaaacttaa taaggaagga ttgtctgttc ctgactcctg gaagggaggt 960
ctcgagggag ttgattacag taccggccca gctaaaaaca ttcatttgaa cctttatagc 1020
gaacaaaact ttactattac acctatttac aatgtctatg gagagatcaa aggtgagaat 1080
gctgacgaag ttatcattat tggtaaccat cgtgacgctt ggattaaggg aggtgcttct 1140
gaccctaaca gtggatctgc tgctttgatt gaacttagta gaggtttgca cgccctaacc 1200
aaaacaggat ggaagccaca ccgtactatt gtactagctt cctgggatgc tgaggaatat 1260

-continued

```
ggcttgattg gatctactga gtttggagaa cagtttgaga agttccttca gaagaaggtc   1320

gttgcctatt tgaacgttga cgttgctgta gctggaactc atcttcattt gggtgcctcg   1380

ccatctttgt tcaaactatt gaaggataat gccaaagaaa tcactttcaa gaattcaacc   1440

gagactttgt atgacaacta tgttaaagat catggcaacg acattatttc gaccttagga   1500

agtggaagtg actacactgt ctttttggat catttgggaa ttccttcgct tgatattggt   1560

ttcattgctg gaaaaggtga cccagtatat cactatcatt caaactatga ttcgtaccac   1620

tggatcagta ctagtggtga tcctggattt gagtatcata atgtactggc caaatatttg   1680

ggttcgttgg ttttgaatct ctctgagaga gaggtgttgt acctgaagct tcatgattat   1740

gctaccgaat tgctcaagta cctcttggaa gcctacgccc aaatgccaga ggaatgggac   1800

gatgaagtaa ttggtttcag atcttcctcg tgtcatcgtg cgaaagcatc tcatcatggt   1860

aaggatcctc atcatgaggg aagacgccat cacggaaaag gattccattc taaaggaggg   1920

cctcatcatg gggaacgcca tcacggaaaa ggattccacg ctgaaggggg accccaccat   1980

gagaaaggac cgcatcacga aaaagggctc cacgtcgaag gagagcccca tcatcagaaa   2040

ggacctcact ttgaaaaagg attccatcat gacatggaga tgtaccataa gaaattggct   2100

catcacggta aagaacccaa gacgaagcta aagcacttga agaaacaagt tgagagttta   2160

atcatcgatt tcgccaatac cactcaaaca tatgacgctt acactgactt ccttcagaag   2220

caacatgaga ttagggattc tctttcattc tgggagaaaa tcaagctaca ttttaagatc   2280

aaggcagcta acttcaaact taaatatttt gagcgagttt tccttcatga aaatggctta   2340

aagaacagag aatggttcaa acatattgta tatgctgcag gaaggaacac tggttacgcc   2400

ggacaaagac tgcctggtct tgtggaagcc attgaagaca agaatctgca tgatgcagta   2460

aaatggcttc acatcctttc caagaagatt gatagtctac agaagtcatt agagtag      2517
```

<210> SEQ ID NO 14
<211> LENGTH: 888
<212> TYPE: DNA
<213> ORGANISM: Pichia pastoris

<400> SEQUENCE: 14

```
atgagattac ttcacatttc attgctatca attatctcag tattgaccaa ggccaacgct     60

gaatgttgtt acaccaacac acatactacc actgaagtct ggtatactac agtatatgct    120

cgagatgtta gtgaagagac ttcttccaca ctggctggtg gaagtgcaac tgtcagctca    180

gaagtgagtt cgacaattga atctagcgtt gccacttccg ctaccaccga atcttcaagt    240

gagacatcag ggtccacatc tgggtccaca tctgccactg aatcatcaac tggtagtagc    300

tcgctagcaa ccagttcatc gataaccagt tcagagtctt ccaccattac acaaaccaca    360

ggacaagagt caacaagccc aaccccatcg tcctcagaga caggttcttc tactactact    420

ccctacgata taagtccaac ggcaagttcc gactttgatg cttttaaata tcaaattctt    480

gatgaacaca acataaaaag agctctacat ggagttgacg gattagagtg ggatgaagaa    540

gtatatgctg ccgcccaagc atatgctgac gcatacactt gtgacggaac cttggttcac    600

tctggaaata gtctgtacgg agaaaactta gcgtatggtt actcaaccag agggactgtt    660

gatgcctggt acagtgaaat tgaatattat gactttaata acccaggtta taccccaggt    720

gttggacatt tcactcaagt agtttggaaa agcaccacaa agctcggctg cgctttcaag    780

tactgcaatg actattacgg agcctacgtg gtatgcaact actcaccacc aggaaattat    840

gtcaacgagg gatacttcga agccaatgtg ttaccactgg tagattaa                 888
```

<210> SEQ ID NO 15
<211> LENGTH: 681
<212> TYPE: DNA
<213> ORGANISM: Pichia pastoris

<400> SEQUENCE: 15
atgagttatc ccctaggtct gggtcgtaca gcttataggt tcatcccgag gtcaatctgt 60
tcaagacgat ccatctcatc ccatgcatta cctccaacgc cctccaactc accaccagca 120
ggagatttat tcaccaaact gctgaacgaa cgcatcatat atttagcagg aggcattgat 180
gatgcgcaag caacatctat cacggctcaa ttgctgtatc tggaatcgca gtcaacgtcg 240
aaacaaatca acatttacat caactcacca ggaggttctg tcacggcagg gctggccatc 300
tacgacacaa tccagtatat ccgagcgcca gtttccacgg tttgcttagg acaggcatgc 360
tccatggcat ccctcttgct tgcaagcgga acgcatggca aacgtttgat cttgccaaac 420
gctaccataa tggtgcatca accatcttcg gcaaacggaa ttaagggaca ggccactgat 480
atcgagatat atgcccgtca tatcatcaat accaaacaga aattgcaaac tttataccta 540
aaacacatgt ctccaaccat gacggtggat gaaatcactg cacttttgga gagagatcgg 600
ttcatggagc cagaggaggc agtgtctctt ggactggcgg accgtgtatt agagaggaaa 660
cccccggttg tatctgacta a 681

<210> SEQ ID NO 16
<211> LENGTH: 1659
<212> TYPE: DNA
<213> ORGANISM: Pichia pastoris

<400> SEQUENCE: 16
atgacagata ccaaggagtt agccacgttg ctggagaact tgttgaaatt gcaaaaatca 60
ggaagtcttg gtgaaattgt gggtcaagca cagcgcattt atcatgacat ttctgacctc 120
tcagtcctat ctggattatc aaccccagaa gtgctctctc ctcacacatc tccagatgtc 180
cccgagagag ttccatctga agtcaactta gacaattcca atctggcaac tgatgtcaac 240
gaaaaggaga agtattttga cgattttgca aatgactaca tcgagtttac ctacaagaac 300
cccaccacct accatttggt gcaatctgtg gcggaattgt tgaagaaaag cggattcgaa 360
tatcttcctg aagcagctga ctggtccaaa ttattcgacc ctgaaaagac gggagcgtat 420
ttcacaatcc ggaatggaac ctctttagct gccttcacaa ttggtagttt ctggtcccca 480
gccaagggag taggagctat cggaagtcac atcgatgctc tcacaactaa gctgaagcca 540
gtctccaata agagtaaggt tgatggctac gagttgttgg gagtttcccc ctatgctggt 600
gctttgtctg acgtctggtg ggatagagat ttgggtattg gtggaagagt aatttacaaa 660
aatgaatctt ccggcaagct ttccaccact ttggttaaca gtacacctca tcctgttgct 720
catattccaa ctttggcccc tcattttggt actccctcca acggtccatt caacaaggaa 780
acccaagcag ttcccgttgt aggattttct gacggaaacg acgaggagaa acccactgag 840
gatgaacaaa agtctccttt gattggtaag cattctttaa aactactccg ctacatatct 900
aagctagcag gagtgccagt gtcctccttg attgatttcg atttggacat attcgatgtc 960
caaaaaggta ctaggggcgg tctttccaat gagttcattt acgccccaag agtggatgat 1020
cgtatttgtt cttactctgc tctacaagcg cttatcagac gtcacaagga tcccgaatcc 1080
tttgtcacag acgactcttt caatcttgtt gccctttatg acaacgagga gatcggatct 1140
ctctccagac agggagccaa gggtggtcta cttgagtcga ccatttccag agcaatcgct 1200
gcattgaaaa tttcagagcc agggactctg caaagactat atgcaaattc agtgattctt 1260
tctgcagatg tcacacattt gttaaatccc aatttcaccg aagtgtactt ggagcaccac 1320
aagccactgc caaacacagg gattgcactt gcgctggatt cgaatggcca tatggccaca 1380
gatttgttag gcaaggtcgt tgttgagcag ctggctaaac tcaatgatga taaagtgcag 1440
tacttccaga ttcggaacga ttcaaggtct ggagggacca ttggacccag tatttccagt 1500
agtactggcg ctagaaccat tgatcttgga attccccaat tgtccatgca cagtattcgt 1560
gctaccgtgg gatacaaaga tgttggcctc gctgtcaagt tttccaagg gttctttaaa 1620 aattggagaa aagttgtcga cggcattgaa gagttttaa 1659

<210> SEQ ID NO 17
<211> LENGTH: 3552
<212> TYPE: DNA
<213> ORGANISM: Pichia pastoris

<400> SEQUENCE: 17
atgacttcgg tatttttggg tgtttataga gccctatttg attaccaagc tcaaaatgac 60
gaagaactaa ctgtgcatga gaatgatcta ctatacgtat tggaaaagtc cgaaattgat 120
gactggtgga aagttaaaca acgagttatc ggagttaatg tcgaggaacc aataggtctg 180
gtacccagta cttatattga gcctgctaca cctatcgggt cagctgttgc actgtatgat 240
tatgacagac aaacagaaga agaaattact ttcaaggaga atgacacctt tgacgtgtac 300
gacaccgacg atcaggagtg gatcttggtt ggcctgaaca atatccattt tggtttcgtg 360
cctgcaaact acatacaaat ttctttgggt acgacggcac ctgcttctaa caatccacca 420
atacttagtc ccgccagctt ccctccacct cctcaacgga tcaacaactc ctctgttccc 480
tctctcaaag atgctgaacc agcaagaaat ctagaggacg ataatgctta tgaagaggag 540
gaagatgtac ctccaccaat gccaacgcga ccaactgcca ctacagctac atctaatatc 600
tctgctcctc aggactctga atccgaagag gaaccttcta gtagtagcag aaggccaagt 660
ggccgttcaa gggcggatga tgattttgta aaaggagact atttcacttg ggatgttcag 720
gaaattaatg gccgcaaaaa gaggaaagct gtcctgggta tcggaaatgg tagtatttat 780
gtccaagcag agggacattc ttctaagaaa tgggatatca ggaatttgac aaatttcagt 840
aacgaaaaaa agcacgtctt ttttgacttt accaacccct cggcatccta tgaacttcat 900
gcaggctcca aggacgcagc agatgccatc ctgtcaattg ttggtgattt gaaaggtgct 960
tcttcaatgc gtgctttgaa agaggtgaag gctgcatctt ctgccccaaa aaccaagact 1020
ggtaaagtca gttacaactt cgatgctgaa agtcccgatg agttgtcgat tagggagggt 1080
gatgttgtct acatattgaa cgataaagaa tcctctgagt ggtggatagt tcaggacgtt 1140
aatactaaca agaaaggtgt tgttccagct agctacatag agttgattag cgggggtgga 1200
tctactttag ccagcattgg ctcttctatt tccaaaggtt ctaagaaagc ttttggatcc 1260
tccagaaaac gtaaggaaaa agagcgtaag catttggaag agcaacgtgc cgctaaaaga 1320
gaaaccgaaa gggaacgtca aagacttcga tccaaggaag aaagggatag gctaagaaag 1380
ttagatgaaa aggaaagaag gaaaaagcaa aaagctactc cacaggatga agaccaaccc 1440
gagactagca aacctaatcc tcatagagtg cgtacctgga ttgacagttc aggatccttc 1500
aaagttgaag cagagtattt gggagttgtt gacggtaaga ttcatctgca taaaacaaac 1560
ggtgtaaaga ttgccgtagc ggctcctaag ttgtcactag aggatttaga gtatgtggaa 1620
agaatcactg gaatgtcgtt agaaaaatac aagccaaagc caaaatctag tggttcctat 1680
tccagacctt ccaaaaagcc atcctctaga gaatcttcac caaaggagtc cagccgctcc 1740
ggagttaaac aatcagttcc caagattgat cctcccaaag acccagatta tgattggttt 1800
caatttttct tgggttgcga tattgatccg aataattgtc agcgatacag tgtggttttc 1860
attaatgaac aactggatga gagtagtttg caagacctca ctccatccct actaagatcg 1920
ctagggttaa gagaaggtga tattttgaga gttcaaaaat tcttggataa caagtttggt 1980
cgaaccaaag ctcaagaatc tgctaccaat ggtggtttat ttaccaagag tgatggtaca 2040
ttgaagaaca ataggtccac tgatgttcta acaagtacag ttgtaacgcg agaaacttta 2100
agtcctacta aggccgaggc taagagcaaa agaattgatg acgaagcatg ggctctcaaa 2160
cccgctgccg aatctagctc tcaaatggat caattctcca gacctgtcag tgcaatgagc 2220
aaacaattga ctggatccat acaagatctc gtcaacttga aacctttggg ggacaatgca 2280
aacaacgctt cggtagccca caaagctgaa acaccaaaca ctacccagga caaaccttct 2340
gctcctgtct tggaacctgt gaagactgga gctgcaaggg gacctgtgca agcgcaacca 2400
acaagtggtg gtttcgtcac tgcacaacct actggtgctc tagttgcaat gcctacaggt 2460
ttcatgccca ttacgatggt gcccgtaaag acaggaggaa ctatagctct tcaacccact 2520
ggtggattcg tttcgttgca aagaactggt ggggtacttc cgcaggttac agggggactt 2580
gttcccgttc agactggtgg gttagtaatg cctcagacct catttggtgt aactccaact 2640
ttgcagccaa caggagggat tctacctgct cagaggacag gtggattggt tcctgttcaa 2700
aggacggggg ggctaattcc cgtccaacaa actggaagat tagttcctgt tcaacaaact 2760
ggaggattga ttcctgttca aaggactgga ggattagttc ccgttcagag aactggaaac 2820
ttacaacctg tacctacaac ctcttttgga agtcaaccaa caggaacttt tgtgcctcaa 2880
tcttcctttg gtaatcagtt ggccaccaat ttgaataacc cgcaaaccac attcggctct 2940
caaccaacag gaggtttccc tcagacatca tttgcacaaa atcagtttag acaatcgaca 3000
ggaggtttcc agcagacccc aattgtgcaa caaacagggg gattccccca atactccgct 3060
ggacaacaga cggtaggatt ccctcagaac tcttttggac agcagacagg aggaattgcc 3120
caaaactcat ttggacaaca gacaggaggt tatcaaacag gttttcaagg aaatggatcg 3180
attccaatgc cccagtcctc attcggtgct tcaaatctgg gattcaatgg tgctacgcag 3240
cagaactaca acattggcat gggccaatct ttgccagcag cttctatccc tcccccttcaa 3300 ccctcttaca cctcatcact caatggaatg tcaaacatgc ttcagaacgt aagcatctct 3360
cagcagccac aacaagccca gccaatgacg acttttggag cacctgtggc ccagcctccg 3420
ttacaggctc aaccaactgg ctttggtttt ggtaactcgc cctatggagg tcagaaccca 3480
ctccaatctc agccaacagg taaaagagcc aacttatcag cagctaccgc agacaaccca 3540
ttcggcttct ag 3552

<210> SEQ ID NO 18
<211> LENGTH: 1662
<212> TYPE: DNA
<213> ORGANISM: Pichia pastoris

<400> SEQUENCE: 18
atgaccaacc aatcaacagt ggtggattta cgcctttcat ccaagagagt tgttggcaaa 60
ccagtcaagt tgcccacagt cctagcgtgc tcagggtcag attcttccgg tggtgcaggg 120

-continued

```
atcgaagcag atatcaaatc catcacggct tttgggtgct atgcgctaac agcaattaca    180

tctttaactg cccagaatac caaaggtgtc accagtatag aaaacaccga cccaaagttt    240

ttcgaagaga ttttagaggc aaattttgag gacattgaaa tcgatgtggt gaaaactgga    300

ctgttaaacc ctgagtcatc tcgtttattg ctgaaatttt tagataaata ccacaaagga    360

aagccatttg tcctggatcc ggtcttagtg gctacgtctg gttcaatgct tgcagatcaa    420

cacgaattag ggttcaccat tgattctcat tttaagaaag ctactatcat tactccaaat    480

ttcgaagagg catgtgtgat ctactcttac ttgaaaaagc tgaagactgt agatgagttg    540

ggtgaaatag aaactttaga ggatttgaaa ggaatggcca agttcatcca gcaaactaca    600

cattgcaact ctgttcttct taaaggtggc catattccct ggaatagaaa cgagcagttg    660

gttaaaaaaa agggaggaga tccagcatac attactgata ttctttatca gggtcatttg    720

gataaattca cggtaatcaa gacagattac ttgacaagtt ctggaactca tggttctggg    780

tgtacgattg ctgcctcaat tgctgcaaac attgcccgtt cgttgaagat tgaggatgct    840

gtaatttctt cgattagata cgttcatcag gcaatttttg gagcagatga gacgctagga    900

caaggaaaag gccctttgaa tcatgtgttt catatttctc ctcccattaa cggcacaagt    960

gctgagaata actttcttcc gttctatcca ggtcacttct tagattactt actggagcat   1020

cctttggtga gtcccatctg gaagaactac atcaaccacc catttttaga aaacgtagca   1080

acaaataagc tggctaagaa cagattcatc cactacattt gtcaagatta cgtgtatcta   1140

gcttcttatg cccgtgtcca cggcttagct gccggagttg cacctgatat tgaaagcata   1200

aaggcagaag cccatataat cgactccatc atggaagaaa tgcatagaca taaagacgta   1260

ttgaactctc gtggaattgt gaaactggat gaattaagac cctccaaggc ctgcaaacag   1320

tattccgact acctcctaaa cattgcgaag acatcagact gggtggccat aaaaatcgcc   1380

ttagcaccat gcatctttgg ctactattac gctgccattt atgctcggtc gtttatcaag   1440

gatgaagctg acgtggacga agaattcttg aattggatca atacgtatac cggtgattgg   1500

tacaaagatg ctgttgacga ggccagacag tcgctagaaa gccatatgca agctgtttct   1560

cccgtccagt tagcagagct agtcaagatc tttgcagatg tctgtcaatt ggaggtgaac   1620

ttctggactt cgccaatgga actaccagaa caagatctat ga                      1662
```

<210> SEQ ID NO 19
<211> LENGTH: 1008
<212> TYPE: DNA
<213> ORGANISM: Pichia pastoris

<400> SEQUENCE: 19

```
atgcctacag tggtgactaa cgagtcctct ctcttgcaaa caaccgtgag tgttgcacca     60

ttggtgcttt tatctgttgt tgatcactac gaacgagtgg tgcaggcacc caacgcccca    120

actaattcaa acgacaaaag agtcgtgggg gtcattttgg gagacaatac aaacaagaac    180

ttgatcaagg taaccaactc atttgccatc ccgtttgaag aagacgaaaa gaacagggat    240

atttggtttt tggatcacga cttcatcgaa tcgatgatgg aaatgttcaa gaagattaat    300

gccaaagaaa gacttattgg atggtaccac tctggaccaa agttaaagtc atctgatcta    360

caaatcaacg agttattcaa gagattcact ccaaatcctt tgcttttgat tgtggatgta    420

aattccaccg atatagtcga tattcctaca gactcatatt tggcaattga agaaattaga    480

gacgatggct caagtgcaga aaaaacgttt atccatttac catccatcat ccaggccgaa    540

gaagcagaag aaattggagt ggagcatctt ctgagggata tccgagacca ggcgtgcgga    600
```

aatctgtcca taagattgac taacaatttc aaatcgctga agtctttaaa cgatcgcata 660
gccaacattg tccaatattt gcgcaagatt ttaagtggag aattaccaat aaataatgta 720
attcttggaa aattacagga catattcaac ttattgccca acttggttgc cgttcaaggt 780
gatcccacaa aaccagccac tgcaagtgct aaccaactag ccacatcatt caatgtgaag 840
accaatgatg aattaatgat ggtttacatc tccagtttag taagatccat cttggctttc 900
catgatttga tcgacaataa gatcgagaac aagaagaaca acgagaaaga taaggaattc 960
acaccaacag aggaagaacc ccaacaagcg gctatagaat cgaaataa 1008

<210> SEQ ID NO 20
<211> LENGTH: 969
<212> TYPE: DNA
<213> ORGANISM: Pichia pastoris

<400> SEQUENCE: 20
atgacaatgt caaccgaaga tatcatcgcc aggcatagga aggagaaaag ggaccaaatt 60
gcacttatta caaggatgaa gaagcagagc actaagtcaa ccaaaaagga aatcatgaaa 120
caatgctctc tcttggaaga agagctacag gcaagacata agaaggagtt aggtgagtgc 180
aagactgaaa attccgtcga gagaagtagt gagcctactg acgaaaaatc aaatggtgga 240
gaactttttt cccctgaaaa gttattatca atgatgactt taaaacagca aggaactcca 300
agtgagaatc aaggaaacgc aactgttcca aagagaaaac gcaataggca gaaggacaga 360
ttagctagaa gggaagttgc cattaaagag atgcaagcag cagcagcaaa agaggctaac 420
ctccaaacaa atttcaaaga gatagaattg aacaacataa gccaactgtg ccaagttgct 480
cacctggaac catatgatat ccgacctgat gggcattgct tgtttgcatc tataaaagat 540
cagttggagg ttcggcacaa aattgaaaat ataagtatac aagatcttcg gtctctggct 600
gcgagtcata ttaaaaatga tcccgagact tatactcctt tcctttttga tgagaatact 660
atgaaaatca gggacattga tgactatgca aacgagctgg aaaccacggc tttatgggga 720
ggtgatatgg aaattttggc attgagcaaa gagtttgatt gtccaatcag tgtaatgatt 780
agtggaagac ctattcatct tgtcaatgcc gacggttcta aagaggagtt gaagttggtt 840
tattaccgtc atgcatatgg cctaggtgag cattacaact ctttaagaga tagatcagag 900
ataagggagt cttgtatagt tgagcaagag gaaaaagaag cggtagacga tggaaaatca 960
tcttcttga 969

<210> SEQ ID NO 21
<211> LENGTH: 939
<212> TYPE: DNA
<213> ORGANISM: Pichia pastoris

<400> SEQUENCE: 21
atgagactta agatcaagcg ttcaaatgaa cagcggctaa taacattgcc tgacggggct 60
acagtatcgg atttacttaa tgaaattgga tcagcttcta tcaatataaa ggttgggttt 120
cctcctcaga caattgatat ctcagatacc agcaagttgc ttactgatag tggaatcaag 180
aatggtgaaa tgatcattgt cactgatacc attgaaacag aagtgcctgt caacaagaat 240
gaggttgcaa ttgccactgt ctcaaaccag aatgatgcgc cctacgttca aatagacgac 300
atcttcctag tcttgcggaa gattcccgat gataattctt gtttcttcaa ctctgtcggc 360
tactgtatat ttggtcctga ttcaatcaag tatccggatt ctcaacaaga actaagacag 420

```
gccgtcgcta atgtaatcag agagaacaac caaggtattt ataactccgc catcttgggt    480

ggaaagtcaa tcacagagta ttctcagtgg atccaaagca gtaattcctg ggaggagcc    540

atcgaagcac agatattggc agaatacctt gatatcagta tctggacagt ggatattgag    600

tctcttcaag tctacaaatt taatgatgaa atggcttcaa ggttttgcgt tattatgtat    660

agtggtattc attacgacgc tatggctctc aagctggaca catcattaga tgaggaggac    720

tcacaaattt gtgtgtttga taagttcagt gagttgggga ctttgattga agacaacgtt    780

ctcaaattaa ccaaccatct taagaaccag ggctattata cgaatacttc cacattcata    840

ctccaatgtc aaatatgtct cgcaacattg caaggagaaa aagaagcaaa tagccacgca    900

aagaaaactg gccacacaaa ttttggtgaa gtcaattga                          939
```

<210> SEQ ID NO 22
<211> LENGTH: 5528
<212> TYPE: DNA
<213> ORGANISM: Pichia pastoris

<400> SEQUENCE: 22

```
atgtcattgt ctgatcctga ggacagccta agacgtctac ttgtgagttt accctccaat      60

gttaagtacg atgcggagtc ttcggtattg aaaagccgac tgaaccttgc tctatatttc    120

tcgctgacaa agagaggtga atatctgggt tccttggtaa cggacttgcc aatggatttg    180

ccatcatctt attccgaaat cttagaggct gaagatgatt cctactcaag attggctgaa    240

tcaatgtaca aatgccctaa ctataagcat catggaagac cttgtgcaag gcagttcaag    300

caaggagagc cgatataccg gtgctacgaa tgtggttttg acgagacttg tgtaatgtgc    360

atgcattgtt ttaataggga gcaacatcga gaccacgagg tttccatttc aattgcttcg    420

tcctccaacg atggtatctg tgattgtgga gatcctcagg catggaatat cgaattacac    480

tgccagagtg aactggaaca agatgaccat tcaagttcag aagttaatcc agattttaaa    540

tctgctataa gggaaacaat ggatattatt ttagattaca ttttggattg tactattcat    600

tctgcatcta tgcttcctgc tgttcaggac atgatgaagg aagacccatc cgactatgaa    660

atggctattc aatatgcttc agatagttct tctctgccca ttgaaagata tggagtggaa    720

gacacgaatg ttcagtcctg gaacgtagtc ctgtggaacg acgaattcca taattatgat    780

gaggctattg attgcatcca gcaagttagt agatgttcat tgtctaaagg acaagctgac    840

gctcaaaaga ttaatgattt tggattttcc atcataagaa gaagtgaatc cttgccttta    900

ctgatagaaa ggtgcgccaa ggttgaagaa tccgggttta ctattacgat tctttctgat    960

agagatgtta cccgattgat tattattgat actatttttg attggttatt gactctgtta   1020

gaaatttcaa ggccggaaat tcagactgct attagagaaa gtttgtgtga atctcttttg   1080

gaagagtttc atgccgacat tcacgaagga gattttttct accgggaaga tgaatattca   1140

gacacacggg gtttgctgga tttcaaaaac agaattccag ccccattggt ggaggatgta   1200

atgaacgagt tgtctattga tgacttgaag aacagaaaac tatccagttt tcttaatgaa   1260

caaccttcag ctctagtcgg ctcaagagta cagtatttct tctatatgga tctgcggttc   1320

tggaaaaagg caagaaaatc tttgaaattg ctaacgacat ctgttttggt ttcaaacttg   1380

gaatacaaaa agacttttc tgaacagttt gtgaaaatat actcgcatct gttgatattg    1440

atggcaaagg aagatagaga gtggcttctc agcaatgcgg gcaatgctgt agtacaactc   1500

tttacatgtc ctaaaacatc tctccattta ttacaaccac aatatttcag aagcatcatc   1560

gtccccatca ttttgttgtt cgaatcttat actggaaacc atttgctgtg gaaacgacca   1620
```

```
tatcaactct tatcacgtaa gaaaggtctc aaatttggtt taatgcgttc tttaactgat   1680
ctagtgacgt taatcaccac tgcccatcaa tcagaagaac atttggtact ttttcagggt   1740
aagaacttca tttacataat catgcttttt aggatgttcc agagtgccct gacattggtc   1800
agaaaggaag gagaacatat taccagggaa tccactgaat ttttaaccta cctgcaaata   1860
tcttactacc ttaatgatgt catcaaaggt attgttgaaa ttgcgcaggt tcctgaaata   1920
cgtaaacctg aacattggaa agttgtggaa acaaacatac aaatattggc cactttaatt   1980
tcatcagaac cttataagtt tcatatggtg cacgaaaaac aacttattga ccatgacgta   2040
acaaagaaac caacctctct tattaatcca ttgaatggat tactgtctaa catgttaaca   2100
accgtaaggg ccaattcttt ttcattttta actcgtcaag tttctcagat taatttttgg   2160
agtatcaatc ccgaagtctc attttcagat gatttagact atctgaaact ctcatcgaag   2220
agtttagaag caattacttt gagttcacag ataaaaattg gccactggat tagaaatgga   2280
tccatgacta gtaaacaagc gcaattgtac tgcacgaggt tcactcaata tggttacata   2340
gccgacgttc atttgaacca acttgctata ctcgaagaac gcgacgatga tcgtctatta   2400
ttaaacattt tggatagatt caatctaata gattggttct ataacgatca ggacgtgctt   2460
ggtactgttt tcgaagaacg atctttttac ctaatgaatg aattggttaa gtttctttat   2520
aatatgtttt cacacagagt taacttccag tttgaatcaa atttcacaga gaaaacccag   2580
tatgaggtaa cgcaatacat tttatacacg ctttgtaaag gatctttgtc attttcagat   2640
ctgacagccg actttcctat ctccgtggaa gttactgttt ttgacaagat ccttgatgag   2700
gttgctgttt acgaagagcc caaaactatg aatgattctg gaaagtattc tatcaagaaa   2760
agttattaca aaaagatgga tccaatgtct atttatgtgg actcgggtga tttcgatgat   2820
gtatcaacag cgatagtaaa ggaactttca attttaggaa aaataaaaga ggagaatgtt   2880
gtaattgaac ctcagatcag tggaccgaat gaatccaaca gccgtgtctt gagcagattg   2940
aaacggttct tcattagcaa atctgtagtc aaactgtttt ataaattgtt acaatctgct   3000
ctttctgaga gcaatgagac ctacgtcatt gaacttttac atttgattca agcagtttta   3060
ttagatgaac atgaattgta cagaatcgaa gatccagtgc aatactttat tcaaattcct   3120
gtgtgtgatc tactgttatc agttgttgag cacaatgatt tttcacgacc tgtctgcaaa   3180
aaactgaagt tctattgaat tggttgatcc agcgggacga gtcaatcatt gactcattgg   3240
ttgattcttt tggtgaaaag cacattgaaa actttaaaaa atctaaggga tctcaagttc   3300
tggagactaa acgagctaaa caaaagcgtt tagccaagga gagacaagag aagatcaaat   3360
cacgatttgc taaacagcaa aagtctttca tgaagcagaa tttggacgca aaaaagagtg   3420
cggaacatgt aactacacat ttatccaaag acaatgaagg attaggtagt tcctcccagg   3480
actcttttca tgagtgcatt ctttgtcaac gtgctcagga gggcaacgag atgtttggaa   3540
tccctgcata tgttgaaaaa gtttccacgt tttgggattt tcaacctaag gatgagtcaa   3600
cctatacgga aagatgctta acaaccattg aaaatcaaat gaaacaattg catgaagaaa   3660
cggatgccaa caatgaggtt agagaacatc tttattatca aaaagatact cctgtaaaaa   3720
gcatggcacc gatatcttca agacacattg ttaagtcatg cgggcaccac atgcattata   3780
aatgtttttc tgagttacta gaaaacagca ggaagtttag cacttgtccg ctttgtcgct   3840
ctgccattaa tgcttttgtt ccacaatttg ccatgaaaaa cgatgctagc cctgcttttc   3900
aggaggctgc ttcgaatatt agtcactttg aaaagttgaa tttgaatcaa attgtatcga   3960
```

```
aatatcttct caatgattcc ttcttgaaat ttattgcgga agaaagtaag gaccagttca   4020
tgtatttgaa tgagtttaaa gacattttga aagacgcccc agatgcttct gaccacatgt   4080
tgagtgaagg gttatttccc tcatttttgg ccatgtcaac attattgggt aataccctag   4140
caaatactga aattcgtctc agattatccc ccgagaagat tccccagaaa ggaaacttga   4200
agagaaaaga ttcggaatta ataacctcat tacttcaatg tgtctcggtt atctcaatct   4260
tattgaaaca atcttatcct gaagagcagt atctgtctcc atttttgaat aaaccaaatt   4320
cattaattat tgattttgcc atttcacttc tacttggaaa agaagactca cttcaagaaa   4380
ctattgtggg catttacaag caaacaattc tgcattcatt gaatttacta ttgactaacg   4440
ttggagataa tgagcatttc agaaggatgc tgagcggtgc aaactctatt attaatgatt   4500
cagaactggc cattttcaaa aagtttgtgt caacggccac ttttacctct gatgtttcat   4560
tcattacttg caacgaacaa ttattggttg gactgtatat tcttttggag aaaaccacca   4620
cagtgtatct taaacagttg tttctgataa tcagcatgtg cagacccttg gacttatgcc   4680
taaatcgtga ctacgagaat tccaatgatt acgaccacta tttgtttggc caactgtgca   4740
aattttttaa cctttccagt ataatcagtt atttgggatc tggaattcct ggtggaaacc   4800
tattggagga gcaaaatgat cttatattaa aaggacaatc cactctccct tcaacaattg   4860
agtatccagg tctcgtttat cttgtgaatt tgcctagaga actgaacact tttacttttt   4920
caaaatatga cacccaagat gcagttaatc taaacttttc tgtttgttta acgtgtggca   4980
aaagagtgaa acatagcggt gattctgaaa atgaaattga aaacttccct gggtacaatg   5040
gtgttcctct tactttgttt caccatcata agaattgtcc tttctctgga tatggagaag   5100
cacaatgtat cttcttaacc ccaaagttga ataaattgac tgccttacta aagattcagc   5160
ctccacgagg aatttctgat cgctcgctat atcacagtac atttgcattc ccattgagca   5220
gcccatatct aaccacacat ggagagtcac attctggtca tggaggcttg atacgcaaag   5280
cgttcctgaa tagagatcga tttcgaaatc tgaatgagct atggttggat ggtgaactag   5340
ctttgtatat ttcccgaagc cttggggatt ctcaaattgt agcggaacca atcaaccctg   5400
ttatgattac aatgccggga ggtattcagg aggcattaaa tcttgcgttc accactttcc   5460
tcggtgacca agaacccggg gatgatgact tggaagatta tgagtatgac atactgttaa   5520
atagatga                                                             5528
```

<210> SEQ ID NO 23
<211> LENGTH: 3168
<212> TYPE: DNA
<213> ORGANISM: Pichia pastoris

<400> SEQUENCE: 23

```
atgtctgcct ttggtgtggt tccgagtgta ttaaacactg gaaaccagat caagcagaaa     60
aacggaacgc ttttcaagaa atcttctgga gtttacaata aacagcagcg ggatcacaat    120
tccagggata aaaagcgatc agctcgtaaa acaaatacac cgccaacacc gactgagagt    180
acttccgcaa agaagtcatc aactcaatca gacgacaaag tgagtcctga tattttacaa    240
ttgtcgcata ttgagattca atatgtgggc ccacttcttt ccaacccaga atctttggga    300
tatgtgaaac aaaacaataa taccaaaatc aagactccga aatatttagt ggatacagat    360
tcaaacctgg tttttggtcc tgatacaact aataaatggg atattgagaa ccagcacaaa    420
atgatcgaaa tggaatcttc ccatcaaggt gactggcaag gtatttatga acaatttcaa    480
gaaatgaata aagtggagcg tcaaaaaatg gaagatctgg gcttggtggc aaaagaggga    540
```

-continued

```
caaagcatgg acctgacaaa tgctatctca ttcaaaggta gctgcgtgga tatgtgtccc    600
gtttatgata gagtcaagag ggaggtacag agagatgttg atccattgga gagagatcct    660
gccactggta agatatctcg agagagagct ttaaagaaat ttgtgcgtcc ttcaggccaa    720
gcaccgcctc ttccttctga cgtaagacct cctcatattc tggtaaaaag tttaaactat    780
attgtggata atttgctgga taaattaccg caaagtcatt cattaatttg ggatagaacc    840
cgtagtatca gacaagattt tacactacag agctactctg gcttggaagc aattgagtgt    900
aacgaaagaa tttgtcgcat acatctactt tgtgctcata taatgccggg ttctgatcaa    960
tctgacttct ccaagcagca agaaattgaa caattcacaa aatcattgaa aacattaaca   1020
gacatatatg atgttgtcag atccaaagga ggaaaatgtg ccaacgaagc tgaattcagg   1080
gcttataatt tgctggtgca ttttcgggac ccaaatctaa ttcatgaaat ccagaactta   1140
cctactcgaa ttcttaagga cgaacgagtt caacttgctt taatgtttcg aagtctacta   1200
ttgaataata atttcaaaga ataccagagg aacattcctg gttgcttggg ggtttttcag   1260
cagtttttca atatgtgttt tgatccagcc accccattct taatcggatg tgtgctggaa   1320
cttaattttg aagagataag attttacgct ttgaaatcga tctcacgttc ttatcacaag   1380
aaatctgccc ctctaacgac ccagaagtta gcatctatgc tcggatttga ttccgaggat   1440
aagctcctaa ctttcactaa ttatttcaag actcctacgt gtactaattc tagaaatgaa   1500
acgtgcattg atatctcaaa acttagatac gagagtttta cggatttggc tgctccaaag   1560
cagatttaca cttcaagatt agacaacaaa ttaaaaggat tcacctataa ggatgttgtt   1620
gatcaaggat taaataacac atccttgcac atagctaatt tgaaagaaac aatggctcag   1680
aatcaacata ttgcagtgga gaaattaccc aatatctcat ttccacaaca tgctttgtct   1740
tctacccctt tcgaagtaga atcaaagtca gacatagtca gatcttcttc cggatcggct   1800
ccgccccaga ctttgatccc accgattcaa gaaaaagtaa taacttctca aatacagcca   1860
ccaataactc ccgtcgttcc cactgaagaa atccaaactc ttccaaaaat agaggagccc   1920
aggttcaaag atcttccaaa ttttgaaaat gcatgcaaag aggtttcctc tattttaatc   1980
aagaagacta tatctccttt gattgctccc atagtgaaca atcagctaga agagtacaac   2040
cggcgacaaa cggttttaag ggatcaggag agacaaaatc aaagaagaca acttttgatt   2100
tcatcccttc aggaagaatt gtactctgct tttatacgag aacaagtgta tattcaagtg   2160
gttgatactc aagccaaaga gtgctttaac aagaatctga aacggcgaat atttcagaaa   2220
ttcatcgggg gtttaattac attgaaaaac aaacaaatga ataagagaag aaaacttgat   2280
gaaattcaag tcttcaagaa taaggttgtt tcctcaagtc aacttcggta ttcagtttca   2340
agaagtcaaa cggaggacaa ttcaacgtca aactcgagtg acgaggaagc atcagctgtt   2400
cagatgaata ttactctttc accatctgtg gatccacttt ggtcacccat agatattaag   2460
tttatattag actccaattt aaagttgttt gaggataaca aggataaata ctggaatttc   2520
atgtttgcga ttgccgattg gactattcta ccaagcaaat ggcttcgtta caaattccaa   2580
cttcaaaacc ccagtctcat aaatactgtt gaatcctcaa attacaaagc caaattacgg   2640
gctctaccca gtgacaaact tcttacaagg gaatacatgg agcactgtcg atttttggta   2700
tttcaagtcg gaaaggttga tgaatcatca aacctgaaag aatctttgtt cagagactca   2760
cagtttatta accgattaat gaaatatgcc aagaagtact cgcaatacca gattggagta   2820
cttgtcttat attatcatga ggatgactct tttgataaac agaaaattat tgatcttttg   2880
```

ttattagaac aatacacaaa taagttagtc aactcactcg agatagttga catgaacaaa 2940
ctcacaaatg atgaactgat aaaagcattg accacgctag tccacaacta taaggataaa 3000
ggtatcaaca aatcggtacc aacatcttcc accaaaggac acaccactag cattatggaa 3060
caggatatga cagtatacag ctacagcacg tccaattcca gggatgctaa gcttaattat 3120
attttgaagc aagcctaccc ccgcaggggg tttcacttga aacaatga 3168

<210> SEQ ID NO 24
<211> LENGTH: 1401
<212> TYPE: DNA
<213> ORGANISM: Pichia pastoris

<400> SEQUENCE: 24
atgtcagaat ggccctcagc tttggaaaat tttgtaagtc attgtttcca gcgtgccaac 60
attgagagct ttccacccgg caaaaaaaaa gaactccaaa aacagttgac gcaaatcatc 120
aatttagcaa ttcttgaaaa caaacttaat tctaataact ggtccaaaca aaagctacca 180
atatttggag aagcaagaga gttagaattg gagcagaaaa tgggaaatgt ttatccaatt 240
actgtttcta gtcgaagaag tgacttgatg catcaagagg cagttcaacc atctgagcct 300
ttagttccct ccgaaagcca acaaaagaaa aagtctagag aattgcgatt taagatcact 360
aaaaaaagtt ctgtatcacc cgcaaataaa atacaagttg cttgtgactt gaattgtaaa 420
cttgtgggaa ctaacacctc tatcgagaaa gattattata gacttacatc tcatccggat 480
ccttccatgg taagaccttt gcctatttta aagaaatcgt tgcagcatct ttacgccaaa 540
tatcaaagtc tagaacgttt caaagctctc agcaaggcag agtacagcta tttttgaat 600 caactgaaat ccctaaggca agacctcaca gtgcaagaca ttcagaatca gttcactgtt 660
aaagtttacg aatttaatac tcaattggcg attcaaaatg aagattttgg tgagcttaat 720
caatgtttga ctcagctggc gcaattgtac actgtatcaa ctatgggtca tacttattac 780
tattctgata ctggcaaata caaccaagag cacaactgtt ttcttgccaa ggatctttgt 840
gaggatcgaa accatatcaa tatgttcaaa tttacgagtt atagaatttt atattttctt 900
ctcatagacg ccccctggga attgctaaaa ataaggcagg atttattcaa ccgtggtcaa 960
cagtatgcaa ttcgtcacaa caaatttctt ttgaagtcat tcaagctttc ggatctcata 1020
accgccatgg attatattca tatcaaggac gaatattcat tcctcgtgaa tatggactca 1080
gatgtctgca atttaaggac agtgtttgat gacgaacata tgactttgaa ccaagacgac 1140
tggtttttct ataagatact ctaccataag attttcttac gagaacagct gaaggccctg 1200
ataactataa gcaaatctta tcgacagata tccctctact acttgaaaaa tctactgatg 1260
gatttagtat tcttggaaaa gaataagtta tctcgtttca ttgagaatgg tgaggtattt 1320
aactgcacga gcgcaagatc attactgctt caaatagaga agaagcagct atcaaagata 1380
gatatcaagg gtcaggtatg a 1401

<210> SEQ ID NO 25
<211> LENGTH: 1075
<212> TYPE: DNA
<213> ORGANISM: Pichia pastoris

<400> SEQUENCE: 25
atggttgact cagagactat caacaaattc atagaagtaa cgggagcctc tgccttccaa 60
gcaattcagt acctagagga gactgatgac tttgaagcgg cagtcaatga ttattattcc 120
tctcaactgg agaatgagaa gggcaagggt aaatcagaac gtccagtcaa tcaaacaaag 180
gcttctgcag ggcccaagat cagaactttc aacgacctaa atagcaactc aaatggggac 240
aacaatcttt tcacaggtgg tgaaaagtcc ggtcttcaag ttgagaaccc agacaaacgt 300
ggggaccctt ttgggttggt caatgatctt ttgaagaaag ctgaggaaac tggccaacaa 360
ccagatacaa ggccccatga agaagctcct gctagacaat ttgttggaac tggccacaag 420
ctgggcagta cggacagtcc ctccgaagtt agtgtctgac cctgcctcaa gaataagaag 480
agctcagaaa gtcagccgac agataacatt ttggaaggac ggattccaag ttggagacgg 540
agatttatac agatatgatg accctgcaaa cgcaagatat ctagccgact tgaacgctgg 600
aagggcacca ctggctcttc tagatgtcga gattgggcaa gaggtagatg tcacagtgca 660
taaaaagata gaaaaaaatt tcactcctcc taagaaagcc cgagttggct ttcaaggtaa 720
aggtcagaga ttagggtctc cagtaccggg cgacataaag ctcagtcaat ctcctgaggt 780
gcaacaagaa acacaagagg aagctgagga ggaaaagcaa aaggaggagg ccgagcagct 840
gggaactggg gattctcccg ttcagattag actcgccaat ggtcagagaa ttgttcatag 900
attcaattct actgattctg ttgctcaatt atatgcattt gtcaatgaac atagtccctc 960
cgccagagaa tttgtgcttt ctctagcttt cccggtgaaa cctattgaga acaatgagga 1020
cacactcaag gatgctggac tcataaacgc tgttgttgtc caaagatgga aataa 1075

<210> SEQ ID NO 26
<211> LENGTH: 897
<212> TYPE: DNA
<213> ORGANISM: Pichia pastoris

<400> SEQUENCE: 26
atgggcgtga tacttccaga cgatggtaag caatcgggag gccaaccaaa tagaagggct 60
aaagtcctga gccgattttt accaccagaa catcaaagac cttcaatcgg cctcttcctg 120
ggacctttta ctccagcagc tgataatgag attgccctgt ggacttgcat tggcgctcag 180
ctctttagtg ggctggcatt gcttagaatg agccgaagat ttgttttttc gcccgatcaa 240
tctgtaagaa ggtttctctt taagactttt cataatgtgg taggtgcagc cctgatattt 300
gggagcggat tagaagggac taggatgctt ctacctgagg atccttggaa agaagaagct 360
agaaaagcaa gaatattggc ccaattgaaa ggtgagcccg ttagttggtg gtatggaccc 420
aagagtttta ttccttctgg aaggttagaa tacacaaaac agatgcagtt tcacaacttt 480
gaagtcatgc ataaatcacc cgaaaaaata gcccgagctc tcatgattaa ggacaaactc 540
aaggaggaaa caaataccct ttattcgtcc attcatgaga aagcggaaca acagactatt 600
cgactctcta aagatctaca gaacaacgtt cccctcaaag gggtaacgtc atatgttcct 660
caatttagca cttcaaatac ggacaccaag ttatatttga aaaatgttag cttgaagacc 720
catgccgacc tggaaaaggt ctgggcagaa cacaatcctt gggacatcct ggaagagaaa 780
atttctccaa tttccgtaat tgcactgcca aagtttaacc caattatatc tgaggttgaa 840
cctgacaagc agcaaccatc tacgggtgat atcaaataca ttagtgacag aaaataa 897

<210> SEQ ID NO 27
<211> LENGTH: 1530
<212> TYPE: DNA
<213> ORGANISM: Pichia pastoris

<400> SEQUENCE: 27
atgaaatatt tgccactcgt tgctaccctg gcctcttcgg ccctcgctgc tggcatcaac 60

-continued

```
ttcgcccaat tactggacca gaagccactg gacattgccg ataatgttaa atgggaattg    120

aagcctgagg tcgactctgc tgctcttcaa agtgcagtca atgagctaga cttgaaaatc    180

gaagccagct atttgtttaa agttgcacat ggttccgtct ttgaatacgg acatcctacc    240

agagtcatcg gttctcctgg tcactggtcc acaatcaacc atgtcctcga cacattacat    300

aacttcaaac actactacga cgttgacgtt cagccatttg aagcctttac cggtatcctt    360

aagtctttct cattgaccat taacggagtt gcaccaaagt ctgcagaagc tttagattta    420

actcctccta ctcctggcgg ttttccagtg accggtccag tcgttttagt tgataattat    480

ggttgtcaag cttctgacta tccattcaac gtgactaacg gaattgcctt aattcaaagg    540

ggttcttgtt cattcggtca aaaatcagaa cttgctggtc tccgtggagc caaagccgct    600

ctcatttaca acaacgtgcc aggtagtgct aagggaacct taggtgcccc aactcctcat    660

caggtaccat cgttgtcact ttctcaggaa gatggagagg ccgtcaagcg tcagcttctg    720

acttctggaa gcgtaattgc aactgtcgct gtcgattcct acgttaagaa gttcaaaacc    780

aagaatgtga ttgctaccac tcgttacggt aatgatagca acattgtgat gctaggtgca    840

cattcagact ctgttgctgc tggaccaggt atcaatgacg atggttctgg taccatctct    900

cttttgaacg tggccaaata cctaactaaa ttcaaagtta ataacaaggt tcgtttcgct    960

tggtgggcag ctgaagaaga aggattactt ggatccgact actacgtttc aaagttaacc   1020

cccaaggaga aatctcagat tcgtttgttt atggactacg atatgatggc ttcccctaac   1080

tacgcctacc aggtctataa tgccactaac agcgagaacc cagttggatc tgaggagctt   1140

aagaatttat acattgactg gtacgttgaa cagggtctga actacactct agttccattt   1200

gatggccgat ccgactatga tggattcatc aagagcggta ttcccggagg tggtattgct   1260

accggagcag aaggtttgaa gaccgaagag gaggctgaac tatttggtgg tgaagctgga   1320

gttgcatatg acccatgtta ccactctctt tgtgacgatt tggccaaccc tgactatgtt   1380

ccatgggttg tcaatactaa attaattgcc cacagtgtcg ccacttatgc aaagagcttg   1440

gacggattcc cattgcgtga ggagcctagc ccattcaaga tgactgccca gtcaaacttc   1500

aagtaccacg gtccaaaact tgtcctttag                                    1530
```

```
<210> SEQ ID NO 28
<211> LENGTH: 513
<212> TYPE: DNA
<213> ORGANISM: Pichia pastoris

<400> SEQUENCE: 28

atgctcaaac actccttaaa aacagggttg gtctttctca cttggatacc ggtgatttat     60

acggtaaagg aacacctgat atacgttgga aaggtggaag gatcctcaat gtcacccact    120

ttgaatcccg ttaaaggtta ttctgactat gtgattttat ggaagttaaa cttcaaagag    180

tcactcaaag tgggagacgt ggtttttata aggtctcctg tagatccaga gaagttatat    240

gctaaacgta taaaggctgt tcaaggggat accgtggtga ctaggcatcc ataccccaaa    300

gacaaagtgt ccattccaag aaaccatctt tgggtagaag gagacaatat acacagcgtg    360

gatagtaaca actttggtcc gatatcgttg ggccttgtat taggaagagc aactcacgta    420

atttttcccc tgaacaggat aggtaatatc tctggtgaag gggtagaga agttagggag    480

gattatttaa gagcggagga cagtccgatg taa                                 513

<210> SEQ ID NO 29
<211> LENGTH: 915
```

<212> TYPE: DNA
<213> ORGANISM: Pichia pastoris

<400> SEQUENCE: 29
atggtttctg aaattcagct tagattagct gttattattt atgatatact ctgttcggcg 60
tcttatgttc tagtcatcca tttgagacca accagagccc ttccgcatca acccatagac 120
cgtaacaatc ctctaacgat taaagaaagg tgccagcgag ccagtgtgtt gactgctaca 180
catgtattat tattgcctat tcttttaaaa gtgttgagac tgtcagaaat tgcggaaact 240
acggcgaaac ttggaatagt ggtgggatat cacaaccaga gctggtcttt ctctaacctc 300
caagatgata ttgtcagcat tttcaaagct ttaggtttga ccatgattct cttttctggt 360
cctattgtag attattttta ctattcaaac tcaacagaag taatcaagca agatctggcg 420
tatgtcgtta gcctcgaggg tatgcgtgat ctacttgtgg gacccatcac tgaggaactt 480
ctttatcggt catgttccat ttcattaatg ctagtagcta acgattacgc caacaaattt 540
ctgttcggcc aacactggtt aataatggta tcatcactct acttcggtat agcacatctt 600
catcatgctg ttgaactgta tcattgtaaa agatattcat taactaccat aaccatatca 660
actgccttcc aatggtcata tacaacgtta tttggaatat atgcaagctt tctatacttg 720
cgaacaggat ctgtatggtc agcaatagtt gttcattcat tttgcaacat gatggggttt 780
ccccggttga catttggacg tgatgaagcg agagattgga aagtgggtta ctatgtgttg 840
ctcgctctag gttccgtcct attcaaaaag tttctttact ctctaacaga atctaaccat 900
acgcttcttc tataa 915

<210> SEQ ID NO 30
<211> LENGTH: 2451
<212> TYPE: DNA
<213> ORGANISM: Pichia pastoris

<400> SEQUENCE: 30
atgtatcccg aacacaagta tcgggagtat caacggaggg tgcccttatg gcagtactcc 60
ctgttggtga ttgtactgct atacgggtct catttgctta tcagcaccat caacttgata 120
cactataacc acaaaaatta tcatgcacac ccagtcaata gtggtatcgt tcttaatgag 180
tttgctgatg acgattcatt ctctttgaat ggcactctga acttggagaa ctggagaaat 240
ggtacctttt cccctaaatt tcattccatt cagtggaccg aaataggtca ggaagatgac 300
cagggatatt acattctctc ttccaattcc tcttacatag taaagtcttt atccgaccca 360
gactttgaat ctgttctatt caacgagtct acaatcactt acaacggtga agaacatcat 420
gtggaagacg tcatagtgtc caataatctt caatatgcat tggtagttac ggataagaga 480
cataattggc gccattcttt ttttgcgaat tactggctgt ataaagtcaa caatcctgaa 540
caggttcagc ctttgtttga tacagatcta tcgttgaatg gtcttattag ccttgtccat 600
tggtctccgg attcttccca agttgcattt gtgttggaaa ataacatata tttgaagcat 660
cttaacaact ttttctgattc aaggattgat caactaactt atgatggagg cgaaaacata 720
ttttatggca aaccagattg ggtttatgaa gaagaagtgt ttgaaagcaa ctctgctatg 780
tggtggtctc caaatggaaa gtttttatca atattgcgaa ctaatgacac ccaagtgcct 840
gtctatccta ttccatattt tgttcagtct gatgctgaaa cagctatcga tgaataccct 900
cttctgaaac acataaaata cccaaaggca ggatttccca atccagttgt tgatgtgatt 960
gtatacgatg ttcaacgcca gcacatatct aggttacctg ctggtgatcc tttctacaac 1020

```
gatgagaaca ttaccaatga ggacagactt atcactgaga tcatctgggt tggtgattca   1080

cggttcctga ccaagattac gaacagggaa agtgacttgt tagcatttta tctggtagac   1140

gctgaggcta acaatagtaa gctggtaaga ttccaagatg ctaagagcac caagtcttgg   1200

tttgaaattg aacacaacac attgtatatt cctaaggata cttcagtggg aagggcacaa   1260

gatggctaca tcgacaccat agatgttaac ggctacaacc atttagccta tttctcacca   1320

ccagacaacc cagaccccaa ggtcattctt acgcgtggtg attgggaagt cgttgacagt   1380

ccatctgcat ttgacttcaa aagaaatttg gtttacttta cagcaaccaa gaaatcctca   1440

atagaaagac atgtttattg tgttgggata gacgggaaac aattcaacaa tgtaactgat   1500

gtttcatcag atggatacta cagtacaagc ttttcccctg gagcaagata tgtattgcta   1560

tcacaccaag gtccccgtgt accttatcaa aagatgatag atcttgtcaa aggcaccgaa   1620

gaaataatcg aatctaacga agatttgaaa gactccgttg ctttatttga tttacctgat   1680

gtcaagtacg gcgaaatcga gcttgaaaaa ggtgtcaagt caaactacgt tgagatcagg   1740

cctaagaact tcgatgaaag caaaaagtat ccggttttat tttttgtgta tgggggggcca   1800

ggttcccaat tggtaacaaa gacattttct aagagtttcc agcatgttgt atcctctgag   1860

cttgacgtca ttgttgtcac ggtggatgga agagggactg gatttaaagg tagaaaatat   1920

agatccatag tgcgggacaa cttgggtcat tatgaatccc tggaccaaat cacggcagga   1980

aaaatttggg cagcaaagcc ttacgttgat gagaatagac tggccatttg ggggttggtct   2040

tatggaggtt acatgacgct aaaggtttta gaacaggata aaggtgaaac attcaaatat   2100

ggaatgtctg ttgcccctgt gacgaattgg aaattctatg attctatcta cacagaaaga   2160

tacatgcaca ctcctcagga caatccaaac tattataatt cgtcaatcca tgagattgat   2220

aatttgaagg gagtgaagag gttcttgcta atgcacggaa ctggtgacga caatgttcac   2280

ttccaaaata cactcaaagt tctagattta tttgatttac atggtcttga aaactatgat   2340

atccacgtgt tccctgatag tgatcacagt attagatatc acaacggtaa tgttatagtg   2400

tatgataagc tattccattg gattaggcgt gcattcaagg ctggcaaata a            2451
```

```
<210> SEQ ID NO 31
<211> LENGTH: 1866
<212> TYPE: DNA
<213> ORGANISM: Pichia pastoris

<400> SEQUENCE: 31

atgaaaccgt atcaccatgc aaaaagccgc ccaataggca gctacctgta ttttggggtg     60

tttaccgtag cattgacatt tctgacgtgg cttaaatatg acgcagagct gtttgctcag    120

caggttcact cgaaagacat ttatgaccca cagttcaaca ttacgttgcc aattgatggc    180

ccaacattta ccccatcaaa gaactattca attagtgttc aaaatgcagc agtggcgtcc    240

gatatagaac aatgttcaaa attaggtgta tctattctgc agcaaggtgg caatgcggcc    300

gattcagcag tcaccgtggc cctgtgtatc ggaacaatca attcgtattc gtccggtata    360

gggggaggag gattcattgt ctctaagtta attgataatc ctaccgctct gagttttgat    420

tgtcgagaaa tggctccttc taaaagtttc aaagaaatgt tcaactatca tgaggagaag    480

gccagagtag gtggtttggc tgtcgccatt ccaggagagt taaagggact ctatgaactg    540

tttcagcacc atggttctgg taatgttgag tggaaagatt tgattttgcc cgttgctgag    600

ttggctgagg tgggatggac tgtcgatccg ctgttttcta gtgcattgaa atctattgag    660

caccatattt acgagcattc atatgattgg gcctttgcat tgaatgaaga cggaaaaatt    720
```

aaaaaaagag gtgactggat taatcgtccc atgttggcta ctacgttgag gagaatagct 780
gaaagtggca acgttgatct attctatgac ccagagagcg atatagtaca aagcatggtg 840
aatgctacta gaaagtatgg aggaatcctt gaagcctcag actttgcaaa atatagagtt 900
cgaattgaag aatcgttgac attgcataac tttacatctg acggccttac ggtttatacg 960
tccaatgggg catcctcagg gttggtgctc cttgctgggt tgaagctcat ggacttattc 1020
gaagatttca aggaatttca taatgatttc ggggctgttg agtctcaaag gcttgttgaa 1080
acgatgaagt ggatggcttc agtaagaagc aaccttggag atttgaacat ttactccacc 1140
aacgaaactg aaattgacga tcataggaag aggtacgaca gatacaaatc agatgagtgg 1200
gcaatagaaa ctcatgccaa aattaatgat tcccacacac ttccttcttg gaaagattat 1260
gctccagcct ttctacctaa tgatcctcat ggtacatctc atttcagtat cgttgaccaa 1320
tacggtaatg cggtggctat gacaaccact gttaaccttg gatttggatc taaaatacac 1380
gatcctatat cagggattat tctaaatgat gaaatggacg atttttcagt tccaacatca 1440
tctaatgcat ttggtttgca tccatcaatc tataattggg tagagcctta caaaagacct 1500
ctctcttcat gtgctcctac cgtaattgtt gattctctgg gagtacctca ttttgtcatc 1560
ggggcagcag gagggtccaa gatcactacc acagttttac aagcaattat aagagtttac 1620
cattatcacc tggatctttt agacgtcatt gcatatccac gctttcatca tcaactactt 1680
ccggaagaag ttcttctgga gtttccacga gataataaac taatacgcca tctaaaagaa 1740
agagggcatg atgttagagt ccaagcacca atatccacca tgaatggtat cctacgaaaa 1800
agaggtggaa gcctgatagc agttagtgat cactggagaa agcttggtcg accttggggc 1860
ttttga 1866

<210> SEQ ID NO 32
<211> LENGTH: 1605
<212> TYPE: DNA
<213> ORGANISM: Pichia pastoris

<400> SEQUENCE: 32
atgaaatcgg ttatttggag ccttctatct ttgctagcat tgtcgcaggc attgactatt 60
ccattgctgg aagagcttca acagcaaaca ttttttagca agaaaaccgt tcctcaacaa 120
gttgctgaat tggtgggcac ccattactct aaggatgaga taatcagtct atggaaggac 180
attgagctgg atgtacccag ggaaaagatc caagaggcct tcgataagtt cgtaaaacaa 240
tcaactgcca cttcccccgt tagaaatgaa tttcccttgt ctcagcaaga ttgggtgaca 300
gtgaccaaca ccaagtttga taattatcaa ttgagggtta aaaaatccca ccctgaaaag 360
ctaaacattg ataaggtaaa gcaatcttcg ggatacctgg atatcattga tcaagataag 420
catcttttct attggttttt tgaatcccga aatgatccgt ccacagaccc aatcatccta 480
tggttgaatg gtggacccgg ctgctcttct attacagggt tgctattcga aaagattggc 540
cccagttaca tcaccaaaga gattaagccg gaacataatc cttattcatg gaacaacaat 600
gctagtgtta tcttccttga gcaaccggtt ggagtaggat tttcttactc ttctaagaaa 660
gtcggtgata ctgcaactgc tgccaaagat acatatgtgt ttttggagct tttcttccaa 720
aagtttcctc agttcctgac ctctaatctg cacattgctg gggaatcgta tgctggccat 780
tatttgccca agattgcttc tgagattgtg tctcacgcag acaagacgtt tgacctttca 840
ggagtcatga tcggtaatgg tcttactgat cctctaattc agtataagta ctatcagcca 900
atggcctgtg gaaaaggtgg ctacaagcag gtcatttcgg acgaggaatg tgatgaattg 960
gatagggtct atccaagatg tgaacgttta acgcgggcat gttatgagtt ccaaaattca 1020
gttacttgtg ttccggcaac actttattgc gaccaaaagc tactgaagcc gtacactgac 1080
actggcttga atgtctatga tattcgtaca atgtgcgatg aagggactga tttgtgttac 1140
aaagaactgg aatacgtgga gaagtacatg aaccagcctg aagtgcagga agccgtgggc 1200
tctgaagtca gttcttacaa aggttgtgac gatgatgtct tcttaagatt ttttgtactct 1260 ggcgatggat ctaagccttt ccaccagtat atcacggatg ttctcaatgc aagtattccg 1320
gttctgattt acgcaggtga taaagattat atctgtaatt ggctaggaaa ccaagcttgg 1380
gtcaatgagc tagaatggaa cttgtctgag gaattccagg caactccgat tcgaccgtgg 1440
ttcactttgg acaataacga ttatgcagga aacgtacaaa cttatggaaa cttttccttt 1500
ctaagagtat ttgatgctgg tcacatggtt ccttacaatc aaccagtcaa cgcacttgac 1560
atggttgtca gatggacaca cggtgatttc tcatttggtt attaa 1605

<210> SEQ ID NO 33
<211> LENGTH: 2520
<212> TYPE: DNA
<213> ORGANISM: Pichia pastoris

<400> SEQUENCE: 33
atgactcaat tagatgtcga atcattgatt caagaactca cactaaatga aaaggttcaa 60
cttctgtccg gatcagactt ttggcacacc accccagtta gacgtctagg aattccaaag 120
atgagattat ctgacggtcc taacggcgtc cgaggaacca agtttttcaa tggagttcca 180
accgcatgtt ttccttgtgg tactggatta ggtgccactt tcgataaaga acttctaaaa 240
gaagctggct ccttgatggc agacgaagct aaagcaaaag ctgcctcggt agttttgggt 300
cctacagcta acattgctcg aggccccaac ggaggaagag gcttcgaatc ttttggagag 360
gatccagtgg ttaatggatt atctagtgct gcaatgatta atggattgca aggtaaatat 420
attgcggcta ccatgaaaca ttatgtttgt aacgatttag agatggatcg taattgcatt 480
gatgcacagg tgtctcacag agctctaaga gaagtgtacc ttcttccatt ccaaattgcg 540
gtaagagatg caaatcctcg cgctatcatg actgcttata ataaagcaaa cggtgaacat 600
gtatctcagt caaagtttct tctagatgag gttttgagaa aagaatgggg ctgggatggt 660
ttgttaatgt ccgattggtt cggtgtgtac gatgcaaagt cttctatcac taatggtctt 720
gacctggaaa tgcctggtcc acctcagtgc agagtccatt cggcaaccga tcatgccatc 780
aattctgggg agatacacat aaatgatgtc gatgagcggg tgcgaagcct cttaagttta 840
attaactatt gtcaccagag tggcgtcact gaggaggatc cggagacatc cgataacaac 900
accccagaga ccatcgaaaa actcagaaaa atcagtagag aatcaatcgt cttgctgaag 960
gatgatgaca ggaacagaag tatccttcct ctgaagaagt cagataaaat tgccgtgatt 1020
ggaaacaatg ctaagcaggc tgcatattgc ggaggaggtt ctgcttctgt tctctcgtac 1080
catactacaa ctcctttcga ctctatcaaa tcacgattgg aagattcaaa cactccagct 1140
tacaccatcg gtgctgatgc ttacaagaac cttccgcctt tgggccctca gatgacagac 1200
agcgatggaa aaccggggtt cgacgccaaa ttttttgttg gctcgcctac atctaaagat 1260
agaaagctga ttgatcactt tcagttgacc aattcacaag tcttcctggt tgactactat 1320
aatgaacaga tccctgaaaa caaagagttt tacgtagacg ttgaagggca attcattcct 1380
gaggaagatg gaacctataa ctttggcttg accgtattcg gaacgggaag attattcgtg 1440
gatgataagc tggtttccga tagtagccaa aaccagaccc ctggagattc ctttttttgga 1500 ctagcagctc aagaggttat cgggtccatt catttggtca agggtaaagc atataaaata 1560
aaggttcttt atggatccag tgtcaccaga acatatgaaa ttgcagccag tgttgctttt 1620
gaaggaggag catttacttt tggtgcagca aaacaaagaa atgaagatga agaaattgct 1680
agagctgtgg aaattgctaa ggcaaatgat aaagtggtgt tgtgcatagg tctaaatcaa 1740
gactttgaaa gtgagggatt cgacaggccg gatatcaaaa ttcctggagc aaccaacaag 1800
atggtaagtg ctgttttgaa ggctaaccct aacactgtga tcgtcaacca aacaggaacc 1860
ccagtcgaga tgccatgggc cagtgacgct ccagtgatct tgcaggcttg gtttgggggg 1920
tctgaggcag ggaccgctat agctgatgta ctattcggtg actacaaccc tagcggaaaa 1980
ctaacggtta cttttccctt gagatttgag gataaccctg catatctcaa cttccaatcc 2040
aataagcaag catgttggta tggggaagac gtttatgtgg gctacagata ttacgagacc 2100
atagacaggc ctgtgttatt cccatttggc cacggattgt cattcaccga atttgatttt 2160
accgacatgt ttgtcaggct tgaagaagaa aaccttgaag ttgaggttgt agtcagaaac 2220
acaggaaagt atgatggtgc tgaagttgtg cagttgtacg tagcaccagt atccccatcc 2280
ctgaaaaggc ccatcaaaga actcaaggaa tatgctaaga ttttcttagc cagtggtgag 2340
gcaaaaacag ttcacctgag cgttcctatt aagtatgcca cttcgttctt tgacgaatat 2400
cagaagaaat ggtgctccga gaaaggagag tacacaatct tactgggatc cagctcagca 2460
gatattaaag tttcgcaatc tattacttta gaaaaaacaa ctttttggaa aggtttatag 2520

<210> SEQ ID NO 34
<211> LENGTH: 5004
<212> TYPE: DNA
<213> ORGANISM: Pichia pastoris

<400> SEQUENCE: 34
atgttcctca aaagtctcct tagttttgcg tctatcctaa cgctttgcaa ggcctgggat 60
ctggaagatg tacaagatgc accaaagatc aaaggtaatg aagtacccgg tcgctatatc 120
attgagtatg aagaagcttc cacttcagca tttgctaccc aactgagagc tgggggatat 180
gactttaaca tccaatacga ctactcaact ggttcccttt tcaacggagc atctgttcaa 240
atcagcaacg ataacaaaac cactttccag gatttgcaaa gtttgcgtgc agtcaaaaat 300
gtttacccag ctactctcat tacattagat gaaacatttg agcttgctga cacgaagcca 360
tggaaccctc atggaattac cggtgtcgat tctttgcatg agcaaggata tactggtagt 420
ggtgttgtta ttgcagttat cgatactggt gttgactata cacaccctgc tctgggtggt 480
ggtatcggag ataatttccc tatcaaagct ggttatgatt tgtcttccgg tgatggtgtc 540
atcacgaatg atcctatgga ttgtgacggt catggtacct ttgtatcctc catcattgtt 600
gcaaataaca aagatatggt tggtgttgca ccagatgctc agattgtcat gtacaaagtg 660
ttcccctgtt ctgatagtac ttcgactgac atagttatgg cgggtatgca aaaggcctat 720
gatgatggtc acaagattat ttcgctatca ctgggatctg actcggggtt ttccagtact 780
ccagcttcct taatggccag caggattgct caagacagag ttgttttggt ggctgctggt 840
aactctggag aacttggtcc attctatgcc tcctcccctg cttctgggaa acaagtcatt 900
tcagttggat ctgttcaaaa cgaacaatgg acaacctttc cagtaacctt tacctcttca 960
aacggtgaat caagggtttt tccttacctc gcttacaatg gtgcacagat tggatttgat 1020

```
gccgagcttg aggttgattt taccgaagaa agaggatgcg tctatgaacc agagatctcc   1080
gcagataatg cgaataaagc tattttgtta agaaggggcg tcggctgtgt tgaaaacttg   1140
gaattcaatt tattgtctgt ggctggttac aaggcttact tcttgtacaa ctcattttca   1200
agaccatgga gtctcttgaa tatttctcca ctgattgagc tagacaacgc ttactctctt   1260
gttgaagagg aagttggaat atgggtgaaa acccaaatcg acgccggtaa caccgtcaag   1320
ttaaaggtga gcacgagtga ccaaatgttg ccatctgata aagagtattt gggagttgga   1380
aagatggatt attactcctc tcaaggacct gcttatgagc ttgaattttt cccaacgata   1440
tccgctccag gtggagacag ttggggcgct tggcccggtg ggcaatacgg tgttgcctca   1500
ggaacaagtt ttgcttgccc ctatgttgca ggtcttacag ctctttatga atcgcagttt   1560
ggaattcaag atccccagga ctatgtgaga aaattagtct ccacagctac cgatcttcaa   1620
ttatttgact ggaacgcagt gaaacttgag acctctatga atgctccact tattcaacag   1680
ggagctggtc tagtgaacgc tcttggtttg tttgagacta agactgtgat cgtgtctgct   1740
ccttatttgg agctcaatga caccatcaat agagccagtg agtataccat tcaaattaag   1800
aatgagaact ctgagactat tacctatcaa gttgttcacg ttccgggaac tactgtctac   1860
tctagatcag cttctgggaa catcccatac ctggtcaatc aagattttgc accttacggt   1920
gatagtgatg ctgcgacagt tgctctatcc acagaagagt tggttttggg accaggagaa   1980
gttggtgaag tcactgtgat cttctctaca gaagaaattg atcaagaaac tgctccaatt   2040
attcagggta agattacatt ttatggtgat gtcataccga ttgctgttcc ttatatggga   2100
gttgaagttg atattcattc ctgggagcct ctcattgaga ggcctttatc agtgagaatg   2160
tatttggatg atggttcctt agcatatgtt gatgatgatc ctgattatga gttcaatgtg   2220
tatgactggg attctcctag attttatttt aacctgagat atgcaaccaa agaagtatcg   2280
attgacttgg tgcaccctga ttatagcatt gagaacgact acgaatggcc tttagtttcc   2340
ggacacaaca actattatgg tcccgtggga tacgactacg attatacctc gggtcaagcc   2400
tttttgcctc gttactttca acaacgtatt aacgaacttg gatatctttc tttttccaga   2460
tttgctaact tttctgtagt tcctgctggt gaatacaaag ctctatttag agttttgcta   2520
ccatatggag acttttggaa caaagaagac tggcaattgt ttgaatcccc agtgtttaac   2580
gtcctcgctc caccgaatga agaaaacact actgaagagc caactgagga atccagcgag   2640
gagcctaccg aagagtcaac gtctgagtca actgaagagc cctcttctga gtcaactgag   2700
aaatctagcg aggtgccaac tgaagaaatt actgaagatg caacatccac aattgatgat   2760
gatgaagcat ccaccgaaag ctctactgaa gaaccaagtg ctcagcccac cggtccttac   2820
tctgatttga ctgtcggtga ggccattacc gacgttagtg tcaccagttt gaggacaact   2880
gaagcatttg gatacacttc cgactggttg gttgtgtctt tcactttcaa cactactgac   2940
agagatatta ctctcccacc ttacgctgtt gtacaagtaa ctatcccaaa tgaacttcaa   3000
ttcattgctc atccagaata cgccccatac cttgagccct cattgcaagt tttctacact   3060
aagaatgaaa gattaattat gactagtcag ttcaactacg acaccagagt catcgacttc   3120
aagtttgaca atcgagacca agtaataact caagtggagg gagttgttta tttcacgatg   3180
aaactagaac aagatttcat ttctgcattg gccccaggtg aatacgattt tgaatttcat   3240
acatccgttg attcttatgc ttcgaccttt gactttattc cattgattag atccgagcca   3300
atcaaattga tagcaggtgc accagacgaa gttgaatggt ttattgatat tccaagtgca   3360
tacagcgatt tggcaacgat agatattagt tctgatatcg atactaatga taatttgcag   3420
```

```
cagtacttct atgattgctc aaagctcaag tacactattg gaaaagagtt tgatcagtgg   3480
ggtaatttta cagctggatc agatggtaac caatacagca ataccaccga tgggtatgtt   3540
ccaattactg attctaccgg ctctccagta gctgaagttc aatgtttaat ggaaagtatc   3600
tcattgagtt tcacaaatac tcttgctgag gatgaagtat tgagagttgt tcttcactct   3660
tctgcgttta gacgtggttc attcaccatg gccaacgtgg taaacgttga cattacagct   3720
ggtggattgg caaaaagaga actcttctct tatatattgg atgaaaatta ctatgctagt   3780
actggatctg aggggttggc atttgacgta tttgaagttg ctgatcaggt cgaggagcca   3840
actgaggagt caacctcaga ggaatctact gaacaggaaa cttccaccga ggaacctacc   3900
gaggaatcaa ctgaacctac tgaggaatct acccaggaac ctactgaaga gcccaccgac   3960
gagcctactt ctgagtcaac tgaggaacct tctgaggagc caacttctga cgatctctca   4020
attgacccaa ctgctgtacc taccgatgaa cctactgaag agccaactga ggagcctact   4080
tctgagtcaa ctgaggaacc ttctgaggag ccaacttctg acgatctctc aattgaccca   4140
actgctgtac ctaccgatga acctactgaa gagccaactg aggagccgac ctctgagact   4200
accgatgatc catcgatagc acctactgct gtgccaactt ccgacacatc ttctggacaa   4260
tcggtggtta ctcaaaacac tacagtcact cagactacca tcacttcagt ctgtaatgtt   4320
tgtgctgaga cccctgtaac aatcacttac actgcaccag ttgtgactaa gccagtttct   4380
tacaccaccg ttacttcagt ttgccatgta tgtgcagaga caccaatcac agttaccttg   4440
acgttgccat gtgaaaccga agacgtgaca aagactgccg gccctaagac tgtcacttac   4500
accgaagttt gcaactcctg tgctgacaag cctatcactt acacctacat cgctccagag   4560
tacactcaag gtgccgaacg tacaacagtt acatcggttt gcaacgtttg tgctgagaca   4620
cctgtaacgc taacatacac tgcgccgaaa gccagtcgtc atacagttcc ttcacaatat   4680
tcaagtgccg gagagctcat ttcatccaag ggatcacga ttcctactgt tcctgcccgt   4740
ccaactggta cttatagtaa gtctgttgac actagccaac gtacactcgc taccattaca   4800
aaatcttcag atgagtctaa cactgttacc actactcaag ccacacaagt tttgagcggt   4860
gaatccagtg gaattcaagc tgcttcaaac agcacgagca tctcagctcc aactgtcact   4920
acagctggga acgagaactc tggatctaga ttttcgtttg ctggactatt cacagttctg   4980
cctcttatct tgttcgttat ataa                                          5004
```

<210> SEQ ID NO 35
<211> LENGTH: 1335
<212> TYPE: DNA
<213> ORGANISM: Pichia pastoris

<400> SEQUENCE: 35

```
atgcagtttg cttccttact gcttctcttg tatattttct tggggcaaat ttatcctact     60
gaagcagcaa aatattttgt tcgtctgaag aagcctcaca cactagacct cttgttcaaa    120
caggatgaag cagatgcatc tgctgagaac cgaatctctc ttcatggttt aagggaccga    180
atcaaaaaaa agatctcttt tggaacgttc gaaggttttg ttggtgaatt cacaacagaa    240
cttgtagaaa aactaaaaaa gaattcgttg attgcagaca taactcctga cattatcgtc    300
tcatcttgcg atatcgaatt gcagtccccc gctcctgatc acctggctag gttatccaaa    360
gaaggtgccg taagagcaca agatcgtctt cttggaccgg aatttttcta cgatggtgac    420
tggactggag aaggcgtcaa tgtatacgtg atagacacgg gtatcagggt aaatctagat    480
```

```
gaatttgagg gcagagcatc atttggtgct gattttacag gcactgggaa agatgactct    540

gttggtcatg gaacccacgt agctggtctt attggctcca aaacttttgg agtggccaaa    600

aatatcaact tgatatccgt aaaagctctc tctggtaatg ggagcggttc gctttcagag    660

gtcctacagg cgattgaatt cgcagtcaag catatgaaag ccagtcgtaa gccaggtgtt    720

gctaacttgt ctctaggtgc accaaaaaat tcaatccttg aaaaagcgat tgaagaggca    780

ttcaagaacg gtttagtcat agtagcagca gctggcaatg ccttcgtgga tgcctgtaac    840

acatcccctg caaactctcc atatgcaatc accgttggag ctataggtga tcacaacgat    900

gaaataacta gattttccaa ctggggagcc tgtgtcgatc tttttgcagg aggggacaca    960

attgtaagtg taggacttct caatggagtc gctgtccgca tgtctggaac ttcgatgtct   1020

gctccaatag tcgcaggctt agccggaata ttacttgacc agggtgtggc cccagaagat   1080

gtaaaaggta agttaataga gctctcagat gaagggaaga tcaacgataa tactggaatt   1140

ctaaagccgg gaactccaaa ccgaatagcc aacaatggaa ttcgaaaaag tgattatgaa   1200

gatcaaaaag aaaatgacaa tgatgaagac gatgaagacg gggaagacaa tctagaagac   1260

attgaagagg acgaggatta ttgggatgaa gagagaaggt atagggaata tgcggtatct   1320

agtttagtct tctaa                                                     1335
```

<210> SEQ ID NO 36
<211> LENGTH: 546
<212> TYPE: DNA
<213> ORGANISM: Pichia pastoris

<400> SEQUENCE: 36

```
atgttcaaca ttatccaacg gatacagagt ttgagcaatt tttatttaac ggtttccatt     60

ctattatgta ttgttacaac agttgtctca attattagta tgttcttgga tgaaacgtcc    120

agtattcctg cccaattaag caatgttgta atatcaacaa atttaaagta tagcagatcg    180

tttggttcag tcggtggtag acctaaagaa aactccaaga ttttatttga tcttgatatg    240

gatctggctc cattattcaa ttggaatact aaacaactgt ttgtacaatt ggtagcagag    300

taccctacct ctgttgccga tgatggtgcg aaggtgacct attgggatag cataattact    360

gagaaaaagt acgcaagagt gcatgtcaat aagcagaggg gaaaatactc agtttgggac    420

gtgtcggact cctttcaagg ccgcaatgct acggttaaac tgaaatggaa cttacagccc    480

tatgtcggct ttctattctt tggacaaact aagggagaga ttgaggtggc ctatcctgca    540

acataa                                                               546
```

<210> SEQ ID NO 37
<211> LENGTH: 870
<212> TYPE: DNA
<213> ORGANISM: Pichia pastoris

<400> SEQUENCE: 37

```
atgagtgtca tagtgcatcc tcttgcacta ttgacaataa tcgacgagtt ccagagacga     60

ggtcgcaaca acgattccat aatattcggt gggttacttg gtaaacatga tgaatccacc    120

aaccaaatat ctgttgttaa cagctttgtg ataccattga tcgataatca gtttttgaat    180

aaagagtact tgcaggacat gctactcaaa ttttctatca ttaattccaa ctttcgattc    240

gtaggttact atcacgttca atctttaaac ggtaccgaaa ctcaacagta tgacttgaac    300

gctattaacc tagtatgcca agatgataat aggccttcgt cctttgtcca ttggatagta    360

acagatccaa aagagttcaa atcattctcg atgtattact tggatgattc aatggttcaa    420
```

```
ctcgtcaatt ccaatattca acattacatt tctaaaccat tgccctatga atttaaaaac    480

cttctgtctg agaaaattgc tatcgacaca atcctcaagc aatccaggct agaaaaagac    540

ttatccacca aaaactcact gaagaaatta aacaatagtt atatcgacat tcattcctca    600

ctgaacgttc tctataaatc agtcaatagg cttattcgtt acctcaaaaa atgctcaaaa    660

tcagaagttt caattgacta tgacacagtt caggaaatga atactgtaat actgaaaatt    720

gaaaggctta aattgatacc ccaagtcaag gaggagtttg acttagtgac tctttcacta    780

ctggtagaca atcttgatca gatggatcat cttttgtatc tccggaaaca agtggaacag    840

tacaaaatat ctgaatcaat gtatagttag                                    870
```

<210> SEQ ID NO 38
<211> LENGTH: 1167
<212> TYPE: DNA
<213> ORGANISM: Pichia pastoris

<400> SEQUENCE: 38

```
atgaaatttc actcgattgt cttcacattt tcactcgttt tgagttcact ggcgttgtcg     60

ataccatggg tgtctgacca catggtccag catctttttg ccgacccttc aatcagtaaa    120

ggtcctgatg tagatctcgt tggctacat aagcatttgg tcagcatcaa atctctttcg    180

ggctatgaac aagaagtagt atcgtggttg gccgattatc tagccagtag gggtcttact    240

gtggagttga acaaggtcga ggacgaaact gaacgttaca atttgtatgc ttatttggga    300

accacccgca acactaaggt tgtgctaact tctcacttag acacagttcc cccttatctt    360

ccctacaaag ttgaggaagg tggctatatc tttggcagag gaagctgtga tgctaaggga    420

tcagttgcgg cacaagtgat tgccttccta aatctcttgg aagagggctc catcaaagaa    480

ggtgatgtca gtcttttgta cgtcgttggt gaagagattg gaggtgatgg aatgcgcaca    540

gctagcaaga ccttgggtgc taaatgggac actgccattt ttggagaacc taccgagaac    600

aagcttgcca ttggacacaa gggaattgca ctgtttgacc tgaagattac aggaaaatcc    660

tgtcattctg gataccctga gctgggaatt gatgccgacg ctatgttggt ccagattttg    720

cacaagttgc tttttgagac ttcttggcct gtcagtgatt tgctgggaaa ctccacagtc    780

aacgcgggac agatcaacgg aggagtagct gctaatgtta tttcttcgga agcacatgcc    840

aaggttttaa tccgcgtggc taaagacatt gacgctgtag agaagctgat ctacgaggcc    900

attgccccct tcgaggagta tacagacatt acctttcact ccaaagaaga tgctactttc    960

ttggattaca aggttgaagg gttcgagaac tacattgcag cctacagtac cgatgtacca   1020

ttcctagtga cgggctccaa tttgaccaga tatttgtacg gaccaggaag catcatggtg   1080

gctcatgggc ctgatgaaat ggtcaaggtt tcagacctgc aggatagtgt tgacggatac   1140

aagcgattag tctccgtctc actttag                                       1167
```

<210> SEQ ID NO 39
<211> LENGTH: 1776
<212> TYPE: DNA
<213> ORGANISM: Pichia pastoris

<400> SEQUENCE: 39

```
atgccagaga aaaagaaaca aaaaaaagag tcgacatctc cattcaaggg taacctagtt     60

gggatctcat tggtagctgt ggcattgttt gccatctacc agtacctcta cccaagctcg    120

ttttcctctc agcctgaaac cccagcccca gttttcgatc tgagcagtga attagaagca    180
```

ttgtgtcccg tgtaccctgc agtcagatct tccgacttcg aaaaggatcg ccccatctta 240
gagagaattc tgaacgatcc ctcatttaga atcgcttctg ctcaaaaact gagtaaggct 300
gttcagatcg atacccaagt gttcgacgaa caattggacg tggctcaaga ccctgaagtt 360
tggaccaaat tcgtcaagtt ccatgaatat ttggaggcaa ctttccccac cgtttactcc 420
caattgaagg tcgacaaaat caacacctat ggcttggttt tcacttggga aggctcagac 480
cctagtctga aaccactcat gttcttggct caccaagacg tggttccagt ccagaaagat 540
actcttcagg attggtcata tcccccttc gaaggacgta tcgccgatga cagagtttgg 600
ggacgtggat cagctgattg caagagttta ctgattgcat tactggaaac cgtagaattg 660
ctggtagatg aagggtactc accaaagaga ggtgtcatcc tcgcatttgg attcgacgaa 720
gaagcttcag gtacctacgg tgctcacaat atctccaagt tttgcttga gaaatatggg 780 ccagatagta ttgccctcat tttggatgaa ggtgaggctg tcagttacgt ggacaagaaa 840
caaactaccc tcgttgcaaa gattgctacg caggaaaagg gttaccttga cctagaggtc 900
gcattgacca ctgtaggagg ccattcttct gtccccccta agcacactgc aattggcctt 960
atttccaagt tggtcacaca tatcgaagat catccattgg acccagaaat tagtaccaga 1020
aatcctctgg tacagttttc gaactgtctt ggtgcagctg ggggctttgag agatgacttc 1080 aagactgctc ttgttgcata cagcaaggat ccgtcgaaca acattgtcaa acaaggtgtg 1140
attaaaggta tttccaagat tgcatttttc ttcggttctt tgattaccac aacacaagcc 1200
accgatctta ttttcggtgg agagaagatc aatgctttgc ctgaaagtgc tagagtagtt 1260
atcaaccata gagtggacgt tgagcgtgat tcagcccaaa tcatagacag attgattcac 1320
ttccacgttg ttcctattgc caaggagcac ggtttcaagg tcacttacag tgactatggt 1380
agtgacaaag ttgaaactgt ctacgagcca gaaggagttg cctcattggg agaattccac 1440
gtttctcctt tctccagagt ctgggagcct gctccagaat ctccatccga cgacaatgtc 1500
tggtccatca tttctggtac cactcgtacg atatttgagg agtttgtgga cccctcggct 1560
aaacttattg caagtccata catgatgcct ggtaacaccg acactcgaca ctactggccg 1620
ctgacaaaga atatctatag atacgttcca ggtattgtag atatttacaa ggctaagata 1680
cactcggtag atgaatctac cgaggttgat gcccacttgc aagttatagc tttctaccac 1740
gagttcatca aggttgccag cgaatgggag ctttga 1776

<210> SEQ ID NO 40
<211> LENGTH: 1275
<212> TYPE: DNA
<213> ORGANISM: Pichia pastoris

<400> SEQUENCE: 40
atgaaatcct ctaaagaact atacaaggag gctctcaact atgaatactc ttccgcggtt 60
tctttcaagg cctgggttcg aagtgctcaa atcattttgc gacatgcccg gcagtttgct 120
gaacaaagat acatcagtga gtgctataag ttgtctgttc gttttgtaga cttgattgtg 180
aacaagatgg ccacgcataa agagctcaag caattgaaga aaataaatgc accagtatat 240
ctcacctatt tggatttggc tacgaagaaa gtcccagatg tcatcaagga atgtgaggcc 300
ttgaagacaa ttttggatga tgagtaccaa agctacctca aactgcaaca attgaaacga 360
cagaagcaga aagaccaatt gatccatcat cagaatcagg ctcaaacgca taaattacgt 420
agatcttcat caatattgaa agatcatatc aacgctgttg atgaaagagc gctgttgaaa 480
caactacagc agttgacata ccatgatcgt gaattcgcaa ccgcaataac ggagatgcca 540

```
aattatccag agatccccca gctgagtatt tcaacgaatc agaacactag atcagaggca    600

cccccacttc caccaagagt atcgcaggaa cagtcattag caccagtatc actagattca    660

tcacaggcag atttacaaca caaaactgtt aacttcaccg aagctgggca accattacga    720

acagtattta tttcagatag actccaatct gagttcctta gactagcgga accaaacacg    780

atacaaaagc tagagacttg tggcatcctt tgtggaaagc tcgtcagaaa tgcattcttc    840

atcacccatt tggttatacc agatcaagag tcgacaccaa acacatgtaa tacaagaaat    900

gaggaaaagt tattcgacac tatagatcag cttgatttat ttgtccttgg atggatacat    960

acccacccaa cacaatcatg cttcctgtct tccatagact tacatacaca gaattcgtac   1020

cagatcatgt taagcgaagc aattgccatt gtgtgtgcac cagcacctca gttttctcat   1080

cattcttttg gatgttttcg gctaacccat cctccgggaa ttccaaccat tacacaatgc   1140

actaggacgg gatttcatcc tcatgaggaa cccaatctgt atgtgacttg taatcgaaag   1200

aacatgggcg acgtgcaagg cggacacgtt gtgatcaaga atcatttacc gtttgaaaag   1260

cttgatctaa gataa                                                     1275
```

<210> SEQ ID NO 41
<211> LENGTH: 1347
<212> TYPE: DNA
<213> ORGANISM: Pichia pastoris

<400> SEQUENCE: 41

```
atgactagtt ctgtagataa agtgagtcag aaggtcgctg acgtaaaact gggctcctcc     60

aagtcaacaa agaataacaa gagcaaaggt aaaggaaaat ccaacaagaa tcaagtggtt    120

gaggatgatg atgaggatga ttttgaaaag gccttggagc ttgcaatgca attagatgca    180

caaaaactag ctcagaaaaa agctgatgat gtgcctcttg ttgaagaaga agagaaaaaa    240

gttgaggaaa agattgaaca gcaatatgac cccatttcca ctttttaccc tgatggaaac    300

tatccccaag gagaagttgt ggattacaaa gatgacaact tgtaccgtac tactgatgaa    360

gaaaagcgag ctttggatcg agagaagaat aacaagtgga atgaatttcg taaaggtgct    420

gaaattcata ggagagttcg aaaactggca aaggatgaga tcaaaccggg aatgtcaatg    480

atcgagatcg ccgaactaat cgaaaacgca gttcgtggat atagtggtga agacggactc    540

aagggtggta tgggatttcc ttgtggtctt tctttgaacc attgtgctgc gcactattct    600

cctaatgcta acgacaaact tgtcttaaat tatgaagacg tcatgaaagt agattttggt    660

gtccatgtga acggtcacat tatcgatagt gcattcacgt taacattcga tgacaaatat    720

gatgatctgt tgaaagctgt caaggatgct accaatactg gtattcgtga agcaggtatt    780

gatgtgagat tgaccgacat tggtgaagcc atccaagaag taatggagtc ctacgaagtt    840

actttagacg gagaaacata ccaagttaaa cctatcaaga atctttgtgg ccataacatc    900

ggccagtata gaattcatgg tggtaagtct gttcccatag tgaagaattt tgacaacacc    960

aagatggagg aaggtgaaac ctttgcaatt gaaacctttg gcagtacagg aaggggtcat   1020

gtgataggac aaggtgaatg ctctcactac gccaagaatc cagatgcccc cgccaatgct   1080

atctccagca ttcgtgtgaa ccgtgctaaa caattgctaa agactatcga tgagaacttt   1140

ggtactcttc cattctgtcg tcgctacata gatcgtcttg gagaagaaaa gtacttattg   1200

gcattgaacc agttggttaa atctggagtt gttagcgatt atccaccctt ggtagatgtc   1260

aaggggtcat acactgccca atacgagcac accatccttt tgagacctaa tgttaaggaa   1320
```

-continued

```
gttgtatccc gcggtgaaga ctactag                                        1347


<210> SEQ ID NO 42
<211> LENGTH: 1119
<212> TYPE: DNA
<213> ORGANISM: Pichia pastoris

<400> SEQUENCE: 42

atgattcaca gctgtgctag tgctgagtgc tcaaaagcga ctgaatctac cttaaaatgt     60

cccttgtgtc taaaacaagg tcagatccaa tatttttgta accaaaaatg tttcaagaat    120

ggatggaaga tccacaaagc ggttcacgcc aaagatggtg atatagatgg ttcgtacaac    180

ccctttccca actttgccta caccggtgag ctcagaccag catatccctt gtctgtgaga    240

cgagaggttc cagagaacat tactctccca gattatgctc ttgatggagt accagtctca    300

gaaatcaaaa ataacagaat gaacaagatc aatttggtaa cggagccaga agacctggcc    360

aagctaaaaa atgtttgccg tttagcacga gaggttctag atgctgcggc tgcatctatc    420

aaaccaggag ttaccactga tgagatagat gaaatcgttc atagtgaaac aatcaagaga    480

gaagcatacc cctccccttt aaattacttc aattttccca aatctgtttg cacatccgtt    540

aatgaagtca tctgccacgg tatacctgat cgtagaccgc tccaggatgg tgacatcgtg    600

aacctggatg ttaccottta taaagatgga tttcatgcag atctgaatga aacgtactat    660

gttggagaga aggccaagac taacaaagat ctggtcaacc tcgtcgagac aaccagagaa    720

gctcttgctg aagctatccg tttagtgaaa cccggcatgc cgttccgtca aattggtact    780

gttatcgaaa actatgtgac tgaaagaggc tgtgaaactg ttcgttctta cactggtcat    840

ggtatcaata ctttgttcca cactgaacca accattccgc attacgctcg taacaaagct    900

gttggagtag ccaaaccagg agtggtattc actatcgaac caatgttgac tctgggcact    960

catcgtgacg tggtttggcc cgacaactgg accgccgtta ccgctgatgg aggaccaagt   1020

gcccaatttg aacataccct tttggttacg gaagatggtg tggagattct cactggcaga   1080

acggaaactt cgccaggcgg tgccatctca agactataa                          1119


<210> SEQ ID NO 43
<211> LENGTH: 1605
<212> TYPE: DNA
<213> ORGANISM: Pichia pastoris

<400> SEQUENCE: 43

atgctctata agaccacctt gtcaatagca cacacgagtg tgatattgtt gtcattgata     60

accgccataa gttgctttga gttgcatctt cctcagaagg tttctcatat agtagacagt    120

ttacaatata cttgcggcca atttttgcaa aagcagcaga tctttgcact ctataacaag    180

caaaatttca ccgaaatagt gaaccagaat atcaagggaa tagaggagag agttttgtct    240

gagttgcttg aagaaagatt agagaatgaa tcccagaatg attattatac cgccaattct    300

caaaattggc ctatcgactt ggatcagtac tcagaatcat ttgtaataag gatcacatct    360

gaagatgagt ttatcaagta cttgatcttc aaggaagcta aagctttgca tatttccata    420

tgggagcaat ctgttggttt gatagatttg aaggttgacc gtgatcagat gcaccgccta    480

ctttacaacg tggagtcacg catactggaa cgaagaacga gaagtgttga cagtccagtt    540

tctgaatata aagtacaatt gatgattgga gatcttccac agcgaatcta cgaaacatat    600

ccttcgacaa aagtgacatc tttgcaagcc ctaggagagt tcccttcttt ccagaaccta    660

agtaatgctt tttttgagga ttttagaacg ctggaaacta tatacgactg gttcgaagaa    720
```

```
atacagaagg aatttcctaa gctagtgtcg atcaactgga ttgggcaaac ttatgaaggt    780
cgtgatctga aggctcttca cgttagaggg aagcactctg gcaacaaaac agtagtcgtt    840
acaggtggaa tgcatgcgcg tgaatggata tcagtaacca gtgcatgcta tgccgttcac    900
aaactgctcc aaaactatgc tgacggacac cacaaggaag cgaaatacct ggacaagttg    960
gactttttgt ttgttccagt tttgaatcct gatggatacg aatatagctt taacgaagac   1020
aggttgtgga ggaagaacag acaagaaact tatatgcccc gatgttttgg tatagacatt   1080
gaccattcat ttgattatca tttcgtgaaa tcagaagact taccctgtgg agaggaatat   1140
tcgggtgagt cccctttcga aagtatagaa agtgaagtgt ggaataattt cctgaacaga   1200
accaaagaag aacataagat ctacggctat atcgacttac actcgtattc gcaaacggtg   1260
ctgtatccct atgcgtactc atgcgaaatc ttaccaaggg acgaggaaaa cctgattgag   1320
ctaggttacg gtattgcaag ggccataaga aagagtacag ggaaaaaata tcaagtgttg   1380
aaggcatgcg aagacaggga tgcagatcta ttgcctgatt tgggaggagg aaccgcttta   1440
gattatatgt accacaaccg tgcatactgg gcgtttcaga tcaaattgag ggattccggt   1500
aatcatggct ttctccttcc caaaaagttt atatacccag ttggaacaga ggtttatgcc   1560
tcaattcagt acttttgttc ttttgtgctg aatttagaag gctaa                   1605
```

<210> SEQ ID NO 44
<211> LENGTH: 1191
<212> TYPE: DNA
<213> ORGANISM: Pichia pastoris

<400> SEQUENCE: 44

```
atgaaattga ccataacatt agcccataac gatcaaatct tggacattga tgtgtccagt     60
gaaatgctac tatctgacct caaagtcctg ttggagttgg aaacttccgt acttaaaaac    120
gaccaacaat tattttacaa taacaacctg ctcactggag atgactcgcc actggaagat    180
ttaggactca aagataatga actcataatt ctgagcaaag tcgaagcaca tagtgatgtc    240
aattcacact tgaactctgt tagagaacag ttgatacaaa acccgctata ccaggccagt    300
ttacctccaa gtcttagaga taagctcgac gaccctcaag gcttcaaaga agaagtggaa    360
aaactaatcc aattggggca gtttggacaa tacgggcctt cccgtacttc cgtccaacag    420
gaattagaca gactacaaag agatcctgac aatccacaaa atcagaaacg aattatggag    480
ctcattaacg aacaagctat agaggaaaat atgaatactg cttttgaaat ctcacctgaa    540
tctttcgttt ccgtgaatat gctctatata aatgtggaaa ttaatggtgt ccattgtaaa    600
gcattcgtcg atagtggagc ccaaacgacc ataatgtccc ctaaactcgc agagaaatgc    660
aaccttgcga atctaattga taaaaggttc cgaggagtcg cacagggtgt aggaagttct    720
gaaatcattg gtcgtatcca ttctgctccc ataaaaatcg aagatattat tgttccctgc    780
tcattcactg ttttggatac caaggttgac cttctattcg gacttgatat gttgagaaga    840
catcagtgtg tgattgacct taagaacaac tgtttacaaa ttgcagacag aaagacagaa    900
tttttaggag aagcagacat cccaaaggaa ttctttaacc aaccaatgga agctccatcc    960
acagctcctg tcccaaaacc tgtacaacct cctcaacaac tcggtcagcg gccggctgga   1020
agccctccct ccacaattca aagaccagca gtacaaccgc cacctgtgga tatacctcca   1080
gaaaaaatcc agcagttgat caaccttgga ttcggagaag aggagtcgaa agaagcactt   1140
attagatcta gaggaaatgt ggaagttgca gcggctttgt tattcaacta g            1191
```

<210> SEQ ID NO 45
<211> LENGTH: 1553
<212> TYPE: DNA
<213> ORGANISM: Pichia pastoris

<400> SEQUENCE: 45
atgccaaacc ttccttctag cttgaacaag atgactgctc aagccgtgaa atacgcaaac 60
ggtatgtcat ctgccctctc ccgtgtttga gactctatcc actaacttta gattttatca 120
ccttcctgaa caattcacct actccatacc atgctgtcga ctccgtaaag tccaaattgg 180
tagagtcggg gtttaacgag ctcagtgaga gagttaattg ggccggaaaa gtcaagaaga 240
atggcgctta ctttgtgact cgtaacaatt cgtccattat agccttcact gttggcgggc 300
actggcagcc aggtaacgga gtgtcaattg ttggagccca tactgattcc ccaaccttga 360
gaatcaaacc catatcccat tcgactaagg agggatttaa ccaagttgga attgaaactt 420
atggtggagg cttgtggcat acgtggtttg acagagattt aggagtagct ggacgagtgt 480
ttattgaaga agaagaatct ggtaacattg tgtccaagtt agtcaagatc gataaaccag 540
tattgagaat ccccacacta gccatacacc ttaccaaaga gagagctaag tttgagttta 600
ataaggaaac tcaattccat ccaatctcat cgcttgaaaa ctcctctgaa aaggagaaaa 660
acaaagatga ggaacatgac gcttgtgcag gagaagattt gactacggag gagtttaagt 720
caattcaatc tgttgtggag agacacaaca aacaattgct tgatctggtg gctgcagatc 780
ttgattgctc tatatcccag atagtggact ttgaattgat tcttttcgac cacaacaaac 840
cagtactcgg aggtttgaat gaagaatttg tgttctcagg aagattggac aacctaactt 900
cttgtttctg tgccactgaa gcgcttataa atgccagtaa agataccaac aggttagatc 960
tggatactaa tattcaactg atctctctgt ttgaccacga agagattgga tcagtttctg 1020
ctcaaggagc tgattcttca tttctacctg acatacttca gcgtataaca agactaactg 1080
gtaatgaggt tagcaccgat ctggaaggac aaccaaattc tttctttta gagtcaatgg 1140 ccaaatcttt cctactatct tcagatatgg cacatggtgt gcatcccaac tatggggaag 1200
tctatgagaa gctaaatagg ccaagaatca acgagggacc agtgatcaaa ataaacgcta 1260
atcaaaggta cagcaccaat tccccaggta ttgttttgct caagaagatt ggtgagttgg 1320
gaaaggtccc cttgcaattg tttgttgtta gaaacgactc tccctgtggg tcaacaattg 1380
gtccaatgtt gagtgctaaa cttggacttc gaacgctgga cctcgggaac cccccagctct 1440 ccatgcattc tatcagagaa actggaggtg ctcgtgacgt taaaaagttg gtcgatcttt 1500
tcgaaagcta ttttgagaat tattacacct tggagcctaa gattaaggta taa 1553

<210> SEQ ID NO 46
<211> LENGTH: 1413
<212> TYPE: DNA
<213> ORGANISM: Pichia pastoris

<400> SEQUENCE: 46
atgaacaaag gtccgaaaga attggagggc cgcaagtatc cagcaagagc ccatgcactg 60
acggtcaaaa atcactttat ccaaaagaag gctgacattt caagtcgttc tgcaatcttt 120
attagtggcg aagatctcaa gttgtatcct tactgtgacc aaacagctcc tctcagacag 180
aatcgttatt tcttttatct gtcaggttgt aatatccctg gatcccatgt cctttttgac 240
ttggacgccg aattgttaat tctggtgcta ccagaaattg attgggatga tgtcatgtgg 300
agtgggatgc ctctttcgat tgaagatgcc tacaagacgt ttgatgtgga caaggtggta 360

```
tatcttaaag atttgcaagg ctttttgtcg tcgtttggaa aaatatatac aactgacatc    420

aatgatgaaa attctaagtt tggcaatcta ctaacagaga aagatcctga cttgttctgg    480

gctctggatg aatccagatt gatcaaagac gactatgaac tcactctaat gagacatgcg    540

tcaaaaattt ctgacaattc ccattacgct gtcatgtcgg ctcttccaat tgaaactgac    600

gaaggccata ttcacgctga gtttgtttat cattcgttaa gacagggatc taaatttcaa    660

agttatgacc cgatttgttg cagtggacca aactgtagta cccttcatta tgttaagaat    720

gacgattcta tggagaataa acacaccgtt ctaatcgatg ctggtgcaga atggaacaac    780

tatgctagtg acgttacaag atgttttccc atcaatggag attggacgaa agagcatctt    840

gagatctata atgctgtttt ggatatgcag gaccaagtta tgaagaagat taagcctgaa    900

gcccattggg atgagctaca ccttttggca catcgtgttc tcattaagca tttttgagc    960

ctcggcatat ttcataacgg aacagaggat gagatatttg agagtggagt ctcagtatca   1020

ttctttcctc atgggctggg tcacctttta ggaatggata ctcatgatgt tggtgggcac   1080

cccaactatg atgatccaaa ccctctattg agatacctaa gattgagaag agtgttgaaa   1140

gaaaatatgg tagttacgaa cgaacctgga atctacttct ctccctatct tgttgaattg   1200

ggactgaagg atgataataa ggcaaaatat gtcaacaagg atgtactgga aaagtattgg   1260

tatgtcggag gtgtgagaat tgaagacgat attcttgtta cgaaagatgg gtatgaaaac   1320

ttcaccaaga ttactagcga ccccgaagaa atttccaaaa tcgttaaaaa ggggttggag   1380

aagggtaaag acgggttcca taatgttgta tga                                1413
```

<210> SEQ ID NO 47
<211> LENGTH: 2612
<212> TYPE: DNA
<213> ORGANISM: Pichia pastoris

<400> SEQUENCE: 47

```
atgacatctc ggacagctga gaacccgttc gatatagagc ttcaagagaa tctaagtcca     60

cgttcttcca attcgtccat attggaaaac attaatgagt atgctagaag acatcgcaat    120

gattcgcttt cccaagaatg tgataatgaa gatgagaacg aaaatctcaa ttatactgat    180

aacttggcca agttttcaaa gtctggagta tcaagaaaga gctgtatgct aatatttggt    240

atttgctttg ttatctggct gtttctcttt gaccttgtat gcgagggaca atcgattttc    300

caatttgaac gagtacgttc cagattcaaa cagccacgga actgcttctg ccaccacgtc    360

taatcgttga accaaaacag actgaattac ctgaaagcaa agattctaac actgattatc    420

aaaaaggagc taaattgagc cttagcggct ggagatcagg tctgtacaat gtctatccaa    480

aactgatctc tcgtggtgaa gatgacatat actatgaaca cagttttcat cgtatagatg    540

aaaagaggat tacagactct caacacggtc gaactgtatt taactatgag aaaattgaag    600

taaatggaat cacgtataca gtgtcatttg tcaccatttc tccttacgat tctgccaaat    660

tcttagtcgc atgcgactat gaaaaacact ggagacattc tacgtttgca aaatatttca    720

tatatgataa ggaaagcgac caagaggata gctttgtacc tgtctacgat gacaaggcat    780

tgagcttcgt tgaatggtcg ccctcaggtg atcatgtagt attcgttttt gaaaacaatg    840

tatacctcaa acaactctca actttagagg ttaagcaggt aacttttgat ggtgatgaga    900

gtatttacaa tggtaagcct gactggatct atgaagagga agttttaagt agcgacagag    960

ccatatggtg gaatgacgat ggatcgtact ttacgttctt gagacttgat gacagcaatg   1020
```

tcccaacctt caacttgcag cattttttg aagaaacagg ctctgtgtcg aaatatccgg 1080
tcattgatcg attgaaatat ccaaaaccag gatttgacaa ccccctggtt tctttgttta 1140
gttacaacgt tgccaagcaa aagttagaaa agctaaatat tggagcagca gtttctttgg 1200
gagaagactt cgtgctttac agtttaaaat ggatagacaa ttcttttttc ttgtcgaagt 1260
tcacagaccg cacttcgaaa aaaatggaag ttactctagt ggacattgaa gccaattctg 1320
cttcggtggt gagaaaacat gatgcaactg agtataacgg ctggttcact ggagaatttt 1380
ctgtttatcc tgtcgttgga gataccattg gttacattga tgtaatctat tatgaggact 1440
acgatcactt ggcttattat ccagactgca catccgataa gtatattgtg cttacagatg 1500
gttcatggaa tgttgttgga cctggagttt tagaagtgct tgaagataga gtctacttta 1560
tcggcaccaa agaatcatca atggaacatc acttgtatta tacatcatta acgggaccca 1620
aggttaaggc tgttatggat atcaaagaac ctgggtactt tgatgtaaac attaagggaa 1680
aatatgcttt actatcttac agaggcccca aactcccata ccagaaattt attgatcttt 1740
ctgaccctag tacaacaagt cttgatgaca ttttatcgtc taatagagga attgtcgagg 1800
ttagtttagc aactcacagc gttcctgttt ctacctatac taatgtaaca cttgaggacg 1860
gcgtcacact gaacatgatt gaagtgttgc ctgccaattt taatcctagc aagaagtacc 1920
cactgttggt caacatttat ggtggaccgg gctcccagaa gttagatgtg cagttcaaca 1980
ttgggtttga gcatattatt tcttcgtcac tggatgcaat agtgctttac atagatccga 2040
gaggtactgg aggtaaaagc tgggctttta aatcttacgc tacagagaaa ataggctact 2100
gggaaccacg agacatcact gcagtagttt ccaagtggat ttcagatcac tcatttgtga 2160
atcctgacaa aactgcgata tgggggtggt cttacggtgg gttcactacg cttaagacat 2220
tggaatatga ttctggagag gttttcaaat atggtatggc tgttgctcca gtaactaatt 2280
ggcttttgta tgactccatc tacactgaaa gatacatgaa ccttccaaag gacaatgttg 2340
aaggctacag tgaacacagc gtcattaaga aggtttccaa ttttaagaat gtaaaccgat 2400
tcttggtttg tcacgggact actgatgata acgtgcattt tcagaacaca ctaaccttac 2460
tggaccagtt caatattaat ggtgttgtga attacgatct tcaggtgtat cccgacagtg 2520
aacatagcat tgcccatcac aacgcaaata aagtgatcta cgagaggtta ttcaagtggt 2580
tagagcgggc atttaacgat agatttttgt aa 2612

<210> SEQ ID NO 48
<211> LENGTH: 2127
<212> TYPE: DNA
<213> ORGANISM: Pichia pastoris

<400> SEQUENCE: 48
atgacctgcc aaagtgtaga agagctggat gctattgttg aatcaaagct tagggaggtt 60
gataataaag tttcgaacgg aaatgttgac ttcatcaaac aatatctgat tcaggcgatg 120
aactattatg acaagtatag atctgaaatc aaaaaaattg gacccacaga aaagaaccct 180
aaatactatt gttttcaaga ggcagcgtat gttaactaca aagcttccca agctttacta 240
agagagagaa tacccaagct gcctggcttt ggaggatata aatctgcgta ttcaaaaatc 300
tatcgtgaac tgatagaaat ggtagagggg caagaacatg agattgccca gataaaaagc 360
ggcttaagga aaaacttttg tgatgataca ttagttcttc gactgagaag tttaaaatca 420
ccatctgcta ctcagcccaa aagtttaccg gattctacac ccacttcaca atttaaacca 480
aaaccttcaa agccttttag tatcacaatc aatgaggaat acatttcggt tgaccaattg 540

-continued

```
tcacgccttc ttaaaacgaa cccgaatgac atactcctca ttgatctacg gtctcgtcaa    600
gagtacgacg tgtatcacat tgaagatggc tccggggtgg acatgtcaat atgtatagaa    660
ccaatgagta tcagaaacgg atacacagca gaggatcttt atcaactttc aatggccgtc    720
aatccagatt atgaaaggag attgttcaag aatcggtctc agtatgaact gttggtatgt    780
tatggtaatt atgacaacga ggctactgtt caaatgttca tgactatcat gaataaagat    840
acttccctca agaggcggag cgtctatttg aaatccggaa ttaagggctg gaatcaggat    900
ctgagttttc aagattcgaa accgaatggg tacttaacta gtacgactga ctacttcagt    960
aacactccga aacacacaat tacgcccaaa tcatcaaaat caagttcaaa acctacttta   1020
aaaactactg tcaactctgg gcctgcccac actgttggga tcaataatct aggaaataca   1080
tgttacatga attgcatact tcaatgccta ttagaaagtg ataagtttgt ttcatttttt   1140
ttacaaggcg attataagaa acatatcaat attaatagcc gattaggctc gagaggtata   1200
ttggctacag gatttcattt gttagtgcta ttaatatcca gatcatctgg taaaacagtg   1260
actccttctt catttgccaa agatgtttca acagtgaata agaattttaa gttaggagag   1320
caacaggatt gttttgaatt tttagatttt ctcctggata gtttacatga agacctgaat   1380
gaatgtggga atgaaccacc aatcgcagaa ctcacacctg aagaggaaaa gcttagggaa   1440
gctttaccta tcaggattgc ttcgaccatt gaatgggaaa ggtatttaaa aaacaatttt   1500
agcatagtag aagatgtgtt tcaagggcag tacttctcca gattggaatg tacagtctgt   1560
aaaagcactt caactactta taactcattc agttcactgt ccttgccaat cccattagat   1620
cgacaaaatg tcacactaga tgactgtttc caggcttttt gttctgtaga agaattgaac   1680
ggagatgaca gatggcattg tccaagctgt aaaaaaaagc aggtcgcttt taagaaactt   1740
ggtatctcta gactaccaag tgttctgatc gttcacttta aaaggtttca ggtcaagtgg   1800
gaaacaggtc atataatcaa gatagacaag tttatcagtt atccgttcaa gctatcaatg   1860
gacaaatatt ggcccaaagc tcaatcagaa gaagaactaa gaaacttgga gaagctacca   1920
tcgagaaatc agaatccccc tttcaattat cgattgacag ggtggctaa tcattttggg    1980
accagaacat catctggtca ctacacatca tatgttcaaa aaggtggcca atggtattac   2040
tttgacgata gtgctgtgac tagcaatgtt gatcgtcata aaatcgtaaa tgggaacgcc   2100
tatgttttat tttatcgacg tagttag                                       2127
```

<210> SEQ ID NO 49
<211> LENGTH: 669
<212> TYPE: DNA
<213> ORGANISM: Pichia pastoris

<400> SEQUENCE: 49

```
atggaagccg tgaatttaca aattgaatgg attagacagg tgcctccagt tactgtggct     60
cttgtagcat ccatgtcaat gacctatttt ttgcaacgca tagatgtatt atcctcaaat    120
atgttcgtgt ttgaaagaca tcgtgtgttt aatgagatgg cctattctcg tttgatacta    180
agtttcttct tcagcgccca ttcgtttgtt ggattctttt ggacattgta cacattattt    240
cagaattcac aggcactcga gctgacctat gaaaactcaa tcgattacct ctactcattg    300
gtgataatag caggtttgat cgtggcatgg gcctcatact tggggggtcc gttcatgctg    360
ggatgggttc tagctgacgt cttgagaacc atatggtgca aacagaatcc caacgaaaga    420
atgtctattt tggggctagt ttccttcaag gcaggatact ttccatttgt aatacttgcc    480
```

atttcatggc tagaaggaag ttcaagaaat cttctattaa tgctaattag ccaaactgtc 540
agtcaggctt atatttttgg acaccatatg atgcccgaac tacacgggat cgatctgttt 600
ctgcctatat ggaaattcca gtgtttcaga cgtcagagac aaccaccaat tcatcagcat 660
caagactaa 669

<210> SEQ ID NO 50
<211> LENGTH: 927
<212> TYPE: DNA
<213> ORGANISM: Pichia pastoris

<400> SEQUENCE: 50
atgtcaaagg tggtggtatt cctaaatgga ttattggcaa taacctttac gtttgaactt 60
ctctctgttt taagcgtgcc aatcaccaag catatccaac tttgttctta tcaaggatat 120
aagtttggcg tgtttggata ttgcaccgag aataatatct gcacaacgat aggaatcggt 180
tatcatcgaa attcaataga cgaattgaga ggcttttcat taccaagtaa tgcaagaagc 240
tctatatcaa gcttgttggt ggttcatttg attggctgtg tttgcacctt tattttatgg 300
gttctaagtc tcatgttgaa tatggataga tttcacagat cattatggtt cttattaacg 360
tgtctagtat ggacttgtgc tttctttttt tttacattat tctccttcct ggtagacgtg 420
ttactatttg tgccacacgt tgcgtttgga ggttggttga tgttggtaag tactgtattt 480
ttggcattta caggaaccat tttttgcatc atgcgaagaa ctgtcagctc aagaaaaact 540
catttgaaga actacaacgg gggaagtaca agtttgatgc ggctgcagac gtatatctcc 600
aatagctcta gaggaagctc tgtaaccaat gatgaatacg tctggtttca agaaactcca 660
ttacaagacc tctacccccc agacaatccc aattacgacg acatctacgg aacgactgaa 720
cacgaactaa cccgcttgga cacaatatct cttgaaaggc caagaatagg ccttatcaca 780
aacgaaaatg ccagcggcga tggtggggta gtttccccac cacagaatga cagtacactt 840
ctggaatctt cgggcagaat taggaatggg ccactgggag accgaagtga atttcccaac 900
ggatcaacaa gcgaactttc tgcataa 927

<210> SEQ ID NO 51
<211> LENGTH: 714
<212> TYPE: DNA
<213> ORGANISM: Pichia pastoris

<400> SEQUENCE: 51
atgaaataca gtgaccaatt aatagaagag tacaaagaat tatggttaac agcgacatct 60
aatgagctta ctagagaatg gtgccaggga actctccacc tgagcaaatt atacgtttac 120
ttgacacaag acttaaagta ttttggggat ggatttcgac ttttaggcaa aaccatttcg 180
ttatgtcgcc gtaggcaatc gcttgtgtca ttaggcaaac atgtggggat gctcagtaat 240
agtgagaaca cgtacttcgt ggattgtatt aacgatctta ctgaacagtt attaagagat 300
gggatgtaca atgctgaaga attagaagaa atcagtggtt taacgttacc tgccgtggaa 360
aggtaccttt tattcatgag atcgatggta gagtcttcta caataactta tgcagaaatg 420
attactgtga tgtttgtaat ggaacaagtc tatctggatt ggtcaaataa tggactgaga 480
agtaaacctg acaacttgca ttggtggttc aatgaatgga ttgatataca tagtggggag 540
aactttgaaa gctggtgcca gtttttaaag gatgaggtag accgctgtat acaggagttg 600
aaggatgcta atagagatga tctcgtggcg agggttgagg agatttttag agaaacatta 660
gaacttgaag tcgaattctt taaaagttgt tacgatatca cggacgatga atga 714

<210> SEQ ID NO 52
<211> LENGTH: 357
<212> TYPE: DNA
<213> ORGANISM: Pichia pastoris

<400> SEQUENCE: 52
atgcactcga aatttaggtg ggtatgtgtc gatactcaat tctgcacaca ccaccaaaat 60
ctgtcgcctt tctcttatat ctccaacccg agtccaatgt cattttctta ccttgaaggc 120
aacatcgatt ttaaaggaca ggaacttgca aacaggatca ctaaaaaact aatcacattt 180
ggtgcaatta ttagttttct ggtaggattt ttgagtgaca acatcttata cactgtatac 240
actttcgcag cttttggttt attgactgct tctttggtta ttccccccttt tagcttctac 300 aaaaagaacc ctgtaacatg gttaccaaag aaatccaaaa tagagattca gcattga 357

<210> SEQ ID NO 53
<211> LENGTH: 3423
<212> TYPE: DNA
<213> ORGANISM: Pichia pastoris

<400> SEQUENCE: 53
atgacagact ctgttaactc tgatgattct gatctggaaa tcatagaggt gactgagcct 60
actccaaaag tggacctttt ggccccccaat ccagcattta attttactgc ccccataagc 120
aacagtaacg gcacaactcc aataaggaga aaacttgatg accaatccaa ctccaattct 180
tttgccagac tggaatcgtt acgggaatca tcagtgaaac cacaagctag tacgttcaat 240
agtagtaggt tcatccccca agccgaccaa ttttccaata atcagaataa tgaacttgat 300
aacaacaatg gattcgccga ctggatttct aagtcccaac ctgaatttcc ctttccactt 360
aatgatggac caaaaaagtc cagcaatcaa cctacaaact caaattttga agagatcatc 420
gatttaactg aagatatcga gataaataca tctgtccccg catctacatc atcttctacc 480
ccagttccct ccagcacaca gaatcagagc catcatatag ccaacaacaa cacagcacaa 540
gatgcgcata tcttccaagg gaaacgacct ctccaatcat attcagatga tgaagacgaa 600
gatttgcaaa ttgtaggatc caatattgtt cagcagcctc taggaattat gccaggaact 660
ttcaacgccc ctgcaaacat actccatttt gacggttcaa accagaatga acaagccaga 720
tggctggact tgcggataaa agatttgtta gataatcttc acaatcttcg agttcatgct 780
cagtcgaata ttatggagat caataggttc atttccactt tggggcattt aaacagagaa 840
gtttcagagc tcaatctaag atatcaatct atcgtgaaca atcctcaggc gaccgctaat 900
aatcaaggat acctcactca gcttttgaac aggattcagg agcttactaa tgaaaaagcg 960
cacatattta gagagatgga tacatccaag ataaaacagc aggagattca cagaagaatc 1020
catgctctct cgtcaacaat tgacaaactg aaaaaagatc gtgaacttat ctttcgaaat 1080
gctcaaaatg cttttcacgg tgatatgaag aatgaagttt tggaaggcca gtctttcatg 1140
gatgcaattc atagggcaaa tagcttgggt tatgcttcaa atatttattc tcgttctgat 1200
gaagacgctg gaagcttaca acggcttctt gaaaatatcc agcccgatat ggaggacaaa 1260
gacgatgatg aattggctaa aactccgaag gagttcaata ttcaactgct gaagcatcag 1320
agagttgggt tagattggct acttcggatg gagaagtcaa ccaacaaagg aggcatttta 1380
gcagatgcca tgggcctggg aaaaaccatc caggctatta gtattattta cgcaaacaaa 1440
tggaaaacac aagaagaagc cgaagaggag gcaaaacttg aagagaaggt tagatccgaa 1500

-continued aagtctacat cagaaacgaa tggagaggtc agcaaaacgt caacggcaaa gtcggaaaag 1560
aaacccatcc aaggagacga aggatatttc aaaactacgt taataatagc accagtttct 1620
cttctacatc agtgggagtc tgaaatcttg ttaaagacga aaccagaata caggctaaaa 1680
gttttcattt atcacaagca aaaaatgtcc tcgtttgaag agctccaaca gtatgatata 1740
gtattaacat cgtatggaac tctgtcttct caaatgaaga agcattttga agaggcaatt 1800
aaggaggcag acctacagcc caactcttca tccataccag cagaagactc tggaggcata 1860
tctttcaagt caccattttt tgcaaaagaa acaaagtttc ttcgagtcat tctagacgaa 1920
gcccataaga tcaaaggaaa aaatacaatc acttcgaagg cagtcgcttt ggtgaagtct 1980
aaatacagat ggtgtttaac gggcacaccg ctacaaaata aaattgaaga actatggcct 2040
ctacttcgat tcttgagaat taagccatat tatgatgaaa agcgatttag aactggcata 2100
gtattaccta taaagagttc catgtcaggc aaatatgatt ccacagacaa gaagattgct 2160
atgaggaaac ttcatgccct acttaaagca atcttgttga aacgaaacaa agattcgaag 2220
attgatggag agcccattct caagttaccc aagaagcata tcattgacac attcatagaa 2280
atggaagcaa aagagttaga cttttacaag gatctggaag gacagacagc caaaaaagcc 2340
gaaaagatgc taaacgctgg aaagggacaa ggaaatcatt attctggtat tcttatcttg 2400
ctattgagac tgagacaaac ttgttgccac catttcctcg tgaagttatc tgagatgaag 2460
caagaagcca aattgaaaca ggaagttgct accaagatgc cacaattggc cacacaacta 2520
tctcctgctg tggtaaggag aattaacatt gaagcagagg ccggatttac gtgtcctata 2580
tgtttggata acatcataaa tgagaatgct tgtatattat acaaatgtgg acatgttgtt 2640
tgtcaagatt gcaaagacga tttcttcacc aattatcaag agaatgaaac tgatgacggt 2700
cttagagtgt ccaaatgtgt gacctgtcgt ttgcctgtca acgaaagcaa tgtaatcagt 2760
ttcccagtct acgacaagat tgtgaaccag catatttcag tgatggatat agttaaaagt 2820
gagtctccag tgttgtcaaa aattgaaatg attcaacaac tgatccggga gaacaaaggc 2880
gtcttcgaat cgtctgccaa gatcgataaa gcagtggaaa tgatacaaga gttactgaga 2940
gacaatccag gggagaagat catagttttt agtcaattca caactctctt cgatgtcata 3000
gaggtaatac tcaaagagaa caacattaaa ttcattagat atgacgggtc aatgtctctt 3060
agcaatagag atgctgccat tcaagagttt tatgagagta cggagaaaaa cgtaatgctt 3120
ctttctttga aagcagggaa cgtggggttg acattgactt gcgcctcccg tgtcataata 3180
atggacccat tttggaaccc atatgtggaa gaccaggcca tggatagagc ccatagaatt 3240
ggccagttaa gagaagtttt cgtctatcga atgttgatca agaacaccgt cgaagataga 3300
attttgacca ttcaaaatac gaaaagagaa atagttgaaa acgctctgga taaccagagt 3360
ttgaatacga tatccaagct tggcaggaac gagttggctt tcttatttgg tatcggcaat 3420
tga 3423

<210> SEQ ID NO 54
<211> LENGTH: 1080
<212> TYPE: DNA
<213> ORGANISM: Pichia pastoris

<400> SEQUENCE: 54
atggagtgta aaaaagtcaa agatcgccta gtcacggaat acttaaagat tgaatgtagt 60
cgacttaacc gaaggatacg ctccctgaaa aatccaaaag ttgagcaagc cctactgcaa 120
ttcaagaact cacgtttggc tcacatgaga aaggctcatc tggatggaat aagaaaccca 180

```
cagtatacgg atgacgccat ctttcaggca ttggaaacca tggatttgga ccacatattt    240

gagaaggcag gtagtcttta caactcacag caacaagatg aatcaaaaaa agattccctg    300

gatgaaacag atttcaccgt ggtggcgttg ctagattggt tcaagaatga cttcttcaaa    360

tgggtaaaca agccaccttg tcctgtttgc catagtgaag atgaaagccg cataagaatg    420

gtcggatctg caaggcccac tagtgaagaa ttgtcgtacg gagcaggggt cgtagaggtg    480

tttaattgtg accattgtag ctgtgcaatc agatttccaa gatataacga ccctaagaag    540

ctcctgagaa ctagagctgg acgatgtggg gaatggaata actgttttct gttgtgtcta    600

aaagccttgg gtctgaaagc tagatgtgtg aggaatgtgg aagatcatgt atggagtgaa    660

tactactcgg aacatctcaa gcggtgggtc catctggata gttgcgagaa tgcctttgat    720

caaccagaac tatactgcaa aggttggggg aaaaagatga gctattgttt tgcttttgat    780

gacactctca tagaagatgt gagtgccaag tacattactc aaggtagact gcctaaaatg    840

ctagacgacg aaaccatcag aatatgcttg tattttttca accaggaagc tcttaagatg    900

gtgagtgaaa atccagaggc attctactcc gctttggtta agtatcacag atgtctgtct    960

gcgaatagaa aagagagcgg gtcaaaatca cgagccgtga atgctagttt gacttcattg   1020

ttaccacgac aatctggtag cgcatcctgg acgtctgaga gaggcgaaaa cggactttag   1080
```

<210> SEQ ID NO 55
<211> LENGTH: 819
<212> TYPE: DNA
<213> ORGANISM: Pichia pastoris

<400> SEQUENCE: 55

```
atgcctataa aggggcggtt caccaaaaag aagccaaaaa ggaaagatga gccaaatcga     60

ccgtccccca cccagttcat caaaaaaata gcctcattga aaaagcagac caggagagat    120

gaggccctgg atgtgctaca cgaactagca gttgttgtgt cacctttgat gaaagagaac    180

ggtttcactg ttggattatt atgcgaaatg ttcccgaaga atgcctcttt attggggctg    240

aatgtgaata tgggttcaaa gatcatgatc cgattgagac ctagccacaa catgaacttg    300

tttttgccaa aaagagagat catcggtaca atgctccatg agttaaccca taatcgcttt    360

tcggcccatg atgtaaggtt ttatgacttt cttgagggtc tcaagagcag gttttttgag    420

attcaggtga aaggatcttt acaaactaca gggtatgtta actttagtga agttctatct    480

ggtaatgcgg cgagagggca actgattcaa aaggaaaaag agaaaggaca aagattgggt    540

ggtaataagc atgcaaaacc tatgagagtc ctaatcttgg aggcggccga gaagagaatg    600

atagactcta aatggtgcgg aggagctagc aatgaagtag gccttccaaa aattgaagat    660

ctaatggacg atgaagaagc tcaacactct gaactaaagg aagagaatac aaagaaggtc    720

agaaaaattg ttcaacctag caaaaagaaa attgtagatt tggaaaacct accgaatggc    780

aagtccatta ttattgatct aactaatgac gatgactaa                           819
```

<210> SEQ ID NO 56
<211> LENGTH: 1719
<212> TYPE: DNA
<213> ORGANISM: Pichia pastoris

<400> SEQUENCE: 56

```
atggaacaca attgtctgaa agtcaatgaa ttggcgctcc agttggctca atcactgcag     60

aacagcaaag tcagcacagc tgatcctcta aagaagagga caagcagcta cagaggcctg    120
```

-continued

```
agtagcgagc ctataatcac agaggaagaa ccaacaatca agggcgacta taatagattt    180
tacagtcagt cttcagataa gcaagtattg gacaataaac catggttgca ggatggaaac    240
tatttcaaga ctgtatacat ttcaacgata gcactactga agatgatgtc tcatgcccgg    300
tccggtggtt caattgagat tatgggcatg ctgacaggta aggtgtttgc caacacatta    360
gtcgtaatgg attgctactt acttccggtt gaaggtacag agacacgagt gaatgctcaa    420
gcggaaggat atgagttcat ggtctcttat ttggataact taaaggaaat caagcataac    480
gagaatatca taggatggta tcactctcat cctggttatg ggtgctggtt gagtggaatt    540
gatgttgcca ctcagaattt aaaccaaaag tttcaagatc cctacctggc gatagtgatt    600
gatcctgaaa gatcagtcag acaaggattt gttgagattg gagcattcag aacgtttgct    660
gagccagccg ttggaagatc gtcgtcgtca gtttcctctg caagtggtgc aggaattagt    720
gatgttgcgt tttcttccgg tagaaacagt gcatctggaa tgtcctcagt tctgagtgca    780
agtaatatta gcattgccga agagctaagc aaacaatcga tcacccaaaa tgtttttgac    840
agaactacta caaagattcc caagggcaaa atgactgatt ttggagctca ttcaggaaaa    900
tattactcgc tagaggttaa ggttttcaga tctccactgg aggagaaact actggatacg    960
tttggttcta aaacctggat taaaggttta acgaactact ccaacgttgt taatgccgag   1020
gaaactcaag tggagttaat gcataaaata atggaagcca cggagaactt acggaaggaa   1080
tctccttcta aattgccatc tttggtgatg ggaacctga tttattcagg tgcctctcaa    1140
ggaacaacag ggaaccgcaa gcgctcaatg tccaaatctt ctatttattc gggtttacaa   1200
gcttcatcgg gtatacccag ttctaggtat cctacgaagg gaaaaaatat gagtggatct   1260
caattcaatg atgacccgct agcaagatca ctggataaaa taccgccaga tagtccagat   1320
caacagtacg atggcgcatt atccattcaa caaccgaaaa gagcatataa tacacatact   1380
tctagagcag gtgggttggc cagcgttctg tcctctggga gtatggatcc tcaaagttac   1440
tccatggtag gacgaatgag tctaactaat caatcgccgg ggacagctct gagaggccta   1500
aatacacctc ccaacaaacg accgcagaga aaccctggtc atacaagctc aggtcaagga   1560
ggaacgcctg gaggagtcag tcggtccaaa gagaaaatta acaagccaat aggtataagc   1620
atgattagca aggatttcaa ggttgtcatc tcacaacagg tcaaccagat gctacgtcgt   1680
cacgtccaga atgacctttt tggatccaat agtccctaa                          1719
```

<210> SEQ ID NO 57
<211> LENGTH: 2181
<212> TYPE: DNA
<213> ORGANISM: Pichia pastoris

<400> SEQUENCE: 57

```
atggatcatg cccaacgatt gctagaacta agtttttaca atcaaagtct gggcaaatca     60
gtgatagcaa agaaatacag aatagaatcc tctcgatatt tgaatgaaca actggacaag    120
tccttgacaa gagataatga tctgattgga ttatgccgta tagcattaga caacaagttg    180
accatatcag ataagattat atggatgagc tctcaagttg aagacaactt ctttccgcca    240
gtttttcaag gcttgaagac gtatattgat agcgacgaga tttatcaaga gaaactttta    300
agcgtaccag cggattttga accaatagtt gaatggaaga gttgcacaga gttgcccaat    360
gaatggtcaa acaatggtgt ggacaattta tttcaggatt ctttagatga ctgttcgttt    420
gtagcttcat ttctatcctg caacaatatt ggtatccctc tcatggataa agtcattccc    480
cacaaaaact cgttcaaata tgcggttaga ctgactttca atggttgcga aaggttggtg    540
```

```
tttattgata gccgtttgcc tttgcttagg aatacttcca agactttacg agtgtcaagt    600
ttttctaaca aagatctctt atggcctagc atcatcgaaa aagctttcct gaaaatgtgt    660
gatgatgggt acaagttttc aggatcaaat tcagccattg caaactatgc tttgactggc    720
tggatccctg aagtcattaa aacttcttca tgtacaatag cagatattag ccgattgcat    780
gaggattttc ggaacggaaa cgtagtacta tgcttgggaa cgggcaatct gaccgagcga    840
gaatgcaaac agtatggatt gatccccaat catgactatg ctgtcactaa actatcattt    900
acgaatgatt cagaatacaa gtttgacatt cgtaatccgt ggactaaagg gcagaaagca    960
gtgacaatta cagatctttc aacctttgaa gttatctacg caaacagaaa tcctataatg   1020
ttttcgcaca tgaaccagct aagcggtatc tgtcaaagtc aggttaatga agagttcata   1080
gatctaattc ttaaccattc gcagtatacc ctaggcaatg acggtaattc tacaattgat   1140
gtgattcttt tctttgaaag acattcgtta agaaagaaaa tcagtgcaga gtctcgtatt   1200
gagattttcc aatcagaagg cgaaagacta atctccagaa gaaataaagc aagcaaggaa   1260
tgtgtttcta ataataccaa ctttcatttc ataacaatcg aactgaaacc gttagaaaag   1320
gtaactgtgg taatagatat cggcgagtct tcgattcgaa gccatccatt tactctaaag   1380
gcttttgcca atgattcaac tataactttg aacaaagcac tttctagacc tggttgtttc   1440
aagcaaatgg acctagagct aacgccctta aactctggtg ggaattggga taattatgct   1500
tattacaaaa atccacaact catagtcact cttcacggag attcaacgga tgaagctcca   1560
tttgaatctg ctgttttcag caaaagtgat aagaccctat ttacgtatac agtgttttgg   1620
aaaagtgacg atccagactt tcctttcatc actgacgcaa gcaagaacaa gctcgtaagc   1680
acagacaata agtataaata cagatcatgt acaagatcaa gagttgtttc ttgcgacaaa   1740
agctatttgt tcgtgctgag ctcctacgaa cctgatgcaa ttgagtcttt caaagtattt   1800
tttcaatgtt cccacgattt ttctatagag tgggctgaga cgtcgcttgg gcttttcaca   1860
aaggaagaaa ctttctcctg gaaggaccaa ttagtcaagg agttcattat tcaagtctat   1920
aacccttcaa agttgaaagt tcacgcagta aacaccaaca acaaacgcag atcaaaacta   1980
aattgctctc tctcattcca aaacacatta atcagctctt tgcaagacta cacagacaat   2040
ctctatggat gctttattag cgggaacttg gagattcccg gcaagtatct attacaagtt   2100
cataaaaaca ttatatctaa cgaagaatgt ttggtcgaaa ttggatctag ttcgtcattt   2160
gagttatggg aacatcatta a                                             2181
```

<210> SEQ ID NO 58
<211> LENGTH: 1137
<212> TYPE: DNA
<213> ORGANISM: Pichia pastoris

<400> SEQUENCE: 58

```
atgttgaaaa ctcgatttca ttccagaaag ggttttgtaa tctacagtgg agatgatgaa     60
gagagtgacg aagagagtaa acaatggatg tttcccgagt cgacctttgt aaccaatggg    120
tttgaccaat tgttcaaggt gagaaatgtc aataccatta atgacgacga tgacggctac    180
caatcgttcg atcaaccgga ttgggcgcaa gatttaaccg cagatactca gtatcttgct    240
ttaggtgacg aaggggagaa tcatcgttca caacaagaga taggcaacag gaaaagagcc    300
aacaaaaagc aaaagaagcc aactaaagca aagacaaaac gtcaacaaag acgcacagcc    360
aaaaatgatc aatccacgga acgatctgcc atttcacaac cttctaactt aagtacactg    420
```

```
aactccttac tcaaatctgt tcggtctgaa ctttccaatt ctgatgggag tccccacaca    480

ttctacgatg tatctctcta tgaagaagat ctgaacaacc tagctgatga cgaatggttg    540

aacgataata acgtctcgtt tatctacgag tacattgaaa gattttacat tacccgttgt    600

ttgagcgaca agcttcaatt ttcatcaaag aagatggtca attctcaaat aatactcctc    660

cgaccttcta tggttttttt gctggcacat tcaactccaa aagatatcca ggattttctc    720

ccaccgttgg ataagtctgg ctttatattc cttcctctga acgacaatga tgatctggaa    780

atggctgaag gtggatccca ttggtgtctt ttagttgtag ctgttcacga taacaaatgt    840

ttcctctatg actcattaga gaatgccaat ctcacagagt ctgttgcgct tgtgtctaag    900

ctgtccactc tgctaaacag gcgaatacaa ctcgttgaaa atacacattg tcctcaacaa    960

ctcaatggca gtgattgtgg agtaatcaca acccaaatta cagcactact ggtatcccga   1020

ctgctttgtg ttttgccggg acatcctata aatttggatc ttcaaaatgt agctatcaac   1080

gcaataagcg ggagaatctt catgttaaaa ctcctccaac atgttctgaa caattaa      1137
```

<210> SEQ ID NO 59
<211> LENGTH: 408
<212> TYPE: DNA
<213> ORGANISM: Pichia pastoris

<400> SEQUENCE: 59

```
atggcaccac cagtccctgt atatacgaga gatgaagtca agatgcaatt tccacagtac     60

atgatgaaat ttttgccttc aaactgtgag ctgtactcca tcatccagaa ccaatgtacc    120

ttctctgctg acgagataat atgtgtgccc ttcaagaggg tgtttgccaa atgccggagg    180

ggaaaccaag aagccaagag gaacataata ccagagaatg gaggactgaa tttaactgga    240

aagaaactaa tcccaagaga atacacagtc attgaagtta cggactccct aacgaacaag    300

tacgacaata gtagcctcat ggacagattt tttgaggcag aaagagattt aatgataagg    360

tttcaagaat atgaggaacg gaacagtaag gaaggagaaa taaagtag                 408
```

<210> SEQ ID NO 60
<211> LENGTH: 1449
<212> TYPE: DNA
<213> ORGANISM: Pichia pastoris

<400> SEQUENCE: 60

```
atgctcagac agtttgctgg aagggagttc aagcgtcggt tttctacggg aatcaagacg     60

atgccaacaa agcttaccaa actgccaaat ggtattcgtg tcgtaacgga cgaagctccg    120

ggccatttta gtgccatggg cattttcgtt gatgctggtt caagatatga gagccagttt    180

ccagaattaa ccggccactc tcacatcatc gatagacttg cattcaaatc aacatccaaa    240

ttcgatggga aatctatggt agaaaacacc aatcatttag gtggcaactt tatgtgtgcc    300

tcttcaagag agtcattgat ataccaggct tcagtgttca acaaagatgt ggacaagatg    360

gctgaaatcc tcagttctac agtcaaagaa cctttattta ctgaggagga agtttctaat    420

cagatagcaa cagcagatta tgagttggat gagttatggc tgcaacctga cctaattctt    480

cccgaattgt ctcaacaggt agcttatgga tcaaaaaatt tgggttcccc gctgctctgt    540

ccgaaggagt ctttagcaaa catctcaaga gaatcccttt tgaagtatcg tgaaatattt    600

tttagacctg agaacttggt cgttgctatg ttgggagttc cccacgagaa ggccttggaa    660

cttgttgata aaaatttagg cgatatgaaa tctgtcggtt ccagtccagt ggtcaaagaa    720

cctgctaaat atacaggagg agaactttct ttgcctccag ttcctcctat gggtgggctt    780
```

```
cccgagtttc atcacatata tcttacattt gaaggtgtcc ccgtggactc tgacgatgtc    840

tactcactgg ctactttgca gatgctcgtc ggtggtggtg gatctttctc tgctggtggt    900

ccaggaaaag gaatgtatgc cagagcatac acgcgagttc tgaatcagta cggttttatt    960

gaaagttgca attcatatat acacaatttc tcagactcgg ggctgtttgg tctctcaatt   1020

tcaagcattc cgcaggcaaa taaagttgtt gcagaactct taggtcatga actgagctgc   1080

ttgttttctg aaaatccggg caaaggtgct cttaccaatg ccgaagtaaa ccgtgccaaa   1140

aatcagctac ggtcttcttt gttgatgaac ttggagagca agatggttca attagaagaa   1200

ctaggaagac acattcaagt ttatggcaga aaagttgatg tcacagagat gtgtgataaa   1260

atcagcaaag ttacaaagga agatctagtt gcaattgcaa agaaagtctt gaccggaagc   1320

aacccgacta tagttgttca aggtgacaga gaatcttatg gagacattga gggtactttg   1380

gcatcttttg gagttggttt agatgccgct tccaaagctt caaagaaaaa aacgagaggt   1440

tggttctaa                                                           1449
```

<210> SEQ ID NO 61
<211> LENGTH: 390
<212> TYPE: DNA
<213> ORGANISM: Pichia pastoris

<400> SEQUENCE: 61

```
atggcaatta tcaagttcaa cgcaggcaaa gtcaagattg acgaggaaac caagctttgt     60

acacccttgg caacaagagg agaaataatc gtccaattgt cggctgaggg cgaagagttt    120

tatgatttca aatgggtccc tactgagaac acagctggtg aaggtaacca gtcagagaca    180

ttcttggtca ttccgggcga tgtgacgtgg aaacacgtca aaagttgtaa agatggtaga    240

gttttcaaat tgacattttt gagtagtggg gcaaagagtt tgttctggat gcaagatgat    300

aatggaaacg aggatgaccc atcagagttg acaaccaaag ataaggaaat tagtgaaaaa    360

attaccaagt tgttcgacga agaagagtga                                     390
```

<210> SEQ ID NO 62
<211> LENGTH: 2184
<212> TYPE: DNA
<213> ORGANISM: Pichia pastoris

<400> SEQUENCE: 62

```
atgaaacact tggctgtcca taagtacaag gtaggagcca tcgcagctgg cttggttgtc     60

tcctataaaa tctttgccta ccgcgctgcg tcttcctcct cctcaaacgt catcaacttg    120

accaatatgg caaaaactcc aatcacttta aaaccccctc aggctccact ccgctgggac    180

catactccag agcagatcct tgccgaaact gataagtata tatctaccag tcaagaggtt    240

gacgattggg tggcaaacag ctttgccact gccaatgtgg acaccatcaa gaaaatagcc    300

gccgctgaga atgaacaata cttgccactg tgtcaattga gtttttatca acatatctcg    360

gataaccagg acgttcgtaa tgccagtact gttagtgagg agaaaattga taagttctcc    420

atcgaatcca accttagaga agatgtgttc aaaacagtga acaaagtgtt caaacaggtt    480

caagaagatt cggaactcca aaagaccttg gacccagaat ttaggcgttt actagaaaaa    540

ttgaacctag gttacgtgag atctggttta gatttatccc aggagaagag agaccaagtc    600

aagagtttga aacaagaact atcaaccatt tcaatcaagt ttaataagaa cttgggagag    660

gaaactgaac acatttggtt caccactgag gagttaaaag gtgttccaga atcagttgtt    720
```

gagcagtttg aaactaagaa tgagaatgat gttacttacc acaagatgac atacaagtat 780
cctgacctgt tcccggtact aaaatatgcc gttaatccag ctacgagaca aagagctttt 840
gtcggggatc aaaacaagat acctgaaaat tcaggattac ttgtgaaagc cgtcaatttg 900
agaaacgaac ttgcaaaagt tttgggttat gatacctatg ctgactatat cctggaagtg 960
aagatggcca agaactccaa gaatgttttt gaatttcttg atgatgtaag ggaaaaactc 1020
agacctctcg gagagaagga actgcaaaga atgttgactc tcaaggctaa cgacccaaat 1080
gctgttgata aggaaaatta ctacgtctgg gatcatcgtt actatgataa caagcttctt 1140
gaatctgaat acaaagtgga tgagcaaaag ctggctgaat actttccaat ggagtccacc 1200
attgaaaaaa tgcttgccat ttacgagcac ttgttcaatt tgcagtttca acaagttgac 1260
gattcggaga aacaagtttg gcatccagat gtaaaacaat tctccgtttg gaaaatcgat 1320
aaccctgatt ctcctgaatt tgtgggctgg atctattttg atttgcatcc aagagaagga 1380
aaatacggtc acgctgctaa ttttggaatc ggtcctagtt acatcaaaga agatgggagt 1440
aaaaattatc ctgtcactgc tttggtttgc aacttttcta aaccatcaaa ggataagcca 1500
tccctattga agcacaatga agtcactaca ttcttccatg agctaggaca tggtatccat 1560
gatttaattg ggcaaactag gtatgctcgt ttccatggta cttcagttgc tcgtgatttc 1620
gttgaatgtc cttcacagat tctagagtac tggacctgga ctagagatca actcaagtct 1680
ctttcccaac attacaagac aggagaagcc ctctccgatg aactcattga ttcgctagtc 1740
aagtccaagc atgtcaatgg cgccattttc aatcttaggc agttacactt tggtctcttt 1800
gacatgaaac tacatactgc caaagagcct gaatctttag atgtgacaag gttgtggaac 1860
gaattacgtg aggaagtcgc tctggttaag aatggtgacc aaattacgaa aggatacggt 1920
tcatttggac acctaatggg cggttatgct gctggttact acggatacct gtattctcaa 1980
gtgtttgcca gtgacattta ttacaccttt ttcaaagctg atccaatgag tacagctcaa 2040
ggtatcaagt accgtgatat cattcttgcc agaggtggat caagagagga gctagataat 2100
ctcaaggaat tacttggaag agagcctaca tctgatgcct ttatgactga gcttggagta 2160
gaaaatggtg cgtccaagtt gtaa 2184

<210> SEQ ID NO 63
<211> LENGTH: 2766
<212> TYPE: DNA
<213> ORGANISM: Pichia pastoris

<400> SEQUENCE: 63
atgcgttttt tggtctcatc ctttcggccc ttcagacata caatttcgtc gcatatctca 60
atgggccagg ctctgtctgc cattcgtgta tttcataaaa attctcactc acgtacccaa 120
ggtttaaggc gccactctca ctactgttgc caccgcaaga tagatatgag tacttctact 180
aaacttccag agcgtcaatt gctaccagcc aatgttaggc ctaccaaata tgatttgaca 240
ttggagccct tatttttctac cttcaagttt aacggagaag agactataca tttagatgtt 300
caggaggact ccagttctat tacgctacac gctctagaca tcgatctcca agattcacta 360
ttgataactt caaacaagtc taagactccc ccgcttcatg tgacaagcaa tgatgatgac 420
caatcgctca cttttcaatt caaagagggt actctagtaa agggagataa ggtgcagctg 480
cagttgaaat ttgttggtga attgaatgat aagatggccg gtttttaccg ctcttcatat 540
gaagagaatg gagaaactaa atatttggca actacccaga tggagccaac agattgtcgt 600
cgtgctttcc cttcctttga tgagccatcg ctaaaagccg tattcaacat tgccctcatt 660

```
gctgatcaga aacttacttg tctctcaaac atggacgtga aagaggaaca atctctcgga    720
gatagaagga agaaggtgat attcaatccc actccactaa tttctactta cctaattgct    780
tttattgttg gtgatttaaa atatattgaa gccgactata actatcgcat tcctgtcaga    840
gtttatgcca cccctggttt agagaagcag ggtcgttttt ctgtcgagct tgctgctaaa    900
acattagaat tctttgagca acagtttgat attgattatc ctcttccaaa gatggacatg    960
gtggcgattc atgatttcag tgcaggagct atggaaaact ttgggcttgt tacctataga   1020
gttgttgatt tgctgtacga tgaaaaaaat tcaaatttgg ctactaagca acgtgttgca   1080
gaagttgtcc aacacgaatt ggcgcatcag tggtttggta atcttgtcac aatggagtgg   1140
tgggagggcc tttggctgaa tgaaggcttt gctacatgga tgtcttggta ctcttgtgac   1200
aagtttttcc ctgattggaa agtatgggaa caatatgtta cagattcttt acaacaggct   1260
ctggctctgg acgctctacg tgcttctcac cctattgaag ttcctgtgaa aagggccgac   1320
gagatcaatc aaatttttga cgcaatttcc tattctaaag gatcctcctt gctaaaaatg   1380
atctccaaat ggctcggaga ggatgtgttc attaagggag tctccagtta tttaaaaaag   1440
cacaggtatg gtaatacgaa aaccaccgat ttgtgggaat cgctttctga ggtgtctgga   1500
aaagatgtgg tcaaagttat gagtatctgg actggtaaaa ttggatttcc aatcatctca   1560
gtaactgaaa atgcaaaccg tatcactttt actcagaaca gatatttaac tactggtgat   1620
gtaactcctg aagaggatac gacgatttat cctgtttttt tgggactcaa aacagaaagc   1680
tcaactgatg agtcgctggt ccttgactca aggtcaatgt cagtagatat ccagaattct   1740
gactttttca aagttaatgc tgaacaagcc ggtatttaca ggaccaatta tgcaccagag   1800
agatggatca aacttggaaa gcaacctcac cttctaagtg tagaagaccg tgctggtttg   1860
gttgcggatg cgggcgctct ggctagttct ggtcactcat ctacaaggaa ctttttgaac   1920
cttgtaaatt catggaaaga tgagtctagc tttgttgtct gggacgaaat aacttcccgt   1980
gttgcagctt taaaagcagc ttggttattt gaatcccaat ctgacattga cgccctgaat   2040
gctttcgtaa gagaccttat ttctacgaag atcaaaagta tcggatggtc attcaatgat   2100
aatgaaccat tccttgaaca aagactaaag agccttctat atgctactgc tgctggtgca   2160
aaagtaccag gagtagttaa atcagcattg ataaactttc aaaaatacgt tgctggtgat   2220
aagactgcca ttcaccctaa cataaaggca gttacgtttc aaactgttgc ggcccaagga   2280
tctgaaaagg aatgggatca gttactcgac atctacaaga accctgtatc tattgatgag   2340
aaaattattg ctcttaggtc tctcggaagg tttgaagatc ccatcttgat cgcaaagacc   2400
ctggcactgt tatttgatgg ttccgtaagg tcacaagata tttacgtacc aatgcaaggc   2460
cttcgtgcga ctaagatagg agtagagtca cttttcaagt ggttgactct taattgggac   2520
aagatttata aattgcttcc acctggtctg tcaatgcttg gttctgtggt tactatcagt   2580
acttctgggt tcacttcctt ggatgatcaa aagcgtgtca aagatttctt tgcatcaaag   2640
gataccaaag gcttcgacca gggtttggcc caggcgttag acaccatcca atccaaggca   2700
agttgggtac aacgtgactc taggaatgta tccgattggc tacgtgagca gggatacaaa   2760
aaatag                                                              2766
```

<210> SEQ ID NO 64
<211> LENGTH: 1803
<212> TYPE: DNA
<213> ORGANISM: Pichia pastoris

<400> SEQUENCE: 64
atgataagga tatccttgct gaaaagagca ctgtttccct acgggcgact accaatgcat 60
aatggtaggt ggtattcaga cataggtggc ggaaattcaa ggaatcggaa cgaacagaaa 120
ccaaaattgc ctgtaccaac tagtaatgaa gttaaggaca atgagtcaaa cccggacttc 180
tttattaaaa acggctttag atcagctgat attgcagaga catcctttgt gaaagacaag 240
ggtgctacag tcgaagagga acgtaataca tcggacagtt cacacgaatc tcctcaactt 300
aattttaagg aaaccaacga cgaaacgaat tcaacgatcc aaccaccagt ggcaaaatta 360
cccaccccaa agcaattgaa acaatacctg gataggttca tcgtgggaca agagaagtgc 420
aagaagataa tgtcggtcgc agtttacact cattatgttc gaataaataa ccaggctcag 480
aaacggaatc agaaggtcga ttcctctgaa gaaaatgttg agaatgggtt tccaaatgtt 540
actaaagaat ttgaggacga aaatgaccca gattatgttc cggatttgga gaaatcaaat 600
gttcttttgc tgggaccgtc tggatcaggc aagaccctga ttgctaagac tctcgctaaa 660
tgtctgcagg ttccatttat aattcaagat tgtacctcct tgacccaggc tggttatgtt 720
ggcgaggata ttgagagctg tattgaaaag ttgctaattg attcagacta cgatattgaa 780
aggtgtgaaa agggaattat tgtgctggat gaaatagaca agttggccaa gccctctgtc 840
tatacaggaa ccaaagatat tgcaggagag ggtgttcaac aaggcctttt aaaactggtt 900
gaaggtacta cagttacggt tcaatgcaag aggagcaatg ctcctgatca taatcagttc 960
ggattgaatg gcaaagctac aaatcaggac aaggaaaatt atatcgttga cactacaaat 1020
atcttatttt taaccctggg agcgtttgtg aacctagata agattgttgc ttataggctg 1080
aagcagaact ctattggatt cgatactgat gagtcgaaag atatttctga aacagactca 1140
gtttccgaca aatctacatt agaatatgtt acacttccag atggatcaaa agtttcagct 1200
ctggaacttg tgtcttctac ggatctacag aattatgggt tgattccaga actgatcggc 1260
aggcttccga ttgtatcttc actttctcct ttaacagttg atgatcttgt ggctgtcctg 1320
actgagccca ggaactcgat actaaagcaa tatgtgcatt tctttgacac tgtcaatgtc 1380
aaacttgcta tcacttccaa ggcaatcaga aggatagccg agatctcgat caagaatggt 1440
acaggtgcaa gaggtctcag agccattttg gagaaactgc tactcaatgc caagtatgat 1500
tgccctggta gtagtatttc atttgtgtta gttgatacag atgttataag taagtctatc 1560
gatgagaata aggaaacggg ggaattcgtc ttcaaagatg gtgagccaaa gtattactcg 1620
cgtggagaat tattttcctt tttcaatgag ttatcaaaag aagacgaaaa actcaagaca 1680
tcaattgaaa agatgtgcca aataccactt tccaagaatc gcatagttta ctccgaagag 1740
gagcaggcaa ggttggattc ttctaaacct ctcgccgtga agcactatga acctttcatt 1800
tga 1803

<210> SEQ ID NO 65
<211> LENGTH: 2322
<212> TYPE: DNA
<213> ORGANISM: Pichia pastoris

<400> SEQUENCE: 65
atgagcttca acctgctaag tgttccttta cgaacgtcaa agccgatacc gttaggcgaa 60
agcctaaaag agcttatcaa caatcagtac taccagacat ctgctgcgtt caaatcggat 120
atcgaagaga tcgaccaact aagaaatgat gtcctatcaa tagaaccaaa caatgatgga 180
cttgcattgc tcaagagata ctatgtacag ttagccagca ttagccaaaa actccctgat 240

```
tattttatgg agtatccctg gtttggaaca ttaggatacc aagtaactgg ccccgtagct    300
ctaaaatccc tctatttcga aagaatcaat atagcgtaca acatcgcagc gacgtattca    360
atcataggtt taaacgagcc cagagctaca ggagaaggct tgaaaaaatc atgcatttat    420
tttcagtata gtagtggggc attcgaaagt gtactgaagc tagtggagca aaaaccgaaa    480
gagctgacac ttcccattga tcttagtgtt aacattatga aaaccctggc taaactcatg    540
ctggctcagg cccaggaatg tttttggcaa aaggctgttt ctaacacttt aaaagataac    600
gttattgcaa ggttggcctt tcaagtatct caattttacg atgaagctct gtctatggct    660
tacaagtgcg atattttaaa gtctgaatgg atagaacata tgagttgcaa gaagctgcat    720
tttaaggctg cggcccaatt tagacttgct tgtgtggcag tcgctgcttc tagacatgga    780
gaggaaatag caagattaag gattgcaaat accatttgcg aaacagcatc tagagaagcc    840
aagtatcacc ttccctctgt atcttccgat ttggagagtc tttcgaagat aatcaaagac    900
tctttaagaa gaagtgaacg tgataatgat ctaatatatc tgcaggaagt tcctaatgaa    960
tcagatcttc ctccaattgt tgcagcatct atggttgaac ctaagccaat agttgagtta   1020
aattcagctg aatgtgcgaa agatacaaag aaatacggca aatccttttt ccatgatctt   1080
atgccatact tagtgattga aattgcacag gcatttagag agaggcagga ttcttatgtt   1140
gtaaagcata tcaaggagcc catggagatg ctgacaaaga ttcttcacac aatccttgct   1200
gaaaatggac ttccggcgtt gatagatacc atacaaaggc ctcaaagatt gccaaccaac   1260
atccttgaac attgtcaaat actcaatgaa aggggtggca tggacaaact taaggtattt   1320
ttcgaagata tcagcaagct aagacacaaa agtgagcaag ttctccaaaa ctgtgtcgaa   1380
ttgctacaaa tggaagagtc cgaaaatgag gaaatgagaa ggaagcatgg atcacagagg   1440
tggaattttg ctgactctag ggaggcatca gcagatgtca ggaaaagtgt acaggcacta   1500
gagggctatt tgaaacaggc ccatgatggt gatcaagtga tctggaatga cttcgaacaa   1560
ttgaagccac tactaagcat gatgagtgct cctaattcaa ctaaattact ggaagaattt   1620
gtaccaaatt caaaattcgt cagacttcct ccagaattga accgaatcgt taacgaatta   1680
agagctgatg ttaatcaggt caaaaagctc gcatcgcaaa gggaaacttt tattaataca   1740
gttaaagtaa aaagcaccga cctgtccata ttgcccttgg tagtttccca ttataagaaa   1800
ttacaacaaa acaacattaa tacgatcacg acggaattgt tcgaagaagt gttcagacga   1860
caggttagca acttcgattc tgatatcaga tttgttcaaa aacacaggga caaccaaatc   1920
gagttagaga agcatattaa atctttggtc caacaattca atcagcttag agggaatata   1980
gatgcctcgc aagaacgcca aaatgcactt cagttgttgg acgatgccta taacggatac   2040
cttgatttgg taaacaacct cacacaggga cttagttttt acaatgattt cactggaaag   2100
gcaaatgatg tctatttgag atgtcaagaa ttctacaact ttcgtaaaca agaagccatg   2160
aagctggagc aggaaatata tgctgtattt gaacaaggta aatctcctca gaaaaaacaa   2220
ctagaagatc aggtttcaga tcaaccaaaa agtgaagtca agtcttcaaa gggttattct   2280
aatgagctgt ggaaccccga cgttggaatt aaatttggct ag                      2322
```

<210> SEQ ID NO 66
<211> LENGTH: 960
<212> TYPE: DNA
<213> ORGANISM: Pichia pastoris

<400> SEQUENCE: 66

-continued

```
atggtggcct ctcttcacat tgtcaatccg aatttggcct ccgctttcag tttgcctccc     60

aggtcaaaca ctttgagcgt ttccatacac gcttcggctt tgttacagat cctggaatca    120

agttacttcg accagaataa gaatggtcgt atcataggaa ccctcctagg ttctaggtct    180

gaagagacaa cggaggttca agtcaaagac tctttcatag tttcccacac ggaggacgga    240

gacgagttta ccattgattc ttctcaacgt gaatttgtcg ccatccacaa gaagtctagc    300

ccaagagact cagtcgtagg atggttttcc attaactcta aggtcgacag ctttatcgga    360

ctggtccatg actttttctc aaagggtcca gatagcacac acccgtaccc tgccatatat    420

ttgagtatcc agttatgtga cgagagcgga tccttcgtag agccagtttt caaggcgtac    480

gttgcctccc cagtgggatg ttatggagct ctggcaagtc acttagacct tgaaaaagct    540

ggctcttttg tcttctctga agtcccaacc aaggtcatat actctgctaa cgaaaaaagt    600

ctgctggctc atttcaagaa caacgttgtg gaacccaaag ttccaatacc acaaaacgac    660

acaaatcaac taatttcaca actcaacaaa ctcgacgttt ccattgacca gttaatagac    720

tacgttgaca aagtcatttc aggatctctg gatagaaatg atgtgaagaa tgatgagatt    780

ggccgtttcc tgttgaccaa cttagtttcc cttccaactt ctccttcaaa ggaagagctt    840

tcatcttcca taagctctca tatccaggac tcactgatga tcgactactt ggcctccgcc    900

gtgaaaactc aattagatgt tagctccaaa ttaatgaacc tggtacaaga tgataaatag    960
```

<210> SEQ ID NO 67
<211> LENGTH: 599
<212> TYPE: PRT
<213> ORGANISM: Pichia pastoris

<400> SEQUENCE: 67

```
Met Leu Lys Asp Gln Phe Leu Leu Trp Val Ala Leu Ile Ala Ser Val
1               5                   10                  15

Pro Val Ser Gly Val Met Ala Ala Pro Ser Glu Ser Gly His Asn Thr
            20                  25                  30

Val Glu Lys Arg Asp Ala Lys Asn Val Val Gly Val Gln Gln Leu Asp
        35                  40                  45

Phe Ser Val Leu Arg Gly Asp Ser Phe Glu Ser Ala Ser Ser Glu Asn
    50                  55                  60

Val Pro Arg Leu Val Arg Arg Asp Asp Thr Leu Glu Ala Glu Leu Ile
65                  70                  75                  80

Asn Gln Gln Ser Phe Tyr Leu Ser Arg Leu Lys Val Gly Ser His Gln
                85                  90                  95

Ala Asp Ile Gly Ile Leu Val Asp Thr Gly Ser Ser Asp Leu Trp Val
            100                 105                 110

Met Asp Ser Val Asn Pro Tyr Cys Ser Ser Arg Ser Arg Val Lys Arg
        115                 120                 125

Asp Ile His Asp Glu Lys Ile Ala Glu Trp Asp Pro Ile Asn Leu Lys
    130                 135                 140

Lys Asn Glu Thr Ser Gln Asn Lys Asn Phe Trp Asp Trp Leu Val Gly
145                 150                 155                 160

Thr Ser Thr Ser Ser Pro Ser Thr Ala Thr Ala Thr Gly Ser Gly Ser
                165                 170                 175

Gly Ser Gly Ser Gly Ser Gly Ser Gly Ser Ala Ala Thr Ala Val Ser
            180                 185                 190

Val Ser Ser Ala Gln Ala Thr Leu Asp Cys Ser Thr Tyr Gly Thr Phe
        195                 200                 205
```

-continued

```
Asp His Ala Asp Ser Ser Thr Phe His Asp Asn Asn Thr Asp Phe Phe
    210                 215                 220

Ile Ser Tyr Ala Asp Thr Thr Phe Ala Ser Gly Ile Trp Gly Tyr Asp
225                 230                 235                 240

Asp Val Ile Ile Asp Gly Ile Glu Val Lys Glu Leu Ser Phe Ala Val
                245                 250                 255

Ala Asp Met Thr Asn Ser Ser Ile Gly Val Leu Gly Ile Gly Leu Lys
            260                 265                 270

Gly Leu Glu Ser Thr Tyr Ala Ser Ala Ser Ser Val Ser Glu Met Tyr
        275                 280                 285

Gln Tyr Asp Asn Leu Pro Ala Lys Met Val Thr Asp Gly Leu Ile Asn
    290                 295                 300

Lys Asn Ala Tyr Ser Leu Tyr Leu Asn Ser Lys Asp Ala Ser Ser Gly
305                 310                 315                 320

Ser Ile Leu Phe Gly Gly Val Asp His Glu Lys Tyr Ser Gly Gln Leu
                325                 330                 335

Leu Thr Val Pro Val Ile Asn Thr Leu Ala Ser Ser Gly Tyr Arg Glu
            340                 345                 350

Ala Ile Arg Leu Gln Ile Thr Leu Asn Gly Ile Asp Val Lys Lys Gly
        355                 360                 365

Ser Asp Gln Gly Thr Leu Leu Gln Gly Arg Phe Ala Ala Leu Leu Asp
    370                 375                 380

Ser Gly Ala Thr Leu Thr Tyr Ala Pro Ser Ser Val Leu Asn Ser Ile
385                 390                 395                 400

Gly Arg Asn Leu Gly Gly Ser Tyr Asp Ser Ser Arg Gln Ala Tyr Thr
                405                 410                 415

Ile Arg Cys Val Ser Ala Ser Asp Thr Thr Ser Leu Val Phe Asn Phe
            420                 425                 430

Gly Gly Ala Thr Val Glu Val Ser Leu Tyr Asp Leu Gln Ile Ala Thr
        435                 440                 445

Tyr Tyr Thr Gly Gly Ser Ala Thr Gln Cys Leu Ile Gly Ile Phe Ser
    450                 455                 460

Ser Gly Ser Asp Glu Phe Val Leu Gly Asp Thr Phe Leu Arg Ser Ala
465                 470                 475                 480

Tyr Val Val Tyr Asp Leu Asp Gly Leu Glu Val Ser Leu Ala Gln Ala
                485                 490                 495

Asn Phe Asn Glu Thr Asp Ser Asp Val Glu Ala Ile Thr Ser Ser Val
            500                 505                 510

Pro Ser Ala Thr Arg Ala Ser Gly Tyr Ser Ser Thr Trp Ser Gly Ser
        515                 520                 525

Ala Ser Gly Thr Val Tyr Thr Ser Val Gln Met Glu Ser Gly Ala Ala
    530                 535                 540

Ser Ser Ser Asn Ser Ser Gly Ser Asn Met Gly Ser Ser Ser Ser Ser
545                 550                 555                 560

Ser Ser Ser Ser Ser Ser Thr Ser Ser Gly Asp Glu Glu Gly Gly Ser
                565                 570                 575

Ser Ala Asn Arg Val Pro Phe Ser Tyr Leu Ser Leu Cys Leu Val Val
            580                 585                 590

Ile Leu Gly Val Cys Ile Val
        595
```

<210> SEQ ID NO 68
<211> LENGTH: 562
<212> TYPE: PRT

```
<213> ORGANISM: Pichia pastoris

<400> SEQUENCE: 68

Met Ile Ile Asn His Leu Val Leu Thr Ala Leu Ser Ile Ala Leu Ala
1               5                   10                  15

Asn Asp Tyr Glu Ser Leu Asp Leu Arg His Ile Gly Val Leu Tyr Thr
            20                  25                  30

Ala Glu Ile Gln Ile Gly Ser Asp Glu Thr Glu Ile Glu Val Ile Val
        35                  40                  45

Asp Thr Gly Ser Ala Asp Leu Trp Val Ile Asp Ser Asp Ala Ala Val
    50                  55                  60

Cys Glu Leu Ser Tyr Asp Glu Ile Glu Ala Asn Ser Phe Ser Ser Ala
65                  70                  75                  80

Ser Ala Lys Phe Met Asp Lys Ile Ala Pro Pro Ser Gln Glu Leu Leu
                85                  90                  95

Asp Gly Leu Ser Glu Phe Gly Phe Ala Leu Asp Gly Glu Ile Ser Gln
            100                 105                 110

Tyr Leu Ala Asp Lys Ser Gly Arg Val Ser Lys Arg Glu Glu Asn Gln
        115                 120                 125

Gln Asp Phe Asn Ile Asn Arg Asp Glu Pro Val Cys Glu Gln Phe Gly
    130                 135                 140

Ser Phe Asp Ser Ser Ser Ser Asp Thr Phe Gln Ser Asn Asn Ser Ala
145                 150                 155                 160

Phe Gly Ile Ala Tyr Leu Asp Gly Thr Thr Ala Asn Gly Thr Trp Val
                165                 170                 175

Arg Asp Thr Val Arg Ile Gly Asp Phe Ala Ile Ser Gln Gln Ser Phe
            180                 185                 190

Ala Leu Val Asn Ile Thr Asp Asn Tyr Met Gly Ile Leu Gly Leu Gly
        195                 200                 205

Pro Ala Thr Gln Gln Thr Thr Asn Ser Asn Pro Ile Ala Ala Asn Arg
    210                 215                 220

Phe Thr Tyr Asp Gly Val Val Asp Ser Leu Arg Ser Gln Gly Phe Ile
225                 230                 235                 240

Asn Ser Ala Ser Phe Ser Val Tyr Leu Ser Pro Asp Glu Asp Asn Glu
                245                 250                 255

His Asp Glu Phe Ser Asp Gly Glu Ile Leu Phe Gly Ala Ile Asp Arg
            260                 265                 270

Ala Lys Ile Asp Gly Pro Phe Arg Leu Phe Pro Tyr Val Asn Pro Tyr
        275                 280                 285

Lys Pro Val Tyr Pro Asp Gln Tyr Thr Ser Tyr Val Thr Val Ser Thr
    290                 295                 300

Ile Ala Val Ser Ser Ser Asp Glu Thr Leu Ile Ile Glu Arg Arg Pro
305                 310                 315                 320

Arg Leu Ala Leu Ile Asp Thr Gly Ala Thr Phe Ser Tyr Leu Pro Thr
                325                 330                 335

Tyr Pro Leu Ile Arg Leu Ala Phe Ser Ile His Gly Gly Phe Glu Tyr
            340                 345                 350

Val Ser Gln Leu Gly Leu Phe Val Ile Arg Thr Ser Ser Leu Ser Val
        355                 360                 365

Ala Arg Asn Lys Val Ile Glu Phe Lys Phe Gly Glu Asp Val Val Ile
    370                 375                 380

Gln Ser Pro Val Ser Asp His Leu Leu Asp Val Ser Gly Leu Phe Thr
385                 390                 395                 400
```

```
Asp Gly Gln Gln Tyr Ser Ala Leu Thr Val Arg Glu Ser Leu Asp Gly
                405                 410                 415

Leu Ser Ile Leu Gly Asp Thr Phe Ile Lys Ser Ala Tyr Leu Phe Phe
            420                 425                 430

Asp Asn Glu Asn Ser Gln Leu Gly Ile Gly Gln Ile Asn Val Thr Asp
        435                 440                 445

Asp Glu Asp Ile Glu Val Val Gly Asp Phe Thr Ile Glu Arg Asp Pro
    450                 455                 460

Ala Tyr Ser Ser Thr Trp Ser Ser Asp Leu Pro His Glu Thr Pro Thr
465                 470                 475                 480

Arg Ala Leu Ser Thr Ala Ser Gly Gly Gly Leu Gly Thr Gly Ile Asn
                485                 490                 495

Thr Ala Thr Ser Arg Ala Ser Ser Arg Ser Thr Ser Gly Ser Thr Ser
            500                 505                 510

Arg Thr Ser Ser Thr Ser Gly Ser Ala Ser Gly Thr Ser Ser Gly Ala
        515                 520                 525

Ser Ser Ala Thr Gln Asn Asp Glu Thr Ser Thr Asp Leu Gly Ala Pro
    530                 535                 540

Ala Ala Ser Leu Ser Ala Thr Pro Cys Leu Phe Ala Ile Leu Leu Leu
545                 550                 555                 560

Met Leu


<210> SEQ ID NO 69
<211> LENGTH: 207
<212> TYPE: PRT
<213> ORGANISM: Pichia pastoris

<400> SEQUENCE: 69

Met Val Ala Ser His Val Asn Asn Ala Ser Ala Ser Arg Ser Asn Thr
1               5                   10                  15

Ser Val Ser His Ala Ser Ala Ser Ser Tyr Asp Asn Lys Asn Gly Arg
            20                  25                  30

Gly Thr Gly Ser Arg Ser Thr Thr Val Val Lys Asp Ser Val Ser His
        35                  40                  45

Thr Asp Gly Asp Thr Asp Ser Ser Arg Val Ala His Lys Lys Ser Ser
    50                  55                  60

Arg Asp Ser Val Val Gly Trp Ser Asn Ser Lys Val Asp Ser Gly Val
65                  70                  75                  80

His Asp Ser Lys Gly Asp Ser Thr His Tyr Ala Tyr Ser Cys Asp Ser
                85                  90                  95

Gly Ser Val Val Lys Ala Tyr Val Ala Ser Val Gly Cys Tyr Gly Ala
            100                 105                 110

Ala Ser His Asp Lys Ala Gly Ser Val Ser Val Thr Lys Val Tyr Ser
        115                 120                 125

Ala Asn Lys Ser Ala His Lys Asn Asn Val Val Lys Val Asn Asp Thr
    130                 135                 140

Asn Ser Asn Lys Asp Val Ser Asp Asp Tyr Val Asp Lys Val Ser Gly
145                 150                 155                 160

Ser Asp Arg Asn Asp Val Lys Asn Asp Gly Arg Thr Asn Val Ser Thr
                165                 170                 175

Ser Ser Lys Ser Ser Ser Ser Ser His Asp Ser Met Asp Tyr Ala Ser
            180                 185                 190

Ala Val Lys Thr Asp Val Ser Ser Lys Met Asn Val Asp Asp Lys
        195                 200                 205
```

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
acctattgtt taccttcctg 20

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
gaattctctc acttaatctt tagctcccat gctcatcttg 40

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
gcggccgcaa gaagttgatt gtttatttgt aggcggtgcc 40

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
gggctatccg ccttatcttg 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
aataacttca tgactgcatt 20

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gaattctctc acttaatctt agtttaaata atatggagat 40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
gcggccgcaa gaagttgatt attggagaaa aggaatacac 40

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
ggcatctccg tctggtgcag 20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
caaggttcga aactgcagct 20

<210> SEQ ID NO 79
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
ctcacttaat cttctgtact ctgaagagag agcaaaccaa tggcaa 46

<210> SEQ ID NO 80
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
agaagttgat tgagactttc aacgagggtc ctttggcaat cattggt 47

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
accccaggac caggtatttc 20

<210> SEQ ID NO 82

<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
tactacaggc tggctgttcc 20

<210> SEQ ID NO 83
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
ctcacttaat cttctgtact ctgaagaagt ccaactgttg aacgcc 46

<210> SEQ ID NO 84
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
agaagttgat tgagactttc aacgagggtc cccttcagct accttt 46

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
tccctgctaa gccctaatcg 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86
aagttgtatg gccgtcctca 20

<210> SEQ ID NO 87
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 87
ctcacttaat cttctgtact ctgaagtgag tcttggttgt gtcggt 46

<210> SEQ ID NO 88
<211> LENGTH: 46

<212> TYPE: DNA
<213> ORGANISM: Artificial Sequence
<220> FEATURE:
<223> OTHER INFORMATION: Description of Artificial Sequence: Synthetic
primer

<400> SEQUENCE: 88
agaagttgat tgagactttc aacgaggcct cctgtttgat cggttc 46

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 89
gtgccatggt gacgttacag 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 90
cggagttata ggggacgctt 20

<210> SEQ ID NO 91
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 91
ctcacttaat cttctgtact ctgaagcgtc acatcatagc cgttctc 47

<210> SEQ ID NO 92
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
agaagttgat tgagactttc aacgagcgtc aaaagtggtc gtggac 46

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
tggcccagtt acacggaata 20

<210> SEQ ID NO 94
<211> LENGTH: 20
<212> TYPE: DNA

<213> ORGANISM: Artificial Sequence
<220> FEATURE:
<223> OTHER INFORMATION: Description of Artificial Sequence: Synthetic
primer

<400> SEQUENCE: 94
gtcgatcgtt ggtgtgtgac 20

<210> SEQ ID NO 95
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
ctcacttaat cttctgtact ctgaaggagc cgactttgac atcgac 46

<210> SEQ ID NO 96
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 96
agaagttgat tgagactttc aacgagagcg aagagactgg ttccaa 46

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 97
agctgttcta accgtcctca 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 98
cttggaatat ctgtgggcgc 20

<210> SEQ ID NO 99
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 99
ctcacttaat cttctgtact ctgaagtcat gaccagcagt tgttca 46

<210> SEQ ID NO 100
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 100
agaagttgat tgagactttc aacgagatgc tgcaggaagg aacact 46

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 101
caaactctgc acctccaagc 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
ctctgattgc acgagaaggc 20

<210> SEQ ID NO 103
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
ctcacttaat cttctgtact ctgaagtgaa aggcgattgg agttgc 46

<210> SEQ ID NO 104
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
agaagttgat tgagactttc aacgagctgg ctctgcttct ggtact 46

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 105
gatgttgagg cgggcataag 20

<210> SEQ ID NO 106
<211> LENGTH: 20
<212> TYPE: DNA
<213> ORGANISM: Artificial Sequence
<220> FEATURE:

<223> OTHER INFORMATION: Description of Artificial Sequence: Synthetic
primer

<400> SEQUENCE: 106
tttcaacggg gttctacgga 20

<210> SEQ ID NO 107
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 107
ctcacttaat cttctgtact ctgaaggtgg tagtatgtgt gttggtgt 48

<210> SEQ ID NO 108
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 108
agaagttgat tgagactttc aacgagctgc gctttcaagt actgca 46

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 109
tgtcttcctc gtcttcctcg 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 110
cgggcaataa tcagtggagc 20

<210> SEQ ID NO 111
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 111
ctcacttaat cttctgtact ctgaagcgtt ggaggtaatg catggg 46

<210> SEQ ID NO 112
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
agaagttgat tgagactttc aacgagggcg gaccgtgtat tagaga 46

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
tcagagaagc cagtggaagg 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
ttcctcggcc tctttatgct 20

<210> SEQ ID NO 115
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
ctcacttaat cttctgtact ctgaagcaac gtggctaact ccttgg 46

<210> SEQ ID NO 116
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
agaagttgat tgagactttc aacgaggttg tcgacggcat tgaaga 46

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
tcggttcaaa gcccctaagt 20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
aggtgtgaaa tgcgctgatc 20

<210> SEQ ID NO 119
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
ctcacttaat cttctgtact ctgaagaaac caacaacgcc tggtac 46

<210> SEQ ID NO 120
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
agaagttgat tgagactttc aacgagtcac aggctgaagg atcgaa 46

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
ccatggtgtg ttttccggtt 20

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
tgagggacaa agtaatgggg t 21

<210> SEQ ID NO 123
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
ctcacttaat cttctgtact ctgaagaccg aagtcatggt tggaaa 46

<210> SEQ ID NO 124
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
agaagttgat tgagactttc aacgagctac cgcagacaac ccattc 46

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 125
cgctccctca tcgagtactt 20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 126
cagacatcgt ggaaactgcc 20

<210> SEQ ID NO 127
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 127
ctcacttaat cttctgtact ctgaagtatc tgcttcgatc cctgca 46

<210> SEQ ID NO 128
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 128
agaagttgat tgagactttc aacgagttct cccgtccagt tagcag 46

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 129
atttcagaag ctccgcatcc 20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 130
acaaaagcac gcgattgaga 20

<210> SEQ ID NO 131
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
ctcacttaat cttctgtact ctgaagacac tcacggttgt ttgcaa 46

<210> SEQ ID NO 132
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
agaagttgat tgagactttc aacgagaacc ccaacaagcg gctata 46

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
acccggatct gctagtgaag 20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
cgtatgctcg tgtgactgtg 20

<210> SEQ ID NO 135
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
ctcacttaat cttctgtact ctgaagttcc tatgcctggc gatgat 46

<210> SEQ ID NO 136
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
agaagttgat tgagactttc aacgagaggg agtcttgtat agttgagca 49

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
agcaggggta ttttcacgga 20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
agcatgattg tgttgggtgg 20

<210> SEQ ID NO 139
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
ctcacttaat cttctgtact ctgaagaatc cgatactgta gccccg 46

<210> SEQ ID NO 140
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
agaagttgat tgagactttc aacgaggcaa agaaaactgg ccacac 46

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
ggaaggccct attcacgact 20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
caccatttcc ctgctgtgtc 20

<210> SEQ ID NO 143
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
ctcacttaat cttctgtact ctgaagtcaa taccgaagac tccgca 46

<210> SEQ ID NO 144
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
agaagttgat tgagactttc aacgagggga ggtattcagg aggcat 46

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
gctcgatcag atattgtccg c 21

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
agcagctctc caatcagtgt 20

<210> SEQ ID NO 147
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
ctcacttaat cttctgtact ctgaagctgg aattgtgatc ccgctg 46

<210> SEQ ID NO 148
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
agaagttgat tgagactttc aacgagtttt gaagcaagcc tacccc 46

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
caggatccag ccgctaaaac 20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
tgaacaagca gccacatcac 20

<210> SEQ ID NO 151
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
ctcacttaat cttctgtact ctgaagtgag ggccattctg acatact 47

<210> SEQ ID NO 152
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
agaagttgat tgagactttc aacgaggtga ggtatttaac tgcacgag 48

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
tcgcctacat agtctgcaca 20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
acctcatgcc atgtctgtca 20

<210> SEQ ID NO 155
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
ctcacttaat cttctgtact ctgaagttga ctgccgcttc aaagtc 46

<210> SEQ ID NO 156
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
agaagttgat tgagactttc aacgagccgc cagagaattt gtgctt 46

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
tagaggtgaa cgtttggcct 20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
aatccatcac ctccacccag 20

<210> SEQ ID NO 159
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
ctcacttaat cttctgtact ctgaaggctg ctggagtaaa aggtcc 46

<210> SEQ ID NO 160
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
agaagttgat tgagactttc aacgagcaag cagcaaccat ctacgg 46

<210> SEQ ID NO 161

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
aacctcatcc actgtcagca 20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
ggaagacaaa gttcgctccg 20

<210> SEQ ID NO 163
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
ctcacttaat cttctgtact ctgaagtcat agttgagagc ctccttgt 48

<210> SEQ ID NO 164
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
agaagttgat tgagactttc aacgagacaa tgcactagga cgggat 46

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
cttgaatcag gcgacgtacc 20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
cccagctctc tttcactcca 20

<210> SEQ ID NO 167
<211> LENGTH: 46

<212> TYPE: DNA
<213> ORGANISM: Artificial Sequence
<220> FEATURE:
<223> OTHER INFORMATION: Description of Artificial Sequence: Synthetic
primer

<400> SEQUENCE: 167
ctcacttaat cttctgtact ctgaagttga agagcagcag agtcga 46

<210> SEQ ID NO 168
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 168
agaagttgat tgagactttc aacgagttaa ttgcccacag tgtcgc 46

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 169
accttccaca gtcgacgaat 20

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 170
acaaacagtc aaatgcacgg a 21

<210> SEQ ID NO 171
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 171
ctcacttaat cttctgtact ctgaagtcct tccacctttc caacgt 46

<210> SEQ ID NO 172
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 172
agaagttgat tgagactttc aacgaggggg tagagaagtt agggagg 47

<210> SEQ ID NO 173
<211> LENGTH: 20
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 173
ggaactacaa ctggaggcct 20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tagtgccggt tccatggatt 20

<210> SEQ ID NO 175
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ctcacttaat cttctgtact ctgaagggtc tatgggttga tgcgga 46

<210> SEQ ID NO 176
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
agaagttgat tgagactttc aacgagatgt gttgctcgct ctaggt 46

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cgacaaacac accaaggtcc 20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gttgttggag tgagcgatgg 20

<210> SEQ ID NO 179
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 179
ctcacttaat cttctgtact ctgaagcctc cgttgatact cccgat 46

<210> SEQ ID NO 180
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 180
agaagttgat tgagactttc aacgagtgca ttcaaggctg gcaaat 46

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 181
gcatatggag tggtgtgcag 20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 182
cgggtagcat tgaacgtacg 20

<210> SEQ ID NO 183
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 183
ctcacttaat cttctgtact ctgaagatgc tacggtaaac acccca 46

<210> SEQ ID NO 184
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 184
agaagttgat tgagactttc aacgagactg gagaaagctt ggtcga 46

<210> SEQ ID NO 185
<211> LENGTH: 20
<212> TYPE: DNA
<213> ORGANISM: Artificial Sequence
<220> FEATURE:

<223> OTHER INFORMATION: Description of Artificial Sequence: Synthetic primer

<400> SEQUENCE: 185
aggcaccaga agaaagagct 20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 186
ggacacgttt ggagcttctt 20

<210> SEQ ID NO 187
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 187
ctcacttaat cttctgtact ctgaaggccc accaattcag caactt 46

<210> SEQ ID NO 188
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 188
agaagttgat tgagactttc aacgaggatg ctggtcacat ggttcc 46

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 189
aaccgccaat agtttcagcc 20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 190
ggatgagaaa gcggcttctg 20

<210> SEQ ID NO 191
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 191
ctcacttaat cttctgtact ctgaaggtgc caaaagtctg atccgg 46

<210> SEQ ID NO 192
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 192
agaagttgat tgagactttc aacgagtgcc acttcgttct ttgacg 46

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 193
acggatcagt gatggcgtat 20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 194
atgggatctg gacgacgttt 20

<210> SEQ ID NO 195
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 195
ctcacttaat cttctgtact ctgaagagct ggatcacaaa cattcgg 47

<210> SEQ ID NO 196
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 196
agaagttgat tgagactttc aacgagcttt gagtgttggt ccctgc 46

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 197
cggctaccaa gtcagacctt 20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
gttgcccatt acgtcctgtg 20

<210> SEQ ID NO 199
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
ctcacttaat cttctgtact ctgaagcctt tgatctttgg tgcatcttg 49

<210> SEQ ID NO 200
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
agaagttgat tgagactttc aacgagcact acagctggga acgaga 46

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
acgggttgga aaagttgagc 20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
agtggggttg gagattggag 20

<210> SEQ ID NO 203
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
ctcacttaat cttctgtact ctgaagacga ttccagcata gcctgt 46

<210> SEQ ID NO 204
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 204
agaagttgat tgagactttc aacgagctgg tagccgcaaa acttca 46

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 205
gcgttgaatc ctcctcgttc 20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 206
ctgtggggtc tgaacatcct 20

<210> SEQ ID NO 207
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 207
ctcacttaat cttctgtact ctgaagagct gctagggttc attgagt 47

<210> SEQ ID NO 208
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 208
agaagttgat tgagactttc aacgagctcc cttgggtacg tcaact 46

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 209
tggcagtctt cacatgtcct 20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 210
agctggtcaa gtctggtacc 20

<210> SEQ ID NO 211
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 211
ctcacttaat cttctgtact ctgaaggagg tctagtgtgt gaggct 46

<210> SEQ ID NO 212
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 212
agaagttgat tgagactttc aacgagagaa ggtataggga atatgcggt 49

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 213
tagccacaac cctgatgacg 20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 214
tacactggga cgcagatgtt 20

<210> SEQ ID NO 215
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 215
ctcacttaat cttctgtact ctgaagtgct caaactctgt atccgttg 48

<210> SEQ ID NO 216
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 216
agaagttgat tgagactttc aacgagcttt caaggccgca atgcta 46

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 217
cttcctttgc agttggtggt 20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 218
gggtctttgg ctttggtgag 20

<210> SEQ ID NO 219
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 219
ctcacttaat cttctgtact ctgaagcgtc tctggaactc gtcgat 46

<210> SEQ ID NO 220
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 220
agaagttgat tgagactttc aacgagcccc aagtcaagga ggagtt 46

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 221
gagtccaatc acggccaatc 20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 222
tgcttcttcg gacagatcgt 20

<210> SEQ ID NO 223
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
ctcacttaat cttctgtact ctgaagtact gattgaaggg tcggca 46

<210> SEQ ID NO 224
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
agaagttgat tgagactttc aacgagttgt acggaccagg aagcat 46

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 225
ttcctctgcc tcttccttgg 20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
agcatgcaaa cacgaggtac 20

<210> SEQ ID NO 227
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
ctcacttaat cttctgtact ctgaagagag gaaaacgagc ttgggt 46

-continued

<210> SEQ ID NO 228
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 228
agaagttgat tgagactttc aacgagatca aggttgccag cgaatg 46

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 229
accctacaga accgcaatga 20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 230
acagcccaaa tagagacgca 20

<210> SEQ ID NO 231
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 231
ctcacttaat cttctgtact ctgaagagga gcccagtttt acgtca 46

<210> SEQ ID NO 232
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 232
agaagttgat tgagactttc aacgagtatc ccgcggtgaa gactac 46

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 233
gtgttgctaa gcctgtggac 20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 234
tcctcctttc gacgcttctt 20

<210> SEQ ID NO 235
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 235
ctcacttaat cttctgtact ctgaagacag ctgtgaatca tgaagtttt 49

<210> SEQ ID NO 236
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 236
agaagttgat tgagactttc aacgagattc tcactggcag aacgga 46

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 237
ttttcacgtt gaggccactg 20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 238
agctccgcag taacaggaat 20

<210> SEQ ID NO 239
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 239
ctcacttaat cttctgtact ctgaagtcaa agcaacttat ggcggt 46

<210> SEQ ID NO 240

<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
agaagttgat tgagactttc aacgagctct tcgcagcacc agaaag 46

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
tcgttgttgc tggtgttctg 20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
agtttgaagg cacgttggtc 20

<210> SEQ ID NO 243
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
ctcacttaat cttctgtact ctgaagactc caacaggact ttgaggt 47

<210> SEQ ID NO 244
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
agaagttgat tgagactttc aacgagaaat gtggaagttg cagcgg 46

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
aggttgatcg ccgtcttgta 20

<210> SEQ ID NO 246
<211> LENGTH: 20

<212> TYPE: DNA
<213> ORGANISM: Artificial Sequence
<220> FEATURE:
<223> OTHER INFORMATION: Description of Artificial Sequence: Synthetic
primer

<400> SEQUENCE: 246
tcttcatgag gtggtaggcg 20

<210> SEQ ID NO 247
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 247
ctcacttaat cttctgtact ctgaagagag ggcagatgac ataccg 46

<210> SEQ ID NO 248
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 248
agaagttgat tgagactttc aacgaggaga aactggaggt gctcgt 46

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 249
caaggcattc agttgaccgt 20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 250
accaacgagc cttacagaca 20

<210> SEQ ID NO 251
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 251
ctcacttaat cttctgtact ctgaagtttt gaccgtcagt gcatgg 46

<210> SEQ ID NO 252
<211> LENGTH: 46
<212> TYPE: DNA

<213> ORGANISM: Artificial Sequence
<220> FEATURE:
<223> OTHER INFORMATION: Description of Artificial Sequence: Synthetic
primer

<400> SEQUENCE: 252
agaagttgat tgagactttc aacgaggtcg gaggtgtgag aattga 46

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 253
tgggaactat gtggctcctc 20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 254
cgagctatca gtactcccgg 20

<210> SEQ ID NO 255
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 255
ctcacttaat cttctgtact ctgaagggtt ctcagctgtc cgagat 46

<210> SEQ ID NO 256
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 256
agaagttgat tgagactttc aacgagtagc attgcccatc acaacg 46

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 257
gtgggaagac tattgatgcg a 21

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 258
gggaaatcgc tgaggtgtac 20

<210> SEQ ID NO 259
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 259
ctcacttaat cttctgtact ctgaagaggt catctggaag ctttgc 46

<210> SEQ ID NO 260
<211> LENGTH: 49
<212> TYPE: DNA
<213> ORGANISM: Artificial Sequence
<220> FEATURE:
<223> OTHER INFORMATION: Description of Artificial Sequence: Synthetic
primer

<400> SEQUENCE: 260
agaagttgat tgagactttc aacgagggtg gccaatggta ttactttga 49

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 261
ataagagccc cgatacaggc 20

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 262
cttgacacac tttgctcctg a 21

<210> SEQ ID NO 263
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 263
ctcacttaat cttctgtact ctgaagagta gctgacctgt tgtgcc 46

<210> SEQ ID NO 264
<211> LENGTH: 46
<212> TYPE: DNA
<213> ORGANISM: Artificial Sequence
<220> FEATURE:

<223> OTHER INFORMATION: Description of Artificial Sequence: Synthetic
primer

<400> SEQUENCE: 264
agaagttgat tgagactttc aacgagggac accatatgat gcccga 46

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 265
cagatcaagt ccaagtccgc 20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 266
agagactttg cgagagtccc 20

<210> SEQ ID NO 267
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 267
ctcacttaat cttctgtact ctgaagtgca atatccaaac acgcca 46

<210> SEQ ID NO 268
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 268
agaagttgat tgagactttc aacgagactt ctggaatctt cgggca 46

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 269
ggatgtttgg gccattgtga 20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 270
caatctctcg cttcatcacg 20

<210> SEQ ID NO 271
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 271
ctcacttaat cttctgtact ctgaagtcgc tgttaaccat aattctttg 49

<210> SEQ ID NO 272
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 272
agaagttgat tgagactttc aacgaggcga gggttgagga gatttt 46

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 273
ggccatggca ctattttgtt 20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 274
acgtacttcc cgcccaataa 20

<210> SEQ ID NO 275
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 275
ctcacttaat cttctgtact ctgaagccca cctaaatttc gagtgca 47

<210> SEQ ID NO 276
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 276
agaagttgat tgagactttc aacgagacac tttcgcagct tttggt 46

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 277
tcctccttgc catgaagagg 20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 278
gcctgatgaa gatgatgccg 20

<210> SEQ ID NO 279
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 279
ctcacttaat cttctgtact ctgaagaggc tcagtcacct ctatga 46

<210> SEQ ID NO 280
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 280
agaagttgat tgagactttc aacgagtgat caagaacacc gtcgaag 47

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 281
tccctttgtt ggtcgtacga 20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 282
tggttcaact tgtagcgcat 20

<210> SEQ ID NO 283
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 283
ctcacttaat cttctgtact ctgaaggggc ttgctcaact tttgga 46

<210> SEQ ID NO 284
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 284
agaagttgat tgagactttc aacgagcgac aatctggtag cgcatc 46

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 285
atgctcgtac aaagacccca 20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 286
tgagatctcc aagtgcagca 20

<210> SEQ ID NO 287
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
ctcacttaat cttctgtact ctgaaggacg gtcgatttgg ctcatc 46

<210> SEQ ID NO 288
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
agaagttgat tgagactttc aacgagtgaa gaagctcaac actctgaac 49

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 289
tgattgacgg caccctgtat 20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 290
caataattca gctgcgccct 20

<210> SEQ ID NO 291
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 291
ctcacttaat cttctgtact ctgaagcctc tgtagctgct tgtcct 46

<210> SEQ ID NO 292
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 292
agaagttgat tgagactttc aacgagagga gtcagtcggt ccaaag 46

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 293
tgtgggctgg gatgtgtaat 20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 294
agcacggtca agtaaatcgc 20

<210> SEQ ID NO 295
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
ctcacttaat cttctgtact ctgaagtgct atcactgatt tgccca 46

<210> SEQ ID NO 296
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
agaagttgat tgagactttc aacgagggag attcccggca agtatc 46

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
ggctttctga ctacctgggt 20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 298
aaagggaaga agggtgcagt 20

<210> SEQ ID NO 299
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 299
ctcacttaat cttctgtact ctgaagaagg tcgactcggg aaacat 46

<210> SEQ ID NO 300
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 300
agaagttgat tgagactttc aacgagtggt atcccgactg ctttgt 46

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 301
tggaatggct cgagaatggt 20

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 302
accaacaggc tgaacactag a 21

<210> SEQ ID NO 303
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 303
ctcacttaat cttctgtact ctgaagtcgt cagcagagaa ggtaca 46

<210> SEQ ID NO 304
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 304
agaagttgat tgagactttc aacgagacgg actccctaac gaacaa 46

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 305
tctgatggtt ggctttgctt 20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 306
cggtttgtgg cccatctatg 20

<210> SEQ ID NO 307
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 307
ctcacttaat cttctgtact ctgaagaaaa ccgacgcttg aactcc 46

<210> SEQ ID NO 308
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 308
agaagttgat tgagactttc aacgagaagt cttgaccgga agcaac 46

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 309
gggccttaac aaacaccaca 20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 310
tagaggcgga aaggaacgag 20

<210> SEQ ID NO 311
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 311
ctcacttaat cttctgtact ctgaagttgc caagggtgta caaagc 46

<210> SEQ ID NO 312
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 312
agaagttgat tgagactttc aacgagacca agttgttcga cgaaga 46

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
caacacatac caggcgaagg 20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
ccctcctccg ccatcattat 20

<210> SEQ ID NO 315
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
ctcacttaat cttctgtact ctgaagtagg agacaaccaa gccagc 46

<210> SEQ ID NO 316
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
agaagttgat tgagactttc aacgagggag tagaaaatgg tgcgtcc 47

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
aatggctcca aatcacaggc 20

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
gctttgagga atgcgtgaag a 21

<210> SEQ ID NO 319

<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 319
ctcacttaat cttctgtact ctgaaggtag tgagagtggc gcctta 46

<210> SEQ ID NO 320
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 320
agaagttgat tgagactttc aacgagtggg tacaacgtga ctctagg 47

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 321
acactcttaa ggctcgtcgt 20

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 322
ctcctccact tcagtatccg t 21

<210> SEQ ID NO 323
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 323
ctcacttaat cttctgtact ctgaagttcc ttgaatttcc gccacc 46

<210> SEQ ID NO 324
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 324
agaagttgat tgagactttc aacgaggagc aggcaaggtt ggattc 46

<210> SEQ ID NO 325
<211> LENGTH: 20

<212> TYPE: DNA
<213> ORGANISM: Artificial Sequence
<220> FEATURE:
<223> OTHER INFORMATION: Description of Artificial Sequence: Synthetic
primer

<400> SEQUENCE: 325
ctgggcagca aataacggtt 20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 326
ccaaagttgg ctccgagtag 20

<210> SEQ ID NO 327
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 327
ctcacttaat cttctgtact ctgaagccta acggtatcgg ctttga 46

<210> SEQ ID NO 328
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 328
agaagttgat tgagactttc aacgagggca aaatcctttt ccatga 46

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 329
gaagaaggcc aagtgtgata 20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 330
gacgagacgc tgttcctttc 20

<210> SEQ ID NO 331
<211> LENGTH: 46
<212> TYPE: DNA

<213> ORGANISM: Artificial Sequence
<220> FEATURE:
<223> OTHER INFORMATION: Description of Artificial Sequence: Synthetic
primer

<400> SEQUENCE: 331
ctcacttaat cttctgtact ctgaagtgtg aagagaggcc accatt 46

<210> SEQ ID NO 332
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 332
agaagttgat tgagactttc aacgagtgat cgactacttg gcctcc 46

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 333
aacaacattc aagctgccgt 20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 334
atcggcaaag atgaagcgac 20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 335
gctggacact tctgagctca 20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 336
acttgtcagg acgatacgga 20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 337
ccggtctccc tggaaataga 20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 338
gcgaggtcct tgtcaatgag 20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 339
acaagaactc gggctccttt 20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 340
ttgcagcgct ccataatgtc 20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 341
gctgattctg agaacgctgg 20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 342
gccattcttc ggtgcagtag 20

<210> SEQ ID NO 343
<211> LENGTH: 20
<212> TYPE: DNA
<213> ORGANISM: Artificial Sequence
<220> FEATURE:

<223> OTHER INFORMATION: Description of Artificial Sequence: Synthetic
primer

<400> SEQUENCE: 343
tagagttgtc ccaaacggca 20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 344
cgtggttctc gaggctctat 20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 345
ggagttggaa cgtcgtagga 20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 346
agttgtccgt cattagccct 20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 347
tgttcccttt cggctagaca 20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 348
acggttgagg gcattacgta 20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 349
ttgtcttcca ccccttcgtt 20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 350
ggttggcctt ggacattgtt 20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 351
tgctcttcgg tactcatgct 20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 352
tttggccatg ctgagctttt 20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 353
aagcccgatc acttgcattt 20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 354
cacctaatgt ttggcacccc 20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 355
atcccagact gacatcgcaa 20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 356
ccgccagaaa ttcatgccat 20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 357
tcgtttcact gtaccatgca 20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 358
accagtccgc attttcactg 20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 359
gtggacagct gcaatcgtag 20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 360
caactgggaa gcctgcattt 20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 361
ccttgcatat ccgtttgcca 20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 362
ggaggttcag gagcaggaat 20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 363
cggtttcatc tgttgcctcc 20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 364
gtcgcccatg ttctttcgat 20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 365
caaacaggct ggaaaccaca 20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 366
aatctccacg ttcagttgcg 20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 367
tcatcccttg aaaaccccga 20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 368
ttgtggaggg agattcaggc 20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 369
aaggtaagga acgtgcttgc 20

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 370
gttctactgt tcacgtgctc t 21

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 371
accggttaga atacatgctg c 21

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 372
cgaaaagaag ctggactccg 20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 373

-continued ttccatcgta cgaccagtgt 20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 374
agcgatgagg ccaacagtat 20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 375
tgtccagccc aaaagactga 20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 376
ctcctggggc tcgtactaag 20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 377
cctcaataac gacggccttg 20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 378
ccttttcctg atcagtgggg 20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 379
tgttggggaa tgaaacacga 20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 380
gaaggacgag tagggttgct 20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 381
tcctgatctg gctcgtttgt 20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 382
acctccaact cctgaaagca 20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 383
cctcgagtct gggctttaca 20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 384
ggagagatgc cagaccaagt 20

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 385
agcctgttct actgcatacg t 21

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 386
ccatttcttg taccctgggc 20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 387
gcagaaaagg cgcgaatttc 20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 388
gggaaaggat gtggaccaac 20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 389
tggccaagag tgtccaattg 20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 390
taacagatgg cgcacgtaga 20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 391
ccttgcgttc ccaggtaaag 20

-continued

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 392
tgtggtatgg tttggggcta 20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 393
actcccgttc ctccatgttc 20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 394
acggtacaaa aggcgtttca 20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 395
agtcaaactc ggtggtaggt 20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 396
cggttatcat gtgcctgctc 20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 397
atgttgctgc tccgaaatcc 20

<210> SEQ ID NO 398

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 398
gatctgctgg ccttgagagt 20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 399
ctatgtcctg gtgtttgccg 20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 400
gccaatgatg atctcgcagg 20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 401
gcctttgata tgccgtcgtt 20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 402
tcgagtaatg cttcccacca 20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 403
agctttcaca acagcgatcg 20

<210> SEQ ID NO 404
<211> LENGTH: 20

<212> TYPE: DNA
<213> ORGANISM: Artificial Sequence
<220> FEATURE:
<223> OTHER INFORMATION: Description of Artificial Sequence: Synthetic
primer

<400> SEQUENCE: 404
tgattgcttc tgggttgctg 20

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 405
caaaaccggc gtaaaatggc 20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 406
ttgtgctgca tctgtgtgag 20

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 407
agcctacaag tggttacagg t 21

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 408
ggaaaccgac cagcctaaag 20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 409
agtcgcacca ggttatcaca 20

<210> SEQ ID NO 410
<211> LENGTH: 20
<212> TYPE: DNA

<213> ORGANISM: Artificial Sequence
<220> FEATURE:
<223> OTHER INFORMATION: Description of Artificial Sequence: Synthetic
primer

<400> SEQUENCE: 410
ggaaagctgc ccagaaactc 20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 411
tgagaggatt cgttgtggct 20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 412
ctatgtcgaa gtagcggtgc 20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 413
agagtggcac tgctatcgaa 20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 414
cgtacaaact tggcagctgt 20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 415
gctgtgttgt aaattccggc 20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
acaacccgga agacaactct 20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
tgtcgttgcc ttcccgatat 20

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
gaagatggga gagggtgctt 20

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
cttgttgacg acggtagcag 20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
ccctagtctc gttcgaaggg 20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
ggcacagcag gttttcgtat 20

<210> SEQ ID NO 422
<211> LENGTH: 21
<212> TYPE: DNA
<213> ORGANISM: Artificial Sequence
<220> FEATURE:

<223> OTHER INFORMATION: Description of Artificial Sequence: Synthetic
primer

<400> SEQUENCE: 422
ggagattctg atgctacccc a 21

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 423
tggagccatc agatcaggac 20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 424
cctgttcttg caagccttca 20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 425
taagacatgc gaccaccaga 20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 426
catggccaat gtcgaactgt 20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 427
agctggctga aaaggtgttg 20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 428
ctcagtgttg gaaagcaccc 20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 429
tagggaatct ttggtggcgt 20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 430
ggaacctaga gcgagcaaca 20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 431
caggctctat tgtcgacgtg 20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 432
ggaggtgatg acaatgccac 20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 433
ctgtgaagct cctcctacgt 20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 434
ggacactgct ggacaagaga 20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 435
tactgacgcc gaagagctag 20

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 436
ccgatcgcaa aatagtggca 20

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 437
gttgtggttg tatgcggtca 20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 438
caataactcc actggtgccg 20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 439
tcgttatact ccagcgtgct 20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 440

gggctcaaaa tctggaacca                                              20


<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441

caatgcagta ctcaccggtg                                              20


<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442

aagctgacga cccccttagac                                             20


<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443

ctatcgtgtc tgggctgcta                                              20


<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444

aaggagattg ccgcaactct                                              20


<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445

gtggagtcag agtcgagagg                                              20


<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
```

cccagctttt atacggcttg g 21

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 447
cagcaaaagc tcgtgatcca 20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 448
tgcgggtagt cgattgatgt 20

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 449
tcacgtatct cagcaacagg a 21

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 450
ggacctagga aatacgccca 20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 451
actccagttc cacaagtcca 20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 452
actgccaacc gtttactcca 20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 453
gcgcggaaga ttaaagtcgt 20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 454
ttggactcga tcgatgaggg 20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 455
tgatgacttc caagatgcgc 20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 456
tcacctggag caactgatgt 20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 457
gtttggtacg cttgtaggcc 20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 458
gatgagcaag catccattca 20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 459
aaagacagga gcgtgagcat 20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 460
ctcaacttcg cttgcccttt 20

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 461
tgggaaacag aacgatgaac t 21

<210> SEQ ID NO 462
<211> LENGTH: 2835
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 462
ggtggttacg gtccaggcgc tggtcaacaa ggtccaggaa gtggtggtca acaaggacct 60
ggcggtcaag gaccctacgg tagtggccaa caaggtccag gtggagcagg acagcagggt 120
ccgggaggcc aaggacctta cggaccaggt gctgctgctg ccgccgctgc cgctgccgga 180
ggttacggtc caggagccgg acaacagggt ccaggtggag ctggacaaca aggtccagga 240
tcacaaggtc ctggtggaca aggtccatac ggtcctggtg ctggtcaaca gggaccaggt 300
agtcaaggac ctggttcagg tggtcagcag ggtccaggag gacagggtcc ttacggccct 360
tctgccgctg cagcagcagc cgctgccgca ggaggatacg gacctggtgc tggacaacga 420
tctcaaggac caggaggaca aggtccttat ggacctggcg ctggccaaca aggacctggt 480
tctcagggtc caggttcagg aggccaacaa ggcccaggag gtcaaggacc atacggacca 540
tccgctgcgg cagctgcagc tgctgcaggt ggatatggcc caggagccgg acaacagggt 600
cctggttcac aaggtccagg atctggtggt caacagggac caggcggcca gggaccttat 660
ggtccaggag ccgctgcagc agcagcagct gttggaggtt acggccctgg tgccggtcaa 720
caaggcccag gatctcaggg tcctggatct ggaggacaac aaggtcctgg aggtcagggt 780
ccatacggac cttcagcagc agctgctgct gcagccgctg gtggttatgg acctggtgct 840

```
ggtcaacaag gaccgggttc tcagggtccg ggttcaggag gtcagcaggg ccctggtgga    900
caaggacctt atggacctag tgcggctgca gcagctgccg ccgcaggtgg ttacggtcca    960
ggcgctggtc aacaaggtcc aggaagtggt ggtcaacaag gacctggcgg tcaaggaccc   1020
tacggtagtg gccaacaagg tccaggtgga gcaggacagc agggtccggg aggccaagga   1080
ccttacggac caggtgctgc tgctgccgcc gctgccgctg ccggaggtta cggtccagga   1140
gccggacaac agggtccagg tggagctgga caacaaggtc caggatcaca aggtcctggt   1200
ggacaaggtc catacggtcc tggtgctggt caacagggac caggtagtca aggacctggt   1260
tcaggtggtc agcagggtcc aggaggacag ggtccttacg gcccttctgc cgctgcagca   1320
gcagccgctg ccgcaggagg atacggacct ggtgctggac aacgatctca aggaccagga   1380
ggacaaggtc cttatggacc tggcgctggc caacaaggac ctggttctca gggtccaggt   1440
tcaggaggcc aacaaggccc aggaggtcaa ggaccatacg gaccatccgc tgcggcagct   1500
gcagctgctg caggtggata tggcccagga gccggacaac agggtcctgg ttcacaaggt   1560
ccaggatctg gtggtcaaca gggaccaggc ggccagggac cttatggtcc aggagccgct   1620
gcagcagcag cagctgttgg aggttacggc cctggtgccg gtcaacaagg cccaggatct   1680
cagggtcctg gatctggagg acaacaaggt cctggaggtc agggtccata cggaccttca   1740
gcagcagctg ctgctgcagc cgctggtggt tatggacctg gtgctggtca acaaggaccg   1800
ggttctcagg gtccgggttc aggaggtcag cagggccctg gtggacaagg accttatgga   1860
cctagtgcgg ctgcagcagc tgccgccgca ggtggttacg gtccaggcgc tggtcaacaa   1920
ggtccaggaa gtggtggtca acaaggacct ggcggtcaag gaccctacgg tagtggccaa   1980
caaggtccag gtggagcagg acagcagggt ccgggaggcc aaggacctta cggaccaggt   2040
gctgctgctg ccgccgctgc cgctgccgga ggttacggtc caggagccgg acaacagggt   2100
ccaggtggag ctggacaaca aggtccagga tcacaaggtc ctggtggaca aggtccatac   2160
ggtcctggtg ctggtcaaca gggaccaggt agtcaaggac ctggttcagg tggtcagcag   2220
ggtccaggag gacagggtcc ttacggccct tctgccgctg cagcagcagc cgctgccgca   2280
ggaggatacg gacctggtgc tggacaacga tctcaaggac caggaggaca aggtccttat   2340
ggacctggcg ctggccaaca aggacctggt tctcagggtc caggttcagg aggccaacaa   2400
ggcccaggag gtcaaggacc atacggacca tccgctgcgg cagctgcagc tgctgcaggt   2460
ggatatggcc caggagccgg acaacagggt cctggttcac aaggtccagg atctggtggt   2520
caacagggac caggcggcca gggaccttat ggtccaggag ccgctgcagc agcagcagct   2580
gttggaggtt acggccctgg tgccggtcaa caaggcccag gatctcaggg tcctggatct   2640
ggaggacaac aaggtcctgg aggtcagggt ccatacggac cttcagcagc agctgctgct   2700
gcagccgctg gtggttatgg acctggtgct ggtcaacaag gaccgggttc tcagggtccg   2760
ggttcaggag gtcagcaggg ccctggtgga caaggacctt atggacctag tgcggctgca   2820
gcagctgccg ccgca                                                    2835
```

<210> SEQ ID NO 463
<211> LENGTH: 945
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 463

-continued

```
Gly Gly Tyr Gly Pro Gly Ala Gly Gln Gln Gly Pro Gly Ser Gly Gly
1               5                   10                  15

Gln Gln Gly Pro Gly Gly Gln Gly Pro Tyr Gly Ser Gly Gln Gln Gly
            20                  25                  30

Pro Gly Gly Ala Gly Gln Gln Gly Pro Gly Gly Gln Gly Pro Tyr Gly
        35                  40                  45

Pro Gly Ala Ala Ala Ala Ala Ala Ala Ala Ala Gly Gly Tyr Gly Pro
    50                  55                  60

Gly Ala Gly Gln Gln Gly Pro Gly Gly Ala Gly Gln Gln Gly Pro Gly
65                  70                  75                  80

Ser Gln Gly Pro Gly Gly Gln Gly Pro Tyr Gly Pro Gly Ala Gly Gln
                85                  90                  95

Gln Gly Pro Gly Ser Gln Gly Pro Gly Ser Gly Gly Gln Gln Gly Pro
            100                 105                 110

Gly Gly Gln Gly Pro Tyr Gly Pro Ser Ala Ala Ala Ala Ala Ala Ala
        115                 120                 125

Ala Ala Gly Gly Tyr Gly Pro Gly Ala Gly Gln Arg Ser Gln Gly Pro
    130                 135                 140

Gly Gly Gln Gly Pro Tyr Gly Pro Gly Ala Gly Gln Gln Gly Pro Gly
145                 150                 155                 160

Ser Gln Gly Pro Gly Ser Gly Gly Gln Gln Gly Pro Gly Gly Gln Gly
                165                 170                 175

Pro Tyr Gly Pro Ser Ala Ala Ala Ala Ala Ala Ala Ala Gly Gly Tyr
            180                 185                 190

Gly Pro Gly Ala Gly Gln Gln Gly Pro Gly Ser Gln Gly Pro Gly Ser
        195                 200                 205

Gly Gly Gln Gln Gly Pro Gly Gly Gln Gly Pro Tyr Gly Pro Gly Ala
    210                 215                 220

Ala Ala Ala Ala Ala Ala Val Gly Gly Tyr Gly Pro Gly Ala Gly Gln
225                 230                 235                 240

Gln Gly Pro Gly Ser Gln Gly Pro Gly Ser Gly Gly Gln Gln Gly Pro
                245                 250                 255

Gly Gly Gln Gly Pro Tyr Gly Pro Ser Ala Ala Ala Ala Ala Ala Ala
            260                 265                 270

Ala Gly Gly Tyr Gly Pro Gly Ala Gly Gln Gln Gly Pro Gly Ser Gln
        275                 280                 285

Gly Pro Gly Ser Gly Gly Gln Gln Gly Pro Gly Gly Gln Gly Pro Tyr
    290                 295                 300

Gly Pro Ser Ala Ala Ala Ala Ala Ala Ala Ala Gly Gly Tyr Gly Pro
305                 310                 315                 320

Gly Ala Gly Gln Gln Gly Pro Gly Ser Gly Gly Gln Gln Gly Pro Gly
                325                 330                 335

Gly Gln Gly Pro Tyr Gly Ser Gly Gln Gln Gly Pro Gly Gly Ala Gly
            340                 345                 350

Gln Gln Gly Pro Gly Gly Gln Gly Pro Tyr Gly Pro Gly Ala Ala Ala
        355                 360                 365

Ala Ala Ala Ala Ala Ala Gly Gly Tyr Gly Pro Gly Ala Gly Gln Gln
    370                 375                 380

Gly Pro Gly Gly Ala Gly Gln Gln Gly Pro Gly Ser Gln Gly Pro Gly
385                 390                 395                 400

Gly Gln Gly Pro Tyr Gly Pro Gly Ala Gly Gln Gln Gly Pro Gly Ser
                405                 410                 415

Gln Gly Pro Gly Ser Gly Gly Gln Gln Gly Pro Gly Gly Gln Gly Pro
```

-continued

```
            420                 425                 430

Tyr Gly Pro Ser Ala Ala Ala Ala Ala Ala Ala Ala Ala Gly Gly Tyr
        435                 440                 445

Gly Pro Gly Ala Gly Gln Arg Ser Gln Gly Pro Gly Gly Gln Gly Pro
    450                 455                 460

Tyr Gly Pro Gly Ala Gly Gln Gln Gly Pro Gly Ser Gln Gly Pro Gly
465                 470                 475                 480

Ser Gly Gly Gln Gln Gly Pro Gly Gly Gln Gly Pro Tyr Gly Pro Ser
                485                 490                 495

Ala Ala Ala Ala Ala Ala Ala Ala Gly Gly Tyr Gly Pro Gly Ala Gly
            500                 505                 510

Gln Gln Gly Pro Gly Ser Gln Gly Pro Gly Ser Gly Gly Gln Gln Gly
        515                 520                 525

Pro Gly Gly Gln Gly Pro Tyr Gly Pro Gly Ala Ala Ala Ala Ala Ala
    530                 535                 540

Ala Val Gly Gly Tyr Gly Pro Gly Ala Gly Gln Gln Gly Pro Gly Ser
545                 550                 555                 560

Gln Gly Pro Gly Ser Gly Gly Gln Gln Gly Pro Gly Gly Gln Gly Pro
                565                 570                 575

Tyr Gly Pro Ser Ala Ala Ala Ala Ala Ala Ala Ala Gly Gly Tyr Gly
            580                 585                 590

Pro Gly Ala Gly Gln Gln Gly Pro Gly Ser Gln Gly Pro Gly Ser Gly
        595                 600                 605

Gly Gln Gln Gly Pro Gly Gly Gln Gly Pro Tyr Gly Pro Ser Ala Ala
    610                 615                 620

Ala Ala Ala Ala Ala Ala Gly Gly Tyr Gly Pro Gly Ala Gly Gln Gln
625                 630                 635                 640

Gly Pro Gly Ser Gly Gly Gln Gln Gly Pro Gly Gly Gln Gly Pro Tyr
                645                 650                 655

Gly Ser Gly Gln Gln Gly Pro Gly Gly Ala Gly Gln Gln Gly Pro Gly
            660                 665                 670

Gly Gln Gly Pro Tyr Gly Pro Gly Ala Ala Ala Ala Ala Ala Ala Ala
        675                 680                 685

Ala Gly Gly Tyr Gly Pro Gly Ala Gly Gln Gln Gly Pro Gly Gly Ala
    690                 695                 700

Gly Gln Gln Gly Pro Gly Ser Gln Gly Pro Gly Gly Gln Gly Pro Tyr
705                 710                 715                 720

Gly Pro Gly Ala Gly Gln Gln Gly Pro Gly Ser Gln Gly Pro Gly Ser
                725                 730                 735

Gly Gly Gln Gln Gly Pro Gly Gly Gln Gly Pro Tyr Gly Pro Ser Ala
            740                 745                 750

Ala Ala Ala Ala Ala Ala Ala Ala Gly Gly Tyr Gly Pro Gly Ala Gly
        755                 760                 765

Gln Arg Ser Gln Gly Pro Gly Gly Gln Gly Pro Tyr Gly Pro Gly Ala
    770                 775                 780

Gly Gln Gln Gly Pro Gly Ser Gln Gly Pro Gly Ser Gly Gly Gln Gln
785                 790                 795                 800

Gly Pro Gly Gly Gln Gly Pro Tyr Gly Pro Ser Ala Ala Ala Ala Ala
                805                 810                 815

Ala Ala Ala Gly Gly Tyr Gly Pro Gly Ala Gly Gln Gln Gly Pro Gly
            820                 825                 830

Ser Gln Gly Pro Gly Ser Gly Gly Gln Gln Gly Pro Gly Gly Gln Gly
        835                 840                 845
```

Pro Tyr Gly Pro Gly Ala Ala Ala Ala Ala Ala Ala Val Gly Gly Tyr
850 855 860

Gly Pro Gly Ala Gly Gln Gln Gly Pro Gly Ser Gln Gly Pro Gly Ser
865 870 875 880

Gly Gly Gln Gln Gly Pro Gly Gly Gln Gly Pro Tyr Gly Pro Ser Ala
885 890 895

Ala Ala Ala Ala Ala Ala Ala Gly Gly Tyr Gly Pro Gly Ala Gly Gln
900 905 910

Gln Gly Pro Gly Ser Gln Gly Pro Gly Ser Gly Gly Gln Gln Gly Pro
915 920 925

Gly Gly Gln Gly Pro Tyr Gly Pro Ser Ala Ala Ala Ala Ala Ala Ala
930 935 940

Ala
945

<210> SEQ ID NO 464
<211> LENGTH: 315
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 464

Gly Gly Tyr Gly Pro Gly Ala Gly Gln Gln Gly Pro Gly Ser Gly Gly
1 5 10 15

Gln Gln Gly Pro Gly Gly Gln Gly Pro Tyr Gly Ser Gly Gln Gln Gly
20 25 30

Pro Gly Gly Ala Gly Gln Gln Gly Pro Gly Gly Gln Gly Pro Tyr Gly
35 40 45

Pro Gly Ala Ala Ala Ala Ala Ala Ala Ala Ala Gly Gly Tyr Gly Pro
50 55 60

Gly Ala Gly Gln Gln Gly Pro Gly Gly Ala Gly Gln Gln Gly Pro Gly
65 70 75 80

Ser Gln Gly Pro Gly Gly Gln Gly Pro Tyr Gly Pro Gly Ala Gly Gln
85 90 95

Gln Gly Pro Gly Ser Gln Gly Pro Gly Ser Gly Gly Gln Gln Gly Pro
100 105 110

Gly Gly Gln Gly Pro Tyr Gly Pro Ser Ala Ala Ala Ala Ala Ala Ala
115 120 125

Ala Ala Gly Gly Tyr Gly Pro Gly Ala Gly Gln Arg Ser Gln Gly Pro
130 135 140

Gly Gly Gln Gly Pro Tyr Gly Pro Gly Ala Gly Gln Gln Gly Pro Gly
145 150 155 160

Ser Gln Gly Pro Gly Ser Gly Gly Gln Gln Gly Pro Gly Gly Gln Gly
165 170 175

Pro Tyr Gly Pro Ser Ala Ala Ala Ala Ala Ala Ala Ala Gly Gly Tyr
180 185 190

Gly Pro Gly Ala Gly Gln Gln Gly Pro Gly Ser Gln Gly Pro Gly Ser
195 200 205

Gly Gly Gln Gln Gly Pro Gly Gly Gln Gly Pro Tyr Gly Pro Gly Ala
210 215 220

Ala Ala Ala Ala Ala Ala Val Gly Gly Tyr Gly Pro Gly Ala Gly Gln
225 230 235 240

Gln Gly Pro Gly Ser Gln Gly Pro Gly Ser Gly Gly Gln Gln Gly Pro

-continued

```
            245                 250                 255

Gly Gly Gln Gly Pro Tyr Gly Pro Ser Ala Ala Ala Ala Ala Ala Ala
        260                 265                 270

Ala Gly Gly Tyr Gly Pro Gly Ala Gly Gln Gln Gly Pro Gly Ser Gln
    275                 280                 285

Gly Pro Gly Ser Gly Gly Gln Gln Gly Pro Gly Gly Gln Gly Pro Tyr
    290                 295                 300

Gly Pro Ser Ala Ala Ala Ala Ala Ala Ala Ala
305                 310                 315


<210> SEQ ID NO 465
<211> LENGTH: 4324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 465

ggagttgaat cacatcttac tggatagcga gctttttgac gaagtgaaaa tttctaattt     60

taaacaagag gaaggggtca aaaacggaga tatcttatac ttggaaaaag agatgacaat    120

cagtgatttc atcaatttttg tatctagttg gccttctgtg ttttcgtgga agcagcaacg    180

aggaaaggag ggtatcctag atgattttta caacgaactg aacgactgct ttgagggggg    240

taacatgaaa gtaatatgga actccgtcct agtatttgcc aggaggaagc aaagggttgt    300

ataggcttta gtacttatag aggaaacggg gttacgtgca agcgcgcatg cctgagcttt    360

gagggggggg actttcacat ctcttcttct cacacttagc cctaacacag agaataataa    420

aaagcattgc aagatgagtg ttgtcagcaa gcaatacgac atccacgaag gcattatctt    480

tgtaattgaa ttgaccccgg agcttcacgc gccggcttca gaagggaaat ctcagctcca    540

gatcatctta gagaatgtca gtgaggttat ttctgagcta atcattacct tgcccggtac    600

aggaataggg tgttacctta ttaattacga cggtggtcaa aacgacgaaa tttaccccat    660

ttttgagtta caagacctga atttggaaat gatgaaacaa ttgtaccaag tcttggagga    720

ccatgtaagt gggcttaatc ctctcgagaa gcaattccca attgaacaca gtaaaccgtt    780

atcagccact ctgttctttc acttaaggtc tctttttttac atggcgaaga ctcataagcg    840

tactggaaga cattacaact tgaaaaagat tttcttgttc actaataacg ataaacctta    900

caatggaaac tctcagctga gagttccctt gaagaaaacc ctggctgatt acaatgacgt    960

agacattact ttgattccgt ttcttctgaa caagccttca ggtgtcaagt ttgacaagac   1020

ggaatactca gaaattttgt tctatgataa agatgcttgt tcgatgtcaa ttgaggagat   1080

ccgccaacga atttctagac ataaggagat caagcgggtt tacttcacct gtcctttgaa   1140

aatcgcaaat aacttgtgca tttctgtgaa aggttattct atgttttatc atgaaactcc   1200

aaggaagatc aaatttgtcg tcaatgaggg ttcaactttc aaagatgtgg agacaaaatc   1260

tcagtttgtc gatccaacat ccggaaaaga gttttccagt gaacagctga tcaaagcata   1320

tcctctaggt gccgatgctt acattccttt aaactcagag caagtcaaaa caataaatcg   1380

atttaatgat atcatcaata tcccctcttt ggaaattcta ggtttcaggg atatatctaa   1440

ttggttgcca cagtatcagt ttggcaaagc atcgttttta tcccctaata actatggtga   1500

ttttacacat tcgcagagaa catttagttg tcttcagtaa tgtcttgttt cttttgttgc   1560

agtggtgagc cattttgact tcgtgaaagt ttctttagaa tagttgtttc cagaggccaa   1620
```

```
acattccacc cgtagtaaag tgcaagcgta ggaagaccaa gactggcata aatcaggtat   1680
aagtgtcgag cactggcagg tgatcttctg aaagtttcta ctagcagata agatccagta   1740
gtcatgcata tggcaacaat gtaccgtgtg gatctaagaa cgcgtcctac taaccttcgc   1800
attcgttggt ccagtttgtt gttatcgatc aacgtgacaa ggttgtcgat tccgcgtaag   1860
catgcatacc caaggacgcc tgttgcaatt ccaagtgagc cagttccaac aatctttgta   1920
atattagagc acttcattgt gttgcgcttg aaagtaaaat gcgaacaaat taagagataa   1980
tctcgaaacc gcgacttcaa acgccaatat gatgtgcggc acacaataag cgttcatatc   2040
cgctgggtga ctttctcgct ttaaaaaatt atccgaaaaa atttttgacg gctagctcag   2100
tcctaggtac gctagcatta aagaggagaa aatggctaaa ctgacctctg ctgttccggt   2160
tctgaccgct cgtgacgttg ctggtgctgt tgagttctgg accgaccgtc tgggtttctc   2220
tcgtgacttc gttgaagacg acttcgctgg tgttgttcgt gacgacgtta ccctgttcat   2280
ctctgctgtt caggaccagg ttgttccgga caacaccctg gcttgggttt gggttcgtgg   2340
tctggacgaa ctgtacgctg aatggtctga agttgtttct accaacttcc gtgacgcttc   2400
tggtccggct atgaccgaaa tcggtgaaca gccgtggggt cgtgagttcg ctctgcgtga   2460
cccggctggt aactgcgttc acttcgttgc tgaagaacag gactaacacg tccgacggcg   2520
gcccacgggt cccaggcctc ggagatccgt ccccctttc ctttgtcgat atcatgtaat   2580
tagttatgtc acgcttacat tcacgccctc cccccacatc cgctctaacc gaaaaggaag   2640
gagttagaca acctgaagtc taggtcccta tttattttt tatagttatg ttagtattaa   2700
gaacgttatt tatatttcaa atttttcttt tttttctgta cagacgcgtg tacgcatgta   2760
acattatact gaaaaccttg cttgagaagg ttttgggacg ctcgaaggct ttaatttgca   2820
agctgtatta gtttcacttt tcagcaacct ggtcggaaag atccacatca agaatggata   2880
ccaaccccaa gagtatgaaa atccttccct acaatggcac ttcaaaatgt tacgtgacga   2940
ttaccttcaa ttggaacacg atatcgacat cagtgacccc cttgagaaac aaaagtacat   3000
aaacagcctc gatgagacaa aaaccaagat catgaaacta cgggactatg tcaaggaaac   3060
tgccgatgat gacgaccctt cacggcttgc caacactctc aaagagctca accaagagct   3120
gaacaaaatt tccaactttg atatcatcgc caataagaag ccaaagaccc ccacgacagt   3180
agaccctgtt cctactgatg atgacatcat caacgcctgg aaggcaggaa ctctgaacgg   3240
tttcaaggtg gatcaattac gaaaatacgt aaggtcacga aacaactttc tggagacggc   3300
ctccaaaaag gcagatctca tcgccaacat tgacaagtac tttcagcaga agttcaaaga   3360
gactaaggcc tgattcgtgt tccttacttt ttcctcgcaa cgtgtttttt tcccaccaca   3420
ttgcctatgt tgtaatgcaa tgcagatgct ggcccagttt ttgacgattc tcgaaaattg   3480
gcattttcgt cgatgccatt ggccaaactg aaaattcaag acaaaataga ttggatttta   3540
tctgcaacgt cttccaccta cacaaccact ctacaaactt cagacaaaca tgtttataaa   3600
agcagctact agatccaaaa tgacaagttc gttattctct actacgtttg ttgtggcatt   3660
tggattggtg gctagcaaca acctcttgcc atgtcctgtt gaccactcta tgaataacga   3720
gactccgcaa gaattgaaac cattgcaggc tgaatcttct actagaaagt tgaactcttc   3780
cgcttaagtc aaataaaact actgacacag atgatgcaca gaaacaacgg atcacgctct   3840
tgactgatta gtcccgtcat tttggttctc attttcttca cagtcaccta tcaatgtatg   3900
atcacctgga aggatttccc tacgatactt caaatctttt acttgataat attactcatt   3960
atggctcagg aatgcagact gcctgattca agacgctgct cttcttattt aacacttgta   4020
```

```
cactaacccc atggaagcca gggaagggaa taaccatctc tctggtaata aatcggtctt   4080

tatttatgca tagaaaagga atctattata tttcgttcat ttggcactct gctaactgta   4140

gattaacggg tctcgtaaat tcaaaatctt cttccgatca aaccggggtg aaatattact   4200

tctcgtgcat agctaatttt caaataaccg tcctaaaatg aacggtcatt tacctggact   4260

ctcttgccaa atgggcaaca aaacataaag ctgatcagaa cgtaactagt ctctcggaat   4320

ccat                                                                4324
```

<210> SEQ ID NO 466
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 466

```
ggagttgaat cacatcttac tg                                              22
```

<210> SEQ ID NO 467
<211> LENGTH: 1099
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 467

```
gacaactaaa tgttctctgc gaatgtgtaa aatcaccata gttattaggg gataaaaacg     60

atgctttgcc aaactgatac tgtggcaacc aattagatat atccctgaaa cctagaattt    120

ccaaagaggg gatattgatg atatcattaa atcgatttat tgttttgact tgctctgagt    180

ttaaaggaat gtaagcatcg gcacctagag gatatgcttt gatcagctgt tcactggaaa    240

actcttttcc ggatgttgga tcgacaaact gagattttgt ctccacatct ttgaaagttg    300

aaccctcatt gacgacaaat ttgatcttcc ttggagtttc atgataaaac atagaataac    360

ctttcacaga aatgcacaag ttatttgcga ttttcaaagg acaggtgaag taaacccgct    420

tgatctcctt atgtctagaa attcgttggc ggatctcctc aattgacatc gaacaagcat    480

ctttatcata gaacaaaatt tctgagtatt ccgtcttgtc aaacttgaca cctgaaggct    540

tgttcagaag aaacggaatc aaagtaatgt ctacgtcatt gtaatcagcc agggttttct    600

tcaagggaac tctcagctga gagtttccat tgtaaggttt atcgttatta gtgaacaaga    660

aaatcttttt caagttgtaa tgtcttccag tacgcttatg agtcttcgcc atgtaaaaaa    720

gagaccttaa gtgaaagaac agagtggctg ataacggttt actgtgttca attgggaatt    780

gcttctcgag aggattaagc ccacttacat ggtcctccaa gacttggtac aattgtttca    840

tcatttccaa attcaggtct tgtaactcaa aaatggggta aatttcgtcg ttttgaccac    900

cgtcgtaatt aataaggtaa caccctattc ctgtaccggg caaggtaatg attagctcag    960

aaataacctc actgacattc tctaagatga tctggagctg agatttccct tctgaagccg   1020

gcgcgtgaag ctccggggtc aattcaatta caaagataat gccttcgtgg atgtcgtatt   1080

gcttgctgac aacactcat                                                1099
```

<210> SEQ ID NO 468
<211> LENGTH: 549
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 468
tcaggcctta gtctctttga acttctgctg aaagtacttg tcaatgttgg cgatgagatc 60
tgcctttttg gaggccgtct ccagaaagtt gtttcgtgac cttacgtatt ttcgtaattg 120
atccaccttg aaaccgttca gagttcctgc cttccaggcg ttgatgatgt catcatcagt 180
aggaacaggg tctactgtcg tgggggtctt tggcttctta ttggcgatga tatcaaagtt 240
ggaaattttg ttcagctctt ggttgagctc tttgagagtg ttggcaagcc gtgaagggtc 300
gtcatcatcg gcagtttcct tgacatagtc ccgtagtttc atgatcttgg tttttgtctc 360
atcgaggctg tttatgtact tttgtttctc aagggggtca ctgatgtcga tatcgtgttc 420
caattgaagg taatcgtcac gtaacatttt gaagtgccat tgtagggaag gattttcata 480
ctcttggggt tggtatccat tcttgatgtg gatctttccg accaggttgc tgaaaagtga 540
aactaatac 549

<210> SEQ ID NO 469
<211> LENGTH: 552
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 469
ttcagtaatg tcttgtttct tttgttgcag tggtgagcca ttttgacttc gtgaaagttt 60
ctttagaata gttgtttcca gaggccaaac attccacccg tagtaaagtg caagcgtagg 120
aagaccaaga ctggcataaa tcaggtataa gtgtcgagca ctggcaggtg atcttctgaa 180
agtttctact agcagataag atccagtagt catgcatatg gcaacaatgt accgtgtgga 240
tctaagaacg cgtcctacta accttcgcat tcgttggtcc agtttgttgt tatcgatcaa 300
cgtgacaagg ttgtcgattc cgcgtaagca tgcataccca aggacgcctg ttgcaattcc 360
aagtgagcca gttccaacaa tctttgtaat attagagcac ttcattgtgt tgcgcttgaa 420
agtaaaatgc gaacaaatta agagataatc tcgaaaccgc gacttcaaac gccaatatga 480
tgtgcggcac acaataagcg ttcatatccg ctgggtgact ttctcgcttt aaaaaattat 540
ccgaaaaaat tt 552

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 470
cagaggccaa acattccacc 20

<210> SEQ ID NO 471
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 471
ttaaagagga gaaa 14

<210> SEQ ID NO 472
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 472
atggctaaac tgacctctgc tgttccggtt ctgaccgctc gtgacgttgc tggtgctgtt 60
gagttctgga ccgaccgtct gggtttctct cgtgacttcg ttgaagacga cttcgctggt 120
gttgttcgtg acgacgttac cctgttcatc tctgctgttc aggaccaggt tgttccggac 180
aacaccctgg cttgggtttg ggttcgtggt ctggacgaac tgtacgctga atggtctgaa 240
gttgtttcta ccaacttccg tgacgcttct ggtccggcta tgaccgaaat cggtgaacag 300
ccgtggggtc gtgagttcgc tctgcgtgac ccggctggta actgcgttca cttcgttgct 360
gaagaacagg actaa 375

<210> SEQ ID NO 473
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 473
cacgtccgac ggcggcccac gggtcccagg cctcggagat ccgtccccct tttcctttgt 60
cgatatcatg taattagtta tgtcacgctt acattcacgc cctcccccca catccgctct 120
aaccgaaaag gaaggagtta gacaacctga agtctaggtc cctatttatt tttttatagt 180
tatgttagta ttaagaacgt tatttatatt tcaaattttt cttttttttc tgtacagacg 240
cgtgtacgca tgtaacatta tactgaaaac cttgcttgag aaggttttgg gacgctcgaa 300
ggctttaatt tgcaagct 318

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 474
aggagttaga caacctgaag 20

<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 475
gtaactagtc tctcggaatc cat 23

<210> SEQ ID NO 476
<211> LENGTH: 1623
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 476
cttcagagta cagaagatta agtgagagaa ttctaccgtt cgtatagcat acattatacg 60
aagttatttc agtaatgtct tgtttctttt gttgcagtgg tgagccattt tgacttcgtg 120
aaagtttctt tagaatagtt gtttccagag gccaaacatt ccacccgtag taaagtgcaa 180
gcgtaggaag accaagactg gcataaatca ggtataagtg tcgagcactg gcaggtgatc 240
ttctgaaagt ttctactagc agataagatc cagtagtcat gcatatggca acaatgtacc 300
gtgtggatct aagaacgcgt cctactaacc ttcgcattcg ttggtccagt ttgttgttat 360
cgatcaacgt gacaaggttg tcgattccgc gtaagcatgc atacccaagg acgcctgttg 420
caattccaag tgagccagtt ccaacaatct ttgtaatatt agagcacttc attgtgttgc 480
gcttgaaagt aaaatgcgaa caaattaaga gataatctcg aaaccgcgac ttcaaacgcc 540
aatatgatgt gcggcacaca ataagcgttc atatccgctg ggtgactttc tcgctttaaa 600
aaattatccg aaaaaatttt tgacggctag ctcagtccta ggtacgctag cattaaagag 660
gagaaaatga ctactcttga tgacacagcc tacagatata ggacatcagt tccgggtgac 720
gcagaggcta tcgaagcctt ggacggttca ttcactactg atacggtgtt tagagtcacc 780
gctacaggtg atggcttcac cttgagagag gttcctgtag acccaccctt aacgaaagtt 840
ttccctgatg acgaatcgga tgacgagtct gatgctggtg aggacggtga ccctgattcc 900
agaacatttg tcgcatacgg agatgatggt gacctggctg gctttgttgt ggtgtcctac 960
agcggatgga atcgtagact cacagttgag gacatcgaag ttgcacctga acatcgtggt 1020
cacggtgttg gtcgtgcact gatgggactg gcaacagagt ttgctagaga aagaggagcc 1080
ggacatttgt ggttagaagt gaccaatgtc aacgctcctg ctattcacgc atataggcga 1140
atgggtttca ctttgtgcgg tcttgatact gctttgtatg acggaactgc ttctgatggt 1200
gaacaagctc tttacatgag tatgccatgt ccatagcacg tccgacggcg gcccacgggt 1260
cccaggcctc ggagatccgt cccccttttc ctttgtcgat atcatgtaat tagttatgtc 1320
acgcttacat tcacgccctc cccccacatc cgctctaacc gaaaaggaag gagttagaca 1380
acctgaagtc taggtcccta tttatttttt tatagttatg ttagtattaa gaacgttatt 1440
tatatttcaa atttttcttt tttttctgta cagacgcgtg tacgcatgta acattatact 1500
gaaaaccttg cttgagaagg ttttgggacg ctcgaaggct ttaatttgca agctataact 1560
tcgtatagca tacattatac cttgttatgc ggccgcaaga agttgattga gactttcaac 1620
gag 1623

<210> SEQ ID NO 477
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 477
cttcagagta cagaagatta agtgaga 27

<210> SEQ ID NO 478
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 478
taccgttcgt atagcataca ttatacgaag ttat 34

<210> SEQ ID NO 479
<211> LENGTH: 552
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 479
ttcagtaatg tcttgtttct tttgttgcag tggtgagcca ttttgacttc gtgaaagttt 60
ctttagaata gttgtttcca gaggccaaac attccacccg tagtaaagtg caagcgtagg 120
aagaccaaga ctggcataaa tcaggtataa gtgtcgagca ctggcaggtg atcttctgaa 180
agtttctact agcagataag atccagtagt catgcatatg gcaacaatgt accgtgtgga 240
tctaagaacg cgtcctacta accttcgcat tcgttggtcc agtttgttgt tatcgatcaa 300
cgtgacaagg ttgtcgattc cgcgtaagca tgcataccca aggacgcctg ttgcaattcc 360
aagtgagcca gttccaacaa tctttgtaat attagagcac ttcattgtgt tgcgcttgaa 420
agtaaaatgc gaacaaatta agagataatc tcgaaaccgc gacttcaaac gccaatatga 480
tgtgcggcac acaataagcg ttcatatccg ctgggtgact ttctcgcttt aaaaaattat 540
ccgaaaaaat tt 552

<210> SEQ ID NO 480
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 480
ttaaagagga gaaa 14

<210> SEQ ID NO 481
<211> LENGTH: 570
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 481
atgactactc ttgatgacac agcctacaga tataggacat cagttccggg tgacgcagag 60
gctatcgaag ccttggacgg ttcattcact actgatacgg tgtttagagt caccgctaca 120
ggtgatggct tcaccttgag agaggttcct gtagacccac ccttaacgaa agttttccct 180
gatgacgaat cggatgacga gtctgatgct ggtgaggacg gtgaccctga ttccagaaca 240
tttgtcgcat acggagatga tggtgacctg gctggctttg ttgtggtgtc ctacagcgga 300

```
tggaatcgta gactcacagt tgaggacatc gaagttgcac ctgaacatcg tggtcacggt    360

gttggtcgtg cactgatggg actggcaaca gagtttgcta gagaaagagg agccggacat    420

ttgtggttag aagtgaccaa tgtcaacgct cctgctattc acgcatatag gcgaatgggt    480

ttcactttgt gcggtcttga tactgctttg tatgacggaa ctgcttctga tggtgaacaa    540

gctctttaca tgagtatgcc atgtccatag                                      570
```

```
<210> SEQ ID NO 482
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 482

cacgtccgac ggcggcccac gggtcccagg cctcggagat ccgtcccccct tttcctttgt     60

cgatatcatg taattagtta tgtcacgctt acattcacgc cctcccccca catccgctct    120

aaccgaaaag gaaggagtta gacaacctga agtctaggtc cctatttatt tttttatagt    180

tatgttagta ttaagaacgt tatttatatt tcaaattttt cttttttttc tgtacagacg    240

cgtgtacgca tgtaacatta tactgaaaac cttgcttgag aaggttttgg gacgctcgaa    300

ggctttaatt tgcaagct                                                   318
```

```
<210> SEQ ID NO 483
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483

ataacttcgt atagcataca ttataccttg ttat                                  34
```

```
<210> SEQ ID NO 484
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484

gcggccgcaa gaagttgatt gagactttca acgag                                 35
```

```
<210> SEQ ID NO 485
<211> LENGTH: 3869
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 485

tactacaggc tggctgttcc tcgcatggtg tttaatgtcc tgactgggtt ttcgtttatc     60

ggtattaccg gagccacctt gactgtaagg gaacgatact ggactaagag agtaatgcga    120

aaggcaacag cgtttctggc gaacctaatc aatgacggtt acgagtttac tactcctaaa    180

gccagtctta ttttgctaga gcgagtcaac gcttacttaa agggccaggg acctaattat    240

gacatcgatt ttgacgagca ggaggcgttc attaaagaaa tggaggagtt gaggacctct    300
```

```
ggtggatatg agaacagata ctcatattca ggaaccgatg aaacacccag agatccgggt    360
tgcctgtttc ttcccattgc tttaaataaa tggcactttg atgtgctaga ctgcctgagg    420
atatacggta ctcaggaaga tctggaatct aaattattaa gtgttcagca attggtgtta    480
caatgttgca tgaagcacag tggcatgact ccagacatgg tctttgcaac ggaagtagct    540
cagaagccga ccttcgaaga cgacatagtt tgtgatgata ttgacgctta tgcccagggg    600
ggtgattgtc tagattattg ttacacgcca agcaattact ccagaacttt agaaattcat    660
ggcaagattg ctaccttaca acgagagctg gggctatgct ataatattct cggaattttg    720
gaccgttttt ccgattaagg tttttagctc cattgcgcca acccccgctc tccagactcc    780
ttcgttatcc agcattcagc atggacaggt tcaaaaaata aaatttcttg atatgggtcc    840
acttcaaaca tgcgcctacc tgtaggaaaa aaaaagagaa cataaatatg ccgcgaacag    900
aaaacgtaat gtactgttct atatataaac tgttcagatc aatcataaat tctcagtttc    960
aaactttccg ctcagccaga ttttattcgt aaagaacgca tcattggctc tatgttgaag   1020
gatcagttct tgttatgggt tgctttgata gcgagcgtac cggtttccgg cgtgatggca   1080
gctcctagcg agtccgggca taacacggtt gaaaaacgag atgccaaaaa cgttgttggc   1140
gttcaacagt tggacttctt cagagtacag aagattaagt gagagaattc taccgttcgt   1200
atagcataca ttatacgaag ttatttcagt aatgtcttgt ttcttttgtt gcagtggtga   1260
gccattttga cttcgtgaaa gtttctttag aatagttgtt tccagaggcc aaacattcca   1320
cccgtagtaa agtgcaagcg taggaagacc aagactggca taaatcaggt ataagtgtcg   1380
agcactggca ggtgatcttc tgaaagtttc tactagcaga taagatccag tagtcatgca   1440
tatggcaaca atgtaccgtg tggatctaag aacgcgtcct actaaccttc gcattcgttg   1500
gtccagtttg ttgttatcga tcaacgtgac aaggttgtcg attccgcgta agcatgcata   1560
cccaaggacg cctgttgcaa ttccaagtga gccagttcca acaatctttg taatattaga   1620
gcacttcatt gtgttgcgct tgaaagtaaa atgcgaacaa attaagagat aatctcgaaa   1680
ccgcgacttc aaacgccaat atgatgtgcg gcacacaata agcgttcata tccgctgggt   1740
gactttctcg ctttaaaaaa ttatccgaaa aaatttttga cggctagctc agtcctaggt   1800
acgctagcat taaagaggag aaaatgacta ctcttgatga cacagcctac agatatagga   1860
catcagttcc gggtgacgca gaggctatcg aagccttgga cggttcattc actactgata   1920
cggtgtttag agtcaccgct acaggtgatg gcttcacctt gagagaggtt cctgtagacc   1980
cacccttaac gaaagttttc cctgatgacg aatcggatga cgagtctgat gctggtgagg   2040
acggtgaccc tgattccaga acatttgtcg catacggaga tgatggtgac ctggctggct   2100
ttgttgtggt gtcctacagc ggatggaatc gtagactcac agttgaggac atcgaagttg   2160
cacctgaaca tcgtggtcac ggtgttggtc gtgcactgat gggactggca acagagtttg   2220
ctagagaaag aggagccgga catttgtggt tagaagtgac caatgtcaac gctcctgcta   2280
ttcacgcata taggcgaatg ggtttcactt tgtgcggtct tgatactgct ttgtatgacg   2340
gaactgcttc tgatggtgaa caagctcttt acatgagtat gccatgtcca tagcacgtcc   2400
gacggcggcc cacgggtccc aggcctcgga gatccgtccc ccttttcctt tgtcgatatc   2460
atgtaattag ttatgtcacg cttacattca cgccctcccc ccacatccgc tctaaccgaa   2520
aaggaaggag ttagacaacc tgaagtctag gtccctattt atttttttat agttatgtta   2580
gtattaagaa cgttatttat atttcaaatt tttctttttt ttctgtacag acgcgtgtac   2640
```

```
gcatgtaaca ttatactgaa aaccttgctt gagaaggttt tgggacgctc gaaggcttta   2700
atttgcaagc tataacttcg tatagcatac attatacctt gttatgcggc cgcaagaagt   2760
tgattgagac tttcaacgag ggtccccttc agctaccttt ctctctgttt ggtagttatt   2820
ctcggcgtgt gtatagtata gtataaaagg gcctacattg gataggcttc aacattcctc   2880
aataaacaaa catccaacat cgcgcattcc gcatttcgca tttcacattt cgcgcctgcc   2940
ttcctttagg ttctttgaat catcatcaat cgtcgccgtc tacatcagag caggacttat   3000
ctttgccttc cccaaaaatt gccactccgt caaatagatt cttttgaatc cttgactatt   3060
tttgcctaaa taggtttttg ttagtttttc ttcaaagccc aaaagaaact ctatttagat   3120
tcatccagaa acaatctttt tctcacccca tttcgaagtg ccgtggagca cagacataaa   3180
aagatgacta ccgttcaacc tacagggcca gacaggctca ccctgccgca tattctactg   3240
gaattcaacg atggctcctc gcagcatgca gtgatcgagc taagcatgaa cgaggggatt   3300
aatatatcca cccatgagtg gaatccatcc actaatgagc aatcgccacg ggaagagaga   3360
gcaccacccc aacaatccaa tccatcgcat catccagaat catcgaacat agctactcaa   3420
agtcccgctc aggaaaccga gactcagccc ggcattccag gactagatag gcctgccttt   3480
gatacctcgg caacggggtc gtcagaacag gttgacccag tacagggaag gatcctggat   3540
gatattatag gccaatcatt aaggacttcc gaagaagacg ataccgaatc ccgccagaga   3600
ccacgagacc agaagaacat tatgatcacc gtgaattact tgtacgcaga cgacacaaat   3660
tccagaagtg ctaatacaaa caaccagacg cccaataaca cttctagaac ttccgacagt   3720
gaacgtgtgg gctccttatc gttgcacgtt ccggatctac cagataatgc cgacgattac   3780
tatatcgatg tactcattaa actaaccaca agcattgccc tcagcgtcat cacgtccatg   3840
atcaagaaac gattagggct tagcaggga                                      3869
```

<210> SEQ ID NO 486
<211> LENGTH: 1157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 486

```
tactacaggc tggctgttcc tcgcatggtg tttaatgtcc tgactgggtt ttcgtttatc     60
ggtattaccg gagccacctt gactgtaagg gaacgatact ggactaagag agtaatgcga    120
aaggcaacag cgtttctggc gaacctaatc aatgacggtt acgagtttac tactcctaaa    180
gccagtctta ttttgctaga gcgagtcaac gcttacttaa agggccaggg acctaattat    240
gacatcgatt ttgacgagca ggaggcgttc attaaagaaa tggaggagtt gaggacctct    300
ggtggatatg agaacagata ctcatattca ggaaccgatg aaacacccag agatccgggt    360
tgcctgtttc ttcccattgc tttaaataaa tggcactttg atgtgctaga ctgcctgagg    420
atatacggta ctcaggaaga tctggaatct aaattattaa gtgttcagca attggtgtta    480
caatgttgca tgaagcacag tggcatgact ccagacatgg tctttgcaac ggaagtagct    540
cagaagccga ccttcgaaga cgacatagtt tgtgatgata ttgacgctta tgcccagggg    600
ggtgattgtc tagattattg ttacacgcca agcaattact ccagaacttt agaaattcat    660
ggcaagattg ctaccttaca acgagagctg gggctatgct ataatattct cggaattttg    720
gaccgttttt ccgattaagg tttttagctc cattgcgcca acccccgctc tccagactcc    780
```

-continued

```
ttcgttatcc agcattcagc atggacaggt tcaaaaaata aaatttcttg atatgggtcc    840

acttcaaaca tgcgcctacc tgtaggaaaa aaaaagagaa cataaatatg ccgcgaacag    900

aaaacgtaat gtactgttct atatataaac tgttcagatc aatcataaat tctcagtttc    960

aaactttccg ctcagccaga ttttattcgt aaagaacgca tcattggctc tatgttgaag   1020

gatcagttct tgttatgggt tgctttgata gcgagcgtac cggtttccgg cgtgatggca   1080

gctcctagcg agtccgggca taacacggtt gaaaaacgag atgccaaaaa cgttgttggc   1140

gttcaacagt tggactt                                                  1157
```

<210> SEQ ID NO 487
<211> LENGTH: 1089
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 487

```
ggtccccttc agctaccttt ctctctgttt ggtagttatt ctcggcgtgt gtatagtata     60

gtataaaagg gcctacattg gataggcttc aacattcctc aataaacaaa catccaacat    120

cgcgcattcc gcatttcgca tttcacattt cgcgcctgcc ttcctttagg ttctttgaat    180

catcatcaat cgtcgccgtc tacatcagag caggacttat ctttgccttc cccaaaaatt    240

gccactccgt caaatagatt cttttgaatc cttgactatt tttgcctaaa taggtttttg    300

ttagtttttc ttcaaagccc aaaagaaact ctatttagat tcatccagaa acaatctttt    360

tctcacccca tttcgaagtg ccgtggagca cagacataaa aagatgacta ccgttcaacc    420

tacagggcca gacaggctca ccctgccgca tattctactg gaattcaacg atggctcctc    480

gcagcatgca gtgatcgagc taagcatgaa cgaggggatt aatatatcca cccatgagtg    540

gaatccatcc actaatgagc aatcgccacg ggaagagaga gcaccacccc aacaatccaa    600

tccatcgcat catccagaat catcgaacat agctactcaa agtcccgctc aggaaaccga    660

gactcagccc ggcattccag gactagatag gcctgccttt gatacctcgg caacggggtc    720

gtcagaacag gttgacccag tacagggaag gatcctggat gatattatag gccaatcatt    780

aaggacttcc gaagaagacg ataccgaatc ccgccagaga ccacgagacc agaagaacat    840

tatgatcacc gtgaattact tgtacgcaga cgacacaaat tccagaagtg ctaatacaaa    900

caaccagacg cccaataaca cttctagaac ttccgacagt gaacgtgtgg gctccttatc    960

gttgcacgtt ccggatctac cagataatgc cgacgattac tatatcgatg tactcattaa   1020

actaaccaca agcattgccc tcagcgtcat cacgtccatg atcaagaaac gattagggct   1080

tagcaggga                                                           1089
```

<210> SEQ ID NO 488
<211> LENGTH: 3964
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 488

```
gccttctcgt gcaatcagag ctgttgaaag agagaagagg gcacacggaa gctgctgttc     60

aattgtgtga attgaccgga ttacaacctg ctggagtgat aggagagctg gttcgtgacg    120

aggacggctc tatgatgcga ttagacgact gtgttcagtt tggtctccgc cacaacgtaa    180
```

-continued

```
aaattatcaa ccttgaccag atcattgaat acatggattc caagaacagc tagatacgat    240
ggataggaat acagagatat catgattgag gaacgtaaga gctttttcga aagtgtgagt    300
ttgtggtgag ggccaggcgg tggggaggtg gtggggagcc tccttggtcg aatgtagata    360
tagtaagcaa gacacaagag cgcgcgaagt cttcaacgag gcggcgttgg gtcttgtacg    420
caacgtaatg actacacagt tgagcttgtc gcgaaccggt cgacattttg atcatgcata    480
ctatgttgag acaccatctc gtactattgc ggcaaccagc tgtaaatttg actaattaaa    540
gctgatgaag gatgcagggc gtcgtcaatt ttttgattga ttgcatttaa ttgtttgagc    600
cattcaaggc tgaatgcccg gcaccctaga cccttcttgt gagtactata aacccgcagg    660
cagggtaccc ttggccttct gcgagactac cagtcataac gtatatccac aatgtactag    720
taatagcccc ggaaaactct aatcccacag aacgtctaac gcctcctatg tcatcgatac    780
ccattcgcac tactgccatg gcccccctta cgtgatcatt tcacttactc ccgcctaagc    840
ttcgcccaca tgcctgcgtt ttgccaagat ttactgacga gtttggttta ctcatcctct    900
atttataact actagacttt caccattctt caccaccctc gtgccaatga tcatcaacca    960
cttggtattg acagccctca gcattgcact agcaagtgcg caactccaat cgcctttcac   1020
ttcagagtac agaagattaa gtgagagaat tctaccgttc gtatagcata cattatacga   1080
agttatttca gtaatgtctt gtttcttttg ttgcagtggt gagccatttt gacttcgtga   1140
aagtttcttt agaatagttg tttccagagg ccaaacattc cacccgtagt aaagtgcaag   1200
cgtaggaaga ccaagactgg cataaatcag gtataagtgt cgagcactgg caggtgatct   1260
tctgaaagtt tctactagca gataagatcc agtagtcatg catatggcaa caatgtaccg   1320
tgtggatcta agaacgcgtc ctactaacct tcgcattcgt tggtccagtt tgttgttatc   1380
gatcaacgtg acaaggttgt cgattccgcg taagcatgca tacccaagga cgcctgttgc   1440
aattccaagt gagccagttc caacaatctt tgtaatatta gagcacttca ttgtgttgcg   1500
cttgaaagta aaatgcgaac aaattaagag ataatctcga aaccgcgact tcaaacgcca   1560
atatgatgtg cggcacacaa taagcgttca tatccgctgg gtgactttct cgctttaaaa   1620
aattatccga aaaaattttt gacggctagc tcagtcctag gtacgctagc attaaagagg   1680
agaaaatgac tactcttgat gacacagcct acagatatag gacatcagtt ccgggtgacg   1740
cagaggctat cgaagccttg gacggttcat tcactactga tacggtgttt agagtcaccg   1800
ctacaggtga tggcttcacc ttgagagagg ttcctgtaga cccaccctta acgaaagttt   1860
tccctgatga cgaatcggat gacgagtctg atgctggtga ggacggtgac cctgattcca   1920
gaacatttgt cgcatacgga gatgatggtg acctggctgg ctttgttgtg gtgtcctaca   1980
gcggatggaa tcgtagactc acagttgagg acatcgaagt tgcacctgaa catcgtggtc   2040
acggtgttgg tcgtgcactg atgggactgg caacagagtt tgctagagaa agaggagccg   2100
gacatttgtg gttagaagtg accaatgtca acgctcctgc tattcacgca tataggcgaa   2160
tgggtttcac tttgtgcggt cttgatactg ctttgtatga cggaactgct tctgatggtg   2220
aacaagctct ttacatgagt atgccatgtc catagcacgt ccgacggcgg cccacgggtc   2280
ccaggcctcg gagatccgtc cccctttcc tttgtcgata tcatgtaatt agttatgtca   2340
cgcttacatt cacgccctcc ccccacatcc gctctaaccg aaaaggaagg agttagacaa   2400
cctgaagtct aggtccctat ttattttttt atagttatgt tagtattaag aacgttattt   2460
atatttcaaa tttttctttt ttttctgtac agacgcgtgt acgcatgtaa cattatactg   2520
```

```
aaaaccttgc ttgagaaggt tttgggacgc tcgaaggctt taatttgcaa gctataactt   2580

cgtatagcat acattatacc ttgttatgcg gccgcaagaa gttgattgag actttcaacg   2640

agctggctct gcttctggta cttcttcagg tgcatcttct gctactcaaa atgacgaaac   2700

atccactgat cttggagctc cagctgcatc tttaagtgca acgccatgtc tttttgccat   2760

cttgctgctc atgttgtagt agactttttt tttcactgag tttttatgta ctactgatta   2820

cattgtgtag gtgtaatgat gtgcactata atactaatat agtcaaaatg ctacagagga   2880

aagtgcaggt tgcctgtggt ggtttttctt attagcaccc tctgaacact ctttacctct   2940

aacatcctca gccatgctaa tcgcgcataa aataaatctt cgaacttttt tccattttat   3000

gctcataaag cttccttact gtcaccttat caaaagagct tttgccacta aagtagtcac   3060

acccagaatt gctcccgaat atcgtccaac aatgctagga tctgtggaaa gtttgacaaa   3120

taatttgaac accttgagct tgaagcttcc tgaagttaat atccaaggct cctttccaga   3180

aagtaaccca gtggaccttt tgagaaacta catcactcaa gaacttagta aaatttctgg   3240

agttgacaaa gaattgattt tcccagcctt ggaatggggt accacactgg aaaaaggtga   3300

tcttttgatc ccagttcctc gtctgagaat aaagggtgct aatcctaaag atttagccga   3360

acaatgggct gctgcattcc caaagggtgg atatcttaaa gacgttattg cgcaaggacc   3420

tttcttgcag ttctttttta acacatcggt tctgtacaag ttggtgatat ctgatgctct   3480

ggagagaggc gatgactttg gtgcacttcc tctaggaaag ggacaaaaag ttatagtgga   3540

gttttcttct ccaaatattg ccaaaccttt ccacgctggc catcttagaa gtacaatcat   3600

cggtggtttt atttccaatc tgtatgaaaa gctgggtcat gaagttatga ggatgaatta   3660

tttgggagac tggggaaaac aatttggtgt tcttgcagta ggatttgagc gttacggtga   3720

tgaggcaaaa ttaaagactg atccaatcaa ccatttgttt gaggtctatg ttaaaatcaa   3780

ccaagatatt aaggctcaat cagagtctac tgaggagatt gcagaagggc aatcattaga   3840

tgaccaggca agagcttttt tcaagaaaat ggaaaatggc gacgaatcgg ctgtaagctt   3900

gtggaaaaga ttccgtgagt tatccattga gaagtacatt gatacttatg cccgcctcaa   3960

catc                                                                3964
```

<210> SEQ ID NO 489
<211> LENGTH: 1019
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 489

```
gccttctcgt gcaatcagag ctgttgaaag agagaagagg gcacacggaa gctgctgttc     60

aattgtgtga attgaccgga ttacaacctg ctggagtgat aggagagctg gttcgtgacg    120

aggacggctc tatgatgcga ttagacgact gtgttcagtt tggtctccgc cacaacgtaa    180

aaattatcaa ccttgaccag atcattgaat acatggattc caagaacagc tagatacgat    240

ggataggaat acagagatat catgattgag gaacgtaaga gctttttcga aagtgtgagt    300

ttgtggtgag ggccaggcgg tggggaggtg gtggggagcc tccttggtcg aatgtagata    360

tagtaagcaa gacacaagag cgcgcgaagt cttcaacgag gcggcgttgg gtcttgtacg    420

caacgtaatg actacacagt tgagcttgtc gcgaaccggt cgacattttg atcatgcata    480

ctatgttgag acaccatctc gtactattgc ggcaaccagc tgtaaatttg actaattaaa    540
```

```
gctgatgaag gatgcagggc gtcgtcaatt ttttgattga ttgcatttaa ttgtttgagc    600

cattcaaggc tgaatgcccg gcaccctaga cccttcttgt gagtactata aacccgcagg    660

cagggtaccc ttggccttct gcgagactac cagtcataac gtatatccac aatgtactag    720

taatagcccc ggaaaactct aatcccacag aacgtctaac gcctcctatg tcatcgatac    780

ccattcgcac tactgccatg gcccccctta cgtgatcatt tcacttactc ccgcctaagc    840

ttcgcccaca tgcctgcgtt ttgccaagat ttactgacga gtttggttta ctcatcctct    900

atttataact actagacttt caccattctt caccaccctc gtgccaatga tcatcaacca    960

cttggtattg acagccctca gcattgcact agcaagtgcg caactccaat cgcctttca   1019
```

<210> SEQ ID NO 490
<211> LENGTH: 1322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 490

```
ctggctctgc ttctggtact tcttcaggtg catcttctgc tactcaaaat gacgaaacat     60

ccactgatct tggagctcca gctgcatctt taagtgcaac gccatgtctt tttgccatct    120

tgctgctcat gttgtagtag acttttttttt tcactgagtt tttatgtact actgattaca    180

ttgtgtaggt gtaatgatgt gcactataat actaatatag tcaaaatgct acagaggaaa    240

gtgcaggttg cctgtggtgg ttttctttat tagcaccctc tgaacactct ttacctctaa    300

catcctcagc catgctaatc gcgcataaaa taaatcttcg aacttttttc cattttatgc    360

tcataaagct tccttactgt caccttatca aaagagcttt tgccactaaa gtagtcacac    420

ccagaattgc tcccgaatat cgtccaacaa tgctaggatc tgtggaaagt ttgacaaata    480

atttgaacac cttgagcttg aagcttcctg aagttaatat ccaaggctcc tttccagaaa    540

gtaacccagt ggaccttttg agaaactaca tcactcaaga acttagtaaa atttctggag    600

ttgacaaaga attgattttc ccagccttgg aatggggtac cacactggaa aaaggtgatc    660

ttttgatccc agttcctcgt ctgagaataa agggtgctaa tcctaaagat ttagccgaac    720

aatgggctgc tgcattccca aagggtggat atcttaaaga cgttattgcg caaggacctt    780

tcttgcagtt cttttttaac acatcggttc tgtacaagtt ggtgatatct gatgctctgg    840

agagaggcga tgactttggt gcacttcctc taggaaaggg acaaaaagtt atagtggagt    900

tttcttctcc aaatattgcc aaacctttcc acgctggcca tcttagaagt acaatcatcg    960

gtggttttat ttccaatctg tatgaaaagc tgggtcatga agttatgagg atgaattatt   1020

tgggagactg gggaaaacaa tttggtgttc ttgcagtagg atttgagcgt tacggtgatg   1080

aggcaaaatt aaagactgat ccaatcaacc atttgtttga ggtctatgtt aaaatcaacc   1140

aagatattaa ggctcaatca gagtctactg aggagattgc agaagggcaa tcattagatg   1200

accaggcaag agcttttttc aagaaaatgg aaaatggcga cgaatcggct gtaagcttgt   1260

ggaaaagatt ccgtgagtta tccattgaga agtacattga tacttatgcc cgcctcaaca   1320

tc                                                                  1322
```

<210> SEQ ID NO 491
<211> LENGTH: 3932
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 491
gacgagacgc tgttcctttc aacttgtcca cttggactga caagtcaaca cctgttacta 60
attcttttgt catctctcag tatgaagaca cgcgtgttcc tcaatcagcc accagttcta 120
cacatccaaa catacctaaa cacgccaaag agtatccgtt agcaaatggg ccacctgggt 180
ggtgttggaa ttcccattcc agtatgtcga cagaccaacc aatatatcca ggacaccaat 240
atccaccacc gcttcagcag cactaccact ttgcttcacc caggcaacta tcaaactcta 300
gctctgggac gtcatccgtt cctttccaac cacccccctgc tggtcaatta caaccacaag 360
gtaattctat gttcatacac atgccatttt cgctaaatgg cccaccagct gctggacagc 420
aattgatacc accccaagga ctagcctcaa tacctgtcgg ccccggcaac aacagttccc 480
tattggttag ccaaggtgca cctggcggct attctttagc ttcaccagcg ttgtcaccgg 540
tagatgcgac cttcgaagat cccgtcaaga gactgcccaa aaagcggaca aaaactggat 600
gtctcacttg ccgtaagaga cgaatcaaat gtgacgaacg caagccgttc tgtttcaact 660
gtgaaaaaag caaaaaggtg tgtactggtt ttacgcatct attcaaagat ccccctagca 720
aatcctaccc tcccagttca gatggtgcct cccctgttgc caatgaccac cctgtccccc 780
caaggcaaaa ctttggtgaa ttgaggggca gtctgaatta catcatcaac tagaagaatg 840
cttattcctt ttctctactg tataatcacg acgttatgtc ctttaatata agaaacgaca 900
attaaaccac tttaggtgga cataatccat ttctggatgc tgttcgatgt gtagtgtcta 960
aaccgatact gagatttctc tttctctttc tctttttttt tttttcccta ccatttcctt 1020
caagaaaata cacctttcga cagatcatca taaatggtgg cctctcttca cacttcagag 1080
tacagaagat taagtgagag aattctaccg ttcgtatagc atacattata cgaagttatt 1140
tcagtaatgt cttgtttctt ttgttgcagt ggtgagccat tttgacttcg tgaaagtttc 1200
tttagaatag ttgtttccag aggccaaaca ttccacccgt agtaaagtgc aagcgtagga 1260
agaccaagac tggcataaat caggtataag tgtcgagcac tggcaggtga tcttctgaaa 1320
gtttctacta gcagataaga tccagtagtc atgcatatgg caacaatgta ccgtgtggat 1380
ctaagaacgc gtcctactaa ccttcgcatt cgttggtcca gtttgttgtt atcgatcaac 1440
gtgacaaggt tgtcgattcc gcgtaagcat gcatacccaa ggacgcctgt tgcaattcca 1500
agtgagccag ttccaacaat ctttgtaata ttagagcact tcattgtgtt gcgcttgaaa 1560
gtaaaatgcg aacaaattaa gagataatct cgaaaccgcg acttcaaacg ccaatatgat 1620
gtgcggcaca caataagcgt tcatatccgc tgggtgactt tctcgcttta aaaaattatc 1680
cgaaaaaatt tttgacggct agctcagtcc taggtacgct agcattaaag aggagaaaat 1740
gactactctt gatgacacag cctacagata taggacatca gttccgggtg acgcagaggc 1800
tatcgaagcc ttggacggtt cattcactac tgatacggtg tttagagtca ccgctacagg 1860
tgatggcttc accttgagag aggttcctgt agacccaccc ttaacgaaag ttttccctga 1920
tgacgaatcg gatgacgagt ctgatgctgg tgaggacggt gaccctgatt ccagaacatt 1980
tgtcgcatac ggagatgatg gtgacctggc tggctttgtt gtggtgtcct acagcggatg 2040
gaatcgtaga ctcacagttg aggacatcga agttgcacct gaacatcgtg gtcacggtgt 2100
tggtcgtgca ctgatgggac tggcaacaga gtttgctaga gaaagaggag ccggacattt 2160
gtggttagaa gtgaccaatg tcaacgctcc tgctattcac gcatataggc gaatgggttt 2220
cactttgtgc ggtcttgata ctgctttgta tgacggaact gcttctgatg gtgaacaagc 2280
tctttacatg agtatgccat gtccatagca cgtccgacgg cggcccacgg gtcccaggcc 2340
tcggagatcc gtcccccttt tcctttgtcg atatcatgta attagttatg tcacgcttac 2400
attcacgccc tccccccaca tccgctctaa ccgaaaagga aggagttaga caacctgaag 2460
tctaggtccc tatttatttt tttatagtta tgttagtatt aagaacgtta tttatatttc 2520
aaatttttct ttttttctg tacagacgcg tgtacgcatg taacattata ctgaaaacct 2580
tgcttgagaa ggttttggga cgctcgaagg ctttaatttg caagctataa cttcgtatag 2640
catacattat accttgttat gcggccgcaa gaagttgatt gagactttca acgagtgatc 2700
gactacttgg cctccgccgt gaaaactcaa ttagatgtta gctccaaatt aatgaacctg 2760
gtacaagatg ataaatagga actcaaatac aaagcctacc attaatgact gttttatttt 2820
tatactaaag tagctaaagg gtgattatca aggagtggtt aacgatctat tcctagcagg 2880
gcactcagct catcgatctt tccaatatcg gcgtataacg cttccacttc tatcaacgta 2940
tcttcgttaa aaagaccacc tctggtggga actaatcctt ctgctgccgc ctctgctaaa 3000
ctctgtcttc gaatccgttt cttactaaca tcagcttcga cagataagcc actcttcttt 3060
atctttttct tagatcctgt tttgaatctc agggacttta ctggtgccat aacaacttcc 3120
tgttccagta ccttgttctt cttactcttt tttggtatta aagaatgtcc cgccttgagt 3180
cctcgatcat ccttggccat actcaatcgt ctagtagtgc tgttgaaatg ctgtaaagaa 3240
gaggaatatc ttcttaaatg gttggtatct ttttcagcaa ccacaccttt gtttcggaaa 3300
gcggataatg gcacattgct tggattgata gaagaagcta taaaagccca tcctgcgttt 3360
ggagcagttt gattgctctg agttactatg ttcaactgtg tattggcaaa agccttagag 3420
tcgctgtctg attcgcttat attgagtaaa tcatccaggt ccaatagagg aacagaacca 3480
gtctgcttcc cttttggttt tgtacgatcc ctaattgcac ccttcacaga aagttctacc 3540
cgtttggact ttatactgtc tttgttctct gatactgatc gcattgaaaa cccatcaata 3600
atctcaaagg gtttgccaca gtccgaggtg gtccaaattc caatcactgg agggatagga 3660
tccactttgg aagatgccag aacttctttt gcaattttgg taccaatttt tttattggat 3720
gttttgggaa gagcttcatc ttcatcagtg gagttgctgc tttcgttgtc atctactttt 3780
tggtcatctt ctagttcgtc gtcgtctgaa gcaatagcat ctgaggagga cgcatctcct 3840
tcacctttga aaaagtaatt aaataggtag gagtcatcat cagaatcttg ttcttggtct 3900 gatcccttt cgacggcagc ttgaatgttg tt 3932

<210> SEQ ID NO 492
<211> LENGTH: 1072
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 492
gacgagacgc tgttcctttc aacttgtcca cttggactga caagtcaaca cctgttacta 60
attcttttgt catctctcag tatgaagaca cgcgtgttcc tcaatcagcc accagttcta 120
cacatccaaa catacctaaa cacgccaaag agtatccgtt agcaaatggg ccacctgggt 180
ggtgttggaa ttcccattcc agtatgtcga cagaccaacc aatatatcca ggacaccaat 240
atccaccacc gcttcagcag cactaccact ttgcttcacc caggcaacta tcaaactcta 300
gctctgggac gtcatccgtt cctttccaac caccccctgc tggtcaatta caaccacaag 360
gtaattctat gttcatacac atgccatttt cgctaaatgg cccaccagct gctggacagc 420
aattgatacc accccaagga ctagcctcaa tacctgtcgg ccccggcaac aacagttccc 480
tattggttag ccaaggtgca cctggcggct attctttagc ttcaccagcg ttgtcaccgg 540
tagatgcgac cttcgaagat cccgtcaaga gactgcccaa aaagcggaca aaaactggat 600
gtctcacttg ccgtaagaga cgaatcaaat gtgacgaacg caagccgttc tgtttcaact 660
gtgaaaaaag caaaaaggtg tgtactggtt ttacgcatct attcaaagat ccccctagca 720
aatcctaccc tcccagttca gatggtgcct cccctgttgc caatgaccac cctgtccccc 780
caaggcaaaa ctttggtgaa ttgaggggca gtctgaatta catcatcaac tagaagaatg 840
cttattcctt ttctctactg tataatcacg acgttatgtc ctttaatata agaaacgaca 900
attaaaccac tttaggtgga cataatccat ttctggatgc tgttcgatgt gtagtgtcta 960
aaccgatact gagatttctc tttctctttc tctttttttt ttttttccta ccatttcctt 1020
caagaaaata cacctttcga cagatcatca taaatggtgg cctctcttca ca 1072

<210> SEQ ID NO 493
<211> LENGTH: 1237
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 493
tgatcgacta cttggcctcc gccgtgaaaa ctcaattaga tgttagctcc aaattaatga 60
acctggtaca agatgataaa taggaactca aatacaaagc ctaccattaa tgactgtttt 120
atttttatac taaagtagct aaagggtgat tatcaaggag tggttaacga tctattccta 180
gcagggcact cagctcatcg atctttccaa tatcggcgta taacgcttcc acttctatca 240
acgtatcttc gttaaaaaga ccacctctgg tgggaactaa tccttctgct gccgcctctg 300
ctaaactctg tcttcgaatc cgtttcttac taacatcagc ttcgacagat aagccactct 360
tctttatctt tttcttagat cctgttttga atctcaggga ctttactggt gccataacaa 420
cttcctgttc cagtaccttg ttcttcttac tcttttttgg tattaaagaa tgtcccgcct 480
tgagtcctcg atcatccttg gccatactca atcgtctagt agtgctgttg aaatgctgta 540
aagaagagga atatcttctt aaatggttgg tatctttttc agcaaccaca cctttgtttc 600
ggaaagcgga taatggcaca ttgcttggat tgatagaaga agctataaaa gcccatcctg 660
cgtttggagc agtttgattg ctctgagtta ctatgttcaa ctgtgtattg gcaaaagcct 720
tagagtcgct gtctgattcg cttatattga gtaaatcatc caggtccaat agaggaacag 780
aaccagtctg cttccctttt ggttttgtac gatccctaat tgcacccttc acagaaagtt 840
ctacccgttt ggactttata ctgtctttgt tctctgatac tgatcgcatt gaaaacccat 900
caataatctc aaagggtttg ccacagtccg aggtggtcca aattccaatc actggaggga 960
taggatccac tttggaagat gccagaactt cttttgcaat tttggtacca attttttat 1020 tggatgtttt gggaagagct tcatcttcat cagtggagtt gctgctttcg ttgtcatcta 1080
ctttttggtc atcttctagt tcgtcgtcgt ctgaagcaat agcatctgag gaggacgcat 1140
ctccttcacc tttgaaaaag taattaaata ggtaggagtc atcatcagaa tcttgttctt 1200
ggtctgatcc cctttcgacg gcagcttgaa tgttgtt 1237

<210> SEQ ID NO 494
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 494

Ser Gly Ala Gly Gly
1 5

<210> SEQ ID NO 495
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 495

Gly Ser Gly Ala Gly
1 5

<210> SEQ ID NO 496
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 496

Gly Gly Ser Gly Ala
1 5

<210> SEQ ID NO 497
<211> LENGTH: 181
<212> TYPE: PRT
<213> ORGANISM: Aliatypus gulosus

<400> SEQUENCE: 497

Gly Ala Ala Ser Ser Ser Ser Thr Ile Ile Thr Thr Lys Ser Ala Ser
1 5 10 15

Ala Ser Ala Ala Ala Asp Ala Ser Ala Ala Ala Thr Ala Ser Ala Ala
20 25 30

Ser Arg Ser Ser Ala Asn Ala Ala Ala Ser Ala Phe Ala Gln Ser Phe
35 40 45

Ser Ser Ile Leu Leu Glu Ser Gly Tyr Phe Cys Ser Ile Phe Gly Ser
50 55 60

Ser Ile Ser Ser Ser Tyr Ala Ala Ala Ile Ala Ser Ala Ala Ser Arg
65 70 75 80

Ala Ala Ala Glu Ser Asn Gly Tyr Thr Thr His Ala Tyr Ala Cys Ala
85 90 95

Lys Ala Val Ala Ser Ala Val Glu Arg Val Thr Ser Gly Ala Asp Ala
100 105 110

Tyr Ala Tyr Ala Gln Ala Ile Ser Asp Ala Leu Ser His Ala Leu Leu
115 120 125

Tyr Thr Gly Arg Leu Asn Thr Ala Asn Ala Asn Ser Leu Ala Ser Ala
130 135 140

Phe Ala Tyr Ala Phe Ala Asn Ala Ala Ala Gln Ala Ser Ala Ser Ser
145 150 155 160

Ala Ser Ala Gly Ala Ala Ser Ala Ser Gly Ala Ala Ser Ala Ser Gly
165 170 175

Ala Gly Ser Ala Ser
180

<210> SEQ ID NO 498
<211> LENGTH: 126
<212> TYPE: PRT
<213> ORGANISM: Plectreurys tristis

<400> SEQUENCE: 498

Gly Ala Gly Ala Gly Ala Gly Ala Gly Ala Gly Ala Gly Ala Gly Ala
1 5 10 15

Gly Ser Gly Ala Ser Thr Ser Val Ser Thr Ser Ser Ser Ser Gly Ser
20 25 30

Gly Ala Gly Ala Gly Ala Gly Ser Gly Ala Gly Ser Gly Ala Gly Ala
35 40 45

Gly Ser Gly Ala Gly Ala Gly Ala Gly Ala Gly Gly Ala Gly Ala Gly
50 55 60

Phe Gly Ser Gly Leu Gly Leu Gly Tyr Gly Val Gly Leu Ser Ser Ala
65 70 75 80

Gln Ala Gln Ala Gln Ala Gln Ala Ala Ala Gln Ala Gln Ala Gln Ala
85 90 95

Gln Ala Gln Ala Tyr Ala Ala Ala Gln Ala Gln Ala Gln Ala Gln Ala
100 105 110

Gln Ala Gln Ala Ala Ala Ala Ala Ala Ala Ala Ala Ala Ala
115 120 125

<210> SEQ ID NO 499
<211> LENGTH: 239
<212> TYPE: PRT
<213> ORGANISM: Plectreurys tristis

<400> SEQUENCE: 499

Gly Ala Ala Gln Lys Gln Pro Ser Gly Glu Ser Ser Val Ala Thr Ala
1 5 10 15

Ser Ala Ala Ala Thr Ser Val Thr Ser Gly Gly Ala Pro Val Gly Lys
20 25 30

Pro Gly Val Pro Ala Pro Ile Phe Tyr Pro Gln Gly Pro Leu Gln Gln
35 40 45

Gly Pro Ala Pro Gly Pro Ser Asn Val Gln Pro Gly Thr Ser Gln Gln
50 55 60

Gly Pro Ile Gly Gly Val Gly Gly Ser Asn Ala Phe Ser Ser Ser Phe
65 70 75 80

Ala Ser Ala Leu Ser Leu Asn Arg Gly Phe Thr Glu Val Ile Ser Ser
85 90 95

Ala Ser Ala Thr Ala Val Ala Ser Ala Phe Gln Lys Gly Leu Ala Pro
100 105 110

Tyr Gly Thr Ala Phe Ala Leu Ser Ala Ala Ser Ala Ala Ala Asp Ala
115 120 125

Tyr Asn Ser Ile Gly Ser Gly Ala Asn Ala Phe Ala Tyr Ala Gln Ala
130 135 140

Phe Ala Arg Val Leu Tyr Pro Leu Val Gln Gln Tyr Gly Leu Ser Ser
145 150 155 160

Ser Ala Lys Ala Ser Ala Phe Ala Ser Ala Ile Ala Ser Ser Phe Ser
165 170 175

Ser Gly Thr Ser Gly Gln Gly Pro Ser Ile Gly Gln Gln Gln Pro Pro
180 185 190

Val Thr Ile Ser Ala Ala Ser Ala Ser Ala Gly Ala Ser Ala Ala Ala
195 200 205

Val Gly Gly Gly Gln Val Gly Gln Gly Pro Tyr Gly Gly Gln Gln Gln
210 215 220

Ser Thr Ala Ala Ser Ala Ser Ala Ala Ala Ala Thr Ala Thr Ser
225 230 235

<210> SEQ ID NO 500
<211> LENGTH: 182
<212> TYPE: PRT
<213> ORGANISM: Araneus gemmoides

<400> SEQUENCE: 500

Gly Asn Val Gly Tyr Gln Leu Gly Leu Lys Val Ala Asn Ser Leu Gly
1 5 10 15

Leu Gly Asn Ala Gln Ala Leu Ala Ser Ser Leu Ser Gln Ala Val Ser
20 25 30

Ala Val Gly Val Gly Ala Ser Ser Asn Ala Tyr Ala Asn Ala Val Ser
35 40 45

Asn Ala Val Gly Gln Val Leu Ala Gly Gln Gly Ile Leu Asn Ala Ala
50 55 60

Asn Ala Gly Ser Leu Ala Ser Ser Phe Ala Ser Ala Leu Ser Ser Ser
65 70 75 80

Ala Ala Ser Val Ala Ser Gln Ser Ala Ser Gln Ser Gln Ala Ala Ser
85 90 95

Gln Ser Gln Ala Ala Ala Ser Ala Phe Arg Gln Ala Ala Ser Gln Ser
100 105 110

Ala Ser Gln Ser Asp Ser Arg Ala Gly Ser Gln Ser Ser Thr Lys Thr
115 120 125

Thr Ser Thr Ser Thr Ser Gly Ser Gln Ala Asp Ser Arg Ser Ala Ser
130 135 140

Ser Ser Ala Ser Gln Ala Ser Ala Ser Ala Phe Ala Gln Gln Ser Ser
145 150 155 160

Ala Ser Leu Ser Ser Ser Ser Ser Phe Ser Ser Ala Phe Ser Ser Ala
165 170 175

Thr Ser Ile Ser Ala Val
180

<210> SEQ ID NO 501
<211> LENGTH: 180
<212> TYPE: PRT
<213> ORGANISM: Argiope aurantia

<400> SEQUENCE: 501

Gly Ser Leu Ala Ser Ser Phe Ala Ser Ala Leu Ser Ala Ser Ala Ala
1 5 10 15

Ser Val Ala Ser Ser Ala Ala Ala Gln Ala Ala Ser Gln Ser Gln Ala
20 25 30

Ala Ala Ser Ala Phe Ser Arg Ala Ala Ser Gln Ser Ala Ser Gln Ser
35 40 45

Ala Ala Arg Ser Gly Ala Gln Ser Ile Ser Thr Thr Thr Thr Thr Ser
50 55 60

Thr Ala Gly Ser Gln Ala Ala Ser Gln Ser Ala Ser Ser Ala Ala Ser
65 70 75 80

```
Gln Ala Ser Ala Ser Ser Phe Ala Arg Ala Ser Ser Ala Ser Leu Ala
                85                  90                  95

Ala Ser Ser Ser Phe Ser Ser Ala Phe Ser Ser Ala Asn Ser Leu Ser
            100                 105                 110

Ala Leu Gly Asn Val Gly Tyr Gln Leu Gly Phe Asn Val Ala Asn Asn
        115                 120                 125

Leu Gly Ile Gly Asn Ala Ala Gly Leu Gly Asn Ala Leu Ser Gln Ala
    130                 135                 140

Val Ser Ser Val Gly Val Gly Ala Ser Ser Ser Thr Tyr Ala Asn Ala
145                 150                 155                 160

Val Ser Asn Ala Val Gly Gln Phe Leu Ala Gly Gln Gly Ile Leu Asn
                165                 170                 175

Ala Ala Asn Ala
            180


<210> SEQ ID NO 502
<211> LENGTH: 199
<212> TYPE: PRT
<213> ORGANISM: Deinopis spinosa

<400> SEQUENCE: 502

Gly Ala Ser Ala Ser Ala Tyr Ala Ser Ala Ile Ser Asn Ala Val Gly
1               5                   10                  15

Pro Tyr Leu Tyr Gly Leu Gly Leu Phe Asn Gln Ala Asn Ala Ala Ser
            20                  25                  30

Phe Ala Ser Ser Phe Ala Ser Ala Val Ser Ser Ala Val Ala Ser Ala
        35                  40                  45

Ser Ala Ser Ala Ala Ser Ser Ala Tyr Ala Gln Ser Ala Ala Ala Gln
    50                  55                  60

Ala Gln Ala Ala Ser Ser Ala Phe Ser Gln Ala Ala Ala Gln Ser Ala
65                  70                  75                  80

Ala Ala Ala Ser Ala Gly Ala Ser Ala Gly Ala Gly Ala Ser Ala Gly
                85                  90                  95

Ala Gly Ala Val Ala Gly Ala Gly Ala Val Ala Gly Ala Gly Ala Val
            100                 105                 110

Ala Gly Ala Ser Ala Ala Ala Ala Ser Gln Ala Ala Ala Ser Ser Ser
        115                 120                 125

Ala Ser Ala Val Ala Ser Ala Phe Ala Gln Ser Ala Ser Tyr Ala Leu
    130                 135                 140

Ala Ser Ser Ser Ala Phe Ala Asn Ala Phe Ala Ser Ala Thr Ser Ala
145                 150                 155                 160

Gly Tyr Leu Gly Ser Leu Ala Tyr Gln Leu Gly Leu Thr Thr Ala Tyr
                165                 170                 175

Asn Leu Gly Leu Ser Asn Ala Gln Ala Phe Ala Ser Thr Leu Ser Gln
            180                 185                 190

Ala Val Thr Gly Val Gly Leu
        195


<210> SEQ ID NO 503
<211> LENGTH: 171
<212> TYPE: PRT
<213> ORGANISM: Nephila clavipes

<400> SEQUENCE: 503

Gly Ala Thr Ala Ala Ser Tyr Gly Asn Ala Leu Ser Thr Ala Ala Ala
1               5                   10                  15
```

```
Gln Phe Phe Ala Thr Ala Gly Leu Leu Asn Ala Gly Asn Ala Ser Ala
            20                  25                  30

Leu Ala Ser Ser Phe Ala Arg Ala Phe Ser Ala Ser Ala Glu Ser Gln
        35                  40                  45

Ser Phe Ala Gln Ser Gln Ala Phe Gln Gln Ala Ser Ala Phe Gln Gln
    50                  55                  60

Ala Ala Ser Arg Ser Ala Ser Gln Ser Ala Ala Glu Ala Gly Ser Thr
65                  70                  75                  80

Ser Ser Ser Thr Thr Thr Thr Thr Ser Ala Ala Arg Ser Gln Ala Ala
                85                  90                  95

Ser Gln Ser Ala Ser Ser Ser Tyr Ser Ser Ala Phe Ala Gln Ala Ala
            100                 105                 110

Ser Ser Ser Leu Ala Thr Ser Ser Ala Leu Ser Arg Ala Phe Ser Ser
        115                 120                 125

Val Ser Ser Ala Ser Ala Ala Ser Ser Leu Ala Tyr Ser Ile Gly Leu
    130                 135                 140

Ser Ala Ala Arg Ser Leu Gly Ile Ala Asp Ala Ala Gly Leu Ala Gly
145                 150                 155                 160

Val Leu Ala Arg Ala Ala Gly Ala Leu Gly Gln
                165                 170
```

<210> SEQ ID NO 504
<211> LENGTH: 268
<212> TYPE: PRT
<213> ORGANISM: Argiope trifasciata

<400> SEQUENCE: 504

```
Gly Gly Ala Pro Gly Gly Gly Pro Gly Gly Ala Gly Pro Gly Gly Ala
1               5                   10                  15

Gly Phe Gly Pro Gly Gly Gly Ala Gly Phe Gly Pro Gly Gly Gly Ala
            20                  25                  30

Gly Phe Gly Pro Gly Gly Ala Ala Gly Gly Pro Gly Gly Pro Gly Gly
        35                  40                  45

Pro Gly Gly Pro Gly Gly Ala Gly Gly Tyr Gly Pro Gly Gly Ala Gly
    50                  55                  60

Gly Tyr Gly Pro Gly Gly Val Gly Pro Gly Gly Ala Gly Gly Tyr Gly
65                  70                  75                  80

Pro Gly Gly Ala Gly Gly Tyr Gly Pro Gly Gly Ser Gly Pro Gly Gly
                85                  90                  95

Ala Gly Pro Gly Gly Ala Gly Gly Glu Gly Pro Val Thr Val Asp Val
            100                 105                 110

Asp Val Thr Val Gly Pro Glu Gly Val Gly Gly Gly Pro Gly Gly Ala
        115                 120                 125

Gly Pro Gly Gly Ala Gly Phe Gly Pro Gly Gly Gly Ala Gly Phe Gly
    130                 135                 140

Pro Gly Gly Ala Pro Gly Ala Pro Gly Gly Pro Gly Gly Pro Gly Gly
145                 150                 155                 160

Pro Gly Gly Pro Gly Gly Pro Gly Gly Val Gly Pro Gly Gly Ala Gly
                165                 170                 175

Gly Tyr Gly Pro Gly Gly Ala Gly Gly Val Gly Pro Ala Gly Thr Gly
            180                 185                 190

Gly Phe Gly Pro Gly Gly Ala Gly Gly Phe Gly Pro Gly Gly Ala Gly
        195                 200                 205

Gly Phe Gly Pro Gly Gly Ala Gly Gly Phe Gly Pro Ala Gly Ala Gly
```

```
    210                 215                 220

Gly Tyr Gly Pro Gly Gly Val Gly Pro Gly Gly Ala Gly Gly Phe Gly
225                 230                 235                 240

Pro Gly Gly Val Gly Pro Gly Gly Ser Gly Pro Gly Gly Ala Gly Gly
                245                 250                 255

Glu Gly Pro Val Thr Val Asp Val Asp Val Ser Val
            260                 265


<210> SEQ ID NO 505
<211> LENGTH: 420
<212> TYPE: PRT
<213> ORGANISM: Nephila clavipes

<400> SEQUENCE: 505

Gly Val Ser Tyr Gly Pro Gly Gly Ala Gly Gly Pro Tyr Gly Pro Gly
1               5                   10                  15

Gly Pro Tyr Gly Pro Gly Gly Glu Gly Pro Gly Gly Ala Gly Gly Pro
            20                  25                  30

Tyr Gly Pro Gly Gly Val Gly Pro Gly Gly Ser Gly Pro Gly Gly Tyr
        35                  40                  45

Gly Pro Gly Gly Ala Gly Pro Gly Gly Tyr Gly Pro Gly Gly Ser Gly
    50                  55                  60

Pro Gly Gly Tyr Gly Pro Gly Gly Ser Gly Pro Gly Gly Tyr Gly Pro
65                  70                  75                  80

Gly Gly Ser Gly Pro Gly Gly Tyr Gly Pro Gly Gly Ser Gly Pro Gly
                85                  90                  95

Gly Tyr Gly Pro Gly Gly Tyr Gly Pro Gly Gly Ser Gly Pro Gly Gly
            100                 105                 110

Ser Gly Pro Gly Gly Ser Gly Pro Gly Gly Tyr Gly Pro Gly Gly Thr
        115                 120                 125

Gly Pro Gly Gly Ser Gly Pro Gly Gly Tyr Gly Pro Gly Gly Ser Gly
    130                 135                 140

Pro Gly Gly Ser Gly Pro Gly Gly Tyr Gly Pro Gly Gly Ser Gly Pro
145                 150                 155                 160

Gly Gly Phe Gly Pro Gly Gly Ser Gly Pro Gly Gly Tyr Gly Pro Gly
                165                 170                 175

Gly Ser Gly Pro Gly Gly Ala Gly Pro Gly Gly Val Gly Pro Gly Gly
            180                 185                 190

Phe Gly Pro Gly Gly Ala Gly Pro Gly Gly Ala Ala Pro Gly Gly Ala
        195                 200                 205

Gly Pro Gly Gly Ala Gly Pro Gly Gly Ala Gly Pro Gly Gly Ala Gly
    210                 215                 220

Pro Gly Gly Ala Gly Pro Gly Gly Ala Gly Pro Gly Gly Ala Gly Gly
225                 230                 235                 240

Ala Gly Gly Ala Gly Gly Ser Gly Gly Ala Gly Gly Ser Gly Gly Thr
                245                 250                 255

Thr Ile Ile Glu Asp Leu Asp Ile Thr Ile Asp Gly Ala Asp Gly Pro
            260                 265                 270

Ile Thr Ile Ser Glu Glu Leu Pro Ile Ser Gly Ala Gly Gly Ser Gly
        275                 280                 285

Pro Gly Gly Ala Gly Pro Gly Gly Val Gly Pro Gly Gly Ser Gly Pro
    290                 295                 300

Gly Gly Val Gly Pro Gly Gly Ser Gly Pro Gly Gly Val Gly Pro Gly
305                 310                 315                 320
```

```
Gly Ser Gly Pro Gly Gly Val Gly Pro Gly Gly Ala Gly Gly Pro Tyr
                325                 330                 335

Gly Pro Gly Gly Ser Gly Pro Gly Gly Ala Gly Gly Ala Gly Gly Pro
            340                 345                 350

Gly Gly Ala Tyr Gly Pro Gly Gly Ser Tyr Gly Pro Gly Gly Ser Gly
        355                 360                 365

Gly Pro Gly Gly Ala Gly Gly Pro Tyr Gly Pro Gly Gly Glu Gly Pro
    370                 375                 380

Gly Gly Ala Gly Gly Pro Tyr Gly Pro Gly Gly Ala Gly Gly Pro Tyr
385                 390                 395                 400

Gly Pro Gly Gly Ala Gly Gly Pro Tyr Gly Pro Gly Gly Glu Gly Gly
                405                 410                 415

Pro Tyr Gly Pro
            420


<210> SEQ ID NO 506
<211> LENGTH: 376
<212> TYPE: PRT
<213> ORGANISM: Latrodectus hesperus

<400> SEQUENCE: 506

Gly Ile Asn Val Asp Ser Asp Ile Gly Ser Val Thr Ser Leu Ile Leu
1               5                   10                  15

Ser Gly Ser Thr Leu Gln Met Thr Ile Pro Ala Gly Gly Asp Asp Leu
            20                  25                  30

Ser Gly Gly Tyr Pro Gly Gly Phe Pro Ala Gly Ala Gln Pro Ser Gly
        35                  40                  45

Gly Ala Pro Val Asp Phe Gly Gly Pro Ser Ala Gly Gly Asp Val Ala
    50                  55                  60

Ala Lys Leu Ala Arg Ser Leu Ala Ser Thr Leu Ala Ser Ser Gly Val
65                  70                  75                  80

Phe Arg Ala Ala Phe Asn Ser Arg Val Ser Thr Pro Val Ala Val Gln
                85                  90                  95

Leu Thr Asp Ala Leu Val Gln Lys Ile Ala Ser Asn Leu Gly Leu Asp
            100                 105                 110

Tyr Ala Thr Ala Ser Lys Leu Arg Lys Ala Ser Gln Ala Val Ser Lys
        115                 120                 125

Val Arg Met Gly Ser Asp Thr Asn Ala Tyr Ala Leu Ala Ile Ser Ser
    130                 135                 140

Ala Leu Ala Glu Val Leu Ser Ser Ser Gly Lys Val Ala Asp Ala Asn
145                 150                 155                 160

Ile Asn Gln Ile Ala Pro Gln Leu Ala Ser Gly Ile Val Leu Gly Val
                165                 170                 175

Ser Thr Thr Ala Pro Gln Phe Gly Val Asp Leu Ser Ser Ile Asn Val
            180                 185                 190

Asn Leu Asp Ile Ser Asn Val Ala Arg Asn Met Gln Ala Ser Ile Gln
        195                 200                 205

Gly Gly Pro Ala Pro Ile Thr Ala Glu Gly Pro Asp Phe Gly Ala Gly
    210                 215                 220

Tyr Pro Gly Gly Ala Pro Thr Asp Leu Ser Gly Leu Asp Met Gly Ala
225                 230                 235                 240

Pro Ser Asp Gly Ser Arg Gly Gly Asp Ala Thr Ala Lys Leu Leu Gln
                245                 250                 255

Ala Leu Val Pro Ala Leu Leu Lys Ser Asp Val Phe Arg Ala Ile Tyr
            260                 265                 270
```

```
Lys Arg Gly Thr Arg Lys Gln Val Val Gln Tyr Val Thr Asn Ser Ala
        275                 280                 285

Leu Gln Gln Ala Ala Ser Ser Leu Gly Leu Asp Ala Ser Thr Ile Ser
    290                 295                 300

Gln Leu Gln Thr Lys Ala Thr Gln Ala Leu Ser Ser Val Ser Ala Asp
305                 310                 315                 320

Ser Asp Ser Thr Ala Tyr Ala Lys Ala Phe Gly Leu Ala Ile Ala Gln
                325                 330                 335

Val Leu Gly Thr Ser Gly Gln Val Asn Asp Ala Asn Val Asn Gln Ile
            340                 345                 350

Gly Ala Lys Leu Ala Thr Gly Ile Leu Arg Gly Ser Ser Ala Val Ala
        355                 360                 365

Pro Arg Leu Gly Ile Asp Leu Ser
    370                 375


<210> SEQ ID NO 507
<211> LENGTH: 200
<212> TYPE: PRT
<213> ORGANISM: Argiope trifasciata

<400> SEQUENCE: 507

Gly Ala Gly Tyr Thr Gly Pro Ser Gly Pro Ser Thr Gly Pro Ser Gly
1               5                   10                  15

Tyr Pro Gly Pro Leu Gly Gly Gly Ala Pro Phe Gly Gln Ser Gly Phe
            20                  25                  30

Gly Gly Ser Ala Gly Pro Gln Gly Gly Phe Gly Ala Thr Gly Gly Ala
        35                  40                  45

Ser Ala Gly Leu Ile Ser Arg Val Ala Asn Ala Leu Ala Asn Thr Ser
    50                  55                  60

Thr Leu Arg Thr Val Leu Arg Thr Gly Val Ser Gln Gln Ile Ala Ser
65                  70                  75                  80

Ser Val Val Gln Arg Ala Ala Gln Ser Leu Ala Ser Thr Leu Gly Val
                85                  90                  95

Asp Gly Asn Asn Leu Ala Arg Phe Ala Val Gln Ala Val Ser Arg Leu
            100                 105                 110

Pro Ala Gly Ser Asp Thr Ser Ala Tyr Ala Gln Ala Phe Ser Ser Ala
        115                 120                 125

Leu Phe Asn Ala Gly Val Leu Asn Ala Ser Asn Ile Asp Thr Leu Gly
    130                 135                 140

Ser Arg Val Leu Ser Ala Leu Leu Asn Gly Val Ser Ser Ala Ala Gln
145                 150                 155                 160

Gly Leu Gly Ile Asn Val Asp Ser Gly Ser Val Gln Ser Asp Ile Ser
                165                 170                 175

Ser Ser Ser Ser Phe Leu Ser Thr Ser Ser Ser Ser Ala Ser Tyr Ser
            180                 185                 190

Gln Ala Ser Ala Ser Ser Thr Ser
        195                 200


<210> SEQ ID NO 508
<211> LENGTH: 357
<212> TYPE: PRT
<213> ORGANISM: Uloborus diversus

<400> SEQUENCE: 508

Gly Ala Ser Ala Ala Asp Ile Ala Thr Ala Ile Ala Ala Ser Val Ala
1               5                   10                  15
```

```
Thr Ser Leu Gln Ser Asn Gly Val Leu Thr Ala Ser Asn Val Ser Gln
            20                  25                  30

Leu Ser Asn Gln Leu Ala Ser Tyr Val Ser Ser Gly Leu Ser Ser Thr
        35                  40                  45

Ala Ser Ser Leu Gly Ile Gln Leu Gly Ala Ser Leu Gly Ala Gly Phe
    50                  55                  60

Gly Ala Ser Ala Gly Leu Ser Ala Ser Thr Asp Ile Ser Ser Ser Val
65                  70                  75                  80

Glu Ala Thr Ser Ala Ser Thr Leu Ser Ser Ser Ala Ser Ser Thr Ser
                85                  90                  95

Val Val Ser Ser Ile Asn Ala Gln Leu Val Pro Ala Leu Ala Gln Thr
            100                 105                 110

Ala Val Leu Asn Ala Ala Phe Ser Asn Ile Asn Thr Gln Asn Ala Ile
        115                 120                 125

Arg Ile Ala Glu Leu Leu Thr Gln Gln Val Gly Arg Gln Tyr Gly Leu
    130                 135                 140

Ser Gly Ser Asp Val Ala Thr Ala Ser Ser Gln Ile Arg Ser Ala Leu
145                 150                 155                 160

Tyr Ser Val Gln Gln Gly Ser Ala Ser Ser Ala Tyr Val Ser Ala Ile
                165                 170                 175

Val Gly Pro Leu Ile Thr Ala Leu Ser Ser Arg Gly Val Val Asn Ala
            180                 185                 190

Ser Asn Ser Ser Gln Ile Ala Ser Ser Leu Ala Thr Ala Ile Leu Gln
        195                 200                 205

Phe Thr Ala Asn Val Ala Pro Gln Phe Gly Ile Ser Ile Pro Thr Ser
    210                 215                 220

Ala Val Gln Ser Asp Leu Ser Thr Ile Ser Gln Ser Leu Thr Ala Ile
225                 230                 235                 240

Ser Ser Gln Thr Ser Ser Ser Val Asp Ser Ser Thr Ser Ala Phe Gly
                245                 250                 255

Gly Ile Ser Gly Pro Ser Gly Pro Ser Pro Tyr Gly Pro Gln Pro Ser
            260                 265                 270

Gly Pro Thr Phe Gly Pro Gly Pro Ser Leu Ser Gly Leu Thr Gly Phe
        275                 280                 285

Thr Ala Thr Phe Ala Ser Ser Phe Lys Ser Thr Leu Ala Ser Ser Thr
    290                 295                 300

Gln Phe Gln Leu Ile Ala Gln Ser Asn Leu Asp Val Gln Thr Arg Ser
305                 310                 315                 320

Ser Leu Ile Ser Lys Val Leu Ile Asn Ala Leu Ser Ser Leu Gly Ile
                325                 330                 335

Ser Ala Ser Val Ala Ser Ser Ile Ala Ala Ser Ser Ser Gln Ser Leu
            340                 345                 350

Leu Ser Val Ser Ala
        355
```

<210> SEQ ID NO 509
<211> LENGTH: 32
<212> TYPE: PRT
<213> ORGANISM: Euprosthenops australis

<400> SEQUENCE: 509

```
Gly Gly Gln Gly Gly Gln Gly Gln Gly Arg Tyr Gly Gln Gly Ala Gly
1               5                   10                  15

Ser Ser Ala Ala Ala Ala Ala Ala Ala Ala Ala Ala Ala Ala Ala Ala
```

20 25 30

<210> SEQ ID NO 510
<211> LENGTH: 42
<212> TYPE: PRT
<213> ORGANISM: Tetragnatha kauaiensis

<400> SEQUENCE: 510

Gly Gly Leu Gly Gly Gly Gln Gly Ala Gly Gln Gly Gly Gln Gln Gly
1 5 10 15

Ala Gly Gln Gly Gly Tyr Gly Ser Gly Leu Gly Gly Ala Gly Gln Gly
20 25 30

Ala Ser Ala Ala Ala Ala Ala Ala Ala Ala
35 40

<210> SEQ ID NO 511
<211> LENGTH: 42
<212> TYPE: PRT
<213> ORGANISM: Argiope aurantia

<400> SEQUENCE: 511

Gly Gly Tyr Gly Pro Gly Ala Gly Gln Gln Gly Pro Gly Ser Gln Gly
1 5 10 15

Pro Gly Ser Gly Gly Gln Gln Gly Pro Gly Gly Leu Gly Pro Tyr Gly
20 25 30

Pro Ser Ala Ala Ala Ala Ala Ala Ala Ala
35 40

<210> SEQ ID NO 512
<211> LENGTH: 46
<212> TYPE: PRT
<213> ORGANISM: Deinopis spinosa

<400> SEQUENCE: 512

Gly Pro Gly Gly Tyr Gly Gly Pro Gly Gln Gln Gly Pro Gly Gln Gly
1 5 10 15

Gln Tyr Gly Pro Gly Thr Gly Gln Gln Gly Gln Gly Pro Ser Gly Gln
20 25 30

Gln Gly Pro Ala Gly Ala Ala Ala Ala Ala Ala Ala Ala Ala
35 40 45

<210> SEQ ID NO 513
<211> LENGTH: 42
<212> TYPE: PRT
<213> ORGANISM: Nephila clavata

<400> SEQUENCE: 513

Gly Pro Gly Gly Tyr Gly Leu Gly Gln Gln Gly Pro Gly Gln Gln Gly
1 5 10 15

Pro Gly Gln Gln Gly Pro Ala Gly Tyr Gly Pro Ser Gly Leu Ser Gly
20 25 30

Pro Gly Gly Ala Ala Ala Ala Ala Ala Ala
35 40

<210> SEQ ID NO 514
<211> LENGTH: 1800
<212> TYPE: PRT
<213> ORGANISM: Artificial Sequence
<220> FEATURE:
<223> OTHER INFORMATION: Description of Artificial Sequence: Synthetic
polypeptide
<220> FEATURE:

```
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (71)..(90)
<223> OTHER INFORMATION: This region may encompass 6-20 residues
<220> FEATURE:
<221> NAME/KEY: MISC_FEATURE
<222> LOCATION: (97)..(101)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (105)..(109)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (113)..(117)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (121)..(125)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (129)..(133)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (137)..(141)
<223> OTHER INFORMATION: This region may encompass "SGGQQ," "GAGQQ,"
      "GQGPY," "AGQQ" or "SQ," wherein some positions may be absent
```

```
<220> FEATURE:
<221> NAME/KEY: MISC_FEATURE
<222> LOCATION: (145)..(149)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (153)..(157)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (94)..(157)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (161)..(180)
<223> OTHER INFORMATION: This region may encompass 6-20 residues
<220> FEATURE:
<221> NAME/KEY: MISC_FEATURE
<222> LOCATION: (187)..(191)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (195)..(199)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (203)..(207)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (211)..(215)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (219)..(223)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (227)..(231)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (235)..(239)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (243)..(247)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (184)..(247)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (251)..(270)
<223> OTHER INFORMATION: This region may encompass 6-20 residues
<220> FEATURE:
<221> NAME/KEY: MISC_FEATURE
<222> LOCATION: (277)..(281)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (285)..(289)
<223> OTHER INFORMATION: This region may encompass "SGGQQ," "GAGQQ,"
```

"GQGPY," "AGQQ" or "SQ," wherein some positions may be absent
<220> FEATURE:
<221> NAME/KEY: MISC_FEATURE
<222> LOCATION: (293)..(297)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (301)..(305)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (309)..(313)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (317)..(321)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (325)..(329)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (333)..(337)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (274)..(337)
<223> OTHER INFORMATION: This region may encompass 4-8 repeating "GPG-X1" repeating units, wherein X1 is "SGGQQ," "GAGQQ," "GQGPY," "AGQQ" or "SQ," and some positions may be absent
<220> FEATURE:
<221> NAME/KEY: MISC_FEATURE
<222> LOCATION: (341)..(360)
<223> OTHER INFORMATION: This region may encompass 6-20 residues
<220> FEATURE:
<221> NAME/KEY: MISC_FEATURE
<222> LOCATION: (367)..(371)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (375)..(379)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (383)..(387)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (391)..(395)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (399)..(403)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (407)..(411)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (415)..(419)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (423)..(427)

<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (364)..(427)
<223> OTHER INFORMATION: This region may encompass 4-8 repeating
"GPG-X1" repeating units, wherein X1 is "SGGQQ," "GAGQQ,"
"GQGPY," "AGQQ" or "SQ," and some positions may be absent
<220> FEATURE:
<221> NAME/KEY: MISC_FEATURE
<222> LOCATION: (431)..(450)
<223> OTHER INFORMATION: This region may encompass 6-20 residues
<220> FEATURE:
<221> NAME/KEY: MISC_FEATURE
<222> LOCATION: (457)..(461)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (465)..(469)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (473)..(477)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (481)..(485)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (489)..(493)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (497)..(501)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (505)..(509)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (513)..(517)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (454)..(517)
<223> OTHER INFORMATION: This region may encompass 4-8 repeating
"GPG-X1" repeating units, wherein X1 is "SGGQQ," "GAGQQ,"
"GQGPY," "AGQQ" or "SQ," and some positions may be absent
<220> FEATURE:
<221> NAME/KEY: MISC_FEATURE
<222> LOCATION: (521)..(540)
<223> OTHER INFORMATION: This region may encompass 6-20 residues
<220> FEATURE:
<221> NAME/KEY: MISC_FEATURE
<222> LOCATION: (547)..(551)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (555)..(559)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (563)..(567)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (571)..(575)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (579)..(583)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (587)..(591)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (595)..(599)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (603)..(607)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (544)..(607)
<223> OTHER INFORMATION: This region may encompass 4-8 repeating
"GPG-X1" repeating units, wherein X1 is "SGGQQ," "GAGQQ,"
"GQGPY," "AGQQ" or "SQ," and some positions may be absent
<220> FEATURE:
<221> NAME/KEY: MISC_FEATURE
<222> LOCATION: (611)..(630)
<223> OTHER INFORMATION: This region may encompass 6-20 residues
<220> FEATURE:
<221> NAME/KEY: MISC_FEATURE
<222> LOCATION: (637)..(641)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (645)..(649)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (653)..(657)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (661)..(665)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (669)..(673)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (677)..(681)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (685)..(689)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (693)..(697)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (634)..(697)
<223> OTHER INFORMATION: This region may encompass 4-8 repeating
"GPG-X1" repeating units, wherein X1 is "SGGQQ," "GAGQQ,"
"GQGPY," "AGQQ" or "SQ," and some positions may be absent <220> FEATURE:
<221> NAME/KEY: MISC_FEATURE
<222> LOCATION: (701)..(720)
<223> OTHER INFORMATION: This region may encompass 6-20 residues
<220> FEATURE:
<221> NAME/KEY: MISC_FEATURE
<222> LOCATION: (727)..(731)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (735)..(739)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (743)..(747)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (751)..(755)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (759)..(763)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (767)..(771)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (775)..(779)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (783)..(787)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (724)..(787)
<223> OTHER INFORMATION: This region may encompass 4-8 repeating "GPG-X1" repeating units, wherein X1 is "SGGQQ," "GAGQQ," "GQGPY," "AGQQ" or "SQ," and some positions may be absent
<220> FEATURE:
<221> NAME/KEY: MISC_FEATURE
<222> LOCATION: (791)..(810)
<223> OTHER INFORMATION: This region may encompass 6-20 residues
<220> FEATURE:
<221> NAME/KEY: MISC_FEATURE
<222> LOCATION: (817)..(821)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (825)..(829)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (833)..(837)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (841)..(845)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (849)..(853)
<223> OTHER INFORMATION: This region may encompass "SGGQQ," "GAGQQ," "GQGPY," "AGQQ" or "SQ," wherein some positions may be absent

```
<220> FEATURE:
<221> NAME/KEY: MISC_FEATURE
<222> LOCATION: (857)..(861)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (865)..(869)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (873)..(877)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (814)..(877)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (881)..(900)
<223> OTHER INFORMATION: This region may encompass 6-20 residues
<220> FEATURE:
<221> NAME/KEY: MISC_FEATURE
<222> LOCATION: (907)..(911)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (915)..(919)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (923)..(927)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (931)..(935)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (939)..(943)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (947)..(951)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (955)..(959)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (963)..(967)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (904)..(967)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (971)..(990)
<223> OTHER INFORMATION: This region may encompass 6-20 residues
<220> FEATURE:
<221> NAME/KEY: MISC_FEATURE
<222> LOCATION: (997)..(1001)
<223> OTHER INFORMATION: This region may encompass "SGGQQ," "GAGQQ,"
```

"GQGPY," "AGQQ" or "SQ," wherein some positions may be absent
<220> FEATURE:
<221> NAME/KEY: MISC_FEATURE
<222> LOCATION: (1005)..(1009)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1013)..(1017)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1021)..(1025)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1029)..(1033)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1037)..(1041)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1045)..(1049)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1053)..(1057)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (994)..(1057)
<223> OTHER INFORMATION: This region may encompass 4-8 repeating "GPG-X1" repeating units, wherein X1 is "SGGQQ," "GAGQQ," "GQGPY," "AGQQ" or "SQ," and some positions may be absent
<220> FEATURE:
<221> NAME/KEY: MISC_FEATURE
<222> LOCATION: (1061)..(1080)
<223> OTHER INFORMATION: This region may encompass 6-20 residues
<220> FEATURE:
<221> NAME/KEY: MISC_FEATURE
<222> LOCATION: (1087)..(1091)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1095)..(1099)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1103)..(1107)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1111)..(1115)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1119)..(1123)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1127)..(1131)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1135)..(1139)

```
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1143)..(1147)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1084)..(1147)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1151)..(1170)
<223> OTHER INFORMATION: This region may encompass 6-20 residues
<220> FEATURE:
<221> NAME/KEY: MISC_FEATURE
<222> LOCATION: (1177)..(1181)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1185)..(1189)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1193)..(1197)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1201)..(1205)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1209)..(1213)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1217)..(1221)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1225)..(1229)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1233)..(1237)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1174)..(1237)
<223> OTHER INFORMATION: This region may encompass 4-8 repeating
      "GPG-X1" repeating units, wherein X1 is "SGGQQ," "GAGQQ,"
      "GQGPY," "AGQQ" or "SQ," and some positions may be absent
<220> FEATURE:
<221> NAME/KEY: MISC_FEATURE
<222> LOCATION: (1241)..(1260)
<223> OTHER INFORMATION: This region may encompass 6-20 residues
<220> FEATURE:
<221> NAME/KEY: MISC_FEATURE
<222> LOCATION: (1267)..(1271)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (1275)..(1279)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
```

<222> LOCATION: (1283)..(1287)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1291)..(1295)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1299)..(1303)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1307)..(1311)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1315)..(1319)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1323)..(1327)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1264)..(1327)
<223> OTHER INFORMATION: This region may encompass 4-8 repeating “GPG-X1” repeating units, wherein X1 is “SGGQQ,” “GAGQQ,” “GQGPY,” “AGQQ” or “SQ,” and some positions may be absent
<220> FEATURE:
<221> NAME/KEY: MISC_FEATURE
<222> LOCATION: (1331)..(1350)
<223> OTHER INFORMATION: This region may encompass 6-20 residues
<220> FEATURE:
<221> NAME/KEY: MISC_FEATURE
<222> LOCATION: (1357)..(1361)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1365)..(1369)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1373)..(1377)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1381)..(1385)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1389)..(1393)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1397)..(1401)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1405)..(1409)
<223> OTHER INFORMATION: This region may encompass “SGGQQ,” “GAGQQ,” “GQGPY,” “AGQQ” or “SQ,” wherein some positions may be absent
<220> FEATURE:
<221> NAME/KEY: MISC_FEATURE
<222> LOCATION: (1413)..(1417)
<223> OTHER INFORMATION: This region may encompass “SGGQQ,” “GAGQQ,” “GQGPY,” “AGQQ” or “SQ,” wherein some positions may be absent
<220> FEATURE:

-continued

<221> NAME/KEY: MISC_FEATURE
<222> LOCATION: (1354)..(1417)
<223> OTHER INFORMATION: This region may encompass 4-8 repeating
"GPG-X1" repeating units, wherein X1 is "SGGQQ," "GAGQQ,"
"GQGPY," "AGQQ" or "SQ," and some positions may be absent
<220> FEATURE:
<221> NAME/KEY: MISC_FEATURE
<222> LOCATION: (1421)..(1440)
<223> OTHER INFORMATION: This region may encompass 6-20 residues
<220> FEATURE:
<221> NAME/KEY: MISC_FEATURE
<222> LOCATION: (1447)..(1451)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1455)..(1459)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1463)..(1467)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1471)..(1475)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1479)..(1483)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1487)..(1491)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1495)..(1499)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1503)..(1507)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1444)..(1507)
<223> OTHER INFORMATION: This region may encompass 4-8 repeating
"GPG-X1" repeating units, wherein X1 is "SGGQQ," "GAGQQ,"
"GQGPY," "AGQQ" or "SQ," and some positions may be absent
<220> FEATURE:
<221> NAME/KEY: MISC_FEATURE
<222> LOCATION: (1511)..(1530)
<223> OTHER INFORMATION: This region may encompass 6-20 residues
<220> FEATURE:
<221> NAME/KEY: MISC_FEATURE
<222> LOCATION: (1537)..(1541)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1545)..(1549)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1553)..(1557)
<223> OTHER INFORMATION: This region may encompass "SGGQQ," "GAGQQ,"
"GQGPY," "AGQQ" or "SQ," wherein some positions may be absent
<220> FEATURE:
<221> NAME/KEY: MISC_FEATURE
<222> LOCATION: (1561)..(1565)
<223> OTHER INFORMATION: This region may encompass "SGGQQ," "GAGQQ,"
"GQGPY," "AGQQ" or "SQ," wherein some positions may be absent <220> FEATURE:
<221> NAME/KEY: MISC_FEATURE
<222> LOCATION: (1569)..(1573)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1577)..(1581)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1585)..(1589)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1593)..(1597)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1534)..(1597)
<223> OTHER INFORMATION: This region may encompass 4-8 repeating "GPG-X1" repeating units, wherein X1 is "SGGQQ," "GAGQQ," "GQGPY," "AGQQ" or "SQ," and some positions may be absent
<220> FEATURE:
<221> NAME/KEY: MISC_FEATURE
<222> LOCATION: (1601)..(1620)
<223> OTHER INFORMATION: This region may encompass 6-20 residues
<220> FEATURE:
<221> NAME/KEY: MISC_FEATURE
<222> LOCATION: (1627)..(1631)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1635)..(1639)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1643)..(1647)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1651)..(1655)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1659)..(1663)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1667)..(1671)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1675)..(1679)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1683)..(1687)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1624)..(1687)
<223> OTHER INFORMATION: This region may encompass 4-8 repeating "GPG-X1" repeating units, wherein X1 is "SGGQQ," "GAGQQ," "GQGPY," "AGQQ" or "SQ," and some positions may be absent
<220> FEATURE:
<221> NAME/KEY: MISC_FEATURE
<222> LOCATION: (1691)..(1710)

<223> OTHER INFORMATION: This region may encompass 6-20 residues
<220> FEATURE:
<221> NAME/KEY: MISC_FEATURE
<222> LOCATION: (1717)..(1721)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1725)..(1729)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1733)..(1737)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1741)..(1745)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1749)..(1753)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1757)..(1761)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1765)..(1769)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1773)..(1777)
<223> OTHER INFORMATION: This region may encompass "SGGQQ," "GAGQQ," "GQGPY," "AGQQ" or "SQ," wherein some positions may be absent
<220> FEATURE:
<221> NAME/KEY: MISC_FEATURE
<222> LOCATION: (1714)..(1777)
<223> OTHER INFORMATION: This region may encompass 4-8 repeating "GPG-X1" repeating units, wherein X1 is "SGGQQ," "GAGQQ," "GQGPY," "AGQQ" or "SQ," and some positions may be absent
<220> FEATURE:
<221> NAME/KEY: MISC_FEATURE
<222> LOCATION: (1781)..(1800)
<223> OTHER INFORMATION: This region may encompass 6-20 residues
<220> FEATURE:
<221> NAME/KEY: MISC_FEATURE
<222> LOCATION: (1)..(1800)
<223> OTHER INFORMATION: This sequence may encompass 2-20 "GGY-[GPG-X1]n1-GPS-(A)n2" repeating units, wherein X1 is "SGGQQ," "GAGQQ," "GQGPY," "AGQQ" or "SQ," n1 is 4-8 and n2 is 6-20 and some positions may be absent

<400> SEQUENCE: 514

```
Gly Gly Tyr Gly Pro Gly Xaa Xaa Xaa Xaa Xaa Gly Pro Gly Xaa Xaa
1               5                   10                  15

Xaa Xaa Xaa Gly Pro Gly Xaa Xaa Xaa Xaa Xaa Gly Pro Gly Xaa Xaa
            20                  25                  30

Xaa Xaa Xaa Gly Pro Gly Xaa Xaa Xaa Xaa Xaa Gly Pro Gly Xaa Xaa
        35                  40                  45

Xaa Xaa Xaa Gly Pro Gly Xaa Xaa Xaa Xaa Xaa Gly Pro Gly Xaa Xaa
    50                  55                  60

Xaa Xaa Xaa Gly Pro Ser Ala Ala Ala Ala Ala Ala Ala Ala Ala Ala
65                  70                  75                  80

Ala Ala Ala Ala Ala Ala Ala Ala Ala Ala Gly Gly Tyr Gly Pro Gly
                85                  90                  95
```

```
Xaa Xaa Xaa Xaa Xaa Gly Pro Gly Xaa Xaa Xaa Xaa Xaa Gly Pro Gly
            100                 105                 110

Xaa Xaa Xaa Xaa Xaa Gly Pro Gly Xaa Xaa Xaa Xaa Xaa Gly Pro Gly
        115                 120                 125

Xaa Xaa Xaa Xaa Xaa Gly Pro Gly Xaa Xaa Xaa Xaa Xaa Gly Pro Gly
    130                 135                 140

Xaa Xaa Xaa Xaa Xaa Gly Pro Gly Xaa Xaa Xaa Xaa Xaa Gly Pro Ser
145                 150                 155                 160

Ala Ala Ala Ala Ala Ala Ala Ala Ala Ala Ala Ala Ala Ala Ala Ala
                165                 170                 175

Ala Ala Ala Ala Gly Gly Tyr Gly Pro Gly Xaa Xaa Xaa Xaa Xaa Gly
            180                 185                 190

Pro Gly Xaa Xaa Xaa Xaa Xaa Gly Pro Gly Xaa Xaa Xaa Xaa Xaa Gly
        195                 200                 205

Pro Gly Xaa Xaa Xaa Xaa Xaa Gly Pro Gly Xaa Xaa Xaa Xaa Xaa Gly
    210                 215                 220

Pro Gly Xaa Xaa Xaa Xaa Xaa Gly Pro Gly Xaa Xaa Xaa Xaa Xaa Gly
225                 230                 235                 240

Pro Gly Xaa Xaa Xaa Xaa Xaa Gly Pro Ser Ala Ala Ala Ala Ala Ala
                245                 250                 255

Ala Ala Ala Ala Ala Ala Ala Ala Ala Ala Ala Ala Ala Ala Gly Gly
            260                 265                 270

Tyr Gly Pro Gly Xaa Xaa Xaa Xaa Xaa Gly Pro Gly Xaa Xaa Xaa Xaa
        275                 280                 285

Xaa Gly Pro Gly Xaa Xaa Xaa Xaa Xaa Gly Pro Gly Xaa Xaa Xaa Xaa
    290                 295                 300

Xaa Gly Pro Gly Xaa Xaa Xaa Xaa Xaa Gly Pro Gly Xaa Xaa Xaa Xaa
305                 310                 315                 320

Xaa Gly Pro Gly Xaa Xaa Xaa Xaa Xaa Gly Pro Gly Xaa Xaa Xaa Xaa
                325                 330                 335

Xaa Gly Pro Ser Ala Ala Ala Ala Ala Ala Ala Ala Ala Ala Ala Ala
            340                 345                 350

Ala Ala Ala Ala Ala Ala Ala Ala Gly Gly Tyr Gly Pro Gly Xaa Xaa
        355                 360                 365

Xaa Xaa Xaa Gly Pro Gly Xaa Xaa Xaa Xaa Xaa Gly Pro Gly Xaa Xaa
    370                 375                 380

Xaa Xaa Xaa Gly Pro Gly Xaa Xaa Xaa Xaa Xaa Gly Pro Gly Xaa Xaa
385                 390                 395                 400

Xaa Xaa Xaa Gly Pro Gly Xaa Xaa Xaa Xaa Xaa Gly Pro Gly Xaa Xaa
                405                 410                 415

Xaa Xaa Xaa Gly Pro Gly Xaa Xaa Xaa Xaa Xaa Gly Pro Ser Ala Ala
            420                 425                 430

Ala Ala Ala Ala Ala Ala Ala Ala Ala Ala Ala Ala Ala Ala Ala Ala
        435                 440                 445

Ala Ala Gly Gly Tyr Gly Pro Gly Xaa Xaa Xaa Xaa Xaa Gly Pro Gly
    450                 455                 460

Xaa Xaa Xaa Xaa Xaa Gly Pro Gly Xaa Xaa Xaa Xaa Xaa Gly Pro Gly
465                 470                 475                 480

Xaa Xaa Xaa Xaa Xaa Gly Pro Gly Xaa Xaa Xaa Xaa Xaa Gly Pro Gly
                485                 490                 495

Xaa Xaa Xaa Xaa Xaa Gly Pro Gly Xaa Xaa Xaa Xaa Xaa Gly Pro Gly
            500                 505                 510

Xaa Xaa Xaa Xaa Xaa Gly Pro Ser Ala Ala Ala Ala Ala Ala Ala Ala
```

```
        515                 520                 525

Ala Ala Ala Ala Ala Ala Ala Ala Ala Ala Ala Ala Gly Gly Tyr Gly
    530                 535                 540

Pro Gly Xaa Xaa Xaa Xaa Xaa Gly Pro Gly Xaa Xaa Xaa Xaa Xaa Gly
545                 550                 555                 560

Pro Gly Xaa Xaa Xaa Xaa Xaa Gly Pro Gly Xaa Xaa Xaa Xaa Xaa Gly
                565                 570                 575

Pro Gly Xaa Xaa Xaa Xaa Xaa Gly Pro Gly Xaa Xaa Xaa Xaa Xaa Gly
            580                 585                 590

Pro Gly Xaa Xaa Xaa Xaa Xaa Gly Pro Gly Xaa Xaa Xaa Xaa Xaa Gly
        595                 600                 605

Pro Ser Ala Ala Ala Ala Ala Ala Ala Ala Ala Ala Ala Ala Ala Ala
    610                 615                 620

Ala Ala Ala Ala Ala Ala Gly Gly Tyr Gly Pro Gly Xaa Xaa Xaa Xaa
625                 630                 635                 640

Xaa Gly Pro Gly Xaa Xaa Xaa Xaa Xaa Gly Pro Gly Xaa Xaa Xaa Xaa
                645                 650                 655

Xaa Gly Pro Gly Xaa Xaa Xaa Xaa Xaa Gly Pro Gly Xaa Xaa Xaa Xaa
            660                 665                 670

Xaa Gly Pro Gly Xaa Xaa Xaa Xaa Xaa Gly Pro Gly Xaa Xaa Xaa Xaa
        675                 680                 685

Xaa Gly Pro Gly Xaa Xaa Xaa Xaa Xaa Gly Pro Ser Ala Ala Ala Ala
    690                 695                 700

Ala Ala Ala Ala Ala Ala Ala Ala Ala Ala Ala Ala Ala Ala Ala Ala
705                 710                 715                 720

Gly Gly Tyr Gly Pro Gly Xaa Xaa Xaa Xaa Xaa Gly Pro Gly Xaa Xaa
                725                 730                 735

Xaa Xaa Xaa Gly Pro Gly Xaa Xaa Xaa Xaa Xaa Gly Pro Gly Xaa Xaa
            740                 745                 750

Xaa Xaa Xaa Gly Pro Gly Xaa Xaa Xaa Xaa Xaa Gly Pro Gly Xaa Xaa
        755                 760                 765

Xaa Xaa Xaa Gly Pro Gly Xaa Xaa Xaa Xaa Xaa Gly Pro Gly Xaa Xaa
    770                 775                 780

Xaa Xaa Xaa Gly Pro Ser Ala Ala Ala Ala Ala Ala Ala Ala Ala Ala
785                 790                 795                 800

Ala Ala Ala Ala Ala Ala Ala Ala Ala Ala Gly Gly Tyr Gly Pro Gly
                805                 810                 815

Xaa Xaa Xaa Xaa Xaa Gly Pro Gly Xaa Xaa Xaa Xaa Xaa Gly Pro Gly
            820                 825                 830

Xaa Xaa Xaa Xaa Xaa Gly Pro Gly Xaa Xaa Xaa Xaa Xaa Gly Pro Gly
        835                 840                 845

Xaa Xaa Xaa Xaa Xaa Gly Pro Gly Xaa Xaa Xaa Xaa Xaa Gly Pro Gly
    850                 855                 860

Xaa Xaa Xaa Xaa Xaa Gly Pro Gly Xaa Xaa Xaa Xaa Xaa Gly Pro Ser
865                 870                 875                 880

Ala Ala Ala Ala Ala Ala Ala Ala Ala Ala Ala Ala Ala Ala Ala Ala
                885                 890                 895

Ala Ala Ala Ala Gly Gly Tyr Gly Pro Gly Xaa Xaa Xaa Xaa Xaa Gly
            900                 905                 910

Pro Gly Xaa Xaa Xaa Xaa Xaa Gly Pro Gly Xaa Xaa Xaa Xaa Xaa Gly
        915                 920                 925

Pro Gly Xaa Xaa Xaa Xaa Xaa Gly Pro Gly Xaa Xaa Xaa Xaa Xaa Gly
    930                 935                 940
```

-continued

```
Pro Gly Xaa Xaa Xaa Xaa Xaa Gly Pro Gly Xaa Xaa Xaa Xaa Xaa Gly
945                 950                 955                 960

Pro Gly Xaa Xaa Xaa Xaa Xaa Gly Pro Ser Ala Ala Ala Ala Ala Ala
                965                 970                 975

Ala Ala Ala Ala Ala Ala Ala Ala Ala Ala Ala Ala Ala Ala Gly Gly
            980                 985                 990

Tyr Gly Pro Gly Xaa Xaa Xaa Xaa  Xaa Gly Pro Gly Xaa  Xaa Xaa Xaa
        995                 1000                 1005

Xaa Gly  Pro Gly Xaa Xaa Xaa  Xaa Xaa Gly Pro Gly  Xaa Xaa Xaa
    1010                 1015                 1020

Xaa Xaa  Gly Pro Gly Xaa Xaa  Xaa Xaa Xaa Gly Pro  Gly Xaa Xaa
    1025                 1030                 1035

Xaa Xaa  Xaa Gly Pro Gly Xaa  Xaa Xaa Xaa Xaa Gly  Pro Gly Xaa
    1040                 1045                 1050

Xaa Xaa  Xaa Xaa Gly Pro Ser  Ala Ala Ala Ala Ala  Ala Ala Ala
    1055                 1060                 1065

Ala Ala  Ala Ala Ala Ala Ala  Ala Ala Ala Ala Ala  Gly Gly Tyr
    1070                 1075                 1080

Gly Pro  Gly Xaa Xaa Xaa Xaa  Xaa Gly Pro Gly Xaa  Xaa Xaa Xaa
    1085                 1090                 1095

Xaa Gly  Pro Gly Xaa Xaa Xaa  Xaa Xaa Gly Pro Gly  Xaa Xaa Xaa
    1100                 1105                 1110

Xaa Xaa  Gly Pro Gly Xaa Xaa  Xaa Xaa Xaa Gly Pro  Gly Xaa Xaa
    1115                 1120                 1125

Xaa Xaa  Xaa Gly Pro Gly Xaa  Xaa Xaa Xaa Xaa Gly  Pro Gly Xaa
    1130                 1135                 1140

Xaa Xaa  Xaa Xaa Gly Pro Ser  Ala Ala Ala Ala Ala  Ala Ala Ala
    1145                 1150                 1155

Ala Ala  Ala Ala Ala Ala Ala  Ala Ala Ala Ala Ala  Gly Gly Tyr
    1160                 1165                 1170

Gly Pro  Gly Xaa Xaa Xaa Xaa  Xaa Gly Pro Gly Xaa  Xaa Xaa Xaa
    1175                 1180                 1185

Xaa Gly  Pro Gly Xaa Xaa Xaa  Xaa Xaa Gly Pro Gly  Xaa Xaa Xaa
    1190                 1195                 1200

Xaa Xaa  Gly Pro Gly Xaa Xaa  Xaa Xaa Xaa Gly Pro  Gly Xaa Xaa
    1205                 1210                 1215

Xaa Xaa  Xaa Gly Pro Gly Xaa  Xaa Xaa Xaa Xaa Gly  Pro Gly Xaa
    1220                 1225                 1230

Xaa Xaa  Xaa Xaa Gly Pro Ser  Ala Ala Ala Ala Ala  Ala Ala Ala
    1235                 1240                 1245

Ala Ala  Ala Ala Ala Ala Ala  Ala Ala Ala Ala Ala  Gly Gly Tyr
    1250                 1255                 1260

Gly Pro  Gly Xaa Xaa Xaa Xaa  Xaa Gly Pro Gly Xaa  Xaa Xaa Xaa
    1265                 1270                 1275

Xaa Gly  Pro Gly Xaa Xaa Xaa  Xaa Xaa Gly Pro Gly  Xaa Xaa Xaa
    1280                 1285                 1290

Xaa Xaa  Gly Pro Gly Xaa Xaa  Xaa Xaa Xaa Gly Pro  Gly Xaa Xaa
    1295                 1300                 1305

Xaa Xaa  Xaa Gly Pro Gly Xaa  Xaa Xaa Xaa Xaa Gly  Pro Gly Xaa
    1310                 1315                 1320

Xaa Xaa  Xaa Xaa Gly Pro Ser  Ala Ala Ala Ala Ala  Ala Ala Ala
    1325                 1330                 1335
```

```
Ala Ala  Ala Ala Ala Ala Ala  Ala Ala Ala Ala Ala  Gly Gly Tyr
    1340                 1345                 1350

Gly Pro  Gly Xaa Xaa Xaa Xaa  Xaa Gly Pro Gly Xaa  Xaa Xaa Xaa
    1355                 1360                 1365

Xaa Gly  Pro Gly Xaa Xaa Xaa  Xaa Xaa Gly Pro Gly  Xaa Xaa Xaa
    1370                 1375                 1380

Xaa Xaa  Gly Pro Gly Xaa Xaa  Xaa Xaa Xaa Gly Pro  Gly Xaa Xaa
    1385                 1390                 1395

Xaa Xaa  Xaa Gly Pro Gly Xaa  Xaa Xaa Xaa Xaa Gly  Pro Gly Xaa
    1400                 1405                 1410

Xaa Xaa  Xaa Xaa Gly Pro Ser  Ala Ala Ala Ala Ala  Ala Ala Ala
    1415                 1420                 1425

Ala Ala  Ala Ala Ala Ala Ala  Ala Ala Ala Ala Ala  Gly Gly Tyr
    1430                 1435                 1440

Gly Pro  Gly Xaa Xaa Xaa Xaa  Xaa Gly Pro Gly Xaa  Xaa Xaa Xaa
    1445                 1450                 1455

Xaa Gly  Pro Gly Xaa Xaa Xaa  Xaa Xaa Gly Pro Gly  Xaa Xaa Xaa
    1460                 1465                 1470

Xaa Xaa  Gly Pro Gly Xaa Xaa  Xaa Xaa Xaa Gly Pro  Gly Xaa Xaa
    1475                 1480                 1485

Xaa Xaa  Xaa Gly Pro Gly Xaa  Xaa Xaa Xaa Xaa Gly  Pro Gly Xaa
    1490                 1495                 1500

Xaa Xaa  Xaa Xaa Gly Pro Ser  Ala Ala Ala Ala Ala  Ala Ala Ala
    1505                 1510                 1515

Ala Ala  Ala Ala Ala Ala Ala  Ala Ala Ala Ala Ala  Gly Gly Tyr
    1520                 1525                 1530

Gly Pro  Gly Xaa Xaa Xaa Xaa  Xaa Gly Pro Gly Xaa  Xaa Xaa Xaa
    1535                 1540                 1545

Xaa Gly  Pro Gly Xaa Xaa Xaa  Xaa Xaa Gly Pro Gly  Xaa Xaa Xaa
    1550                 1555                 1560

Xaa Xaa  Gly Pro Gly Xaa Xaa  Xaa Xaa Xaa Gly Pro  Gly Xaa Xaa
    1565                 1570                 1575

Xaa Xaa  Xaa Gly Pro Gly Xaa  Xaa Xaa Xaa Xaa Gly  Pro Gly Xaa
    1580                 1585                 1590

Xaa Xaa  Xaa Xaa Gly Pro Ser  Ala Ala Ala Ala Ala  Ala Ala Ala
    1595                 1600                 1605

Ala Ala  Ala Ala Ala Ala Ala  Ala Ala Ala Ala Ala  Gly Gly Tyr
    1610                 1615                 1620

Gly Pro  Gly Xaa Xaa Xaa Xaa  Xaa Gly Pro Gly Xaa  Xaa Xaa Xaa
    1625                 1630                 1635

Xaa Gly  Pro Gly Xaa Xaa Xaa  Xaa Xaa Gly Pro Gly  Xaa Xaa Xaa
    1640                 1645                 1650

Xaa Xaa  Gly Pro Gly Xaa Xaa  Xaa Xaa Xaa Gly Pro  Gly Xaa Xaa
    1655                 1660                 1665

Xaa Xaa  Xaa Gly Pro Gly Xaa  Xaa Xaa Xaa Xaa Gly  Pro Gly Xaa
    1670                 1675                 1680

Xaa Xaa  Xaa Xaa Gly Pro Ser  Ala Ala Ala Ala Ala  Ala Ala Ala
    1685                 1690                 1695

Ala Ala  Ala Ala Ala Ala Ala  Ala Ala Ala Ala Ala  Gly Gly Tyr
    1700                 1705                 1710

Gly Pro  Gly Xaa Xaa Xaa Xaa  Xaa Gly Pro Gly Xaa  Xaa Xaa Xaa
    1715                 1720                 1725

Xaa Gly  Pro Gly Xaa Xaa Xaa  Xaa Xaa Gly Pro Gly  Xaa Xaa Xaa
```

```
    1730                1735                1740

Xaa Xaa  Gly Pro Gly Xaa Xaa  Xaa Xaa Xaa Gly Pro  Gly Xaa Xaa
    1745                1750                1755

Xaa Xaa  Xaa Gly Pro Gly Xaa  Xaa Xaa Xaa Xaa Gly  Pro Gly Xaa
    1760                1765                1770

Xaa Xaa  Xaa Xaa Gly Pro Ser  Ala Ala Ala Ala Ala  Ala Ala Ala
    1775                1780                1785

Ala Ala  Ala Ala Ala Ala Ala  Ala Ala Ala Ala Ala
    1790                1795                1800
```

<210> SEQ ID NO 515
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 515

```
Ser Gly Gly Gln Gln
1               5
```

<210> SEQ ID NO 516
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 516

```
Gly Ala Gly Gln Gln
1               5
```

<210> SEQ ID NO 517
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 517

```
Gly Gln Gly Pro Tyr
1               5
```

<210> SEQ ID NO 518
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 518

```
Ala Gly Gln Gln
1
```

<210> SEQ ID NO 519
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:

```
<221> NAME/KEY: MISC_FEATURE
<222> LOCATION: (1)..(10)
<223> OTHER INFORMATION: This sequence may encompass 2-10 residues

<400> SEQUENCE: 519

Ala Ala Ala Ala Ala Ala Ala Ala Ala Ala
1               5                   10


<210> SEQ ID NO 520
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 6-8 residues

<400> SEQUENCE: 520

His His His His His His His His
1               5


<210> SEQ ID NO 521
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (7)..(11)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (15)..(19)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (23)..(27)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (31)..(35)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (39)..(43)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (47)..(51)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (55)..(59)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (63)..(67)
<223> OTHER INFORMATION: This region may encompass "SGGQQ," "GAGQQ,"
      "GQGPY," "AGQQ" or "SQ," wherein some positions may be absent
<220> FEATURE:
<221> NAME/KEY: MISC_FEATURE
<222> LOCATION: (4)..(67)
<223> OTHER INFORMATION: This region may encompass 4-8 "GPG-X1"
```

-continued

```
      repeating units, wherein X1 is "SGGQQ," "GAGQQ," "GQGPY," "AGQQ"
      or "SQ," and some positions may be absent

<400> SEQUENCE: 521

Gly Gly Tyr Gly Pro Gly Xaa Xaa Xaa Xaa Xaa Gly Pro Gly Xaa Xaa
1               5                   10                  15

Xaa Xaa Xaa Gly Pro Gly Xaa Xaa Xaa Xaa Xaa Gly Pro Gly Xaa Xaa
            20                  25                  30

Xaa Xaa Xaa Gly Pro Gly Xaa Xaa Xaa Xaa Xaa Gly Pro Gly Xaa Xaa
        35                  40                  45

Xaa Xaa Xaa Gly Pro Gly Xaa Xaa Xaa Xaa Xaa Gly Pro Gly Xaa Xaa
    50                  55                  60

Xaa Xaa Xaa Gly Pro Ser
65                  70


<210> SEQ ID NO 522
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 6-20 residues

<400> SEQUENCE: 522

Ala Ala Ala Ala Ala Ala Ala Ala Ala Ala Ala Ala Ala Ala Ala Ala
1               5                   10                  15

Ala Ala Ala Ala
            20
```

MODIFIED STRAINS FOR THE PRODUCTION OF RECOMBINANT SILK

CROSS-REFERENCE TO RELATED APPLICATIONS

This application is a continuation of U.S. Non-Provisional application Ser. No. 15/724,196, filed Oct. 3, 2017, the contents of which is incorporated by reference in its entirety.

SEQUENCE LISTING

The instant application contains a Sequence Listing which has been submitted electronically in ASCII format and is hereby incorporated by reference in its entirety. Said ASCII copy, created on Apr. 7, 2029, is named BTT-012C1_CRF_sequencelisting.txt and is 388,959 bytes in size.

FIELD OF THE INVENTION

The present disclosure relates to methods of strain optimization to produce or enhance production of proteins or metabolites from cells. The present disclosure also relates to compositions resulting from those methods. In particular, the disclosure relates to yeast cells selected or genetically engineered to reduce degradation of recombinant proteins expressed by the yeast cells, and to methods of cultivating yeast cells for the production of useful compounds.

BACKGROUND OF THE INVENTION

The methylotrophic yeast *Pichia pastoris* is widely used in the production of recombinant proteins. *P. pastoris* grows to high cell density, provides tightly controlled methanol-inducible trans gene expression and efficiently secretes heterologous proteins in defined media.

However, during culture of a strain of *P. pastoris*, recombinantly expressed proteins may be degraded before they can be collected, resulting in a mixture of proteins that includes fragments of recombinantly expressed proteins and a decreased yield of full-length recombinant proteins. What is needed, therefore, are tools and engineered strains to mitigate protein degradation in *P. pastoris*.

SUMMARY OF THE INVENTION

In some embodiments, provided herein is a *Pichia pastoris* microorganism, in which the activity of a YPS1-1 protease and a YPS1-2 protease has been attenuated or eliminated, wherein said microorganism expresses a recombinant polypeptide.

In some embodiments, the YPS1-1 protease comprises a polypeptide sequence at least 95% identical to SEQ ID NO: 67. In some embodiments, the YPS1-1 protease comprises SEQ ID NO: 67. In some embodiments, the YPS1-1 protease is encoded by a YPS1-1 gene. In some embodiments, the YPS1-1 gene comprises a polynucleotide sequence at least 95% identical to SEQ ID NO: 1. In some embodiments, the YPS1-1 gene comprises at least 15, 20, 25, 30, 40, or 50 contiguous nucleotides of SEQ ID NO: 1. In some embodiments, the YPS1-1 gene comprises SEQ ID NO: 1. In some embodiments, the YPS1-1 gene is at locus PAS_chr4_0584 of said microorganism.

In some embodiments, the YPS1-2 protease comprises a polypeptide sequence at least 95% identical to SEQ ID NO: 68. In some embodiments, the YPS1-2 protease comprises SEQ ID NO: 68. In some embodiments, the YPS1-2 protease is encoded by a YPS1-2 gene. In some embodiments, the YPS1-2 gene comprises a polynucleotide sequence at least 95% identical to SEQ ID NO: 2. In some embodiments, the YPS1-2 gene comprises at least 15, 20, 25, 30, 40, or 50 contiguous nucleotides of SEQ ID NO: 2. In some embodiments, the YPS1-2 gene comprises SEQ ID NO: 2. In some embodiments, the YPS1-2 gene is at locus PAS_chr3_1157 of said microorganism.

In some embodiments, the YPS1-1 gene or said YPS1-2 gene, or both, has been mutated or knocked out.

In some embodiments, the microorganism expresses a recombinant protein. In some embodiments, the recombinant protein comprises at least one block polypeptide sequence from a silk protein. In some embodiments, the recombinant protein comprises a silk-like polypeptide. In some embodiments, the silk-like polypeptide comprises one or more repeat sequences {GGY-[GPG-$X_1$]$n_1$-GPS-(A)$n_2$}$n_3$ (SEQ ID NO: 514), wherein $X_1$=SGGQQ (SEQ ID NO: 515) or GAGQQ (SEQ ID NO: 516) or GQGPY (SEQ ID NO: 517) or AGQQ (SEQ ID NO: 518) or SQ; n1 is from 4 to 8; n2 is from 6 to 20; and n3 is from 2 to 20. In some embodiments, the silk-like polypeptide comprises comprises a polypeptide sequence encoded by SEQ ID NO: 462.

In some embodiments, the activity of one or more additional proteases in the microorganism has been attenuated or eliminated. In some embodiments, the one or more additional proteases comprises YPS1-5, MCK7, or YPS1-3.

In some embodiments, the YPS1-5 gene is at locus PAS_chr3_0866 of said microorganism.

In some embodiments, the MCK7 protease is encoded by a MCK7 gene comprising a polynucleotide sequence at least 95% identical to SEQ ID NO: 7. In some embodiments, the MCK7 gene comprises at least 15, 20, 25, 30, 40, or 50 contiguous nucleotides of SEQ ID NO: 7. In some embodiments, the MCK7 gene comprises SEQ ID NO: 7. In some embodiments, the MCK7 gene is at locus PAS_chr1-1_0379 of said microorganism.

In some embodiments, the YPS1-3 protease is encoded by a YPS1-3 gene comprising a polynucleotide sequence at least 95% identical to SEQ ID NO: 3. In some embodiments, the YPS1-3 gene comprises at least 15, 20, 25, 30, 40, or 50 contiguous nucleotides of SEQ ID NO: 3. In some embodiments, the YPS1-3 gene comprises SEQ ID NO: 3. In some embodiments, the YPS1-3 gene is at locus PAS_chr3_0299 of said microorganism.

In some embodiments, the one or more additional proteases comprise a polypeptide sequence at least 95% identical to a polypeptide sequence selected from the group consisting of: SEQ ID NO: 68-130. In some embodiments, the one or more additional proteases comprise a polypeptide sequence selected from the group consisting of: SEQ ID NO: 68-130. In some embodiments, the one or more additional proteases are encoded by a polynucleotide sequence at least 95% identical to a polynucleotide sequence selected from the group consisting of: SEQ ID NO: 3-66. In some embodiments, the one or more additional proteases are encoded by a polynucleotide sequence comprising at least 15, 20, 25, 30, 40, or 50 contiguous nucleotides of a polynucleotide sequence selected from the group consisting of: SEQ ID NO: 3-66.

In some embodiments, the microorganism comprises a 3×, 4× or 5× protease knockout.

Also provided herein, according to some embodiments of the invention, is a *Pichia pastoris* engineered microorganism comprising YPS1-1 and YPS1-2 activity reduced by a mutation or deletion of the YPS1-1 gene comprising SEQ ID NO: 1 and the YPS1-2 gene comprising SEQ ID NO: 2, wherein said microorganism further comprises a recombinantly expressed protein comprising a polypeptide sequence encoded by SEQ ID NO: 462.

In some embodiments, also provided herein is cell culture comprising a protease mitigated microorganism as described herein.

Also provided herein, according to some embodiments, is a cell culture comprising a microorganism whose YPS1-1 and YPS1-2 activity has been attenuated or eliminated as described herein, wherein the microorganism recombinantly expresses a protein, wherein said recombinantly expressed protein is less degraded than a cell culture comprising an otherwise identical *Picha pastoris* microorganism whose YPS1-1 and YPS1-2 activity has not been attenuated or eliminated.

In some embodiments, provided herein is a method of producing a recombinant protein with a reduced degradation, comprising: culturing whose YPS1-1 and YPS1-2 activity has been attenuated or eliminated as described herein in a culture medium under conditions suitable for expression of the recombinantly expressed protein; and isolating the recombinant protein from the microorganism or the culture medium.

In some embodiments, the recombinant protein is secreted from said microorganism, and wherein isolating said recombinant protein comprises collecting a culture medium comprising said secreted recombinant protein. In some embodiments, the recombinant protein has a decreased level of degradation as compared to said recombinant protein produced by an otherwise identical microorganism wherein said YPS1-1 and said YPS1-2 protease activity has not been attenuated or eliminated.

Also provided herein is a method of modifying *Pichia pastoris* to reduce the degradation of a recombinantly expressed protein, comprising knocking out or mutating a gene encoding a YPS1-1 protein and a YPS1-2 protein. In some embodiments, the method of modifying *Pichia pastoris* to reduce the degradation of a recombinantly expressed protein further comprises knocking out or mutating one or more additional genes encoding a YPS1-3 protein, a YPS1-5 protein, or an MCK7 protein. In some embodiments, the method of modifying *Pichia pastoris* to reduce the degradation of a recombinantly expressed protein further comprises knocking out one or more genes encoding a protein comprising a polypeptide selected from the group consisting of SEQ ID NO: 68-130.

In some embodiments, the recombinantly expressed protein comprises a polyA sequence comprising at least at least 2, 3, 4, 5, 6, 7, 8, 9, or 10 contiguous alanine residues (SEQ ID NO: 519). In some embodiments, the recombinantly expressed protein comprises a silk-like polypeptide. In some embodiments, the silk-like polypeptide comprises one or more repeat sequences $\{GGY-[GPG-X_1]n_1-GPS-(A)n_2\}n_3$ (SEQ ID NO: 514), wherein $X_1$=SGGQQ (SEQ ID NO: 515) or GAGQQ (SEQ ID NO: 516) or GQGPY (SEQ ID NO: 517) or AGQQ (SEQ ID NO: 518) or SQ; n1 is from 4 to 8; n2 is from 6 to 20; and n3 is from 2 to 20. In some embodiments, the recombinantly expressed protein comprises a polypeptide sequence encoded by SEQ ID NO: 462.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

DETAILED DESCRIPTION

Figure 1:
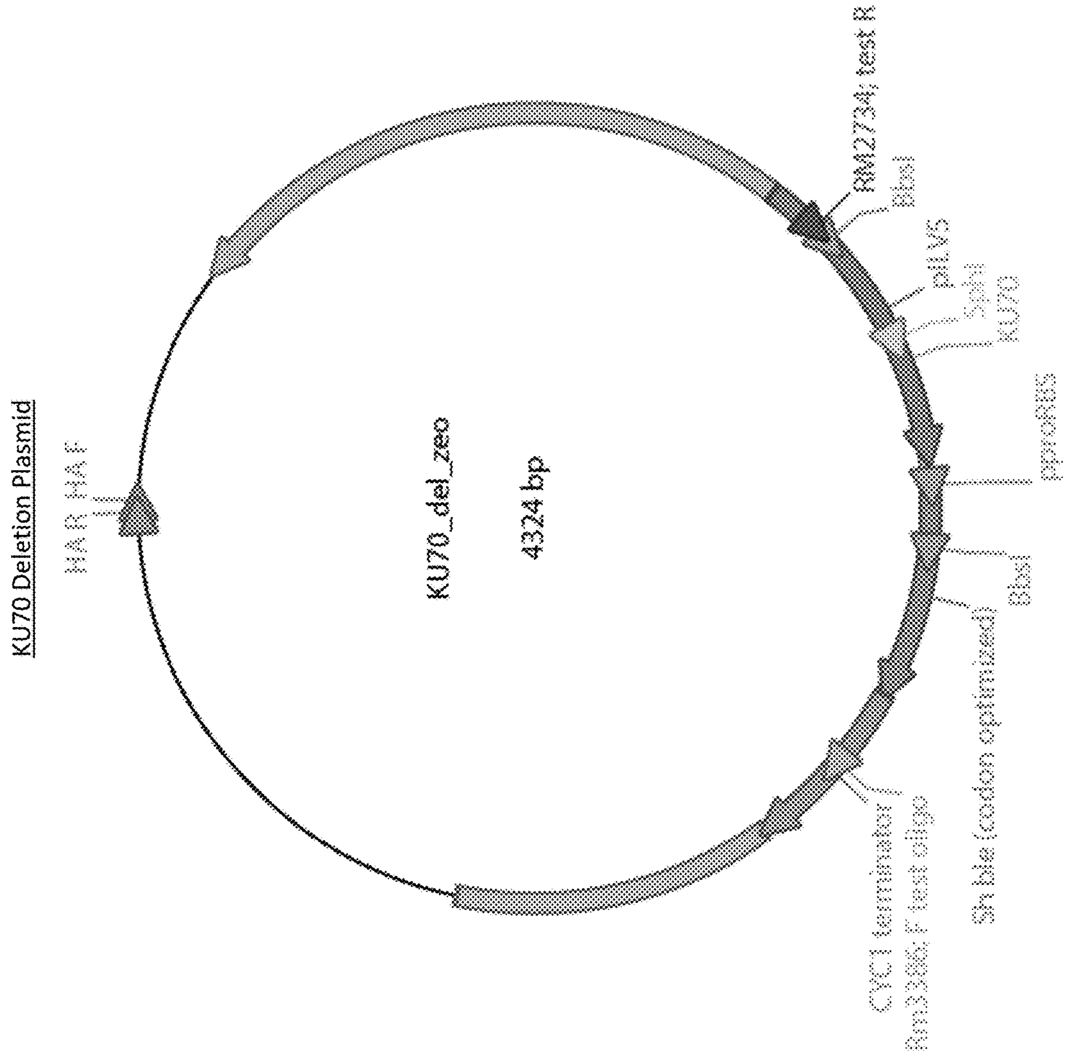
FIG. 1 is a plasmid map for KU 70 deletion with a zeocin resistance marker.

The details of various embodiments of the invention are set forth in the description below. Other features, objects, and advantages of the invention will be apparent from the description and the drawings, and from the claims.

Definitions

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. The terms "a" and "an" includes plural references unless the context dictates otherwise. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

An "isolated" organic molecule (e.g., a silk protein) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

An endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 75%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, inter-nucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique,* 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

The term "deletion" as used herein refers to the removal of one or more nucleotides from a nucleic acid molecule or one or more amino acids from a protein, the regions on either side being joined together.

The term "knock-out" as used herein is intended to refer to a gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "regulatory element" refers to any element which affects transcription or translation of a nucleic acid molecule. These include, by way of example but not limitation: regulatory proteins (e.g., transcription factors), chaperones, signaling proteins, RNAi molecules, antisense RNA molecules, microRNAs and RNA aptamers. Regulatory elements may be endogenous to the host organism. Regulatory elements may also be exogenous to the host organism. Regulatory elements may be synthetically generated regulatory elements.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. Promoters may be endogenous to the host organism. Promoters may also be exogenous to the host organism. Promoters may be synthetically generated regulatory elements.

Promoters useful for expressing the recombinant genes described herein include both constitutive and inducible/repressible promoters. Where multiple recombinant genes are expressed in an engineered organism of the invention, the different genes can be controlled by different promoters or by identical promoters in separate operons, or the expression of two or more genes may be controlled by a single promoter as part of an operon.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The twenty conventional amino acids and their abbreviations follow conventional usage. See *Immunology-A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is sometimes also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A useful algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

Throughout this specification and claims, the word "comprise" or variations such as "comprises" or "comprising," will be understood to imply the inclusion of a stated integer or group of integers but not the exclusion of any other integer or group of integers.

Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Overview

Provided herein are recombinant strains and methods of producing recombinant strains to increase production of a full-length desired product in a target cell, e.g., by reducing protease degradation.

In some embodiments, to attenuate a protease activity in *Pichia pastoris*, the genes encoding these enzymes are inactivated or mutated to reduce or eliminate activity. This can be done through mutations or insertions into the gene itself of through modification of a gene regulatory element. This can be achieved through standard yeast genetics techniques. Examples of such techniques include gene replacement through double homologous recombination, in which homologous regions flanking the gene to be inactivated are cloned in a vector flanking a selectable maker gene (such as an antibiotic resistance gene or a gene complementing an auxotrophy of the yeast strain).

Alternatively, the homologous regions can be PCR-amplified and linked through overlapping PCR to the selectable marker gene. Subsequently, such DNA fragments are transformed into *Pichia pastoris* through methods known in the art, e.g., electroporation. Transformants that then grow under selective conditions are analyzed for the gene disruption event through standard techniques, e.g. PCR on genomic DNA or Southern blot. In an alternative experiment, gene inactivation can be achieved through single homologous recombination, in which case, e.g. the 5' end of the gene's ORF is cloned on a promoterless vector also containing a selectable marker gene. Upon linearization of such vector through digestion with a restriction enzyme only cutting the vector in the target-gene homologous fragment, such vector is transformed into *Pichia pastoris*. Integration at the target gene site is confirmed through PCR on genomic DNA or Southern blot. In this way, a duplication of the gene fragment cloned on the vector is achieved in the genome, resulting in two copies of the target gene locus: a first copy in which the ORF is incomplete, thus resulting in the expression (if at all) of a shortened, inactive protein, and a second copy which has no promoter to drive transcription.

Alternatively, transposon mutagenesis is used to inactivate the target gene. A library of such mutants can be screened through PCR for insertion events in the target gene.

The functional phenotype (i.e., deficiencies) of an engineered/knockout strain can be assessed using techniques known in the art. For example, a deficiency of an engineered strain in protease activity can be ascertained using any of a variety of methods known in the art, such as an assay of hydrolytic activity of chromogenic protease substrates, band shifts of substrate proteins for the selected protease, among others.

Attenuation of a protease activity described herein can be achieved through mechanisms other than a knockout mutation. For example, a desired protease can be attenuated via amino acid sequence changes by altering the nucleic acid sequence, placing the gene under the control of a less active promoter, down-regulation, expressing interfering RNA, ribozymes or antisense sequences that target the gene of interest, or through any other technique known in the art. In preferred strains, the protease activity of proteases encoded at PAS_chr4_0584 (YPS1-1) and PAS_chr3_1157 (YPS1-2) (e.g., polypeptides comprising SEQ ID NO: 67 and 68) is attenuated by any of the methods described above. In some aspects, the invention is directed to methylotrophic yeast strains, especially *Pichia pastoris* strains, wherein a YPS1-1 and a YPS1-2 gene (e.g., as set forth in SEQ ID NO: 1 and SEQ ID NO: 2) have been inactivated. In some embodiments, additional protease encoding genes may also be knocked-out in accordance with the methods provided herein to further reduce protease activity of a desired protein product expressed by the strain.

Production of Recombinant Strains

Provided herein are methods of transforming a strain to reduce activity, e.g., using vectors to deliver recombinant genes or to knock-out or otherwise attenuate endogenous genes as desired. These vectors can take the form of a vector backbone containing a replication origin and a selection marker (typically antibiotic resistance, although many other methods are possible), or a linear fragment that enables incorporation into the target cell's chromosome. The vectors should correspond to the organism and insertion method chosen.

Once the elements of a vector are selected, construction of the vector can be performed in many different ways. In an embodiment, a DNA synthesis service or a method to individually make every vector may be used.

Once the DNA for each vector (including the additional elements required for insertion and operation) is acquired, it must be assembled. There are many possible assembly methods including (but not limited to) restriction enzyme cloning, blunt-end ligation, and overlap assembly [see, e.g., Gibson, D. G., et al., Enzymatic assembly of DNA molecules up to several hundred kilobases. Nature methods, 6(5), 343-345 (2009), and GeneArt Kit (http://tools.invitrogen.com/content/sfs/manuals/geneart_seamless_cloning_and_assembly_man.pdf)]. Overlap assembly provides a method to ensure all of the elements get assembled in the correct position and do not introduce any undesired sequences.

The vectors generated above can be inserted into target cells using standard molecular biology techniques, e.g., molecular cloning. In an embodiment, the target cells are already engineered or selected such that they already contain the genes required to make the desired product, although this may also be done during or after further vector insertion.

Depending on the organism and library element type (plasmid or genomic insertion), several known methods of inserting the vector comprising DNA to incorporate into the cells may be used. These may include, for example, transformation of microorganisms able to take up and replicate DNA from the local environment, transformation by electroporation or chemical means, transduction with a virus or phage, mating of two or more cells, or conjugation from a different cell.

Several methods are known in the art to introduce recombinant DNA in bacterial cells that include but are not limited to transformation, transduction, and electroporation, see Sambrook, et al., Molecular Cloning: A Laboratory Manual (1989), Second Edition, Cold Spring Harbor Press, Plainview, N.Y. Non-limiting examples of commercial kits and bacterial host cells for transformation include NovaBlue Singles™ (EMD Chemicals Inc., NJ, USA), Max Efficiency® DH5α™, One Shot® BL21 (DE3) *E. coli* cells, One Shot® BL21 (DE3) pLys *E. coli* cells (Invitrogen Corp., Carlsbad, Calif., USA), XL1-Blue competent cells (Stratagene, Calif., USA). Non limiting examples of commercial kits and bacterial host cells for electroporation include Zappers™ electrocompetent cells (EMD Chemicals Inc., NJ, USA), XL1-Blue Electroporation-competent cells (Stratagene, Calif., USA), ElectroMAX™ *A. tumefaciens* LBA4404 Cells (Invitrogen Corp., Carlsbad, Calif., USA).

Several methods are known in the art to introduce recombinant nucleic acid in eukaryotic cells. Exemplary methods include transfection, electroporation, liposome mediated delivery of nucleic acid, microinjection into to the host cell, see Sambrook, et al., Molecular Cloning: A Laboratory Manual (1989), Second Edition, Cold Spring Harbor Press, Plainview, N.Y. Non-limiting examples of commercial kits and reagents for transfection of recombinant nucleic acid to eukaryotic cell include Lipofectamine™ 2000, Optifect™ Reagent, Calcium Phosphate Transfection Kit (Invitrogen Corp., Carlsbad, Calif., USA), GeneJammer® Transfection Reagent, LipoTAXI® Transfection Reagent (Stratagene, Calif., USA). Alternatively, recombinant nucleic acid may be introduced into insect cells (e.g. sf9, sf21, High Five™) by using baculo viral vectors.

Transformed cells are isolated so that each clone can be tested separately. In an embodiment, this is done by spreading the culture on one or more plates of culture media containing a selective agent (or lack of one) that will ensure that only transformed cells survive and reproduce. This specific agent may be an antibiotic (if the library contains an antibiotic resistance marker), a missing metabolite (for auxotroph complementation), or other means of selection. The cells are grown into individual colonies, each of which contains a single clone.

Colonies are screened for desired production of a protein, metabolite, or other product, or for reduction in protease activity. In an embodiment, screening identifies recombinant cells having the highest (or high enough) product production titer or efficiency. This includes a decreased proportion of degradation products or an increased total amount of full-length desired polypeptides collected from a cell culture.

This assay can be performed by growing individual clones, one per well, in multi-well culture plates. Once the cells have reached an appropriate biomass density, they are induced with methanol. After a period of time, typically 24-72 hours of induction, the cultures are harvested by spinning in a centrifuge to pellet the cells and removing the supernatant. The supernatant from each culture can then be tested for protease activity and/or protein degradation.

Silk Sequences

In some embodiments, the modified strains with reduced protease activity described herein recombinantly express a silk-like polypeptide sequence. In some embodiments, the silk-like polypeptide sequences are 1) block copolymer polypeptide compositions generated by mixing and matching repeat domains derived from silk polypeptide sequences and/or 2) recombinant expression of block copolymer polypeptides having sufficiently large size (approximately 40 kDa) to form useful fibers by secretion from an industrially scalable microorganism. Large (approximately 40 kDa to approximately 100 kDa) block copolymer polypeptides engineered from silk repeat domain fragments, including sequences from almost all published amino acid sequences of spider silk polypeptides, can be expressed in the modified microorganisms described herein. In some embodiments, silk polypeptide sequences are matched and designed to produce highly expressed and secreted polypeptides capable of fiber formation. In some embodiments, knock-out of protease genes or reduction of protease activity in the host modified strain reduces degradation of the silk like polypeptides.

Provided herein, in several embodiments, are compositions for expression and secretion of block copolymers engineered from a combinatorial mix of silk polypeptide domains across the silk polypeptide sequence space, wherein the block copolymers have minimal degradation. In some embodiments provided herein are methods of secreting block copolymers in scalable organisms (e.g., yeast, fungi, and gram positive bacteria) with minimal degradation. In some embodiments, the block copolymer polypeptide comprises 0 or more N-terminal domains (NTD), 1 or more repeat domains (REP), and 0 or more C-terminal domains (CTD). In some aspects of the embodiment, the block copolymer polypeptide is >100 amino acids of a single polypeptide chain. In some embodiments, the block copolymer polypeptide comprises a domain that is at least 80%, 81%, 82%, 83%, 84%, 85%, 86%, 87%, 88%, 89%, 90%, 91%, 92%, 93%, 94%, 95%, 96%, 97%, 98%, or 99% identical to a sequence of a block copolymer polypeptide as disclosed in International Publication No. WO/2015/042164, "Methods and Compositions for Synthesizing Improved Silk Fibers," incorporated by reference in its entirety.

Several types of native spider silks have been identified. The mechanical properties of each natively spun silk type are believed to be closely connected to the molecular composition of that silk. See, e.g., Garb, J. E., et al., Untangling spider silk evolution with spidroin terminal domains, *BMC Evol. Biol.,* 10:243 (2010); Bittencourt, D., et al., Protein families, natural history and biotechnological aspects of spider silk, *Genet. Mol. Res.,* 11:3 (2012); Rising, A., et al., Spider silk proteins: recent advances in recombinant production, structure-function relationships and biomedical applications, *Cell. Mol. Life Sci.,* 68:2, pg. 169-184 (2011); and Humenik, M., et al., Spider silk: understanding the structure-function relationship of a natural fiber, *Prog. Mol. Biol. Transl. Sci.,* 103, pg. 131-85 (2011). For example:

Aciniform (AcSp) silks tend to have high toughness, a result of moderately high strength coupled with moderately high extensibility. AcSp silks are characterized by large block ("ensemble repeat") sizes that often incorporate motifs of poly serine and GPX. Tubuliform (TuSp or Cylindrical) silks tend to have large diameters, with modest strength and high extensibility. TuSp silks are characterized by their poly serine and poly threonine content, and short tracts of poly alanine. Major Ampullate (MaSp) silks tend to have high strength and modest extensibility. MaSp silks can be one of two subtypes: MaSp1 and MaSp2. MaSp1 silks are generally less extensible than MaSp2 silks, and are characterized by poly alanine, GX, and GGX motifs. MaSp2 silks are characterized by poly alanine, GGX, and GPX motifs. Minor Ampullate (MiSp) silks tend to have modest strength and modest extensibility. MiSp silks are characterized by GGX, GA, and poly A motifs, and often contain spacer elements of approximately 100 amino acids. Flagelliform (Flag) silks tend to have very high extensibility and modest strength. Flag silks are usually characterized by GPG, GGX, and short spacer motifs.

The properties of each silk type can vary from species to species, and spiders leading distinct lifestyles (e.g. sedentary web spinners vs. vagabond hunters) or that are evolutionarily older may produce silks that differ in properties from the above descriptions (for descriptions of spider diversity and classification, see Hormiga, G., and Griswold, C. E., Systematics, phylogeny, and evolution of orb-weaving spiders, *Annu. Rev. Entomol.* 59, pg. 487-512 (2014); and Blackedge, T. A. et al., Reconstructing web evolution and spider diversification in the molecular era, *Proc. Natl. Acad. Sci. USA.,* 106:13, pg. 5229-5234 (2009)). However, synthetic block copolymer polypeptides having sequence similarity and/or amino acid composition similarity to the repeat domains of native silk proteins can be used to manufacture on commercial scales consistent silk-like fibers that recapitulate the properties of corresponding natural silk fibers.

In some embodiments, a list of putative silk sequences can be compiled by searching GenBank for relevant terms, e.g. "spidroin" "fibroin" "MaSp", and those sequences can be pooled with additional sequences obtained through independent sequencing efforts. Sequences are then translated into amino acids, filtered for duplicate entries, and manually split into domains (NTD, REP, CTD). In some embodiments, candidate amino acid sequences are reverse translated into a DNA sequence optimized for expression in *Pichia* (*Komagataella*) *pastoris*. The DNA sequences are each cloned into an expression vector and transformed into *Pichia* (*Komagataella*) *pastoris*. In some embodiments, various silk domains demonstrating successful expression and secretion are subsequently assembled in combinatorial fashion to build silk molecules capable of fiber formation.

Silk polypeptides are characteristically composed of a repeat domain (REP) flanked by non-repetitive regions (e.g., C-terminal and N-terminal domains). In an embodiment, both the C-terminal and N-terminal domains are between 75-350 amino acids in length. The repeat domain exhibits a hierarchical architecture. The repeat domain comprises a series of blocks (also called repeat units). The blocks are repeated, sometimes perfectly and sometimes imperfectly (making up a quasi-repeat domain), throughout the silk repeat domain. The length and composition of blocks varies among different silk types and across different species. Table 1 lists examples of block sequences from selected species and silk types, with further examples presented in Rising, A. et al., Spider silk proteins: recent advances in recombinant production, structure-function relationships and biomedical applications, *Cell Mol. Life Sci.,* 68:2, pg 169-184 (2011); and Gatesy, J. et al., Extreme diversity, conservation, and convergence of spider silk fibroin sequences, *Science,* 291:5513, pg. 2603-2605 (2001). In some cases, blocks may be arranged in a regular pattern, forming larger macro-repeats that appear multiple times (usually 2-8) in the repeat domain of the silk sequence. Repeated blocks inside a repeat domain or macro-repeat, and repeated macro-repeats within the repeat domain, may be separated by spacing elements. In some embodiments, block sequences comprise a glycine rich region followed by a polyA region. In some embodiments, short (~1-10) amino acid motifs appear multiple times inside of blocks. For the purpose of this invention, blocks from different natural silk polypeptides can be selected without reference to circular permutation (i.e., identified blocks that are otherwise similar between silk polypeptides may not align due to circular permutation). Thus, for example, a "block" of SGAGG (SEQ ID NO: 494) is, for the purposes of the present invention, the same as GSGAG (SEQ ID NO: 495) and the same as GGSGA (SEQ ID NO: 496); they are all just circular permutations of each other. The particular permutation selected for a given silk sequence can be dictated by convenience (usually starting with a G) more than anything else. Silk sequences obtained from the NCBI database can be partitioned into blocks and non-repetitive regions.

TABLE 1

Samples of Block Sequences

| Species | Silk Type | Representative Block Amino Acid Sequence |
|---|---|---|
| *Aliatypus gulosus* | Fibroin 1 | GAASSSSTIITTKSASASAAADASAAATASAASRSSANAAASAFAQSFSSILLESGYFCSIFGSSISSSYAAAIASAASRAAAESNGYTTHAYACAKAVASAVERVTSGADAYAYAQAISDALSHALLYTGRLNTANANSLASAFAYAFANAAAQASASSASAGAASASGAASASGAGSAS (SEQ ID NO: 497) |
| *Plectreurys tristis* | Fibroin 1 | GAGAGAGAGAGAGAGAGSGASTSVSTSSSSGSGAGAGAGSGAGSGAGAGSGAGAGAGAGGAGAGFGSGLGLGYGVGLSSAQAQAQAQAAAQAQAQAQAQAYAAAQAQAQAQAQAQAAAAAAAAAAA (SEQ ID NO: 498) |
| *Plectreurys tristis* | Fibroin 4 | GAAQKQPSGESSVATASAAATSVTSGGAPVGKPGVPAPIFYPQGPLQQGPAPGPSNVQPGTSQQGPIGGVGGSNAFSSSFASALSLNRGFTEVISSASATAVASAFQKGLAPYGTAFALSAASAAADAYNSIGSGANAFAYAQAFARVLYPLVQQYGLSSSAKASAFASAIASSFSSGTSGQGPSIGQQQPPVTISAASASAGASAAAVGGGQVGQGPYGGQQQSTAASASAAAATATS (SEQ ID NO: 499) |
| *Araneus gemmoides* | TuSp | GNVGYQLGLKVANSLGLGNAQALASSLSQAVSAVGVGASSNAYANAVSNAVGQVLAGQGILNAANAGSLASSFASALSSSAASVASQSASQSQAASQSQAAASAFRQAASQSASQSDSRAGSQSSTKTTSTSTSGSQADSRSASSSASQASASAFAQQSSASLSSSSSFSSAFSSATSISAV (SEQ ID NO: 500) |
| *Argiope aurantia* | TuSp | GSLASSFASALSASAASVASSAAAQAASQSQAAASAFSRAASQSASQSAARSGAQSISTTTTTSTAGSQAASQSASSAASQASASSFARASSASLAASSSFSSAFSSANSLSALGNVGYQLGFNVANNLGIGNAAGLGNALSQAVSSVGVGASSSTYANAVSNAVGQFLAGQGILNAANA (SEQ ID NO: 501) |
| *Deinopis spinosa* | TuSp | GASASAYASAISNAVGPYLYGLGLFNQANAASFASSFASAVSSAVASASASAASSAYAQSAAAQAQAASSAFSQAAAQSAAAASAGASAGAGASAGAGAVAGAGAVAGAGAVAGASAAAASQAAASSSASAVASAFAQSASYALASSSAFANAFASATSAGYLGSLAYQLGLTTAYNLGLSNAQAFASTLSQAVTGVGL (SEQ ID NO: 502) |
| *Nephila clavipes* | TuSp | GATAASYGNALSTAAAQFFATAGLLNAGNASALASSFARAFSASAESQSFAQSQAFQQASAFQQAASRSASQSAAEAGSTSSSTTTTTSAARSQAASQSASSSYSSAFAQAASSSLATSSALSRAFSSVSSASAASSLAYSIGLSAARSLGIADAAGLAGVLARAAGALGQ (SEQ ID NO: 503) |
| *Argiope trifasciata* | Flag | GGAPGGGPGGAGPGGAGFGPGGGAGFGPGGGAGFGPGGAAGGPGGPGGPGGPGGAGGYGPGGAGGYGPGGVGPGGAGGYGPGGAGGYGPGGSGPGGAGPGGAGGEGPVTVDVDVTVGPEGVGGGPGGAGPGGAGFGPGGGAGFGPGGAPGAPGGPGGPGGPGGPGGVGPGGAGGYGPGGAGGVGPAGTGGFGPGGAGGFGPGGAGGFGPGGAGGFGPAGAGGYGPGGVGPGGAGGFGPGGVGPGGSGPGGAGGEGPVTVDVDVSV (SEQ ID NO: 504) |
| *Nephila clavipes* | Flag | GVSYGPGGAGGPYGPGGPYGPGGEGPGGAGGPYGPGGVGPGGSGPGGYGPGGAGPGGYGPGGSGPGGYGPGGSGPGGYGPGGSGPGGYGPGGSGPGGYGPGGYGPGGSGPGGSGPGGSGPGGYGPGGTGPGGSGPGGYGPGGSGPGGSGPGGYGPGGSGPGGFGPGGSGPGGYGPGGSGPGGAGPGGVGPGGFGPGGAGPGGAAPGGAGPGGAGPGGAGPGGAGPGGAGPGGAGPGGAGGAGGAGGSGGAGGSGGTTIIEDLDITIDGADGPITISEELPISGAGGSGPGGAGPGGVGPGGSGPGGVGPGGSGPGGVGPGGSGPGGVGPGGAGGPYGPGGSGPGGAGGAGGPGGAYGPGGSYGPGGSGGPGGAGGPYGPGGEGPGGAGGPYGPGGAGGPYGPGGEGGPYGP (SEQ ID NO: 505) |
| *Latrodectus hespeina* | AcSp | GINVDSDIGSVTSLILSGSTLQMTIPAGGDDLSGGYPGGFPAGAQPSGGAPVDFGGPSAGGDVAAKLARSLASTLASSGVFRAAFNSRVSTPVAVQLTDALVQKIASNLGLDYATASKLRKASQAVSKVRMGSDTNAYALAISSALAEVLSSSGKVADANINQIAPQLASGIVLGVSTTAPQFGVDLSSINVNLDISNVARNMQASIQGGPAPITAEGPDFGAGYPGGAPTDLSGLDMGAPSDGSRGGDATAKLLQALVPALLKSDVFRAIYKRGTRKQVVQYVTNSALQQAASSLGLDASTISQLQTKATQALSSVSADSDSTAYAKAFGLAIAQVLGTSGQVNDANVNQIGAKLATGILRGSSAVAPRLGIDLS (SEQ ID NO: 506) |
| *Argiope trifasciata* | AcSp | GAGYTGPSGPSTGPSGYPGPLGGGAPFGQSGFGGSAGPQGGFGATGGASAGLISRVANALANTSTLRTVLRTGVSQQIASSVVQRAAQSLASTLGVDGNNLARFAVQAVSRLPAGSDTSAYAQAFSSALFNAGVLNASNIDTLGSRVLSALLNGVSSAAQGLGINVDSGSVQSDISSSSSFLSTSSSSASYSQASASSTS (SEQ ID NO: 507) |

TABLE 1-continued

Samples of Block Sequences

| Species | Silk Type | Representative Block Amino Acid Sequence |
|---|---|---|
| *Uloborus diversus* | AcSp | GASAADIATAIAASVATSLQSNGVLTASNVSQLSNQLASYVSSGLSS TASSLGIQLGASLGAGFGASAGLSASTDISSSVEATSASTLSSSASS TSVVSSINAQLVPALAQTAVLNAAFSNINTQNAIRIAELLTQQVGRQ YGLSGSDVATASSQIRSALYSVQQGSASSAYVSAIVGPLITALSSRG VVNASNSSQIASSLATAILQFTANVAPQFGISIPTSAVQSDLSTISQ SLTAISSQTSSSVDSSTSAFGGISGPSGPSPYGPQPSGPTFGPGPSL SGLTGFTATFASSFKSTLASSTQFQLIAQSNLDVQTRSSLISKVLIN ALSSLGISASVASSIAASSSQSLLSVSA (SEQ ID NO: 508) |
| *Euprosthenops australis* | MaSp1 | GGQGGQGQGRYGQGAGSS (SEQ ID NO: 509) |
| *Tetragnatha hmuiensis* | MaSp1 | GGLGGGQGAGQGGQQGAGQGGYGSGLGGAGQGASAAAAAAAA (SEQ ID NO: 510) |
| *Argiope auranna* | MaSp2 | GGYGPGAGQQGPGSQGPGSGGQQGPGGLGPYGPSAAAAAAAA (SEQ ID NO: 511) |
| *Deinopis spinosa* | MaSp2 | GPGGYGGPGQQGPGQGQYGPGTGQQGQGPSGQQGPAGAAAAAAAAA (SEQ ID NO: 512) |
| *Nephila clavata* | MaSp2 | GPGGYGLGQQGPGQQGPGQQGPAGYGPSGLSGPGGAAAAAAA (SEQ ID NO: 513) |

Fiber-forming block copolymer polypeptides from the blocks and/or macro-repeat domains, according to certain embodiments of the invention, is described in International Publication No. WO/2015/042164, incorporated by reference. Natural silk sequences obtained from a protein database such as GenBank or through de novo sequencing are broken up by domain (N-terminal domain, repeat domain, and C-terminal domain). The N-terminal domain and C-terminal domain sequences selected for the purpose of synthesis and assembly into fibers include natural amino acid sequence information and other modifications described herein. The repeat domain is decomposed into repeat sequences containing representative blocks, usually 1-8 depending upon the type of silk, that capture critical amino acid information while reducing the size of the DNA encoding the amino acids into a readily synthesizable fragment. In some embodiments, a properly formed block copolymer polypeptide comprises at least one repeat domain comprising at least 1 repeat sequence, and is optionally flanked by an N-terminal domain and/or a C-terminal domain.

In some embodiments, a repeat domain comprises at least one repeat sequence. In some embodiments, the repeat sequence is 150-300 amino acid residues. In some embodiments, the repeat sequence comprises a plurality of blocks. In some embodiments, the repeat sequence comprises a plurality of macro-repeats. In some embodiments, a block or a macro-repeat is split across multiple repeat sequences.

In some embodiments, the repeat sequence starts with a Glycine, and cannot end with phenylalanine (F), tyrosine (Y), tryptophan (W), cysteine (C), histidine (H), asparagine (N), methionine (M), or aspartic acid (D) to satisfy DNA assembly requirements. In some embodiments, some of the repeat sequences can be altered as compared to native sequences. In some embodiments, the repeat sequencess can be altered such as by addition of a serine to the C terminus of the polypeptide (to avoid terminating in F, Y, W, C, H, N, M, or D). In some embodiments, the repeat sequence can be modified by filling in an incomplete block with homologous sequence from another block. In some embodiments, the repeat sequence can be modified by rearranging the order of blocks or macrorepeats.

In some embodiments, non-repetitive N- and C-terminal domains can be selected for synthesis. In some embodiments, N-terminal domains can be by removal of the leading signal sequence, e.g., as identified by SignalP (Peterson, T. N., et. Al., SignalP 4.0: discriminating signal peptides from transmembrane regions, *Nat. Methods,* 8:10, pg. 785-786 (2011).

In some embodiments, the N-terminal domain, repeat sequence, or C-terminal domain sequences can be derived from *Agelenopsis aperta, Aliatypus gulosus, Aphonopelma seemanni, Aptostichus* sp. AS217, *Aptostichus* sp. AS220, *Araneus diadematus, Araneus gemmoides, Araneus ventricosus, Argiope amoena, Argiope argentata, Argiope bruennichi, Argiope trifasciata, Atypoides riversi, Avicularia juruensis, Bothriocyrtum californicum, Deinopis Spinosa, Diguetia canities, Dolomedes tenebrosus, Euagrus chisoseus, Euprosthenops australis, Gasteracantha mammosa, Hypochilus thorelli, Kukulcania hibernalis, Latrodectus hesperus, Megahexura fulva, Metepeira grandiosa, Nephila antipodiana, Nephila clavata, Nephila clavipes, Nephila madagascariensis, Nephila Nephilengys cruentata, Parawixia bistriata, Peucetia viridans, Plectreurys tristis, Poecilotheria regalis, Tetragnatha kauaiensis*, or *Uloborus diversus.*

In some embodiments, the silk polypeptide nucleotide coding sequence can be operatively linked to an alpha mating factor nucleotide coding sequence. In some embodiments, the silk polypeptide nucleotide coding sequence can be operatively linked to another endogenous or heterologous secretion signal coding sequence. In some embodiments, the silk polypeptide nucleotide coding sequence can be operatively linked to a 3×FLAG nucleotide coding sequence. In some embodiments, the silk polypeptide nucleotide coding sequence is operatively linked to other affinity tags such as 6-8 His residues (SEQ ID NO: 520).

Silk-Like Polypeptides

In some embodiments, the *P. pastoris* strains disclosed herein have been modified to express a silk-like polypeptide. Methods of manufacturing preferred embodiments of silk-like polypeptides are provided in WO 2015/042164, especially at Paragraphs 114-134, incorporated herein by reference. Disclosed therein are synthetic proteinaceous copolymers based on recombinant spider silk protein fragment sequences derived from MaSp2, such as from the species *Argiope bruennichi*. Silk-like polypeptides are described that include two to twenty repeat units, in which a molecular weight of each repeat unit is greater than about 20 kDa. Within each repeat unit of the copolymer are more than about 60 amino acid residues that are organized into a number of "quasi-repeat units." In some embodiments, the repeat unit of a polypeptide described in this disclosure has at least 95% sequence identity to a MaSp2 dragline silk protein sequence.

In some embodiments, each "repeat unit" of a silk-like polypeptide comprises from two to twenty "quasi-repeat" units (i.e., $n_3$ is from 2 to 20). Quasi-repeats do not have to be exact repeats. Each repeat can be made up of concatenated quasi-repeats. Equation 1 shows the composition of a repeat unit according the present disclosure and that incorporated by reference from WO 2015/042164. Each silk-like polypeptide can have one or more repeat units as defined by Equation 1.

(Equation 1)

(SEQ ID NO: 514)

$\{GGY\text{-}[GPG\text{-}X_1]_{n1}\text{-}GPS\text{-}(A)_{n2}\}_{n3}$.

The variable compositional element $X_1$ (termed a "motif") is according to any one of the following amino acid sequences shown in Equation 2 and $X_1$ varies randomly within each quasi-repeat unit.

(Equation 2)

(SEQ ID NO: 515)

$X_1$ = SGGQQ or (SEQ ID NO: 516)

GAGQQ or (SEQ ID NO: 517)

GQGPY or (SEQ ID NO: 518)

AGQQ or

SQ

Referring again to Equation 1, the compositional element of a quasi-repeat unit represented by "GGY-[GPG-$X_1$]$_{n1}$-GPS" (SEQ ID NO: 521) in Equation 1 is referred to a "first region." A quasi-repeat unit is formed, in part by repeating from 4 to 8 times the first region within the quasi-repeat unit. That is, the value of n1 indicates the number of first region units that are repeated within a single quasi-repeat unit, the value of n1 being any one of 4, 5, 6, 7 or 8. The compositional element represented by "$(A)_{n2}$" (SEQ ID NO: 522) (i.e., a polyA sequence) is referred to as a "second region" and is formed by repeating within each quasi-repeat unit the amino acid sequence "A" $n_2$ times (SEQ ID NO: 522). That is, the value of $n_2$ indicates the number of second region units that are repeated within a single quasi-repeat unit, the value of $n_2$ being any one of 6, 7, 8, 9, 10, 11, 12, 13, 14, 15, 16, 17, 18, 19, or 20. In some embodiments, the repeat unit of a polypeptide of this disclosure has at least 95% sequence identity to a sequence containing quasi-repeats described by Equations 1 and 2. In some embodiments, the repeat unit of a polypeptide of this disclosure has at least 80%, or at least 90%, or at least 95%, or at least 99% sequence identity to a sequence containing quasi-repeats described by Equations 1 and 2.

In additional embodiments, 3 "long" quasi repeats are followed by 3 "short" quasi-repeat units. Short quasi-repeat units are those in which $n_1$=4 or 5. Long quasi-repeat units are defined as those in which $n_1$=6, 7 or 8. In some embodiments, all of the short quasi-repeats have the same $X_1$ motifs in the same positions within each quasi-repeat unit of a repeat unit. In some embodiments, no more than 3 quasi-repeat units out of 6 share the same $X_1$ motifs.

In additional embodiments, a repeat unit is composed of quasi-repeat units that do not use the same $X_1$ more than two occurrences in a row within a repeat unit. In additional embodiments, a repeat unit is composed of quasi-repeat units where at least 1, 2, 3, 4, 5, 6, 7, 8, 9, 10, 11, 12, 13, 14, 15, 16, 17, 18, 19 or 20 of the quasi-repeats do not use the same $X_1$ more than 2 times in a single quasi-repeat unit of the repeat unit.

Thus, in some embodiments, provided herein are strains of yeast that recombinantly express silk-like polypeptides with a reduced degradation to increase the amount of full-length polypeptides present in the isolated product from a cell culture. In some embodiments, the strain expressing a silk-like polypeptide is a *P. pastoris* strain comprises a PAS_chr4_0584 knock-out and a PAS_chr3_1157 knock-out.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

Example 1: Production of Recombinant Yeast Expressing 18B

First, we transformed a strain of *P. pastoris* to abrogate KU70 function to facilitate further editing and engineering. A HIS+ derivative of *Pichia pastoris* (*Komagataella phaffii*) strain GS115 (NRRL Y15851) was electroporated with a DNA cassette consisting of homology arms flanking a zeocin resistance marker and targeting the KU70 locus. A map of the cassette is shown in FIG. 1, and sequences are provided in Table 10. Transformants were plated on YPD agar plates supplemented with zeocin. This resulted in abrogation of KU70 function.

Then, we modified this strain to express a recombinant gene encoding a silk-like polypeptide. A HIS+ derivative of *Pichia pastoris* (*Komagataella phaffii*) strain GS115 (NRRL Y15851) was transformed with a recombinant vector (SEQ ID NO: 462) to cause expression and secretion of a silk-like polypeptide ("18B") (SEQ ID NO: 463). Transformation was accomplished by electroporation as described in PMID 15679083, incorporated by reference herein.

Each vector includes an 18B expression cassette with the polynucleotide sequence encoding the silk-like protein in the recombinant vectors flanked by a promoter (pGCW14) and a terminator (tAOX1 pA signal). The recombinant vectors further comprised dominant resistance markers for selection of bacterial and yeast transformants, and a bacterial origin of replication. The first recombinant vector included targeting regions that directed integration of the 18B polynucleotide sequences immediately 3' of the AOX2 loci in the *Pichia pastoris* genome. The resistance marker in the first vector conferred resistance to G418 (aka geneticin). The second recombinant vector included targeting regions that directed integration of the 18B polynucleotide sequences immediately 3' of the TEF1 loci in the *Pichia pastoris* genome. The resistance marker in the second vector conferred resistance to Hygromycin B.

Example 2: Generating a Library of Single Protease KO Mutants

Figure 2:
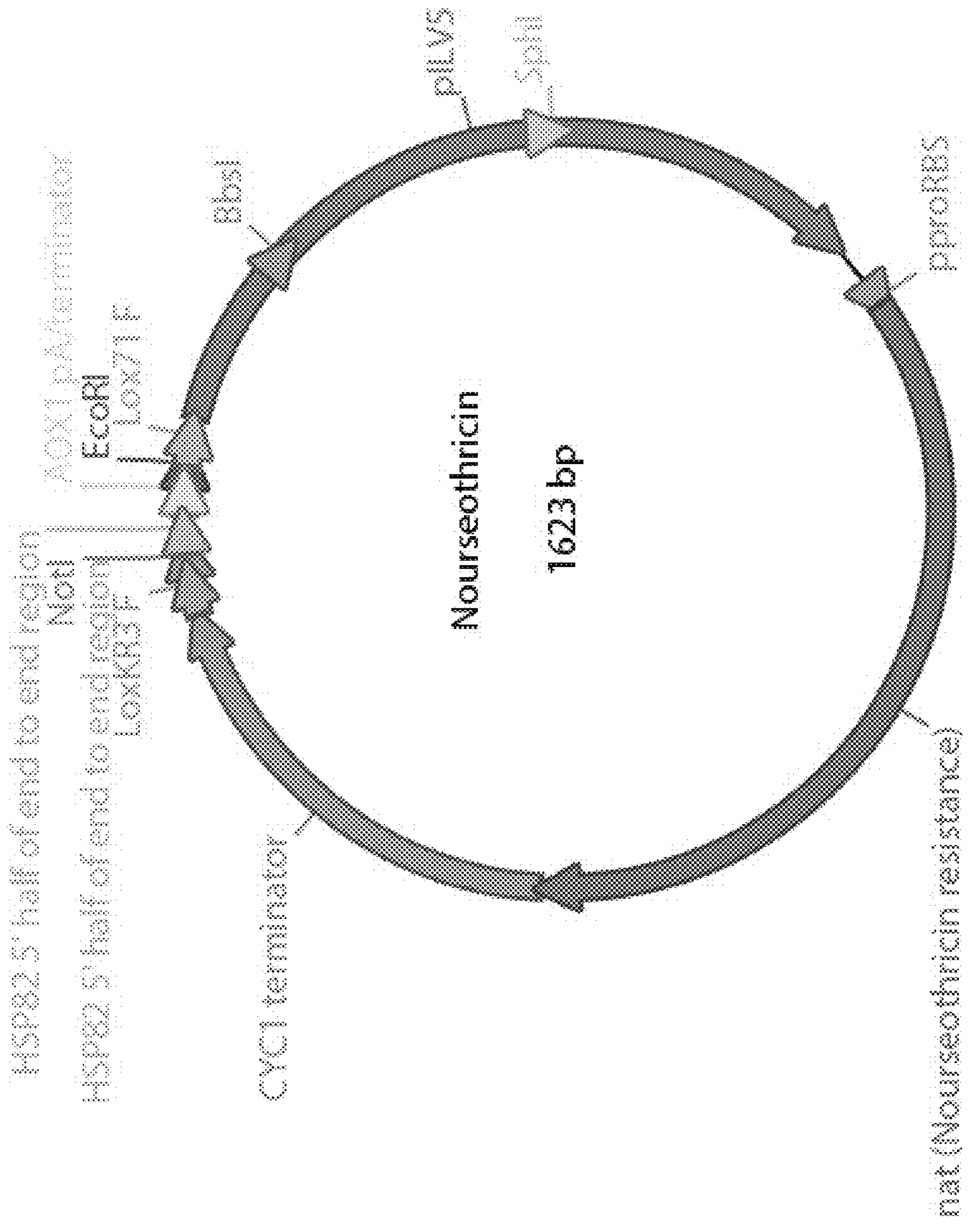
FIG. 2 is a plasmid map of a plasmid comprising a nourseothricin marker used with homology arms for targeted protease gene deletion.

After successful transformation and secretion of 18B in a recombinant *Pichia pastoris* strain, 65 open reading frames (ORFs) encoding proteases were individually targeted for deletion (Table 2). Cells were transformed with vector comprising a DNA cassette with ~1150 bp homology arms flanking a nourseothricin resistance marker. A plasmid map comprising the nourseothricin resistance marker is shown in FIG. 2, and sequences provided in Table 11.

Figure 3A:
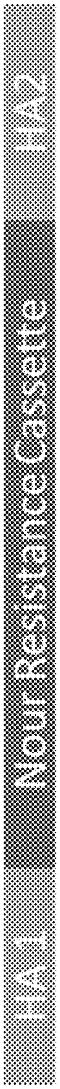
FIG. 3A and FIG. 3B are cassettes for protease knockout with homology arms targeting the desired protease gene flanking a nourseothricin resistance marker.
Figure 3B:
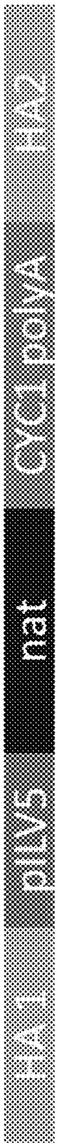

Homology arms used for each target were amplified by the primers provided in Table 7, and inserted into the nourseothricin resistance plasmid. Homology arms were inserted into the nourseothricin plasmid to generate cassettes comprising a nourseothricin resistance marker flanded by 3' and 5' homology arms to the target protease as shown in FIG. 3A and FIG. 3B. In FIG. 3A, the resistance cassette (Nour Resistance Cassette) is shown flanked by homology arms (HA1 and HA2). In FIG. 3B, details of the nourseothricin marker are shown, including the promoter from ILV5 gene from *Saccharomyces cerevisiae* (pILV5), the Nourseothricin acetyltransferase gene from *Streptomyces noursei* (nat), and the polyA signal from CYC1 gene from *Saccharomyces cerevisiae.*

The homology arms in each vector targeted one of the 65 desired protease loci as provided in Table 2. Transformants were plated on YPD agar plates supplemented with nourseothricin, and incubated for 48 hours at 30° C.

TABLE 2

Proteases targeted for deletion in *P. Pastoris* strain

| Protease Gene Symbol | Protease ORF Sequence (SEQ ID NO:) | Protease polypeptide sequence (SEQ ID NO:) |
|---|---|---|
| PAS_chr4_0584 (YPS1-1) | 1 | 67 |
| PAS_chr3_1157 (YPS1-2) | 2 | 68 |
| PAS_chr3_0299 (YPS1-3) | 3 | |
| PAS_chr3_0303 | 4 | |
| PAS_chr3_0866 | 5 | |
| PAS_chr3_0394 | 6 | |
| PAS_chr1-1_0379 (MCK7) | 7 | |
| PAS chr1-1 0174 | 8 | |
| PAS chr1-1 0226 | 9 | |
| PAS_chr3_1087 | 10 | |
| PAS_chr3_0076 | 11 | |
| PAS_chr3_0691 | 12 | |
| PAS_chr3_0815 | 13 | |
| PAS_chr1-4_0164 | 14 | |
| PAS_chr3_0979 | 15 | |
| PAS_chr3_0803 | 16 | |
| PAS_chr2-1_0366 | 17 | |
| PAS_chr3_0842 | 18 | |
| PAS_chr1-3_0195 | 19 | |
| PAS_chr1-4_0052 | 20 | |
| PAS_chr2-2_0057 | 21 | |
| PAS_chr1-3_0150 | 22 | |
| PAS_chr1-3_0221 | 23 | |
| PAS_FragD_0022 | 24 | |
| PAS_chr2-1_0159 | 25 | |
| PAS_chr2-1_0326 | 26 | |
| PAS_chr1-4_0611 | 27 | |
| PAS_chr1-1_0274 | 28 | |
| PAS_chr4_0834 | 29 | |
| PAS_chr3_0896 | 30 | |
| PAS_chr3_0561 | 31 | |

TABLE 2-continued

Proteases targeted for deletion in *P. Pastoris* strain

| Protease Gene Symbol | Protease ORF Sequence (SEQ ID NO:) | Protease polypeptide sequence (SEQ ID NO:) |
|---|---|---|
| PAS_chr3_0633 | 32 | |
| PAS_chr4_0013 | 33 | |
| PAS_chr2-1_0172 | 34 | |
| PAS_chr1-4_0251 | 35 | |
| PAS_chr4_0874 | 36 | |
| PAS_chr3_0513 | 37 | |
| PAS_chr1-1_0127 | 38 | |
| PAS_chr4_0686 | 39 | |
| PAS_chr2-2_0056 | 40 | |
| PAS_chr2-2_0159 | 41 | |
| PAS_chr3_0388 | 42 | |
| PAS_chr3_0419 | 43 | |
| PAS_chr1-3_0258 | 44 | |
| PAS_chr4_0913 | 45 | |
| PAS_chr1-1_0066 | 46 | |
| PAS_chr2-2_0310 | 47 | |
| PAS_chr1-3_0261 | 48 | |
| PAS_chr2-1_0546 | 49 | |
| PAS_chr2-2_0398 | 50 | |
| PAS_chr4_0835 | 51 | |
| PAS_chr1-1_0491 | 52 | |
| PAS_chr2-1_0447 | 53 | |
| PAS_chr1-3_0053 | 54 | |
| PAS_chr3_0200 | 55 | |
| PAS_chr1-3_0105 | 56 | |
| PAS_chr3_0635 | 57 | |
| PAS_chr4_0503 | 58 | |
| PAS_chr2-1_0569 | 59 | |
| PAS_chr3_1223 | 60 | |
| PAS_chr2-1_0597 | 61 | |
| PAS_chr1-1_0327 | 62 | |
| PAS_chr2-2_0380 | 63 | |
| PAS_chr3_0928 | 64 | |
| PAS_chr1-3_0184 | 65 | |

Example 3: Testing Single Protease Knockout Clones for Reduced Protein Degradation Resulting clones were inoculated into 400 µL of Buffered Glycerol-complex Medium (BMGY) in 96-well blocks, and incubated for 48 hours at 30° C. with agitation at 1,000 rpm. Following the 48-hour incubation, 4 µL of each culture was used to inoculate 400 µL of BMGY in 96-well blocks, which were then incubated for 48 hours at 30° C. Guanidine thiocyanate was added to a final concentration of 2.5M to the cell cultures to extract the recombinant protein. After a 5 minute incubation, solutions were centrifuged and the supernatant was sampled and analyzed by western blot.

Figure 4:
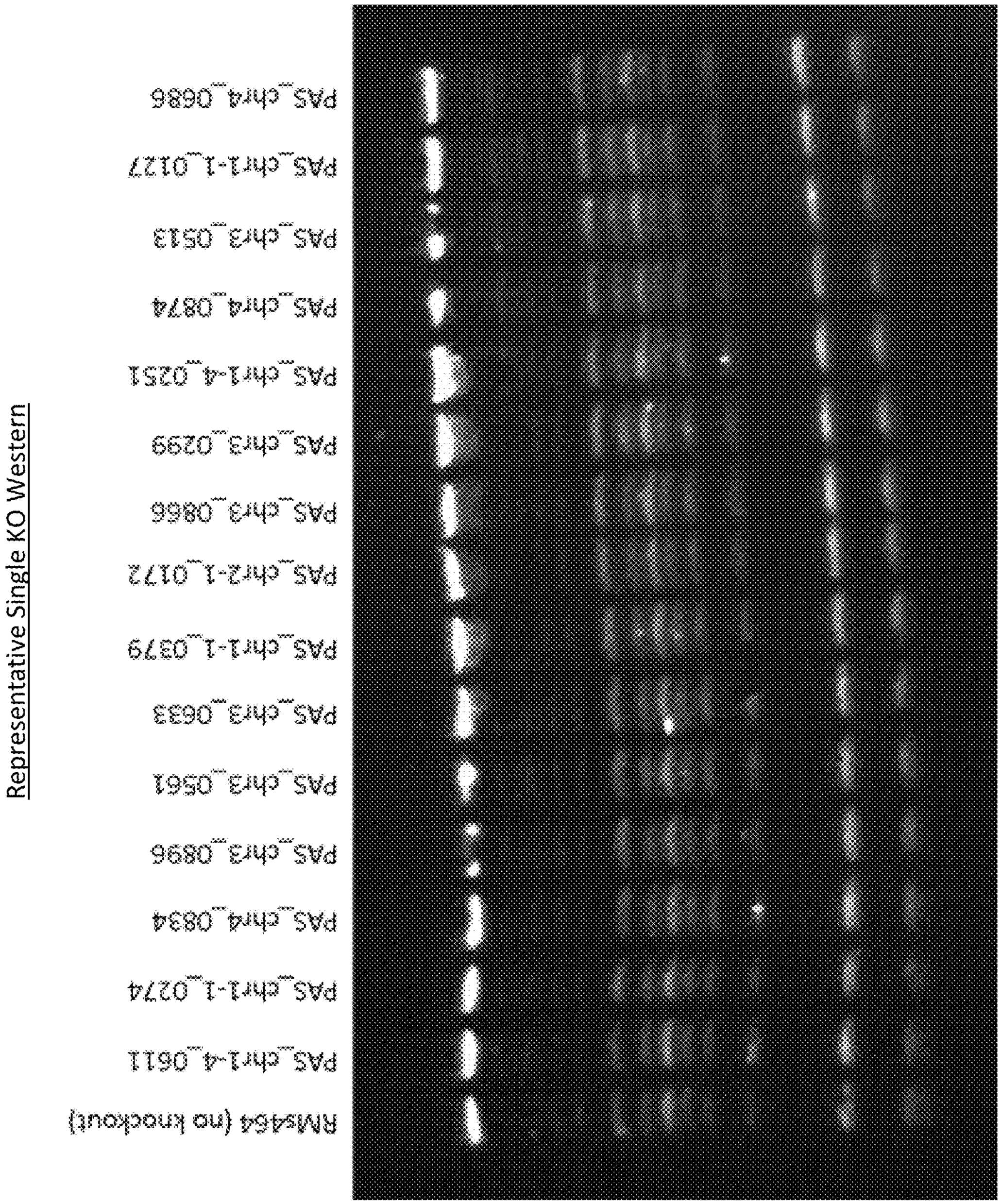
FIG. 4 is a representative western blot of protein isolated from single KO strains to show protein degradation from these strains.

Western blot data for a representative clone of each protease knock-out is shown in FIG. 4. Single protease deletions showed no discernable impact on the distribution of 18B silk fragments detected via western blot.

Example 4: Generating a Library of Protease Double Knock-Outs

In addition to the individual KOs, different pair-wise combinations of proteases were knocked out. These proteases were selected, in part, because they were paralogs that may have compensatory function with respect to each other.

To generate double knockouts, nourseothricin resistance was eliminated from the single protease knock-out strains produced in Example 2, and a second protease deleted by transformation with a second nourseothricin resistance cassette as provided in Example 2. Transformants were plated on YPD agar plates supplemented with nourseothricin, and incubated for 48 hours at 30° C. Double protease knock-outs tested are provided in Table 3.

TABLE 3

Protease double KO strains of *P. Pastoris* expressing silk-like polypeptide

| Double KO Strain | Protease KO 1 | ORF SEQ ID NO: | Protease KO 2 | ORF SEQ ID NO: |
|---|---|---|---|---|
| 1 | PAS_chr1-1_0379 | 7 | PAS_chr3_0299 | 3 |
| 2 | PAS_chr3_0394 | 6 | PAS_chr3_0303 | 4 |
| 3 | PAS_chr4_0584 | 1 | PAS_chr3_1157 | 2 |
| 4 | PAS_chr3_0076 | 11 | PAS_chr1-4_0164 | 14 |
| 5 | PAS_chr4_0584 | 1 | PAS_chr3_0299 | 3 |
| 6 | PAS_chr1-3_0195 | 19 | PAS_chr1-4_0289 | 66 |
| 7 | PAS_chr3_0896 | 30 | PAS_chr2-2_0310 | 47 |
| 8 | PAS_chr3_0394 | 6 | PAS_chr3_1157 | 2 |

Example 5: Testing Double Protease Knockout Clones for Reduced Protein Degradation Resulting clones were inoculated into 400 µL of Buffered Glycerol-complex Medium (BMGY) in 96-well blocks, and incubated for 48 hours at 30° C. with agitation at 1,000 rpm. Following the 48-hour incubation, 4 µL of each culture was used to inoculate 400 µL of BMGY in 96-well blocks, which were then incubated for 48 hours at 30° C. Guanidine thiocyanate was added to a final concentration of 2.5M to the cell cultures to extract the recombinant protein. After a 5 min incubation, solutions were centrifuged and the supernatant was sampled and analyzed by western blot.

Figure 5:
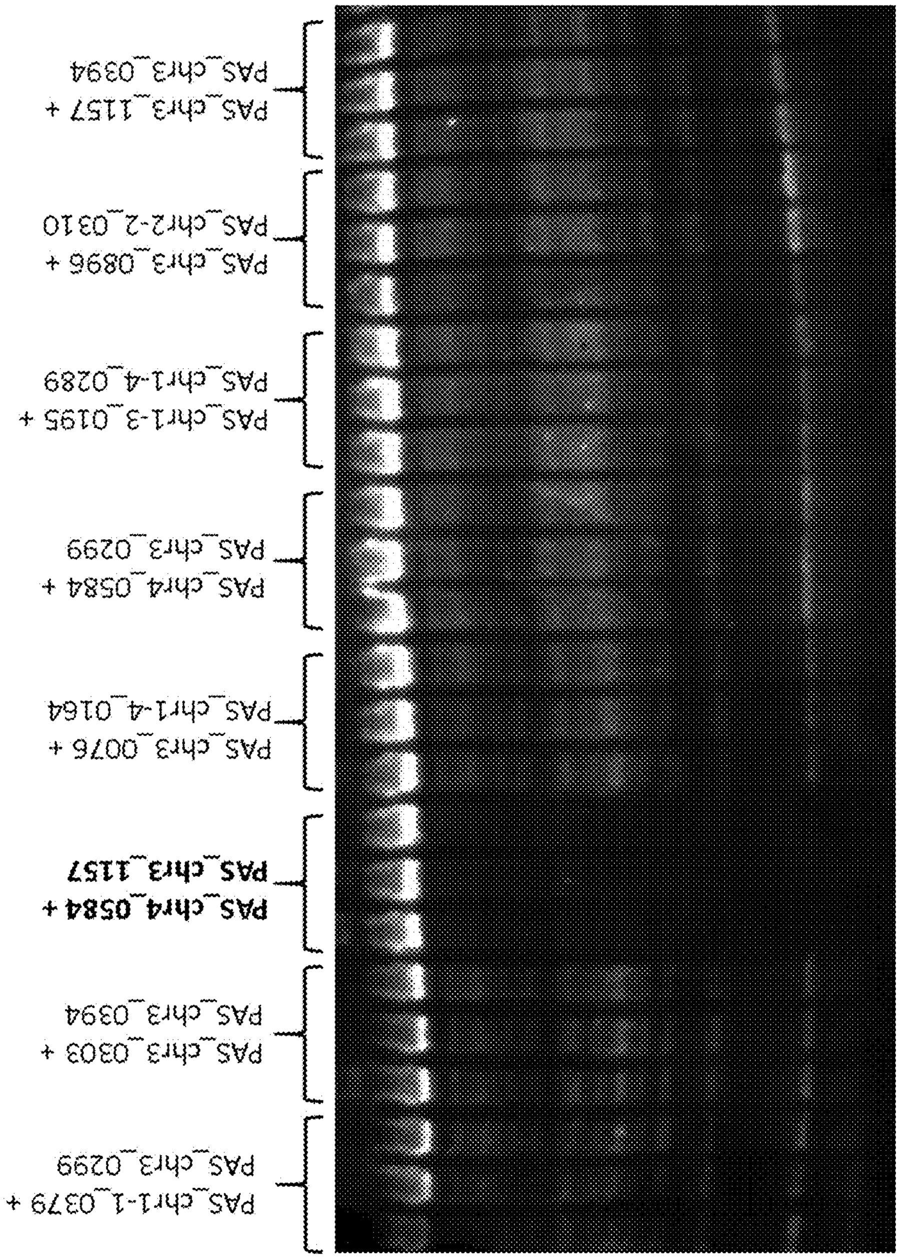
FIG. 5 is a representative western blot of protein isolated from double KO strains to show protein degradation from these strains.

FIG. 5 shows representative results from different protease double knockout strains. As shown, despite the presence of protein degradation in all single knockout strains tested, the combination of PAS_chr4_0584+PAS_chr3_1157 protease knockout (Strain 3 from Table 3) resulted in the near-complete elimination of 18B degradation products. None of the other combinations of proteases resulted in the elimination of degradation products.

Example 6: Additional Protease Knock-Out Strains

As shown in Examples 4 and 5, a modified *Pichia pastoris* cell capable of producing a desired protein (e.g., 18B) was transformed to delete proteases at PAS_chr4_0584 and PAS_chr3_1157 to mitigate degradation of the desired protein. We further knocked out one or more additional proteases to enhance the production of full-length products and minimize degradation.

For each additional knockout, an additional protease gene was deleted from a single protease KO (1× KO), double protease KO (2× KO), triple protease KO (3× KO), or quadruple protease KO (4× KO) by transformation with a nourseothricin resistance cassette with homology arms targeting the desired gene as provided in Example 2. The protease genes knocked out in each strain are shown in Table 4:

TABLE 4

2X-5X KO Strains

| KO Strain | Protease Genes Knocked Out |
|---|---|
| 2X KO | PAS_chr4_0584 (YPS1-1)<br>PAS_chr3_1157 (YPS1-2) |

TABLE 4-continued

| 2X-5X KO Strains | |
|---|---|
| KO Strain | Protease Genes Knocked Out |
| 3X KO | PAS_chr4_0584 (YPS1-1)<br>PAS_chr3_1157 (YPS1-2)<br>PAS_chr3_0866 (YPS1-5) |
| 4X KO | PAS_chr4_0584 (YPS1-1)<br>PAS_chr3_1157 (YPS1-2)<br>PAS_chr3_0866 (YPS1-5)<br>PAS_chr1-1_0379 (MCK7) |
| 5X KO | PAS_chr4_0584 (YPS1-1)<br>PAS_chr3_1157 (YPS1-2)<br>PAS_chr3_0866 (YPS1-5)<br>PAS_chr1-1_0379 (MCK7)<br>PAS_chr3_0299 (YPS1-3) |

The resulting cells were isolated on selective media plates (by auxotrophy or antibiotic resistance marker) and individual clones were isolated for further testing. Individual clones were tested by liquid culture assay under product protein producing conditions as follows: Isolated colonies of each strain were inoculated into 400 μL of Buffered Glycerol-complex Medium (BMGY) in 96-well blocks, and incubated for 48 hours at 30° C. with agitation at 1,000 rpm. Following the 48-hour incubation, 4 μL of each culture was used to inoculate either 400 μL of BMGY or 400 μL of YPD (Yeast Extract Peptone Dextrose Medium) in 96-well blocks, which were then incubated for 48 hours at 30° C. with agitation at 1,000 rpm.

Protein expressed by the cells was isolated and analyzed for degradation as follows: Guanidine thiocyanate was added to a final concentration of 2.5M to the cell cultures to extract the recombinant protein. After a 5 min incubation, solutions were centrifuged and the supernatant was sampled and analyzed by western blot.

Figure 6:
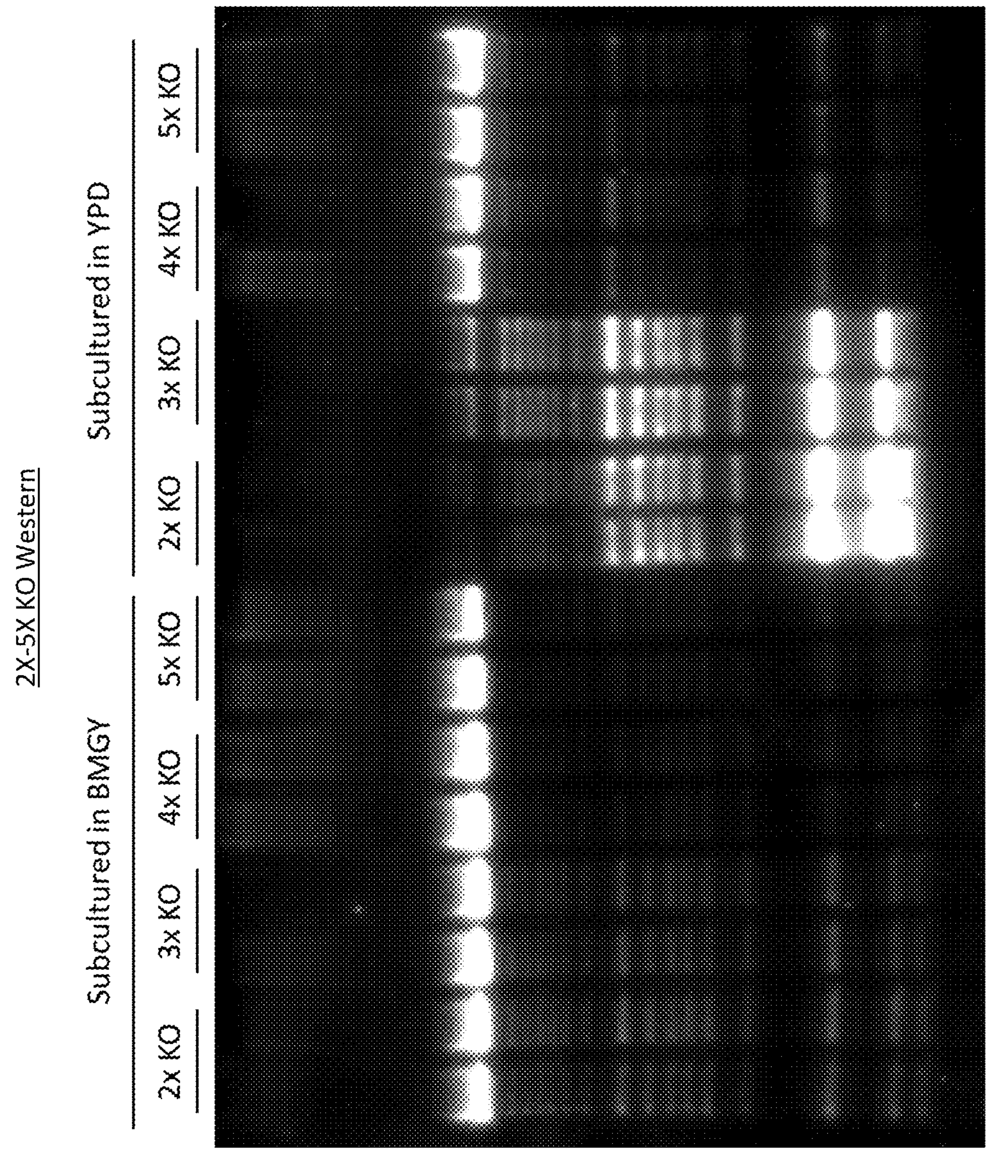
FIG. 6 is a representative western blot of protein isolated from 2×, 3×, 4×, and 5× protease KO strains subcultured in BMGY or YPD to show protein degradation in these strains.

FIG. 6 shows the results of a Western Blot of purified protein from the 2× KO, 3× KO, 4× KO and 5× KO strains inoculated in BMGY or YPD. As shown, the deletion of additional protease genes from the strain having the PAS_chr4_0584+PAS_chr3_1157 protease knockout (Strain 3 from Table 3) resulted in the further elimination of 18B degradation products.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

SEQUENCE LISTING

TABLE 5

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| PAS_chr4_ 0584 | 1 | atgttgaaggatcagttcttgttatgggttgctttgatagcgagcgtaccggtttccggcgtgatggcagctcctagcgagtccgggcataa cacggttgaaaaacgagatgccaaaaacgttgttggcgttcaacagttggacttcagcgttctgaggggtgattccttcgaaagtgcctctt cagagaacgtgcctcggcttgtgaggagagatgacacgctagaagctgagctaatcaaccagcaatcattctacttgtcacgactgaaagtt ggatcacatcaagcggatattggaatcctagtggacacaggatcctctgatttatgggtaatggactcggtaaacccatactgcagtagccg ttcccgcgtgaagagagatatacacgatgagaagatcgccgaatgggatcccatcaatctcaagaaaaatgaaacttctcagaataaaaatt tttgggattggctcgttggaactagcactagttctccttccaccgccacggcaactggtagtggtagtggtagtggtagtggtagtggtagt ggtagtgctgccacagccgtatcggtaagttctgcacaggcaacattggattgctctacgtatggaacgtttgatcacgctgattcctcgac gttccatgacaataatacagactttttcatctcatacgctgataccactttgcttcaggaatctggggttatgacgacgtcattatcgacg gcatagaggtgaaagaactttccttcgccgttgcagacatgaccaattcctctattggtgtgttaggtattggactgaaaggcctagaatcc acatatgctagtgcatcttcggtcagtgaaatgtatcagtatgacaatttgccagccaagatggtcaccgatgggttgatcaacaaaaatgc atactccttgtacttgaactccaaggacgcctcaagtggttccatcctctttggaggtgtggatcatgaaaaatattcgggacaattgttga cagttccagtcatcaacacactcgcttccagtggttacagagaggcaattcgtttacaaattactttaaatggaatagatgtgaaaaagggt tctgaccagggaactcttttacaagggagatttgctgcattattggactctggagctacgctaacgtatgctccttcttctgttttaaattc aattggccggaacctgggcggctcctatgattcgtcaagacaagcttataccattcgttgtgtttctgcatcagataccacttctctggtat tcaattttgggggtgctacagtggaagtttccctgtacgatctacagattgcaacatattacaccggggggaagtgccacgcaatgtcttatt ggaatattcagctctggaagtgatgagtttgtgctcggtgataccttcttgaggtcagcctacgtggtttacgatcttgatgggcttgaagt gtcgcttgcccaagccaacttcaacgaaaccgattctgatgttgaggctattacctccagtgtaccttccgctactcgtgcatccggataca gttctacatggtctggttctgccagcggtacagtttacacttcggttcagatggaatccggtgctgcttccagctccaactcttctggatcg aatatgggttcctcttcctcatcgtcctcttcatcgtcctcgacttccagtggagacgaagaaggagggagctccgccaacagggtcccctt cagctacctttctctctgtttggtagttattctcggcgtgtgtatagtatag |
| PAS_chr3_ 1157 | 2 | atgatcatcaaccacttggtattgacagccctcagcattgcactagcaagtgcgcaactccaatcgcctttcaaggctaacaagttgccatt caaaaagtttatcattccaacgacccaaaggaccgtttaattaagagagatgactacgagtccctcgacttgagacacatcggagtcttgta cactgcagagatccaaattggatctgacgaaactgaaattgaggtcattgtcgacactggttctgccgacttgtgggtcatcgattccgacg ctgccgtctgtgagttatcctacgatgagattgaggccaatagcttttcctcggcttctgccaaattcatggacaagatagctcctccatca caagagctcctggatgggctgagtgagtttggatttgctctcgatggtgaaatttctcaatacctagccgataaatctggacgtgtttcgaa aagagaggaaaatcaacaagatttcaacattaaccgtgacgagcctgtgtgtgaacagtttggttccttcgattctagttcttccgacactt tccaaagcaacaattcagcttttggtattgcttaccttgatggaaccactgctaacggaacttgggtcagggacacagtccgcatcggcgac tttgccatcagccaacagagttttgccttagtcaacatcacagataactacatgggaatcttgggtctcggtcctgctacccaacaaaccac caatagtaacccaattgcagcaaacagatttacttatgatggtgttgtggattcattgcggtcccaaggatttatcaattcagcatcgtttt ctgtttacttgtctccagatgaagataacgagcacgacgaattcagcgacggagaaattttatttggtgctattgatagggccaagatagac gggccatttagactttcccatatgtcaatccttacaaaccagtttaccccgatcaatatacttcctacgttacagtgtccacaattgcggt gtcttcgtcagatgaaactctcattattgaaagacgtcctcgtttggcattaatcgatacaggtgccaccttctcctatttgccaacctacc cattgattcgtttagcgttttccatccatggaggctttgaatatgtttctcaattgggactatttgtcattcgtacaagttctctgtctgtt gctagaaataaggtgattgagttcaagtttggtgaagacgttgtgatccaatccccagtttctgatcatctattggacgtctcaggcctttt tactgatggccaacaatactccgcattaactgtacgtgaaagtcttgacggactttccattctaggtgatacattcatcaaatcggcctact tattctttgacaatgaaaacagccagctgggtattggtcagatcaacgtcactgatgacgaggatattgaggtggtcggtgatttcactatt gaacgagacccagcctactcctctacttggtctagcgatttacctcatgaaacacccactagggctttgagtactgcttcaggggaggcct tggtaccggaataaacacggccacaagtcgtgcaagttctcgttccacatctggctctacttcacgaacttcttctacatctggctctgctt ctggtacttcttcaggtgcatcttctgctactcaaaatgacgaaacatccactgatcttggagctccagctgcatctttaagtgcaacgcca tgtctttttgccatcttgctgctcatgttgtag |
| PAS_chr3_ 0299 | 3 | atgaaccctagcagcttaattctacttgcactcagcattggctactccattgctgagtcaaatttctctttcaaacccagcaagttacctct caaaaaacatcgtgattcttcttccccgcatgaacgatttcttaaacgagatggaccctatcatccgctagaagccgacgcttacttttact |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | acactacgtctatattggttggatcagaagaagaaaaagttgaagtaacagttgatttaggaacctctgatttatgggtcgtcgattacaac<br>accggtttatgtgatagatcctttgacgaaacctatcttaaacgtagtctggatacttctgaggaagattattctgctggagatcttggctc<br>ctcagtcggtgtacgcagcgctagaaaattcttgcgcaaaagggacaccaatcaaactgaggttaatgaagctaactatggtgcttgtccaa<br>attcgattaccttcaatccagaaaactcgtcttctttccagagtaatgatactgctttcaatatcagctactttgatggaaccagtgctagt<br>ggtttttgggctactgatacaatttactttggtgaccttgaggtcagcgagcaatttttgggctggcaaacttaacaataagttatggagg<br>agtcttaggtcttggcccttccaacctacaaacaaccaatgctaaccccaacggtgaggaattcatttacagcggagtcttagattccatgc<br>gtgatcaagggcttatcaactcggcttctttctcaatctatctcaatccagagaatttcagagatgaagataactattctaatgaaggagcg<br>attttgttcggagcaattgataatgcgaagattgacgggtcattgaagctgttaccatacgtgacttcaggtggacactctcagattgatgc<br>taatttcacttacatcaccttgaataatattgccgtggctgacaatgatacagccctgatcgttgagaccaacccccaattggcaatgttga<br>atccaaagtttatatacacctattttccaaacgaagtattgacccggctggtaaactctattgacaatctagaatatgatcctgttgagggg<br>ttatataggataaggagaacaaacattagggatattaacaaaaaaatcatagagtttcaatttggtgacgagattgtgatacattctccctt<br>atcaaattatctgtctgatacatgggttccaagcacaaactacacctatttggagattcaggatagcagagaggatttctttatccttggta<br>atgcatttttcaagtctgcgtatttgtttttgacaatgataacagtgaagtcggtattggccaactaaaggttaccgataaggaggacatc<br>gttccagttggtgaattttctttggatcaagattcagggtactcgtcaacctggtcaacgttctcctatgaaactggttcagctcccttggg<br>tacgtcaactttcgaaacgagtacaaaaactagttcagatggagctgccccgtcggtgtctcacattaacactagttcctacttatttgcgt<br>ttgtactacttttcctttag |
| PAS_chr3_ 0303 | 4 | atgttgcccatccgcttatccaaacttctgcttttgctctccttaaagttgaaattgggtacagctgaagaaaaataccaaaagttggattt<br>aaaaagaattgacaaagactattatgccgtcgatgtcaaagtcggctccgatgagcaggagatcaaagaggtactaatagatacgggttcat<br>ctgatttctggatcttggacaaatcgttctgtaattctccaacatcagaggaagaagagaacagtaacgggcgtagcaacaaggaaagctgt<br>ggagtctatggctcgttcgactccaacaagtcagagacatttcaggcaactggccaagtatttgacgctgcttacggtgacaccacagccga<br>gtcgacaggatcttcaggagttcgaggaattgatcagctacgggtaggagatattcatatagaagaactctattttggactagtgacaaaca<br>ctacaagtttaccacccgttttaggaattgcccagctttccgaagagttcagcaacaactcttatcctaactttccataccagatgaaagag<br>gaaggtctgattgatgttgttgcatactctctctccttgggccaaagtaaaggtgaactactgttcggggctatggaccactcaaaatataa<br>tggaacactattgaaagcccctatattgcaggcgggcacaccaggaatgcaagttcttttaactggagtggcccttacaaatggttcatcaa<br>gcgtcttcaatgagacagacaataaaggttttatctactttgacagtgggactactgcttccactctgccatcagagcactttgatgatctt<br>ttcaaccatcacggatgggcgtacgatggtgatacattgacatattcgattcaatgcgatagtgagggagaaaaatctttacttgacttcac<br>tttagaatataccattgctggtaatattgtcatcaaagtaccatttgaagacattattatgaagaatgaaaatgatggagaatgcctctcaa<br>ccgtaatggtgtcgaaccagacttctttttcatattccgatgacacacccttttttcgttgctggagacgaagttctgttgaacgcttatgtt<br>gtttacaacctagaaacacaagagctggccattgctccagcagtggataatccagaagatactgaagaagatattgagattatctccgcaga<br>ctttgatatttcagaagccagagattatagcgttggattagagttcagaaataccacaattccagctacaactgattacttgccttcctcga<br>tgtcgtcaggttcagtcagcgaagagactggttccaagtctgagagctctacttctgaggactttgctgcagccacgttgaaaccatttaca<br>ttttggggtttcgtcctttttttctttcacttttgatttga |
| PAS_chr3_ 0866 | 5 | atgttagttgctgttgccctagtgttgttactgtctacaggctatgctggaatcgtcgccattgataccgaatatgagttcaccattggttt<br>tcttagtacgatagaaatagggtttcccccacaaagcataacggctcaatgggatacaggatcgtctgacctcttggtcaattccgtgacaa<br>attcacagtgtgctcaggacggatgtagctttggtgcgttcgccttcaacaaatccaccacttattccaatataacaaaccctaacaacctt<br>catgttcagttctcctttgcaagcggcagcgtggttgatgacaaacttgtgagtgacactatttttgtagattccaaggtaatcccacggtt<br>caactttgcactggtatcgaagggagacctgtatggtgataatatttttggtattggaccgagagggaaccagggaacattcgattccaatg<br>gaactccagctttctatgatagctttccttatcacttgaaggccctcggtttaatcaaacgactggcttactcattttacactgggcccacc<br>cagggaaaggtagtatttggaggggtggatcatggaaagtacgatgggtgcctggagaaactcgagattgtccatgacagtgctttttacac<br>actgcttgaggcaattgatgctgatgatacttccgtcttggatgagcaaattcatgttttgtttgatactggtaccgccttgacactttttc<br>ccagctttattgctgaacaactggctgatttttttgaaagctacatattcggacgaatacaatacgtttgtagttccctgcgaccaagatttt<br>gattttgaataccttcattttggttttcgaaacattaagttgtcggtgcgctttaaggatctgtttttagtcattgacgatagtgtttgtgc<br>tgtggggtttgatcaaggggcagatgcaaacaagataacctttgggtcttcacttttaagaaactactacacgctttatgatctagattcca<br>aagaaattttgattgctgacgtcaagcctgatggtccagacgatattgaaatattatcgggtccagttcaacgaatttgtgatgaaaagggt |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gtcagtagcacttcattatggagtagtctgagtatagagtccacgatagaaccagacacttttaccactaagccttctatttcccagacacg gtattcgactagctccattggacctcaaaacatttctaactctttaggtgaatatccttcagtttccgtcactctttctgaacaccataaca ctacttccatagcctcaaattcctcattagaagggaaaccagcaactccaactgttacagaccagtcgtaccagaataataagactacctct accgtaattgctgtgaatttgattacccattcaaccactcattcaaccactcattcacccacctattcaaccactcattctagtaatggatc acgctcaactttagagtacacttcaaccaaggaatcctcggtgaaaatgccctgtgcgttgatcatctccgacacaattccgtacaatgctt ccggtgggaatagtagttatggatcgttaatttcaacatctacggttaacaatgttgaagagaataattcaaacactgttagaccaagaaaa agacagaccttcgtttcgggaaccacttccacgatactactctattcctcaactacgacccaagcatatcagatgttgtcctcaacttcaat cccccgaccatccataaaagccagttcaaatgctggtagccgcaaaacttcaaagacattattaacatttatcatattgtatattttttag |
| PAS_chr3_ 0394 | 6 | atgtaccaggcgttgttggttttgtctctgatatgcttttcgtcggctaattttgttaagctgcgaagcaacgctggtatgttttatgatac tatggctggagttccacgttcagatgaagagttctggttgcgtttggatattaaccaaggtctctcttggactctggatagtagctactact cctgtaatggctcaaatgtttcgtcttccctgtgtttcaattctgctcaaaacgtttacgatgcttccaatagtccaactgcagatttcgtt gatgtctacgcaaacacaactgtaaacaatacagatgaggcatcggccgagagagtaaatcttacaaacaacttatttgctgatggcgttta tatggaagacaattttttacgtcacattgaataatggagcaagaatgactgctacagatctgaaatttttgaatgcccacaatagtagcgccg ctgtggggtctttggcgttggggagttacacctcacaggacgtgccaactttcttacaaagactccaaagcggtggtcttattgaatccaac tcgttttcattggcattaaacgaaatcgattcttcatatggagagctctatttggggacaataaactctaccaagtatgtcgagcctctggt agaattcgatttttattccggtgtcagatcccaatggagtttttggattcgattgggaagatacattccctacagttccgatcagcggattaa gcatgtcttcgaatgacaaacagagaactgtctttttccccaatgagtggaacaacacggtcttaacgggaacatacccacttccaatgatg ttagattcaagaaacatctttatccatcttccattctcttcaatcatacatatagcagtgcagcttaatgcactgtatcttgatacacttca taaatgggccgtgaactgttctgttggtcaactggacgcaactttaaactttcacatgggtaaccttaccgttcatgctcctatcaaggagt tgatttatccagcataccaaggagacaaaaggctgagctttgctaatggagaagatgtttgtattcttgccatggctcctgatgtttacatt ggttatccactgctaggaacccccttttttaaggaatgcagtggttgccgttaatcatgattcaaaaaaggtcgccgttgccaatcttaatag agatagcattcctcccgcttcgaacgtttctgtttcggaatcaatgggagtttatgttcctccacctgtttcaacttcaagaacatcggaga gaccgtccacactagatgagactagtacagccaattttgacaaaagggaagagtctgcaatatcatcaagttcagtcactaacagctcgtct agaaattcttcaaccataacttcttcaggaactcaaaccgagcaaacatcaggcatagctaccatcgaaacagatagcataccaggagctct agggaataatttaactgattattcaacgctgactctaacaatatacaccaattccgaagtggacgaactcaatcctaacatagcaacagcat tcatttccaatggttctatttattcagagccttacccctttccggaactgcagttgctgaatcattcagtgcatcaccttcacaggctgaa ggatcgaactcatcgtcctcaggatcttctttagttttgtgtttctttacatcattggccagtctgttgactgtgagctgtctactactgta a |
| PAS_chr1- 1_0379 | 7 | atgtttgtgatccagctggcattcctatgtctaggcgtcagcctaaccactgcacaacctagttcacctttcaaggcaaataagtttccttt taaaaaggttcactactcatcaaaccctagcgatcgccttattaagcgagacaactataagaagcttgacttgagacatcttggcgtcttgt atactgcggaaattgaaattggttcaggcaaaactgaaatcgaagttattgttgacaccggatctgcagatttgtgggtaattgactcaaat gcagccgtatgcgattgtcctatcttgagatacaaggtacaagtgtttccacccttagtcaaactgccaacgtaacacccctatcaggtaaa cttttgaatggacttcaagaaattggcattgtaactgatggcaaaatttccaaaaagtttcaggaaaaccatcttttgaagagaaacgaggc cttgaattttgatgtcgatctgaataagcccatttgtgatcaatttggatccttcaatccacagtcatcaagaacttttcaaagcaacgaca cagcatttagtatcagatatctggacaactcttttgccaatggatcgtgggtgagggatacggtttatgttggtgattttgaaattgaccag caaagttttgcattggttgatatcacaaataactacatgggaattctgggccttggtccttctagtcagcagacaaccaatagtgatcctac agataacagtttcacttatcttggtattctggattctttgcgggcccaaggattcattaattcagcctcgtactcggtttatctggccccag atggtaagactgatgatactgatcacgatgatggtgagatcctgtttggtgctatcgacgaggctaaaattaatggacagttgaagttgttt ccatatgtcaatccttataaatcggtataccctgaccaatacgcttcatacatcaccgtttccagtattactgtagccagttattttagtag ccgcttggttgaaagaatccctcaattagctcttttagacactggtgccacatttcttacttgccaacttatacgctgatacgtctcgcct atgccatccatcctggttttgagtatgtccgacaactgggtttatttattatagagtcaaacgtactctccagtgcgagacaaagtaccatt gacttccggtttggcaaagacgtagtaattcgatccaatgtttcagaccatctactcgacgtatcacaatacttcacatctggacattatct tgcacttaccatccatgaaagtgtcgatgggcttctcattttgggtgacacgtttatcaagtccacctacttatttttcgacaatgataaca gtgaattgggtattggtcagatcaaaattaccaatgacgaggatattcaagaagttggtgaattcaccttagaacgcgattcagactattct |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | tctacatggtccatttactcttatgaaacttctttggatcccttaagcactggcactggtacggggtcaacctattctcctactcgcagtac<br>tacagctagaagcgaaccgactacgtctcgacgctccaccacccttcaacccagaacaactgtgattccttctattgacaggctttcattga<br>acagcataactagtcatggttcctctactaacggaacctccccaactaatgagacttcttttgctgaggatggaggaactttgacacccgaa<br>gaagcttctttgacaacttcactaaattctgctactatttctgagactacttttgtcgatgttgaaacttctactaccaatggtgcttcagt<br>tgtatctttgagtgttggtccctgcattattgccttcctactactcatctcttaa |
| PAS_chr1-1 0174 | 8 | atgagcatgggagctactgtttcaaaggagtccactgtagacctaacactgccgctgttgcagctgagtccaagactgttgttcctgcctgg<br>agttgtctacaagacgactttcaagttccaggagggggtcaacatcttgctacgttttagagacctgttcgatgagtctttttctgaaagaa<br>atgacgttctaggtgatattgcccgctcgcagaaggaacaacaggaaaacgattatgaccatatcccttttttgagcagcaatgctaagaag<br>agcataggtgtcctgaaagaccaacttgaacttggtgggtctgatgacaagtcacttccctgggttattgcctgtctccctgggttcgacca<br>gtcagaccaggactccattgccactacaatttgtcagataactgaggtgtccgtcgttaaccaggatattgtactatccttcgaagcattaa<br>ccagaggatctttaaaatccaaaaagaccatctccatgaatgaatcaaccatatctgtggaagtggatataccatttactgaggttgaccag<br>accatcagtaacaagctcatcttgacaaatattgataagggtctgcaactactggagaatatcaaacagtttctagtcacctatcaaaatga<br>catgatgaaccttgaagatactaccatggaaaagaactcccgtctaaagtctgcaatgatgattttggctccgttgtctcacttgatctacg<br>ccactgtctcatctcaagaatccactcatgcttatactagactatccaaccagtacaagtccgctaagaaggaattagattcaaccaaaaac<br>agaaagtctttactcaagaagatttgaaaactaatgatattctcacttcagtgttccccttcagtatggttcaaaaggtggatgtcttggg<br>agctatttcaagttctacagacaggatccaaacaactatcgacgcgttggactttgccaatccacttttcgaaacatatttgaacgttgatt<br>atgttctggagacatggaaagattttgacactaagaacggcaaaattgctgccaatttgaccaggtctcaattagtatctaaccacttgaag<br>ggcctcagagtactgattgaagacatccaaggaacttcaagaaggcgggtcagtccttctcagagaactcgtttggcgccttcgcccaatac<br>aaattctgcaaatcaggcaccgaaagctggagaatcagacgacgaaaataaagaattgcgtgattttatcaacaacctctccaaattgaaga<br>tctcagaggatggaaagaggctcgttaccaaagatttcaacagaatgactcaaatgcaaccaagttcatcggagtaccaactgctcagaact<br>tatttagagattattatggatatcccatgggaaacaaaaaatattgtaaaacaacaaattttgatctagacaaggccaaagaaacactaga<br>tcaggaccattacggaatggactccgtcaaagataggatcttagagtatttagcagttcttaaactccacgatcacattaaaacgtccaacc<br>ccaagcaagaagacgaggaaatcaaagccagagcacccattctcttactaacaggtccacctggtgttggtaaaacttcgttaggaaaatct<br>attgcaaaggctctgaacaaaaagttccagcgagtaagtcttggaggattgaaggatgagtccgaaattaagggacatcgcagaacttacgt<br>tggagcaatgccaggactattgacccaagcactgaggaaatctcaatcttttgatccagtgatacttttggatgaaattgacaaggttgtcg<br>atggatcccaaggccctggtagtcgtgtaaacggtgatccagctgctgctttgcttgaagtgttagacccagagcaaaattctaacttctct<br>gaccattatatcgggttcccacttgacttgtctcgtgttgtttttatctgtacgtccaacgatatgagcatgatcagtgccccattaaggga<br>tagaatggaggttattgaactgaatggctacaattatttcgaaaaagtggagattgttaaacaattcttattaccaaagcagatcaaaagaa<br>acggactgcctacgaatgccgaatcaccatcggtggttattcctgacgaagtgattatgtacatcgctgtcaattatactcgggagccaggt<br>attcgtaatttggaacggttaatagggagtatctgtcggggtaaggctattgaatactctagcttgatgagtagtactcaagctccaggcga<br>aattccaaagggatacgtttccaaggtcacggtagataatctttcaaagtacattggaataccccggaattgtctacaggcaagaatatga<br>ggaatgattcagctatctctaaaaagtacggaatcgtgaacggcctcagttacaatagtagcggacatggaagtaccctagtctttgaaatg<br>accggtatacctaatagtactaacactaacatgattacgaccggcagattgggtgatgttcttacagaaagtgtcaagatcgcaagaacaat<br>tataagatcgatgtttagtcacaacttactacaattaaaggatgacgaaacttcaacttctggggatcttttgaagaggtttgacactactc<br>aggttcacatgcatgtgcccgctggtgctattcaaaaagacggacccagtgctggaatcaccattacgctgtgccttctgtcggtgatgcta<br>gagaaacctgtaccaagggatttggccatgactggagagattactttgagagggatggtactgccaattggaggtgttcatgagaagctact<br>aggagcacatttaactggaaccgttaaaagggtgatccttccaagaagtaatcgaagagatgtcattcaagactttatctctaacttggaag<br>ccaataacagaagttctagggataagctactggtagatcttatcaaagaggaggagtcattactgtccaactcaaataaatccgaacgaatt<br>ggagtgttcgggcttcctgaaaaatgggttcaagagaagttgggacttcaagtgagctacgtggaagaattttgggatgttatccagattgt<br>ctggaacgatcaggttgaaattgacagcaccaaattacacgagctagctactaaagagttcgcaaggctatga |
| PAS_chr1-1 0226 | 9 | atgcaattgcgtcattccgttggattggctatcttatctgccatagcagtccaaggattgctaattcctaacattgagtcattacccagcca<br>gtttggtgctaatggtgacagtgaacaaggtgtattagcccaccatggtaaacatcctaaagttgatatggctcaccatggaaagcatccta<br>aaatcgctaaggattccaagggacaccctaagctttgccctgaagctttgaagaagatgaaagaaggccacccttcggctccagtcattact<br>acccattccgcttctaaaaacttaatcccttactcttatattatagtcttcaagaagggtgtcacttcagaggatatcgacttccaccgtga |

TABLE 5-continued

| Protease Gene Symbol/ Locus tag | SEQ ID NO: | Open reading frame nucleotide sequence (5' to 3') |
|---|---|---|
| | | Open reading frame nucleotide sequence for proteases targeted for deletion in *P. pastoris* |
| | | ccttatctccactcttcatgaagagtctgtgagcaaattaagagagtcagatccaaatcactcatttttcgtttctaatgagaatggcgaaa caggttacaccggtgacttctccgttggtgacttgctcaagggttacaccggatacttcacggatgacactttagagcttatcagtaagcat ccagcagttgctttcattgaaagggattcgagagtatttgccaccgattttgaaactcaaaacggtgctccttggggtttggccagagtctc tcacagaaagcctctttccctaggcagcttcaacaagtacttatatgatggagctggtggtgaaggtgttacttcctatgttatcgatacag gtatccacgtcactcacaaagaattccagggtagagcatcttggggtaagaccattccagctggagacgttgatgacgatggaaacggtcac ggaactcactgtgctggtaccattgcttctgaaagctacggtgttgccaagaaggctaatgttgttgccatcaaggtcttgagatctaatgg ttctggttcgatgtcagatgttctgaagggtgttgagtatgccacccaatcccacttggatgctgttaaaaagggcaacaagaaatttaagg gctctaccgctaacatgtcactgggtggtggtaaatctcctgctttggaccttgcagtcaatgctgctgttaagaatggtattcactttgcc gttgcagcaggtaacgaaaaccaagatgcttgtaacacctcgccagcagctgctgagaatgccatcaccgtcggtgcatcaaccttatcaga cgctagagcttacttttctaactacggtaaatgtgttgacattttcgctccaggtttaaacattctttctacctacactggttcggatgacg caactgctaccttgtctggtacttcaatggcctctcctcacattgctggtctgttgacttacttcctatcattgcagcctgctgctggatct ctgtactctaacggaggatctgagggtgtcacacctgctcaattgaaaaagaacctcctcaagtatgcatctgtcggagtattagaggatgt tccagaagacactccaaacctcttggtttacaatggtggtggacaaaacctttcttctttctggggaaaggagacagaagacaatgttgctt cctccgacgatactggtgagtttcactcttttgtgaacaagcttgaatcagctgttgaaaacttggcccaagagtttgcacattcagtgaag gagctggcttctgaacttatttag |
| PAS_chr3_ 1087 | 10 | atgatatttgacggtactacgatgtcaattgccattggtttgctctctactctaggtattggtgctgaagccaaagttcattctgctaagat acacaagcatccagtctcagaaactttaaaagaggccaattttgggcagtatgtctctgctctggaacataaatatgtttctctgttcaacg aacaaaatgctttgtccaagtcgaattttatgtctcagcaagatggttttgccgttgaagcttcgcatgatgctccacttacaaactatctt aacgctcagtattttactgaggtatcattaggtacccctccacaatcgttcaaggtgattcttgacacaggatcctccaatttatgggttcc tagcaaagattgtggatcattagcttgcttcttgcatgctaagtatgaccatgatgagtcttctacttataagaagaatggtagtagctttg aaattaggtatggatccggttccatggaagggtatgtttctcaggatgtgttgcaaattggggatttgaccattcccaaagttgattttgct gaggccacatcggagccggggttggccttcgcttttggcaaatttgacggaattttggggcttgcttatgattcaatatcagtaaataagat tgttcctccaatttacaaggctttggaattagatctccttgacgaaccaaaatttgccttctacttgggggatacggacaaagatgaatccg atggcggtttggccacatttggtggtgtggacaaatctaagtatgaaggaaagatcacctggttgcctgtcagaagaaaggcttactgggag gtctcttttgatggtgtaggtttgggatccgaatatgctgaattgcaaaaaactggtgcagccatcgacactggaacctcattgattgcttt gcccagtggcctagctgaaattctcaatgcagaaattggtgctaccaagggttggtctggtcaatacgctgtggactgtgacactagagact ctttgccagacttaactttaaccttcgccggttacaactttaccattactccatatgactatactttggaggtttctgggtcatgtattagt gctttcacccccatggactttcctgaaccaataggtcctttggcaatcattggtgactcgttcttgagaaaatattactcagtttatgacct aggcaaagatgcagtaggtttagccaagtctatttag |
| PAS_chr3_ 0076 | 11 | atgaagctctccaccaatttgattctagctattgcagcagcttccgccgttgtctcagctgctccagttgctccagccgaagaggcagcaaa ccacttgcacaagcgtgcttactacaccgacacaaccaagactcacactttcactgaggttgttactgtctaccgaactttgaaaccgggcg aaagtatcccaactgactctccaagccacggtggtaaaagtactaaaaagggtaagggtagtaccactcactctggtgctccaggagctacc tctggtgctccaactgacgacaccacttcgactagtggctcagtagggttaccaactagcgcaacttcagttacctcttctacctcctctgc aagtacaacaagcagtggaacttcagccactagcactggtaccggtactagcactagcactagcactggtactggtactggtactacaggca caggaaccactagttccagcactagctcttctgctacttcgactccaaccggttctatcgacgctatcagccagacacttctggatactcac aatgataagcgtgctttgcacggcgtcccagaccttacttggtctaccgaactcgctgactacgcccaaggttacgccgattcatacacttg tggctcttcattagaacacacaggtggaccatacggtgaaaatttggcctctggatactctcctgctggcagtgtagaagcatggtacaacg agatcagcgactacgatttctctaacccaggttattctgctggtaccggtcacttcacccaagttgtctggaaatcaactacacagctgggc tgtggatacaaggagtgcagtaccgacagatactacatcatctgcgaatacgcacctcgtggaaatattgtttctgccggctacttcgaaga caacgtcctgcctcctgtttga |
| PAS_chr3_ 0691 | 12 | Atgactgtgcaaattttgattgtagttaccagtgttgctaagtatgaaagcggaaagctgccaacaggcttgtggttaagtgagttgacaca tatgtatcatagtgcaaaagagaacggctatgatgtgacgattgcgagtccgcaaggcggaaacattccgcttgaccctgaaagcttgaaat caatgctgattgacaagctttcaaaggattatgagacaaaccaagactttatgaagttgttgcaaaacacaaaaagtttgggtgaagtcaca |

TABLE 5-continued

| Open reading frame nucleotide sequence for proteases targeted for deletion in *P. pastoris* | | |
|---|---|---|
| Protease Gene Symbol/ Locus tag | SEQ ID NO: | Open reading frame nucleotide sequence (5' to 3') |
| | | ggacaacagtttgacgttgtttatttggcaggtggacacggaacaatgtatgactttccgaacaacactgttttacaaaacatcatcaaaga<br>acactatgaggcgggcaaaattgttgccgctgtatgtcacggagtttgtgggcttttgaacgtaaaactgtctgatggcgagtatctaatca<br>aagacaaggccattacaggatttaattggtttgaagaagctatagcaggacgcagaaaagaagtaccgttcaaccttgaagcagaattgaat<br>aaaaaaacttcaaaatacgagaaagcttttatcccaatgacgtcaaaagtggtcgtggacgggaacttaatcacaggacagaacccattcag<br>ttcaaaagaaattgcgaaagtggtaatggaacaactgaagcaataa |
| PAS_chr3_0815 | 13 | atgattgatgagaagcaattgaatcaacccaaaaggagcgtcttaagacgtctccatatgctgtttctgccattactagctatctccttttt<br>cctgatatatttaagtgatatcacacagcctctcttccgtgcccgaaaggaagacgaaaacccgttggaaatttacttgaaggcattggaaa<br>cgaatgaagctcacaaatggtcaaaggtgtacacttcgcagcctcatttggccggaaccaactacggattggttgagtttactaagtccaaa<br>tttgaagaatatggatttgaggccagtgtcgatgactacgatgtgtacctgagttaccctattgatcatagtttggaattgtatgagcattc<br>tgaggataaaaatgacaagctcttgtataaggcttcgctgcaagaggacgttctctctgaagacccaactacttcaggcgacgacctgatcc<br>ctaccttccttggttacggtgctaacggcaatgtatctgcagaatacatctacgctaactatggaaccaaagaggactttgaggatttggtg<br>gcccgtggtgttccaatcaaggggaagatcgcagtcattagatatggtcaaatatttagaggcttaaaggtgaaatttgcccaagaatatgg<br>cgcaatcggtgctgtcatatacagtgacccaggcgacgattatggtatcacccctgaaaatggttacaagccttaccctcatggtaaagcca<br>gaaacccaagctctgtgcaaagaggttctgcccaatttttgtctgtttatcccggtgacccaaccacgccaggagttggatcgaagaaggga<br>gtagaaagagttgatcctcatgctacaaccccttccattccagtcttgcctttgagtttcaaagatgccttgccaattttgaagaaacttaa<br>taaggaaggattgtctgttcctgactcctggaagggaggtctcgagggagttgattacagtaccggcccagctaaaaacattcatttgaacc<br>tttatagcgaacaaaactttactattacacctatttacaatgtctatggagagatcaaaggtgagaatgctgacgaagttatcattattggt<br>aaccatcgtgacgcttggattaagggaggtgcttctgaccctaacagtggatctgctgctttgattgaacttagtagaggtttgcacgccct<br>aaccaaaacaggatggaagccacaccgtactattgtactagcttcctgggatgctgaggaatatggcttgattggatctactgagtttggag<br>aacagtttgagaagttccttcagaagaaggtcgttgcctatttgaacgttgacgttgctgtagctggaactcatcttcatttgggtgcctcg<br>ccatctttgttcaaactattgaaggataatgccaaagaaatcactttcaagaattcaaccgagactttgtatgacaactatgttaaagatca<br>tggcaacgacattatttcgaccttaggaagtggaagtgactacactgtctttttggatcatttgggaattccttcgcttgatattggtttca<br>ttgctggaaaaggtgacccagtatatcactatcattcaaactatgattcgtaccactggatcagtactagtggtgatcctggatttgagtat<br>cataatgtactggccaaatatttgggttcgttggttttgaatctctctgagagagaggtgttgtacctgaagcttcatgattatgctaccga<br>attgctcaagtacctcttggaagcctacgcccaaatgccagaggaatgggacgatgaagtaattggtttcagatcttcctcgtgtcatcgtg<br>cgaaagcatctcatcatggtaaggatcctcatcatgagggaagacgccatcacggaaaaggattccattctaaaggagggcctcatcatggg<br>gaacgccatcacggaaaaggattccacgctgaaggggggaccccaccatgagaaaggaccgcatcacgaaaaagggctccacgtcgaaggaga<br>gccccatcatcagaaaggacctcactttgaaaaaggattccatcatgacatggagatgtaccataagaaattggctcatcacggtaaagaac<br>ccaagacgaagctaaagcacttgaagaaacaagttgagagtttaatcatcgatttcgccaataccactcaaacatatgacgcttacactgac<br>ttccttcagaagcaacatgagattagggattctctttcattctgggagaaaatcaagctacattttaagatcaaggcagctaacttcaaact<br>taaatatttgagcgagttttccttcatgaaaatggcttaaagaacagagaatggttcaaacatattgtatatgctgcaggaaggaacactg<br>gttacgccggacaaagactgcctggtcttgtggaagccattgaagacaagaatctgcatgatgcagtaaaatggcttcacatcctttccaag<br>aagattgatagtctacagaagtcattagagtag |
| PAS_chr1-4_0164 | 14 | atgagattacttcacatttcattgctatcaattatctcagtattgaccaaggccaacgctgaatgttgttacaccaacacacatactaccac<br>tgaagtctggtatactacagtatatgctcgagatgttagtgaagagacttcttccacactggctggtggaagtgcaactgtcagctcagaag<br>tgagttcgacaattgaatctagcgttgccacttccgctaccaccgaatcttcaagtgagacatcagggtccacatctgggtccacatctgcc<br>actgaatcatcaactggtagtagctcgctagcaaccagttcatcgataaccagttcagagtcttccaccattacacaaaccacaggacaaga<br>gtcaacaagcccaaccccatcgtcctcagagacaggttcttctactactactccctacgatataagtccaacggcaagttccgactttgatg<br>cttttaaatatcaaattcttgatgaacacaacataaaaagagctctacatggagttgacggattagagtgggatgaagaagtatatgctgcc<br>gcccaagcatatgctgacgcatacacttgtgacggaaccttggttcactctggaaatagtctgtacggagaaaacttagcgtatggttactc<br>aaccagagggactgttgatgcctggtacagtgaaattgaatattatgactttaataacccaggttataccccaggtgttggacatttcactc<br>aagtagtttggaaaagcaccacaaagctcggctgcgctttcaagtactgcaatgactattacggagcctacgtggtatgcaactactcacca<br>ccaggaaattatgtcaacgagggatacttcgaagccaatgtgttaccactggtagattaa |

TABLE 5-continued

| Open reading frame nucleotide sequence for proteases targeted for deletion in *P. pastoris* | | |
|---|---|---|
| Protease Gene Symbol/ Locus tag | SEQ ID NO: | Open reading frame nucleotide sequence (5' to 3') |
| PAS_chr3_ 0979 | 15 | atgagttatcccctaggtctgggtcgtacagcttataggttcatcccgaggtcaatctgttcaagacgatccatctcatcccatgcattacc tccaacgccctccaactcaccaccagcaggagatttattcaccaaactgctgaacgaacgcatcatatatttagcaggaggcattgatgatg cgcaagcaacatctatcacggctcaattgctgtatctggaatcgcagtcaacgtcgaaacaaatcaacatttacatcaactcaccaggaggt tctgtcacggcagggctggccatctacgacacaatccagtatatccgagcgccagtttccacggtttgcttaggacaggcatgctccatggc atccctcttgcttgcaagcggaacgcatggcaaacgtttgatcttgccaaacgctaccataatggtgcatcaaccatcttcggcaaacggaa ttaagggacaggccactgatatcgagatatatgcccgtcatatcatcaataccaaacagaaattgcaaactttatacctaaaacacatgtct ccaaccatgacggtggatgaaatcactgcacttttggagagagatcggttcatggagccagaggaggcagtgtctcttggactggcggaccg tgtattagagaggaaacccccggttgtatctgactaa |
| PAS_chr3_ 0803 | 16 | atgacagataccaaggagttagccacgttgctggagaacttgttgaaattgcaaaaatcaggaagtcttggtgaaattgtgggtcaagcaca gcgcatttatcatgacatttctgacctctcagtcctatctggattatcaaccccagaagtgctctctcctcacacatctccagatgtccccg agagagttccatctgaagtcaacttagacaattccaatctggcaactgatgtcaacgaaaaggagaagtattttgacgattttgcaaatgac tacatcgagtttacctacaagaaccccaccacctaccatttggtgcaatctgtggcggaattgttgaagaaaagcggattcgaatatcttcc tgaagcagctgactggtccaaattattcgaccctgaaaagacgggagcgtatttcacaatccggaatggaacctctttagctgccttcacaa ttggtagtttctggtccccagccaagggagtaggagctatcggaagtcacatcgatgctctcacaactaagctgaagccagtctccaataag agtaaggttgatggctacgagttgttgggagtttcccccctatgctggtgctttgtctgacgtctggtgggatagagatttgggtattggtgg aagagtaatttacaaaaatgaatcttccggcaagctttccaccactttggttaacagtacacctcatcctgttgctcatattccaactttgg cccctcattttggtactccctccaacggtccattcaacaaggaaacccaagcagttcccgttgtaggattttctgacggaaacgacgaggag aaacccactgaggatgaacaaaagtctcctttgattggtaagcattctttaaaactactccgctacatatctaagctagcaggagtgccagt gtcctccttgattgatttcgatttggacatattcgatgtccaaaaaggtactaggggcggtctttccaatgagttcatttacgccccaagag tggatgatcgtatttgttcttactctgctctacaagcgcttatcagacgtcacaaggatcccgaatcctttgtcacagacgactctttcaat cttgttgccctttatgacaacgaggagatcggatctctctccagacagggagccaagggtggtctacttgagtcgaccatttccagagcaat cgctgcattgaaaatttcagagccagggactctgcaaagactatatgcaaattcagtgattctttctgcagatgtcacacatttgttaaatc ccaatttcaccgaagtgtacttggagcaccacaagccactgccaaacacagggattgcacttgcgctggattcgaatggccatatggccaca gatttgttaggcaaggtcgttgttgagcagctggctaaactcaatgatgataaagtgcagtacttccagattcggaacgattcaaggtctgg agggaccattggacccagtatttccagtagtactggcgctagaaccattgatcttggaattccccaattgtccatgcacagtattcgtgcta ccgtgggatacaaagatgttggcctcgctgtcaagtttttccaagggttctttaaaaattggagaaaagttgtcgacggcattgaagagttt taa |
| PAS_chr2- 1_0366 | 17 | atgacttcggtatttttgggtgtttatagagccctatttgattaccaagctcaaaatgacgaagaactaactgtgcatgagaatgatctact atacgtattggaaaagtccgaaattgatgactggtggaaagttaaacaacgagttatcggagttaatgtcgaggaaccaataggtctggtac ccagtacttatattgagcctgctacacctatcgggtcagctgttgcactgtatgattatgacagacaaacagaagaagaaattactttcaag gagaatgacacctttgacgtgtacgacaccgacgatcaggagtggatcttggttggcctgaacaatatccatttggtttcgtgcctgcaaa ctacatacaaatttctttgggtacgacggcacctgcttctaacaatccaccaatacttagtcccgccagcttccctccacctcctcaacgga tcaacaactcctctgttccctctctcaaagatgctgaaccagcaagaaatctagaggacgataatgcttatgaagaggaggaagatgtacct ccaccaatgccaacgcgaccaactgccactacagctacatctaatatctctgctcctcaggactctgaatccgaagaggaaccttctagtag tagcagaaggccaagtggccgttcaagggcggatgatgatttgtaaaaggagactatttcacttgggatgttcaggaaattaatggccgca aaaagaggaaagctgtcctgggtatcggaaatggtagtatttatgtccaagcagagggacattcttctaagaaatgggatatcaggaatttg acaaatttcagtaacgaaaaaaagcacgtctttttttgactttaccaacccctcggcatcctatgaacttcatgcaggctccaaggacgcagc agatgccatcctgtcaattgttggtgatttgaaaggtgcttcttcaatgcgtgctttgaaagaggtgaaggctgcatcttctgccccaaaaa ccaagactggtaaagtcagttacaacttcgatgctgaaagtcccgatgagttgtcgattagggagggtgatgttgtctacatattgaacgat aaagaatcctctgagtggtggatagttcaggacgttaatactaacaagaaaggtgttgttccagctagctacatagagttgattagcggggg tggatctactttagccagcattggctcttctatttccaaaggttctaagaaagcttttggatcctccagaaaacgtaaggaaaaagagcgta agcatttggaagagcaacgtgccgctaaaagagaaaccgaaagggaacgtcaaagacttcgatccaaggaagaaagggataggctaagaaag ttagatgaaaaggaaagaaggaaaaagcaaaaagctactccacaggatgaagaccaacccgagactagcaaacctaatcctcatagagtgcg tacctggattgacagttcaggatccttcaaagttgaagcagagtatttgggagttgttgacggtaagattcatctgcataaaacaaacggtg |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | taaagattgccgtagcggctcctaagttgtcactagaggatttagagtatgtggaaagaatcactggaatgtcgttagaaaaatacaagcca<br>aagccaaaatctagtggttcctattccagaccttccaaaaagccatcctctagagaatcttcaccaaaggagtccagccgctccggagttaa<br>acaatcagttcccaagattgatcctcccaaagacccagattatgattggtttcaatttttcttgggttgcgatattgatccgaataattgtc<br>agcgatacagtgtggttttcattaatgaacaactggatgagagtagtttgcaagacctcactccatccctactaagatcgctagggttaaga<br>gaaggtgatattttgagagttcaaaaattcttggataacaagtttggtcgaaccaaagctcaagaatctgctaccaatggtggtttatttac<br>caagagtgatggtacattgaagaacaataggtccactgatgttctaacaagtacagttgtaacgcgagaaactttaagtcctactaaggccg<br>aggctaagagcaaaagaattgatgacgaagcatgggctctcaaacccgctgccgaatctagctctcaaatggatcaattctccagacctgtc<br>agtgcaatgagcaaacaattgactggatccatacaagatctcgtcaacttgaaacctttgggggacaatgcaaacaacgcttcggtagccca<br>caaagctgaaacaccaaacactacccaggacaaaccttctgctcctgtcttggaacctgtgaagactggagctgcaaggggacctgtgcaag<br>cgcaaccaacaagtggtggtttcgtcactgcacaacctactggtgctctagttgcaatgcctacaggtttcatgcccattacgatggtgccc<br>gtaaagacaggaggaactatagctcttcaacccactggtggattcgtttcgttgcaaagaactggtggggtacttccgcaggttacaggggg<br>acttgttcccgttcagactggtgggttagtaatgcctcagacctcatttggtgtaactccaactttgcagccaacaggagggattctacctg<br>ctcagaggacaggtggattggttcctgttcaaaggacggggggctaattcccgtccaacaaactggaagattagttcctgttcaacaaact<br>ggaggattgattcctgttcaaaggactggaggattagttcccgttcagagaactggaaacttacaacctgtacctacaacctcttttggaag<br>tcaaccaacaggaacttttgtgcctcaatcttcctttggtaatcagttggccaccaatttgaataacccgcaaaccacattcggctctcaac<br>caacaggaggtttccctcagacatcatttgcacaaaatcagtttagacaatcgacaggaggtttccagcagaccccaattgtgcaacaaaca<br>gggggattcccccaatactccgctggacaacagacggtaggattccctcagaactcttttggacagcagacaggaggaattgcccaaaactc<br>atttggacaacagacaggaggttatcaaacaggttttcaaggaaatggatcgattccaatgccccagtcctcattcggtgcttcaaatctgg<br>gattcaatggtgctacgcagcagaactacaacattggcatgggccaatctttgccagcagcttctatccctccccttcaaccctcttacacc<br>tcatcactcaatggaatgtcaaacatgcttcagaacgtaagcatctctcagcagccacaacaagcccagccaatgacgacttttggagcacc<br>tgtggcccagcctccgttacaggctcaaccaactggctttggttttggtaactcgccctatggaggtcagaacccactccaatctcagccaa<br>caggtaaaagagccaacttatcagcagctaccgcagacaacccattcggcttctag |
| PAS_chr3_ 0842 | 18 | atgaccaaccaatcaacagtggtggatttacgcctttcatccaagagagttgttggcaaaccagtcaagttgcccacagtcctagcgtgctc<br>agggtcagattcttccggtggtgcagggatcgaagcagatatcaaatccatcacggcttttgggtgctatgcgctaacagcaattacatctt<br>taactgcccagaataccaaaggtgtcaccagtatagaaaacaccgacccaaagtttttcgaagagattttagaggcaaattttgaggacatt<br>gaaatcgatgtggtgaaaactggactgttaaaccctgagtcatctcgtttattgctgaaatttttagataaataccacaaaggaaagccatt<br>tgtcctggatccggtcttagtggctacgtctggttcaatgcttgcagatcaacacgaattagggttcaccattgattctcattttaagaaag<br>ctactatcattactccaaatttcgaagaggcatgtgtgatctactcttacttgaaaaagctgaagactgtagatgagttgggtgaaatagaa<br>actttagaggatttgaaaggaatggccaagttcatccagcaaactacacattgcaactctgttcttcttaaaggtggccatattccctggaa<br>tagaaacgagcagttggttaaaaaaaagggaggagatccagcatacattactgatattctttatcagggtcatttggataaattcacggtaa<br>tcaagacagattacttgacaagttctggaactcatggttctgggtgtacgattgctgcctcaattgctgcaaacattgcccgttcgttgaag<br>attgaggatgctgtaatttcttcgattagatacgttcatcaggcaatttttggagcagatgagacgctaggacaaggaaaaggccctttgaa<br>tcatgtgtttcatatttctcctcccattaacggcacaagtgctgagaataactttcttccgttctatccaggtcacttcttagattacttac<br>tggagcatcctttggtgagtcccatctggaagaactacatcaaccacccatttttagaaaacgtagcaacaaataagctggctaagaacaga<br>ttcatccactacatttgtcaagattacgtgtatctagcttcttatgcccgtgtccacggcttagctgccggagttgcacctgatattgaaag<br>cataaaggcagaagcccatataatcgactccatcatggaagaaatgcatagacataaagacgtattgaactctcgtggaattgtgaaactgg<br>atgaattaagaccctccaaggcctgcaaacagtattccgactacctcctaaacattgcgaagacatcagactgggtggccataaaaatcgcc<br>ttagcaccatgcatctttggctactattacgctgccatttatgctcggtcgtttatcaaggatgaagctgacgtggacgaagaattcttgaa<br>ttggatcaatacgtataccggtgattggtacaaagatgctgttgacgaggccagacagtcgctagaaagccatatgcaagctgtttctcccg<br>tccagttagcagagctagtcaagatctttgcagatgtctgtcaattggaggtgaacttctggacttcgccaatggaactaccagaacaagat<br>ctatga |
| PAS_chr1-3_0195 | 19 | atgcctacagtggtgactaacgagtcctctctcttgcaaacaaccgtgagtgttgcaccattggtgcttttatctgttgttgatcactacga<br>acgagtggtgcaggcacccaacgccccaactaattcaaacgacaaaagagtcgtgggggtcattttgggagacaatacaaacaagaacttga<br>tcaaggtaaccaactcatttgccatcccgtttgaagaagacgaaaagaacagggatatttggtttttggatcacgacttcatcgaatcgatg |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | atggaaatgttcaagaagattaatgccaaagaaagacttattggatggtaccactctggaccaaagttaaagtcatctgatctacaaatcaa cgagttattcaagagattcactccaaatcctttgcttttgattgtggatgtaaattccaccgatatagtcgatattcctacagactcatatt tggcaattgaagaaattagagacgatggctcaagtgcagaaaaaacgtttatccatttaccatccatcatccaggccgaagaagcagaagaa attggagtggagcatcttctgagggatatccgagaccaggcgtgcggaaatctgtccataagattgactaacaatttcaaatcgctgaagtc tttaaacgatcgcatagccaacattgtccaatatttgcgcaagattttaagtggagaattaccaataaataatgtaattcttggaaaattac aggacatattcaacttattgcccaacttggttgccgttcaaggtgatcccacaaaaccagccactgcaagtgctaaccaactagccacatca ttcaatgtgaagaccaatgatgaattaatgatggtttacatctccagtttagtaagatccatcttggctttccatgatttgatcgacaataa gatcgagaacaagaagaacaacgagaaagataaggaattcacaccaacagaggaagaaccccaacaagcggctatagaatcgaaataa |
| PAS_chr1-4_0052 | 20 | atgacaatgtcaaccgaagatatcatcgccaggcataggaaggagaaaagggaccaaattgcacttattacaaggatgaagaagcagagcac taagtcaaccaaaaaggaaatcatgaaacaatgctctctcttggaagaagagctacaggcaagacataagaaggagttaggtgagtgcaaga ctgaaaattccgtcgagagaagtagtgagcctactgacgaaaaatcaaatggtggagaactttttcccctgaaaagttattatcaatgatg actttaaaacagcaaggaactccaagtgagaatcaaggaaacgcaactgttccaaagagaaaacgcaataggcagaaggacagattagctag aagggaagttgccattaaagagatgcaagcagcagcagcaaaagaggctaacctccaaacaaatttcaaagagatagaattgaacaacataa gccaactgtgccaagttgctcacctggaaccatatgatatccgacctgatgggcattgcttgtttgcatctataaaagatcagttggaggtt cggcacaaaattgaaaatataagtatacaagatcttcggtctctggctgcgagtcatattaaaaatgatcccgagacttatactcctttcct ttttgatgagaatactatgaaaatcagggacattgatgactatgcaaacgagctggaaaccacggctttatggggaggtgatatggaaattt tggcattgagcaaagagtttgattgtccaatcagtgtaatgattagtggaagacctattcatcttgtcaatgccgacggttctaaagaggag ttgaagttggtttattaccgtcatgcatatggcctaggtgagcattacaactctttaagagatagatcagagataagggagtcttgtatagt tgagcaagaggaaaaagaagcggtagacgatggaaaatcatcttcttga |
| PAS_chr2-2_0057 | 21 | atgagacttaagatcaagcgttcaaatgaacagcggctaataacattgcctgacggggctacagtatcggatttacttaatgaaattggatc agcttctatcaatataaaggttgggtttcctcctcagacaattgatatctcagataccagcaagttgcttactgatagtggaatcaagaatg gtgaaatgatcattgtcactgataccattgaaacagaagtgcctgtcaacaagaatgaggttgcaattgccactgtctcaaaccagaatgat gcgccctacgttcaaatagacgacatcttcctagtcttgcggaagattcccgatgataattcttgtttcttcaactctgtcggctactgtat atttggtcctgattcaatcaagtatccggattctcaacaagaactaagacaggccgtcgctaatgtaatcagagagaacaaccaaggtattt ataactccgccatcttgggtggaaagtcaatcacagagtattctcagtggatccaaagcagtaattcctggggaggagccatcgaagcacag atattggcagaataccttgatatcagtatctggacagtggatattgagtctcttcaagtctacaaatttaatgatgaaatggcttcaaggtt ttgcgttattatgtatagtggtattcattacgacgctatggctctcaagctggacacatcattagatgaggaggactcacaaatttgtgtgt ttgataagttcagtgagttggggactttgattgaagacaacgttctcaaattaaccaaccatcttaagaaccagggctattatacgaatact tccacattcatactccaatgtcaaatatgtctcgcaacattgcaaggagaaaaagaagcaaatagccacgcaaagaaaactggccacacaaa ttttggtgaagtcaattga |
| PAS_chr1-3_0150 | 22 | atgtcattgtctgatcctgaggacagcctaagacgtctacttgtgagtttaccctccaatgttaagtacgatgcggagtcttcggtattgaa aagccgactgaaccttgctctatatttctcgctgacaaagagaggtgaatatctgggttccttggtaacggacttgccaatggatttgccat catcttattccgaaatcttagaggctgaagatgattcctactcaagattggctgaatcaatgtacaaatgccctaactataagcatcatgga agaccttgtgcaaggcagttcaagcaaggagagccgatataccggtgctacgaatgtggttttgacgagacttgtgtaatgtgcatgcattg ttttaatagggagcaacatcgagaccacgaggtttccatttcaattgcttcgtcctccaacgatggtatctgtgattgtggagatcctcagg catggaatatcgaattacactgccagagtgaactggaacaagatgaccattcaagttcagaagttaatccagattttaaatctgctataagg gaaacaatggatattattttagattacattttggattgtactattcattctgcatctatgcttcctgctgttcaggacatgatgaaggaaga cccatccgactatgaaatggctattcaatatgcttcagatagttcttctctgcccattgaaagatatggagtggaagacacgaatgttcagt cctggaacgtagtcctgtggaacgacgaattccataattatgatgaggctattgattgcatccagcaagttagtagatgttcattgtctaaa ggacaagctgacgctcaaaagattaatgattttggattttccatcataagaagaagtgaatccttgcctttactgatagaaaggtgcgccaa ggttgaagaatccgggtttactattacgattctttctgatagagatgttacccgattgattattattgatactatttttgattggttattga ctctgttagaaatttcaaggccggaaattcagactgctattagagaaagtttgtgtgaatctcttttggaagagtttcatgccgacattcac gaaggagatttttctaccgggaagatgaatattcagacacacggggtttgctggatttcaaaaacagaattccagccccattggtggagga |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | tgtaatgaacgagttgtctattgatgacttgaagaacagaaaactatccagttttcttaatgaacaaccttcagctctagtcggctcaagag |
| | | tacagtatttcttctatatggatctgcggttctggaaaaaggcaagaaaatctttgaaattgctaacgacatctgttttggtttcaaacttg |
| | | gaatacaaaaagactttttctgaacagtttgtgaaaatatactcgcatctgttgatattgatggcaaaggaagatagagagtggcttctcag |
| | | caatgcgggcaatgctgtagtacaactctttacatgtcctaaaacatctctccatttattacaaccacaatatttcagaagcatcatcgtcc |
| | | ccatcatttgttgttcgaatcttatactggaaaccatttgctgtggaaacgaccatatcaactcttatcacgtaagaaaggtctcaaattt |
| | | ggtttaatgcgttctttaactgatctagtgacgttaatcaccactgcccatcaatcagaagaacatttggtactttttcagggtaagaactt |
| | | catttacataatcatgcttttaggatgttccagagtgccctgacattggtcagaaaggaaggagaacatattaccagggaatccactgaat |
| | | ttttaacctacctgcaaatatcttactaccttaatgatgtcatcaaaggtattgttgaaattgcgcaggttcctgaaatacgtaaacctgaa |
| | | cattggaaagttgtggaaacaaacatacaaatattggccactttaatttcatcagaaccttataagtttcatatggtgcacgaaaaacaact |
| | | tattgaccatgacgtaacaaagaaaccaacctctcttattaatccattgaatggattactgtctaacatgttaacaaccgtaagggccaatt |
| | | ctttttcattttaactcgtcaagtttctcagattaattttggagtatcaatcccgaagtctcattttcagatgatttagactatctgaaa |
| | | ctctcatcgaagagtttagaagcaattactttgagttcacagataaaaattggccactggattagaaatggatccatgactagtaaacaagc |
| | | gcaattgtactgcacgaggttcactcaatatggttacatagccgacgttcatttgaaccaacttgctatactcgaagaacgcgacgatgatc |
| | | gtctattattaaacatttggatagattcaatctaatagattggttctataacgatcaggacgtgcttggtactgttttcgaagaacgatct |
| | | ttttacctaatgaatgaattggttaagtttctttataatatgttttcacacagagttaacttccagtttgaatcaaatttcacagagaaaac |
| | | ccagtatgaggtaacgcaatacattttatacacgctttgtaaaggatctttgtcattttcagatctgacagccgactttcctatctccgtgg |
| | | aagttactgtttttgacaagatccttgatgaggttgctgtttacgaagagcccaaaactatgaatgattctggaaagtattctatcaagaaa |
| | | agttattacaaaaagatggatccaatgtctatttatgtggactcgggtgatttcgatgatgtatcaacagcgatagtaaaggaactttcaat |
| | | tttaggaaaaataaaagaggagaatgttgtaattgaacctcagatcagtggaccgaatgaatccaacagccgtgtcttgagcagattgaaac |
| | | ggttcttcattagcaaatctgtagtcaaactgttttataaattgttacaatctgctctttctgagagcaatgagacctacgtcattgaactt |
| | | ttacatttgattcaagcagttttattagatgaacatgaattgtacagaatcgaagatccagtgcaatactttattcaaattcctgtgtgtga |
| | | tctactgttatcagttgttgagcacaatgatttttcacgacctgtctgcaaaaaactgaagttctattgaattggttgatccagcgggacga |
| | | gtcaatcattgactcattggttgattcttttggtgaaaagcacattgaaaactttaaaaaatctaagggatctcaagttctggagactaaac |
| | | gagctaaacaaaagcgtttagccaaggagagacaagagaagatcaaatcacgatttgctaaacagcaaaagtctttcatgaagcagaatttg |
| | | gacgcaaaaaagagtgcggaacatgtaactacacatttatccaaagacaatgaaggattaggtagttcctcccaggactcttttcatgagtg |
| | | cattctttgtcaacgtgctcaggagggcaacgagatgtttggaatccctgcatatgttgaaaaagtttccacgttttgggattttcaaccta |
| | | aggatgagtcaacctatacggaaagatgcttaacaaccattgaaaatcaaatgaaacaattgcatgaagaaacggatgccaacaatgaggtt |
| | | agagaacatctttattatcaaaaagatactcctgtaaaaagcatggcaccgatatcttcaagacacattgttaagtcatgcgggcaccacat |
| | | gcattataaatgtttttctgagttactagaaaacagcaggaagtttagcacttgtccgctttgtcgctctgccattaatgcttttgttccac |
| | | aatttgccatgaaaaacgatgctagccctgcttttcaggaggctgcttcgaatattagtcactttgaaaagttgaatttgaatcaaattgta |
| | | tcgaaatatcttctcaatgattccttcttgaaatttattgcggaagaaagtaaggaccagttcatgtatttgaatgagtttaaagacatttt |
| | | gaaagacgccccagatgcttctgaccacatgttgagtgaagggttatttccctcatttttggccatgtcaacattattgggtaataccctag |
| | | caaatactgaaattcgtctcagattatcccccgagaagattccccagaaaggaaacttgaagagaaaagattcggaattaataacctcatta |
| | | cttcaatgtgtctcggttatctcaatcttattgaaacaatcttatcctgaagagcagtatctgtctccatttttgaataaaccaaattcatt |
| | | aattattgattttgccatttcacttctacttggaaaagaagactcacttcaagaaactattgtgggcatttacaagcaaacaattctgcatt |
| | | cattgaatttactattgactaacgttggagataatgagcatttcagaaggatgctgagcggtgcaaactctattattaatgattcagaactg |
| | | gccattttcaaaaagtttgtgtcaacggccacttttacctctgatgtttcattcattacttgcaacgaacaattattggttggactgtatat |
| | | tcttttggagaaaaccaccacagtgtatcttaaacagttgtttctgataatcagcatgtgcagacccttggacttatgcctaaatcgtgact |
| | | acgagaattccaatgattacgaccactatttgtttggccaactgtgcaaatttttttaacctttccagtataatcagttatttgggatctgga |
| | | attcctggtggaaacctattggaggagcaaaatgatcttatattaaaaggacaatccactctcccttcaacaattgagtatccaggtctcgt |
| | | ttatcttgtgaatttgcctagagaactgaacacttttacttttcaaaatatgacacccaagatgcagttaatctaaacttttctgtttgtt |
| | | taacgtgtggcaaaagagtgaaacatagcggtgattctgaaaatgaaattgaaaacttccctgggtacaatggtgttcctcttactttgttt |
| | | caccatcataagaattgtcctttctctggatatggagaagcacaatgtatcttcttaaccccaaagttgaataaattgactgccttactaaa |
| | | gattcagcctccacgaggaatttctgatcgctcgctatatcacagtacatttgcattcccattgagcagcccatatctaaccacacatggag |
| | | agtcacattctggtcatggaggcttgatacgcaaagcgttcctgaatagagatcgatttcgaaatctgaatgagctatggttggatggtgaa |
| | | ctagctttgtatatttcccgaagccttggggattctcaaattgtagcggaaccaatcaaccctgttatgattacaatgccgggaggtattca |

TABLE 5-continued

| Protease Gene Symbol/ Locus tag | SEQ ID NO: | Open reading frame nucleotide sequence for proteases targeted for deletion in *P. pastoris*<br>Open reading frame nucleotide sequence (5' to 3') |
|---|---|---|
| | | ggaggcattaaatcttgcgttcaccactttcctcggtgaccaagaacccggggatgatgacttggaagattatgagtatgacatactgttaa<br>atagatga |
| PAS_chr1-3_0221 | 23 | atgtctgcctttggtgtggttccgagtgtattaaacactggaaaccagatcaagcagaaaaacggaacgcttttcaagaaatcttctggagt<br>ttacaataaacagcagcgggatcacaattccagggataaaaagcgatcagctcgtaaaacaaatacaccgccaacaccgactgagagtactt<br>ccgcaaagaagtcatcaactcaatcagacgacaaagtgagtcctgatattttacaattgtcgcatattgagattcaatatgtgggcccactt<br>ctttccaacccagaatctttgggatatgtgaaacaaaacaataataccaaaatcaagactccgaaatatttagtggatacagattcaaacct<br>ggtttttggtcctgatacaactaataaatgggatattgagaaccagcacaaaatgatcgaaatggaatcttcccatcaaggtgactggcaag<br>gtatttatgaacaatttcaagaaatgaataaagtggagcgtcaaaaaatggaagatctgggcttggtggcaaaagagggacaaagcatggac<br>ctgacaaatgctatctcattcaaaggtagctgcgtggatatgtgtcccgtttatgatagagtcaagagggaggtacagagagatgttgatcc<br>attggagagagatcctgccactggtaagatatctcgagagagagctttaaagaaatttgtgcgtccttcaggccaagcaccgcctcttcctt<br>ctgacgtaagacctcctcatattctggtaaaaagtttaaactatattgtggataatttgctggataaattaccgcaaagtcattcattaatt<br>tgggatagaacccgtagtatcagacaagattttacactacagagctactctggcttggaagcaattgagtgtaacgaaagaatttgtcgcat<br>acatctactttgtgctcatataatgccgggttctgatcaatctgacttctccaagcagcaagaaattgaacaattcacaaaatcattgaaaa<br>cattaacagacatatatgatgttgtcagatccaaaggaggaaaatgtgccaacgaagctgaattcagggcttataatttgctggtgcatttt<br>cgggacccaaatctaattcatgaaatccagaacttacctactcgaattcttaaggacgaacgagttcaacttgctttaatgtttcgaagtct<br>actattgaataataatttcaaagaataccagaggaacattcctggttgcttgggggtttttcagcagtttttcaatatgtgttttgatccag<br>ccaccccattcttaatcggatgtgtgctggaacttaattttgaagagataagattttacgctttgaaatcgatctcacgttcttatcacaag<br>aaatctgcccctctaacgacccagaagttagcatctatgctcggatttgattccgaggataagctcctaactttcactaattatttcaagac<br>tcctacgtgtactaattctagaaatgaaacgtgcattgatatctcaaaacttagatacgagagttttacggatttggctgctccaaagcaga<br>tttacacttcaagattagacaacaaattaaaaggattcacctataaggatgttgttgatcaaggattaaataacacatccttgcacatagct<br>aatttgaaagaaacaatggctcagaatcaacatattgcagtggagaaattacccaatatctcatttccacaacatgctttgtcttctacccc<br>tttcgaagtagaatcaaagtcagacatagtcagatcttcttccggatcggctccgccccagactttgatcccaccgattcaagaaaaagtaa<br>taacttctcaaatacagccaccaataactcccgtcgttcccactgaagaaatccaaactcttccaaaaatagaggagcccaggttcaaagat<br>cttccaaattttgaaaatgcatgcaaagaggtttcctctattttaatcaagaagactatatctcctttgattgctcccatagtgaacaatca<br>gctagaagagtacaaccggcgacaaacggttttaagggatcaggagagacaaaatcaaagaagacaacttttgatttcatcccttcaggaag<br>aattgtactctgcttttatacgagaacaagtgtatattcaagtggttgatactcaagccaaagagtgctttaacaagaatctgaaacggcga<br>atatttcagaaattcatcgggggtttaattacattgaaaaacaaacaaatgaataagagaagaaaacttgatgaaattcaagtcttcaagaa<br>taaggttgtttcctcaagtcaacttcggtattcagtttcaagaagtcaaacggaggacaattcaacgtcaaactcgagtgacgaggaagcat<br>cagctgttcagatgaatattactctttcaccatctgtggatccactttggtcacccatagatattaagtttatattagactccaatttaaag<br>ttgtttgaggataacaaggataaatactggaatttcatgtttgcgattgccgattggactattctaccaagcaaatggcttcgttacaaatt<br>ccaacttcaaaaccccagtctcataaatactgttgaatcctcaaattacaaagccaaattacgggctctacccagtgacaaacttcttacaa<br>gggaatacatggagcactgtcgatttttggtatttcaagtcggaaaggttgatgaatcatcaaacctgaaagaatctttgttcagagactca<br>cagtttattaaccgattaatgaaatatgccaagaagtactcgcaataccagattggagtacttgtcttatattatcatgaggatgactcttt<br>tgataaacagaaaattattgatcttttgttattagaacaatacacaaataagttagtcaactcactcgagatagttgacatgaacaaactca<br>caaatgatgaactgataaaagcattgaccacgctagtccacaactataaggataaaggtatcaacaaatcggtaccaacatcttccaccaaa<br>ggacacaccactagcattatggaacaggatatgacagtatacagctacagcacgtccaattccagggatgctaagcttaattatattttgaa<br>gcaagcctacccccgcaggggggtttcacttgaaacaatga |
| PAS_FragD_0022 | 24 | atgtcagaatggccctcagctttggaaaattttgtaagtcattgtttccagcgtgccaacattgagagctttccacccggcaaaaaaaaaga<br>actccaaaaacagttgacgcaaatcatcaatttagcaattcttgaaaacaaacttaattctaataactggtccaaacaaaagctaccaatat<br>ttggagaagcaagagagttagaattggagcagaaaatgggaaatgtttatccaattactgtttctagtcgaagaagtgacttgatgcatcaa<br>gaggcagttcaaccatctgagcctttagttccctccgaaagccaacaaaagaaaaagtctagagaattgcgatttaagatcactaaaaaaag<br>ttctgtatcacccgcaaataaaatacaagttgcttgtgacttgaattgtaaacttgtgggaactaacacctctatcgagaaagattattata<br>gacttacatctcatccggatccttccatggtaagacctttgcctattttaaagaaatcgttgcagcatctttacgccaaatatcaaagtcta<br>gaacgtttcaaagctctcagcaaggcagagtacagctatttttttgaatcaactgaaatccctaaggcaagacctcacagtgcaagacattca |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gaatcagttcactgttaaagtttacgaatttaatactcaattggcgattcaaaatgaagattttggtgagcttaatcaatgtttgactcagc<br>tggcgcaattgtacactgtatcaactatgggtcatacttattactattctgatactggcaaatacaaccaagagcacaactgttttcttgcc<br>aaggatctttgtgaggatcgaaaccatatcaatatgttcaaatttacgagttatagaattttatatttcttctcatagacgcccccctggga<br>attgctaaaaataaggcaggatttattcaaccgtggtcaacagtatgcaattcgtcacaacaaatttcttttgaagtcattcaagctttcgg<br>atctcataaccgccatggattatattcatatcaaggacgaatattcattcctcgtgaatatggactcagatgtctgcaatttaaggacagtg<br>tttgatgacgaacatatgactttgaaccaagacgactggtttttctataagatactctaccataagattttcttacgagaacagctgaaggc<br>cctgataactataagcaaatcttatcgacagatatccctctactacttgaaaaatctactgatggatttagtattcttggaaaagaataagt<br>tatctcgtttcattgagaatggtgaggtatttaactgcacgagcgcaagatcattactgcttcaaatagagaagaagcagctatcaaagata<br>gatatcaagggtcaggtatga |
| PAS_chr2-1_0159 | 25 | atggttgactcagagactatcaacaaattcatagaagtaacgggagcctctgccttccaagcaattcagtacctagaggagactgatgactt<br>tgaagcggcagtcaatgattattattcctctcaactggagaatgagaagggcaagggtaaatcagaacgtccagtcaatcaaacaaaggctt<br>ctgcagggcccaagatcagaactttcaacgacctaaatagcaactcaaatggggacaacaatcttttcacaggtggtgaaaagtccggtctt<br>caagttgagaacccagacaaacgtggggacccttttgggttggtcaatgatcttttgaagaaagctgaggaaactggccaacaaccagatac<br>aaggccccatgaagaagctcctgctagacaatttgttggaactggccacaagctgggcagtacggacagtccctccgaagttagtgtctgac<br>cctgcctcaagaataagaagagctcagaaagtcagccgacagataacattttggaaggacggattccaagttggagacggagatttatacag<br>atatgatgaccctgcaaacgcaagatatctagccgacttgaacgctggaagggcaccactggctcttctagatgtcgagattgggcaagagg<br>tagatgtcacagtgcataaaaagatagaaaaaaatttcactcctcctaagaaagcccgagttggctttcaaggtaaaggtcagagattaggg<br>tctccagtaccgggcgacataaagctcagtcaatctcctgaggtgcaacaagaaacacaagaggaagctgaggaggaaaagcaaaaggagga<br>ggccgagcagctgggaactggggattctcccgttcagattagactcgccaatggtcagagaattgttcatagattcaattctactgattctg<br>ttgctcaattatatgcatttgtcaatgaacatagtccctccgccagagaatttgtgctttctctagctttcccggtgaaacctattgagaac<br>aatgaggacacactcaaggatgctggactcataaacgctgttgttgtccaaagatggaaataa |
| PAS_chr2-1_0326 | 26 | atgggcgtgatacttccagacgatggtaagcaatcgggaggccaaccaaatagaagggctaaagtcctgagccgatttttaccaccagaaca<br>tcaaagaccttcaatcggcctcttcctgggaccttttactccagcagctgataatgagattgccctgtggacttgcattggcgctcagctct<br>ttagtgggctggcattgcttagaatgagccgaagatttgtttttttcgcccgatcaatctgtaagaaggtttctctttaagacttttcataat<br>gtggtaggtgcagccctgatatttgggagcggattagaagggactaggatgcttctacctgaggatccttggaaagaagaagctagaaaagc<br>aagaatattggcccaattgaaaggtgagcccgttagttggtggtatggacccaagagttttattccttctggaaggttagaatacacaaaac<br>agatgcagtttcacaactttgaagtcatgcataaatcacccgaaaaaatagcccgagctctcatgattaaggacaaactcaaggaggaaaca<br>aatacccttattcgtccattcatgagaaagcggaacaacagactattcgactctctaaagatctacagaacaacgttcccctcaaaggggt<br>aacgtcatatgttcctcaatttagcacttcaaatacggacaccaagttatatttgaaaaatgttagcttgaagacccatgccgacctggaaa<br>aggtctgggcagaacacaatccttgggacatcctggaagagaaaatttctccaatttccgtaattgcactgccaaagtttaacccaattata<br>tctgaggttgaacctgacaagcagcaaccatctacgggtgatatcaaatacattagtgacagaaaataa |
| PAS_chr1-4_0611 | 27 | atgaaatatttgccactcgttgctaccctggcctcttcggccctcgctgctggcatcaacttcgcccaattactggaccagaagccactgga<br>cattgccgataatgttaaatgggaattgaagcctgaggtcgactctgctgctcttcaaagtgcagtcaatgagctagacttgaaaatcgaag<br>ccagctatttgtttaaagttgcacatggttccgtctttgaatacggacatcctaccagagtcatcggttctcctggtcactggtccacaatc<br>aaccatgtcctcgacacattacataacttcaaacactactacgacgttgacgttcagccatttgaagcctttaccggtatccttaagtcttt<br>ctcattgaccattaacggagttgcaccaaagtctgcagaagctttagatttaactcctcctactcctggcggttttccagtgaccggtccag<br>tcgttttagttgataattatggttgtcaagcttctgactatccattcaacgtgactaacggaattgccttaattcaaaggggttcttgttca<br>ttcggtcaaaaatcagaacttgctggtctccgtggagccaaagccgctctcatttacaacaacgtgccaggtagtgctaagggaaccttagg<br>tgccccaactcctcatcaggtaccatcgttgtcactttctcaggaagatggagaggccgtcaagcgtcagcttctgacttctggaagcgtaa<br>ttgcaactgtcgctgtcgattcctacgttaagaagttcaaaaccaagaatgtgattgctaccactcgttacggtaatgatagcaacattgtg<br>atgctaggtgcacattcagactctgttgctgctggaccaggtatcaatgacgatggttctggtaccatctctcttttgaacgtggccaaata<br>cctaactaaattcaaagttaataacaaggttcgtttcgcttggtgggcagctgaagaagaaggattacttggatccgactactacgtttcaa<br>agttaacccccaaggagaaatctcagattcgtttgtttatggactacgatatgatggcttcccctaactacgcctaccaggtctataatgcc |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
| --- | --- | --- |
| | | actaacagcgagaacccagttggatctgaggagcttaagaatttatacattgactggtacgttgaacagggtctgaactacactctagttcc atttgatggccgatccgactatgatggattcatcaagagcggtattcccggaggtggtattgctaccggagcagaaggtttgaagaccgaag aggaggctgaactatttggtggtgaagctggagttgcatatgacccatgttaccactctctttgtgacgatttggccaaccctgactatgtt ccatgggttgtcaatactaaattaattgcccacagtgtcgccacttatgcaaagagcttggacggattcccattgcgtgaggagcctagccc attcaagatgactgcccagtcaaacttcaagtaccacggtccaaaacttgtcctttag |
| PAS_chr1-1_0274 | 28 | atgctcaaacactccttaaaaacagggttggtctttctcacttggataccggtgatttatacggtaaaggaacacctgatatacgttggaaa ggtggaaggatcctcaatgtcacccactttgaatcccgttaaaggttattctgactatgtgattttatggaagttaaacttcaaagagtcac tcaaagtgggagacgtggtttttataaggtctcctgtagatccagagaagttatatgctaaacgtataaaggctgttcaaggggataccgtg gtgactaggcatccataccccaaagacaaagtgtccattccaagaaaccatctttgggtagaaggagacaatatacacagcgtggatagtaa caactttggtccgatatcgttgggccttgtattaggaagagcaactcacgtaatttttcccctgaacaggataggtaatatctctggtgaag ggggtagagaagttagggaggattatttaagagcggaggacagtccgatgtaa |
| PAS_chr4_0834 | 29 | atggtttctgaaattcagcttagattagctgttattatttatgatatactctgttcggcgtcttatgttctagtcatccatttgagaccaac cagagcccttccgcatcaacccatagaccgtaacaatcctctaacgattaaagaaaggtgccagcgagccagtgtgttgactgctacacatg tattattattgcctattcttttaaaagtgttgagactgtcagaaattgcggaaactacggcgaaacttggaatagtggtgggatatcacaac cagagctggtctttctctaacctccaagatgatattgtcagcattttcaaagctttaggtttgaccatgattctcttttctggtcctattgt agattatttttactattcaaactcaacagaagtaatcaagcaagatctggcgtatgtcgttagcctcgagggtatgcgtgatctacttgtgg gacccatcactgaggaacttctttatcggtcatgttccatttcattaatgctagtagctaacgattacgccaacaaatttctgttcggccaa cactggttaataatggtatcatcactctacttcggtatagcacatcttcatcatgctgttgaactgtatcattgtaaaagatattcattaac taccataaccatatcaactgccttccaatggtcatatacaacgttatttggaatatatgcaagctttctatacttgcgaacaggatctgtat ggtcagcaatagttgttcattcattttgcaacatgatggggtttccccggttgacatttggacgtgatgaagcgagagattggaaagtgggt tactatgtgttgctcgctctaggttccgtcctattcaaaaagtttctttactctctaacagaatctaaccatacgcttcttctataa |
| PAS_chr3_0896 | 30 | atgtatcccgaacacaagtatcgggagtatcaacggagggtgcccttatggcagtactccctgttggtgattgtactgctatacgggtctca tttgcttatcagcaccatcaacttgatacactataaccacaaaaattatcatgcacacccagtcaatagtggtatcgttcttaatgagtttg ctgatgacgattcattctctttgaatggcactctgaacttggagaactggagaaatggtaccttttcccctaaatttcattccattcagtgg accgaaataggtcaggaagatgaccagggatattacattctctcttccaattcctcttacatagtaaagtctttatccgacccagactttga atctgttctattcaacgagtctacaatcacttacaacggtgaagaacatcatgtggaagacgtcatagtgtccaataatcttcaatatgcat tggtagttacggataagagacataattggcgccattcttttttgcgaattactggctgtataaagtcaacaatcctgaacaggttcagcct ttgtttgatacagatctatcgttgaatggtcttattagccttgtccattggtctccggattcttcccaagttgcatttgtgttggaaaataa catatatttgaagcatcttaacaacttttctgattcaaggattgatcaactaacttatgatggaggcgaaaacatatttatggcaaaccag attgggtttatgaagaagaagtgtttgaaagcaactctgctatgtggtggtctccaaatggaaagtttttatcaatattgcgaactaatgac acccaagtgcctgtctatcctattccatattttgttcagtctgatgctgaaacagctatcgatgaataccctcttctgaaacacataaaata cccaaaggcaggatttcccaatccagttgttgatgtgattgtatacgatgttcaacgccagcacatatctaggttacctgctggtgatcctt tctacaacgatgagaacattaccaatgaggacagacttatcactgagatcatctgggttggtgattcacggttcctgaccaagattacgaac agggaaagtgacttgttagcattttatctggtagacgctgaggctaacaatagtaagctggtaagattccaagatgctaagagcaccaagtc ttggtttgaaattgaacacaacacattgtatattcctaaggatacttcagtgggaagggcacaagatggctacatcgacaccatagatgtta acggctacaaccatttagcctatttctcaccaccagacaacccagaccccaaggtcattcttacgcgtggtgattgggaagtcgttgacagt ccatctgcatttgacttcaaaagaaatttggtttactttacagcaaccaagaaatcctcaatagaaagacatgtttattgtgttgggataga cgggaaacaattcaacaatgtaactgatgtttcatcagatggatactacagtacaagcttttcccctggagcaagatatgtattgctatcac accaaggtccccgtgtaccttatcaaaagatgatagatcttgtcaaaggcaccgaagaaataatcgaatctaacgaagatttgaaagactcc gttgctttatttgatttacctgatgtcaagtacggcgaaatcgagcttgaaaaaggtgtcaagtcaaactacgttgagatcaggcctaagaa cttcgatgaaagcaaaaagtatccggtttatttttgtgtatgggggccaggttcccaattggtaacaaagacattttctaagagtttcc agcatgttgtatcctctgagcttgacgtcattgttgtcacggtggatggaagagggactggatttaaaggtagaaaatatagatccatagtg cgggacaacttgggtcattatgaatccctggaccaaatcacggcaggaaaaatttgggcagcaaagccttacgttgatgagaatagactggc |

TABLE 5-continued

| Protease Gene Symbol/ Locus tag | SEQ ID NO: | Open reading frame nucleotide sequence (5' to 3') |
|---|---|---|
| | | catttggggttggtcttatggaggttacatgacgctaaaggttttagaacaggataaaggtgaaacattcaaatatggaatgtctgttgccc ctgtgacgaattggaaattctatgattctatctacacagaaagatacatgcacactcctcaggacaatccaaactattataattcgtcaatc catgagattgataatttgaagggagtgaagaggttcttgctaatgcacggaactggtgacgacaatgttcacttccaaaatacactcaaagt tctagatttatttgatttacatggtcttgaaaactatgatatccacgtgttccctgatagtgatcacagtattagatatcacaacggtaatg ttatagtgtatgataagctattccattggattaggcgtgcattcaaggctggcaaataa |
| PAS_chr3_ 0561 | 31 | atgaaaccgtatcaccatgcaaaaagccgcccaataggcagctacctgtattttggggtgtttaccgtagcattgacatttctgacgtggct taaatatgacgcagagctgtttgctcagcaggttcactcgaaagacatttatgacccacagttcaacattacgttgccaattgatggcccaa catttaccccatcaaagaactattcaattagtgttcaaaatgcagcagtggcgtccgatatagaacaatgttcaaaattaggtgtatctatt ctgcagcaaggtggcaatgcggccgattcagcagtcaccgtggccctgtgtatcggaacaatcaattcgtattcgtccggtatagggggagg aggattcattgtctctaagttaattgataatcctaccgctctgagttttgattgtcgagaaatggctccttctaaaagtttcaaagaaatgt tcaactatcatgaggagaaggccagagtaggtggtttggctgtcgccattccaggagagttaaagggactctatgaactgtttcagcaccat ggttctggtaatgttgagtggaaagatttgattttgcccgttgctgagttggctgaggtgggatggactgtcgatccgctgttttctagtgc attgaaatctattgagcaccatatttacgagcattcatatgattgggcctttgcattgaatgaagacggaaaaattaaaaaaagaggtgact ggattaatcgtcccatgttggctactacgttgaggagaatagctgaaagtggcaacgttgatctattctatgacccagagagcgatatagta caaagcatggtgaatgctactagaaagtatggaggaatccttgaagcctcagactttgcaaaatatagagttcgaattgaagaatcgttgac attgcataactttacatctgacggccttacggtttatacgtccaatggggcatcctcagggttggtgctccttgctgggttgaagctcatgg acttattcgaagatttcaaggaatttcataatgatttcggggctgttgagtctcaaaggcttgttgaaacgatgaagtggatggcttcagta agaagcaaccttggagatttgaacatttactccaccaacgaaactgaaattgacgatcataggaagaggtacgacagatacaaatcagatga gtgggcaatagaaactcatgccaaaattaatgattcccacacacttccttcttggaaagattatgctccagcctttctacctaatgatcctc atggtacatctcatttcagtatcgttgaccaatacggtaatgcggtggctatgacaaccactgttaaccttggatttggatctaaaatacac gatcctatatcagggattattctaaatgatgaaatggacgattttcagttccaacatcatctaatgcatttggtttgcatccatcaatcta taattgggtagagccttacaaaagacctctctcttcatgtgctcctaccgtaattgttgattctctgggagtacctcattttgtcatcgggg cagcaggagggtccaagatcactaccacagttttacaagcaattataagagtttaccattatcacctggatcttttagacgtcattgcatat ccacgctttcatcatcaactacttccggaagaagttcttctggagtttccacgagataataaactaatacgccatctaaaagaaagagggca tgatgttagagtccaagcaccaatatccaccatgaatggtatcctacgaaaaagaggtggaagcctgatagcagttagtgatcactggagaa agcttggtcgaccttggggcttttga |
| PAS_chr3_ 0633 | 32 | atgaaatcggttatttggagccttctatctttgctagcattgtcgcaggcattgactattccattgctggaagagcttcaacagcaaacatt ttttagcaagaaaaccgttcctcaacaagttgctgaattggtgggcacccattactctaaggatgagataatcagtctatggaaggacattg agctggatgtacccagggaaaagatccaagaggccttcgataagttcgtaaaacaatcaactgccacttcccccgttagaaatgaatttccc ttgtctcagcaagattgggtgacagtgaccaacaccaagtttgataattatcaattgagggttaaaaaatcccaccctgaaaagctaaacat tgataaggtaaagcaatcttcgggatacctggatatcattgatcaagataagcatcttttctattggtttttgaatcccgaaatgatccgt ccacagacccaatcatcctatggttgaatggtggacccggctgctcttctattacagggttgctattcgaaaagattggccccagttacatc accaaagagattaagccggaacataatccttattcatggaacaacaatgctagtgttatcttccttgagcaaccggttggagtaggattttc ttactcttctaagaaagtcggtgatactgcaactgctgccaaagatacatatgtgtttttggagcttttcttccaaaagtttcctcagttcc tgacctctaatctgcacattgctggggaatcgtatgctggccattatttgcccaagattgcttctgagattgtgtctcacgcagacaagacg tttgacctttcaggagtcatgatcggtaatggtcttactgatcctctaattcagtataagtactatcagccaatggcctgtggaaaaggtgg ctacaagcaggtcatttcggacgaggaatgtgatgaattggatagggtctatccaagatgtgaacgtttaacgcgggcatgttatgagttcc aaaattcagttacttgtgttccggcaacactttattgcgaccaaaagctactgaagccgtacactgacactggcttgaatgtctatgatatt cgtacaatgtgcgatgaagggactgatttgtgttacaaagaactggaatacgtggagaagtacatgaaccagcctgaagtgcaggaagccgt gggctctgaagtcagttcttacaaaggttgtgacgatgatgtcttcttaagatttttgtactctggcgatggatctaagcctttccaccagt atatcacggatgttctcaatgcaagtattccggttctgatttacgcaggtgataaagattatatctgtaattggctaggaaaccaagcttgg gtcaatgagctagaatggaacttgtctgaggaattccaggcaactccgattcgaccgtggttcactttggacaataacgattatgcaggaaa cgtacaaacttatggaaactttcctttctaagagtatttgatgctggtcacatggttccttacaatcaaccagtcaacgcacttgacatgg ttgtcagatggacacacggtgatttctcatttggttattaa |

Open reading frame nucleotide sequence for proteases targeted for deletion in *P. pastoris*

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| PAS_chr4_ 1003 | 33 | atgactcaattagatgtcgaatcattgattcaagaactcacactaaatgaaaaggttcaacttctgtccggatcagacttttggcacaccac<br>cccagttagacgtctaggaattccaaagatgagattatctgacggtcctaacggcgtccgaggaaccaagtttttcaatggagttccaaccg<br>catgttttccttgtggtactggattaggtgccactttcgataaagaacttctaaaagaagctggctccttgatggcagacgaagctaaagca<br>aaagctgcctcggtagttttgggtcctacagctaacattgctcgaggccccaacggaggaagaggcttcgaatcttttggagaggatccagt<br>ggttaatggattatctagtgctgcaatgattaatggattgcaaggtaaatatattgcggctaccatgaaacattatgtttgtaacgatttag<br>agatggatcgtaattgcattgatgcacaggtgtctcacagagctctaagagaagtgtaccttcttccattccaaattgcggtaagagatgca<br>aatcctcgcgctatcatgactgcttataataaagcaaacggtgaacatgtatctcagtcaaagtttcttctagatgaggttttgagaaaaga<br>atggggctgggatggtttgttaatgtccgattggttcggtgtgtacgatgcaaagtcttctatcactaatggtcttgacctggaaatgcctg<br>gtccacctcagtgcagagtccattcggcaaccgatcatgccatcaattctggggagatacacataaatgatgtcgatgagcgggtgcgaagc<br>ctcttaagtttaattaactattgtcaccagagtggcgtcactgaggaggatccggagacatccgataacaacaccccagagaccatcgaaaa<br>actcagaaaaatcagtagagaatcaatcgtcttgctgaaggatgatgacaggaacagaagtatccttcctctgaagaagtcagataaaattg<br>ccgtgattggaaacaatgctaagcaggctgcatattgcggaggaggttctgcttctgttctctcgtaccatactacaactcctttcgactct<br>atcaaatcacgattggaagattcaaacactccagcttacaccatcggtgctgatgcttacaagaaccttccgcctttgggccctcagatgac<br>agacagcgatggaaaaccggggttcgacgccaaatttttttgttggctcgcctacatctaaagatagaaagctgattgatcactttcagttga<br>ccaattcacaagtcttcctggttgactactataatgaacagatccctgaaaacaaagagttttacgtagacgttgaagggcaattcattcct<br>gaggaagatggaacctataactttggcttgaccgtattcggaacgggaagattattcgtggatgataagctggtttccgatagtagccaaaa<br>ccagacccctggagattcctttttggactagcagctcaagaggttatcgggtccattcatttggtcaagggtaaagcatataaaataaagg<br>ttctttatggatccagtgtcaccagaacatatgaaattgcagccagtgttgcttttgaaggaggagcatttacttttggtgcagcaaaacaa<br>agaaatgaagatgaagaaattgctagagctgtggaaattgctaaggcaaatgataaagtggtgttgtgcataggtctaaatcaagactttga<br>aagtgagggattcgacaggccggatatcaaaattcctggagcaaccaacaagatggtaagtgctgttttgaaggctaaccctaacactgtga<br>tcgtcaaccaaacaggaaccccagtcgagatgccatgggccagtgacgctccagtgatcttgcaggcttggtttggggggtctgaggcaggg<br>accgctatagctgatgtactattcggtgactacaaccctagcggaaaactaacggttacttttcccttgagatttgaggataaccctgcata<br>tctcaacttccaatccaataagcaagcatgttggtatggggaagacgtttatgtgggctacagatattacgagaccatagacaggcctgtgt<br>tattcccatttggccacggattgtcattcaccgaatttgattttaccgacatgtttgtcaggcttgaagaagaaaaccttgaagttgaggtt<br>gtagtcagaaacacaggaaagtatgatggtgctgaagttgtgcagttgtacgtagcaccagtatccccatccctgaaaaggcccatcaaaga<br>actcaaggaatatgctaagatttcttagccagtggtgaggcaaaaacagttcacctgagcgttcctattaagtatgccacttcgttctttg<br>acgaatatcagaagaaatggtgctccgagaaaggagagtacacaatcttactgggatccagctcagcagatattaaagtttcgcaatctatt<br>actttagaaaaaacaactttttggaaaggtttatag |
| PAS_chr2- 1_0172 | 34 | atgttcctcaaaagtctccttagttttgcgtctatcctaacgctttgcaaggcctgggatctggaagatgtacaagatgcaccaaagatcaa<br>aggtaatgaagtacccggtcgctatatcattgagtatgaagaagcttccacttcagcatttgctacccaactgagagctgggggatatgact<br>ttaacatccaatacgactactcaactggttcccttttcaacggagcatctgttcaaatcagcaacgataacaaaaccactttccaggatttg<br>caaagtttgcgtgcagtcaaaaatgtttacccagctactctcattacattagatgaaacatttgagcttgctgacacgaagccatggaaccc<br>tcatggaattaccggtgtcgattctttgcatgagcaaggatatactggtagtggtgttgttattgcagttatcgatactggtgttgactata<br>cacaccctgctctgggtggtggtatcggagataatttccctatcaaagctggttatgatttgtcttccggtgatggtgtcatcacgaatgat<br>cctatggattgtgacggtcatggtacctttgtatcctccatcattgttgcaaataacaaagatatggttggtgttgcaccagatgctcagat<br>tgtcatgtacaaagtgttcccctgttctgatagtacttcgactgacatagttatggcgggtatgcaaaaggcctatgatgatggtcacaaga<br>ttatttcgctatcactgggatctgactcggggttttccagtactccagcttccttaatggccagcaggattgctcaagacagagttgttttg<br>gtggctgctggtaactctggagaacttggtccattctatgcctcctcccctgcttctgggaaacaagtcatttcagttggatctgttcaaaa<br>cgaacaatggacaacctttccagtaacctttacctcttcaaacggtgaatcaagggtttttccttacctcgcttacaatggtgcacagattg<br>gatttgatgccgagcttgaggttgattttaccgaagaaagaggatgcgtctatgaaccagagatctccgcagataatgcgaataaagctatt<br>ttgttaagaaggggcgtcggctgtgttgaaaacttggaattcaatttattgtctgtggctggttacaaggcttacttcttgtacaactcatt<br>ttcaagaccatggagtctcttgaatatttctccactgattgagctagacaacgcttactctcttgttgaagaggaagttggaatatgggtga<br>aaacccaaatcgacgccggtaacaccgtcaagttaaaggtgagcacgagtgaccaaatgttgccatctgataaagagtatttgggagttgga<br>aagatggattattactcctctcaaggacctgcttatgagcttgaatttttcccaacgatatccgctccaggtggagacagttggggcgcttg |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gcccggtgggcaatacggtgttgcctcaggaacaagttttgcttgcccctatgttgcaggtcttacagctctttatgaatcgcagtttggaa ttcaagatccccaggactatgtgagaaaattagtctccacagctaccgatcttcaattatttgactggaacgcagtgaaacttgagacctct atgaatgctccacttattcaacagggagctggtctagtgaacgctcttggtttgtttgagactaagactgtgatcgtgtctgctccttattt ggagctcaatgacaccatcaatagagccagtgagtataccattcaaattaagaatgagaactctgagactattacctatcaagttgttcacg ttccgggaactactgtctactctagatcagcttctgggaacatcccatacctggtcaatcaagattttgcaccttacggtgatagtgatgct gcgacagttgctctatccacagaagagttggttttgggaccaggagaagttggtgaagtcactgtgatcttctctacagaagaaattgatca agaaactgctccaattattcagggtaagattacattttatggtgatgtcataccgattgctgttccttatatgggagttgaagttgatattc attcctgggagcctctcattgagaggcctttatcagtgagaatgtatttggatgatggttccttagcatatgttgatgatgatcctgattat gagttcaatgtgtatgactgggattctcctagattttattttaacctgagatatgcaaccaaagaagtatcgattgacttggtgcaccctga ttatagcattgagaacgactacgaatggcctttagtttccggacacaacaactattatggtcccgtgggatacgactacgattatacctcgg gtcaagccttttttgcctcgttactttcaacaacgtattaacgaacttggatatctttctttttccagatttgctaacttttctgtagttcct gctggtgaatacaaagctctatttagagttttgctaccatatggagacttttggaacaaagaagactggcaattgtttgaatccccagtgtt taacgtcctcgctccaccgaatgaagaaaacactactgaagagccaactgaggaatccagcgaggagcctaccgaagagtcaacgtctgagt caactgaagagccctcttctgagtcaactgagaaatctagcgaggtgccaactgaagaaattactgaagatgcaacatccacaattgatgat gatgaagcatccaccgaaagctctactgaagaaccaagtgctcagcccaccggtccttactctgatttgactgtcggtgaggccattaccga cgttagtgtcaccagtttgaggacaactgaagcatttggatacacttccgactggttggttgtgtctttcactttcaacactactgacagag atattactctcccaccttacgctgttgtacaagtaactatcccaaatgaacttcaattcattgctcatccagaatacgccccataccttgag ccctcattgcaagttttctacactaagaatgaaagattaattatgactagtcagttcaactacgacaccagagtcatcgacttcaagtttga caatcgagaccaagtaataactcaagtggagggagttgtttatttcacgatgaaactagaacaagatttcatttctgcattggccccaggtg aatacgattttgaatttcatacatccgttgattcttatgcttcgacctttgactttattccattgattagatccgagccaatcaaattgata gcaggtgcaccagacgaagttgaatggtttattgatattccaagtgcatacagcgatttggcaacgatagatattagttctgatatcgatac taatgataatttgcagcagtacttctatgattgctcaaagctcaagtacactattggaaaagagtttgatcagtggggtaattttacagctg gatcagatggtaaccaatacagcaataccaccgatgggtatgttccaattactgattctaccggctctccagtagctgaagttcaatgttta atggaaagtatctcattgagtttcacaaatactcttgctgaggatgaagtattgagagttgttcttcactcttctgcgtttagacgtggttc attcaccatggccaacgtggtaaacgttgacattacagctggtggattggcaaaaagagaactcttctcttatatattggatgaaaattact atgctagtactggatctgaggggttggcatttgacgtatttgaagttgctgatcaggtcgaggagccaactgaggagtcaacctcagaggaa tctactgaacaggaaacttccaccgaggaacctaccgaggaatcaactgaacctactgaggaatctacccaggaacctactgaagagcccac cgacgagcctacttctgagtcaactgaggaaccttctgaggagccaacttctgacgatctctcaattgacccaactgctgtacctaccgatg aacctactgaagagccaactgaggagcctacttctgagtcaactgaggaaccttctgaggagccaacttctgacgatctctcaattgaccca actgctgtacctaccgatgaacctactgaagagccaactgaggagccgacctctgagactaccgatgatccatcgatagcacctactgctgt gccaacttccgacacatcttctggacaatcggtggttactcaaaacactacagtcactcagactaccatcacttcagtctgtaatgtttgtg ctgagacccctgtaacaatcacttacactgcaccagttgtgactaagccagtttcttacaccaccgttacttcagtttgccatgtatgtgca gagacaccaatcacagttaccttgacgttgccatgtgaaaccgaagacgtgacaaagactgccggccctaagactgtcacttacaccgaagt ttgcaactcctgtgctgacaagcctatcacttacacctacatcgctccagagtacactcaaggtgccgaacgtacaacagttacatcggttt gcaacgtttgtgctgagacacctgtaacgctaacatacactgcgccgaaagccagtcgtcatacagttccttcacaatattcaagtgccgga gagctcatttcatccaaggggatcacgattcctactgttcctgcccgtccaactggtacttatagtaagtctgttgacactagccaacgtac actcgctaccattacaaaatcttcagatgagtctaacactgttaccactactcaagccacacaagttttgagcggtgaatccagtggaattc aagctgcttcaaacagcacgagcatctcagctccaactgtcactacagctgggaacgagaactctggatctagattttcgtttgctggacta ttcacagttctgcctcttatcttgttcgttatataa |
| PAS_chr1-4_0251 | 35 | atgcagtttgcttccttactgcttctcttgtatattttcttggggcaaatttatcctactgaagcagcaaaatattttgttcgtctgaagaa gcctcacacactagacctcttgttcaaacaggatgaagcagatgcatctgctgagaaccgaatctctcttcatggtttaagggaccgaatca aaaaaaagatctcttttggaacgttcgaaggttttgttggtgaattcacaacagaacttgtagaaaaactaaaaaagaattcgttgattgca gacataactcctgacattatcgtctcatcttgcgatatcgaattgcagtcccccgctcctgatcacctggctaggttatccaaagaaggtgc cgtaagagcacaagatcgtcttcttggaccggaatttttctacgatggtgactggactggagaaggcgtcaatgtatacgtgatagacacgg gtatcagggtaaatctagatgaatttgagggcagagcatcatttggtgctgattttacaggcactgggaaagatgactctgttggtcatgga |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | acccacgtagctggtcttattggctccaaaacttttggagtggccaaaaatatcaacttgatatccgtaaaagctctctctggtaatgggag cggttcgctttcagaggtcctacaggcgattgaattcgcagtcaagcatatgaaagccagtcgtaagccaggtgttgctaacttgtctctag gtgcaccaaaaaattcaatccttgaaaaagcgattgaagaggcattcaagaacggtttagtcatagtagcagcagctggcaatgccttcgtg gatgcctgtaacacatcccctgcaaactctccatatgcaatcaccgttggagctataggtgatcacaacgatgaaataactagattttccaa ctggggagcctgtgtcgatctttttgcaggaggggacacaattgtaagtgtaggacttctcaatggagtcgctgtccgcatgtctggaactt cgatgtctgctccaatagtcgcaggcttagccggaatattacttgaccagggtgtggccccagaagatgtaaaaggtaagttaatagagctc tcagatgaagggaagatcaacgataatactggaattctaaagccgggaactccaaaccgaatagccaacaatggaattcgaaaaagtgatta tgaagatcaaaaagaaaatgacaatgatgaagacgatgaagacggggaagacaatctagaagacattgaagaggacgaggattattgggatg aagagagaaggtatagggaatatgcggtatctagtttagtcttctaa |
| PAS_chr4_ 0874 | 36 | atgttcaacattatccaacggatacagagtttgagcaatttttatttaacggtttccattctattatgtattgttacaacagttgtctcaat tattagtatgttcttggatgaaacgtccagtattcctgcccaattaagcaatgttgtaatatcaacaaatttaaagtatagcagatcgtttg gttcagtcggtggtagacctaaagaaaactccaagatttatttgatcttgatatggatctggctccattattcaattggaatactaaacaa ctgtttgtacaattggtagcagagtaccctacctctgttgccgatgatggtgcgaaggtgacctattgggatagcataattactgagaaaaa gtacgcaagagtgcatgtcaataagcagaggggaaaatactcagtttgggacgtgtcggactcctttcaaggccgcaatgctacggttaaac tgaaatggaacttacagccctatgtcggctttctattctttggacaaactaagggagagattgaggtggcctatcctgcaacataa |
| PAS_chr3_ 0513 | 37 | atgagtgtcatagtgcatcctcttgcactattgacaataatcgacgagttccagagacgaggtcgcaacaacgattccataatattcggtgg gttacttggtaaacatgatgaatccaccaaccaaatatctgttgttaacagctttgtgataccattgatcgataatcagtttttgaataaag agtacttgcaggacatgctactcaaattttctatcattaattccaactttcgattcgtaggttactatcacgttcaatctttaaacggtacc gaaactcaacagtatgacttgaacgctattaacctagtatgccaagatgataataggccttcgtcctttgtccattggatagtaacagatcc aaaagagttcaaatcattctcgatgtattacttggatgattcaatggttcaactcgtcaattccaatattcaacattacatttctaaaccat tgccctatgaatttaaaaaccttctgtctgagaaaattgctatcgacacaatcctcaagcaatccaggctagaaaaagacttatccaccaaa aactcactgaagaaattaaacaatagttatatcgacattcattcctcactgaacgttctctataaatcagtcaataggcttattcgttacct caaaaaatgctcaaaatcagaagtttcaattgactatgacacagttcaggaaatgaatactgtaatactgaaaattgaaaggcttaaattga taccccaagtcaaggaggagtttgacttagtgactctttcactactggtagacaatcttgatcagatggatcatcttttgtatctccggaaa caagtggaacagtacaaaatatctgaatcaatgtatagttag |
| PAS_chr1- 1_0127 | 38 | atgaaatttcactcgattgtcttcacattttcactcgttttgagttcactggcgttgtcgataccatgggtgtctgaccacatggtccagca tctttttgccgacccttcaatcagtaaaggtcctgatgtagatctcgttgggctacataagcatttggtcagcatcaaatctctttcgggct atgaacaagaagtagtatcgtggttggccgattatctagccagtaggggtcttactgtggagttgaacaaggtcgaggacgaaactgaacgt tacaatttgtatgcttatttgggaaccacccgcaacactaaggttgtgctaacttctcacttagacacagttccccttatcttccctacaa agttgaggaaggtggctatatctttggcagaggaagctgtgatgctaagggatcagttgcggcacaagtgattgccttcctaaatctcttgg aagagggctccatcaaagaaggtgatgtcagtcttttgtacgtcgttggtgaagagattggaggtgatggaatgcgcacagctagcaagacc ttgggtgctaaatgggacactgccatttttggagaacctaccgagaacaagcttgccattggacacaagggaattgcactgtttgacctgaa gattacaggaaaatcctgtcattctggataccctgagctgggaattgatgccgacgctatgttggtccagattttgcacaagttgcttttttg agacttcttggcctgtcagtgatttgctgggaaactccacagtcaacgcgggacagatcaacggaggagtagctgctaatgttatttcttcg gaagcacatgccaaggttttaatccgcgtggctaaagacattgacgctgtagagaagctgatctacgaggccattgccccccttcgaggagta tacagacattacctttcactccaaagaagatgctactttcttggattacaaggttgaagggttcgagaactacattgcagcctacagtaccg atgtaccattcctagtgacgggctccaatttgaccagatatttgtacggaccaggaagcatcatggtggctcatgggcctgatgaaatggtc aaggtttcagacctgcaggatagtgttgacggatacaagcgattagtctccgtctcactttag |
| PAS_chr4_ 0686 | 39 | atgccagagaaaaagaaacaaaaaaaaagagtcgacatctccattcaagggtaacctagttgggatctcattggtagctgtggcattgtttgc catctaccagtacctctacccaagctcgttttcctctcagcctgaaaccccagccccagttttcgatctgagcagtgaattagaagcattgt gtcccgtgtaccctgcagtcagatcttccgacttcgaaaaggatcgccccatcttagagagaattctgaacgatccctcatttagaatcgct tctgctcaaaaactgagtaaggctgttcagatcgatacccaagtgttcgacgaacaattggacgtggctcaagaccctgaagtttggaccaa |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | attcgtcaagttccatgaatatttggaggcaactttccccaccgtttactcccaattgaaggtcgacaaaatcaacacctatggcttggttt tcacttgggaaggctcagaccctagtctgaaaccactcatgttcttggctcaccaagacgtggttccagtccagaaagatactcttcaggat tggtcatatccccctttcgaaggacgtatcgccgatgacagagtttggggacgtggatcagctgattgcaagagtttactgattgcattact ggaaaccgtagaattgctggtagatgaagggtactcaccaaagagaggtgtcatcctcgcatttggattcgacgaagaagcttcaggtacct acggtgctcacaatatctccaagtttttgcttgagaaatatgggccagatagtattgccctcattttggatgaaggtgaggctgtcagttac gtggacaagaaacaaactaccctcgttgcaaagattgctacgcaggaaaagggttaccttgacctagaggtcgcattgaccactgtaggagg ccattcttctgtccccccctaagcacactgcaattggccttatttccaagttggtcacacatatcgaagatcatccattggacccagaaatta gtaccagaaatcctctggtacagttttcgaactgtcttggtgcagctggggctttgagagatgacttcaagactgctcttgttgcatacagc aaggatccgtcgaacaacattgtcaaacaaggtgtgattaaaggtatttccaagattgcatttttcttcggttctttgattaccacaacaca agccaccgatcttattttcggtggagagaagatcaatgctttgcctgaaagtgctagagtagttatcaaccatagagtggacgttgagcgtg attcagcccaaatcatagacagattgattcacttccacgttgttcctattgccaaggagcacggtttcaaggtcacttacagtgactatggt agtgacaaagttgaaactgtctacgagccagaaggagttgcctcattgggagaattccacgtttctcctttctccagagtctgggagcctgc tccagaatctccatccgacgacaatgtctggtccatcatttctggtaccactcgtacgatatttgaggagtttgtggacccctcggctaaac ttattgcaagtccatacatgatgcctggtaacaccgacactcgacactactggccgctgacaaagaatatctatagatacgttccaggtatt gtagatatttacaaggctaagatacactcggtagatgaatctaccgaggttgatgcccacttgcaagttatagctttctaccacgagttcat caaggttgccagcgaatgggagctttga |
| PAS_chr2-2_0056 | 40 | atgaaatcctctaaagaactatacaaggaggctctcaactatgaatactcttccgcggtttctttcaaggcctgggttcgaagtgctcaaat cattttgcgacatgcccggcagtttgctgaacaaagatacatcagtgagtgctataagttgtctgttcgttttgtagacttgattgtgaaca agatggccacgcataaagagctcaagcaattgaagaaaataaatgcaccagtatatctcacctatttggatttggctacgaagaaagtccca gatgtcatcaaggaatgtgaggccttgaagacaattttggatgatgagtaccaaagctacctcaaactgcaacaattgaaacgacagaagca gaaagaccaattgatccatcatcagaatcaggctcaaacgcataaattacgtagatcttcatcaatattgaaagatcatatcaacgctgttg atgaaagagcgctgttgaaacaactacagcagttgacataccatgatcgtgaattcgcaaccgcaataacggagatgccaaattatccagag atcccccagctgagtatttcaacgaatcagaacactagatcagaggcacccccacttccaccaagagtatcgcaggaacagtcattagcacc agtatcactagattcatcacaggcagatttacaacacaaaactgttaacttcaccgaagctgggcaaccattacgaacagtatttatttcag atagactccaatctgagttccttagactagcggaaccaaacacgatacaaaagctagagacttgtggcatcctttgtggaaagctcgtcaga aatgcattcttcatcacccatttggttataccagatcaagagtcgacaccaaacacatgtaatacaagaaatgaggaaaagttattcgacac tatagatcagcttgatttatttgtccttggatggatacatacccacccaacacaatcatgcttcctgtcttccatagacttacatacacaga attcgtaccagatcatgttaagcgaagcaattgccattgtgtgtgcaccagcacctcagttttctcatcattcttttggatgttttcggcta acccatcctccgggaattccaaccattacacaatgcactaggacgggatttcatcctcatgaggaacccaatctgtatgtgacttgtaatcg aaagaacatgggcgacgtgcaaggcggacacgttgtgatcaagaatcatttaccgtttgaaaagcttgatctaagataa |
| PAS_chr2-2_0159 | 41 | atgactagttctgtagataaagtgagtcagaaggtcgctgacgtaaaactgggctcctccaagtcaacaaagaataacaagagcaaaggtaa aggaaaatccaacaagaatcaagtggttgaggatgatgatgaggatgattttgaaaaggccttggagcttgcaatgcaattagatgcacaaa aactagctcagaaaaaagctgatgatgtgcctcttgttgaagaagaagagaaaaaagttgaggaaaagattgaacagcaatatgaccccatt tccactttttaccctgatggaaactatccccaaggagaagttgtggattacaaagatgacaacttgtaccgtactactgatgaagaaaagcg agctttggatcgagagaagaataacaagtggaatgaatttcgtaaaggtgctgaaattcataggagagttcgaaaactggcaaaggatgaga tcaaaccgggaatgtcaatgatcgagatcgccgaactaatcgaaaacgcagttcgtggatatagtggtgaagacggactcaagggtggtatg ggatttccttgtggtctttctttgaaccattgtgctgcgcactattctcctaatgctaacgacaaacttgtcttaaattatgaagacgtcat gaaagtagatttggtgtccatgtgaacggtcacattatcgatagtgcattcacgttaacattcgatgacaaatatgatgatctgttgaaag ctgtcaaggatgctaccaatactggtattcgtgaagcaggtattgatgtgagattgaccgacattggtgaagccatccaagaagtaatggag |

TABLE 5-continued

| Protease Gene Symbol/ Locus tag | SEQ ID NO: | Open reading frame nucleotide sequence (5' to 3') |
|---|---|---|
| | | Open reading frame nucleotide sequence for proteases targeted for deletion in *P. pastoris* |
| | | tcctacgaagttactttagacggagaaacataccaagttaaacctatcaagaatctttgtggccataacatcggccagtatagaattcatgg<br>tggtaagtctgttcccatagtgaagaattttgacaacaccaagatggaggaaggtgaaacctttgcaattgaaacctttggcagtacaggaa<br>ggggtcatgtgataggacaaggtgaatgctctcactacgccaagaatccagatgcccccgccaatgctatctccagcattcgtgtgaaccgt<br>gctaaacaattgctaaagactatcgatgagaactttggtactcttccattctgtcgtcgctacatagatcgtcttggagaagaaaagtactt<br>attggcattgaaccagttggttaaatctggagttgttagcgattatccacccttggtagatgtcaaggggtcatacactgcccaatacgagc<br>acaccatccttttgagacctaatgttaaggaagttgtatcccgcggtgaagactactag |
| PAS_chr3_ 0388 | 42 | atgattcacagctgtgctagtgctgagtgctcaaaagcgactgaatctaccttaaaatgtcccttgtgtctaaaacaaggtcagatccaata<br>tttttgtaaccaaaaatgtttcaagaatggatggaagatccacaaagcggttcacgccaaagatggtgatatagatggttcgtacaacccct<br>ttcccaactttgcctacaccggtgagctcagaccagcatatcccttgtctgtgagacgagaggttccagagaacattactctcccagattat<br>gctcttgatggagtaccagtctcagaaatcaaaaataacagaatgaacaagatcaatttggtaacggagccagaagacctggccaagctaaa<br>aaatgtttgccgtttagcacgagaggttctagatgctgcggctgcatctatcaaaccaggagttaccactgatgagatagatgaaatcgttc<br>atagtgaaacaatcaagagagaagcatacccctcccctttaaattacttcaattttcccaaatctgtttgcacatccgttaatgaagtcatc<br>tgccacggtatacctgatcgtagaccgctccaggatggtgacatcgtgaacctggatgttaccctttataaagatggatttcatgcagatct<br>gaatgaaacgtactatgttggagagaaggccaagactaacaaagatctggtcaacctcgtcgagacaaccagagaagctcttgctgaagcta<br>tccgtttagtgaaacccggcatgccgttccgtcaaattggtactgttatcgaaaactatgtgactgaaagaggctgtgaaactgttcgttct<br>tacactggtcatggtatcaatactttgttccacactgaaccaaccattccgcattacgctcgtaacaaagctgttggagtagccaaaccagg<br>agtggtattcactatcgaaccaatgttgactctgggcactcatcgtgacgtggtttggcccgacaactggaccgccgttaccgctgatggag<br>gaccaagtgcccaatttgaacatacccttttggttacggaagatggtgtggagattctcactggcagaacggaaacttcgccaggcggtgcc<br>atctcaagactataa |
| PAS_chr3_ 0419 | 43 | atgctctataagaccaccttgtcaatagcacacacgagtgtgatattgttgtcattgataaccgccataagttgctttgagttgcatcttcc<br>tcagaaggtttctcatatagtagacagtttacaatatacttgcggccaattttgcaaaagcagcagatctttgcactctataacaagcaaa<br>atttcaccgaaatagtgaaccagaatatcaagggaatagaggagagagttttgtctgagttgcttgaagaaagattagagaatgaatcccag<br>aatgattattataccgccaattctcaaaattggcctatcgacttggatcagtactcagaatcatttgtaataaggatcacatctgaagatga<br>gtttatcaagtacttgatcttcaaggaagctaaagctttgcatatttccatatgggagcaatctgttggtttgatagatttgaaggttgacc<br>gtgatcagatgcaccgcctactttacaacgtggagtcacgcatactggaacgaagaacgagaagtgttgacagtccagtttctgaatataaa<br>gtacaattgatgattggagatcttccacagcgaatctacgaaacatatccttcgacaaaagtgacatctttgcaagccctaggagagttccc<br>ttctttccagaacctaagtaatgctttttttgaggattttagaacgctggaaactatatacgactggttcgaagaaatacagaaggaatttc<br>ctaagctagtgtcgatcaactggattgggcaaacttatgaaggtcgtgatctgaaggctcttcacgttagagggaagcactctggcaacaaa<br>acagtagtcgttacaggtggaatgcatgcgcgtgaatggatatcagtaaccagtgcatgctatgccgttcacaaactgctccaaaactatgc<br>tgacggacaccacaaggaagcgaaatacctggacaagttggactttttgtttgttccagttttgaatcctgatggatacgaatatagcttta<br>acgaagacaggttgtggaggaagaacagacaagaaacttatatgccccgatgttttggtatagacattgaccattcatttgattatcatttc<br>gtgaaatcagaagacttaccctgtggagaggaatattcgggtgagtcccctttcgaaagtatagaaagtgaagtgtggaataatttcctgaa<br>cagaaccaaagaagaacataagatctacggctatatcgacttacactcgtattcgcaaacggtgctgtatccctatgcgtactcatgcgaaa<br>tcttaccaagggacgaggaaaacctgattgagctaggttacggtattgcaagggccataagaaagagtacagggaaaaaatatcaagtgttg<br>aaggcatgcgaagacagggatgcagatctattgcctgatttgggaggaggaaccgctttagattatatgtaccacaaccgtgcatactgggc<br>gtttcagatcaaattgagggattccggtaatcatggctttctccttcccaaaaagtttatatacccagttggaacagaggtttatgcctcaa<br>ttcagtacttttgttcttttgtgctgaatttagaaggctaa |
| PAS_chr1- 3_0258 | 44 | atgaaattgaccataacattagcccataacgatcaaatcttggacattgatgtgtccagtgaaatgctactatctgacctcaaagtcctgtt<br>ggagttggaaacttccgtacttaaaaacgaccaacaattattttacaataacaacctgctcactggagatgactcgccactggaagatttag<br>gactcaaagataatgaactcataattctgagcaaagtcgaagcacatagtgatgtcaattcacacttgaactctgttagagaacagttgata<br>caaaacccgctataccaggccagtttacctccaagtcttagagataagctcgacgaccctcaaggcttcaaagaagaagtggaaaaactaat<br>ccaattggggcagtttggacaatacgggccttcccgtacttccgtccaacaggaattagacagactacaaagagatcctgacaatccacaaa<br>atcagaaacgaattatggagctcattaacgaacaagctatagaggaaaatatgaatactgcttttgaaatctcacctgaatctttcgtttcc |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gtgaatatgctctatataaatgtggaaattaatggtgtccattgtaaagcattcgtcgatagtggagcccaaacgaccataatgtcccctaa<br>actcgcagagaaatgcaaccttgcgaatctaattgataaaaggttccgaggagtcgcacagggtgtaggaagttctgaaatcattggtcgta<br>tccattctgctcccataaaaatcgaagatattattgttccctgctcattcactgttttggataccaaggttgaccttctattcggacttgat<br>atgttgagaagacatcagtgtgtgattgaccttaagaacaactgtttacaaattgcagacagaaagacagaatttttaggagaagcagacat<br>cccaaaggaattctttaaccaaccaatggaagctccatccacagctcctgtcccaaaacctgtacaacctcctcaacaactcggtcagcggc<br>cggctggaagccctccctccacaattcaaagaccagcagtacaaccgccacctgtggatatacctccagaaaaaatccagcagttgatcaac<br>cttggattcggagaagaggagtcgaaagaagcacttattagatctagaggaaatgtggaagttgcagcggctttgttattcaactag |
| PAS_chr4_ 0913 | 45 | atgccaaaccttccttctagcttgaacaagatgactgctcaagccgtgaaatacgcaaacggtatgtcatctgccctctcccgtgtttgaga<br>ctctatccactaactttagattttatcaccttcctgaacaattcacctactccataccatgctgtcgactccgtaaagtccaaattggtaga<br>gtcggggtttaacgagctcagtgagagagttaattgggccggaaaagtcaagaagaatggcgcttactttgtgactcgtaacaattcgtcca<br>ttatagccttcactgttggcgggcactggcagccaggtaacggagtgtcaattgttggagcccatactgattccccaaccttgagaatcaaa<br>cccatatcccattcgactaaggagggatttaaccaagttggaattgaaacttatggtggaggcttgtggcatacgtggtttgacagagattt<br>aggagtagctggacgagtgtttattgaagaagaagaatctggtaacattgtgtccaagttagtcaagatcgataaaccagtattgagaatcc<br>ccacactagccatacaccttaccaaagagagagctaagtttgagtttaataaggaaactcaattccatccaatctcatcgcttgaaaactcc<br>tctgaaaaggagaaaaacaaagatgaggaacatgacgcttgtgcaggagaagatttgactacggaggagtttaagtcaattcaatctgttgt<br>ggagagacacaacaaacaattgcttgatctggtggctgcagatcttgattgctctatatcccagatagtggactttgaattgattcttttcg<br>accacaacaaaccagtactcggaggtttgaatgaagaatttgtgttctcaggaagattggacaacctaacttcttgtttctgtgccactgaa<br>gcgcttataaatgccagtaaagataccaacaggttagatctggatactaatattcaactgatctctctgtttgaccacgaagagattggatc<br>agtttctgctcaaggagctgattcttcatttctacctgacatacttcagcgtataacaagactaactggtaatgaggttagcaccgatctgg<br>aaggacaaccaaattctttctttttagagtcaatggccaaatctttcctactatcttcagatatggcacatggtgtgcatcccaactatggg<br>gaagtctatgagaagctaaataggccaagaatcaacgagggaccagtgatcaaaataaacgctaatcaaaggtacagcaccaattccccagg<br>tattgttttgctcaagaagattggtgagttgggaaaggtccccttgcaattgtttgttgttagaaacgactctccctgtgggtcaacaattg<br>gtccaatgttgagtgctaaacttggacttcgaacgctggacctcgggaacccccagctctccatgcattctatcagagaaactggaggtgct<br>cgtgacgttaaaaagttggtcgatcttttcgaaagctattttgagaattattacaccttggagcctaagattaaggtataa |
| PAS_chr1- 1_0066 | 46 | atgaacaaaggtccgaaagaattggagggccgcaagtatccagcaagagcccatgcactgacggtcaaaaatcactttatccaaaagaaggc<br>tgacatttcaagtcgttctgcaatctttattagtggcgaagatctcaagttgtatccttactgtgaccaaacagctcctctcagacagaatc<br>gttatttcttttatctgtcaggttgtaatatccctggatcccatgtcctttttgacttggacgccgaattgttaattctggtgctaccagaa<br>attgattgggatgatgtcatgtggagtgggatgcctctttcgattgaagatgcctacaagacgtttgatgtggacaaggtggtatatcttaa<br>agatttgcaaggctttttgtcgtcgtttggaaaaatatatacaactgacatcaatgatgaaaattctaagtttggcaatctactaacagaga<br>aagatcctgacttgttctgggctctggatgaatccagattgatcaaagacgactatgaactcactctaatgagacatgcgtcaaaaatttct<br>gacaattcccattacgctgtcatgtcggctcttccaattgaaactgacgaaggccatattcacgctgagtttgtttatcattcgttaagaca<br>gggatctaaatttcaaagttatgacccgatttgttgcagtggaccaaactgtagtacccttcattatgttaagaatgacgattctatggaga<br>ataaacacaccgttctaatcgatgctggtgcagaatggaacaactatgctagtgacgttacaagatgttttcccatcaatggagattggacg<br>aaagagcatcttgagatctataatgctgttttggatatgcaggaccaagttatgaagaagattaagcctgaagcccattgggatgagctaca<br>ccttttggcacatcgtgttctcattaagcatttttttgagcctcggcatatttcataacggaacagaggatgagatatttgagagtggagtct<br>cagtatcattctttcctcatgggctgggtcaccttttaggaatggatactcatgatgttggtgggcaccccaactatgatgatccaaaccct<br>ctattgagatacctaagattgagaagagtgttgaaagaaaatatggtagttacgaacgaacctggaatctacttctctccctatcttgttga<br>attgggactgaaggatgataataaggcaaaatatgtcaacaaggatgtactggaaaagtattggtatgtcggaggtgtgagaattgaagacg<br>atattcttgttacgaaagatgggtatgaaaacttcaccaagattactagcgaccccgaagaaatttccaaaatcgttaaaaaggggttggag<br>aagggtaaagacgggttccataatgttgtatga |
| PAS_chr2- 2_0310 | 47 | atgacatctcggacagctgagaacccgttcgatatagagcttcaagagaatctaagtccacgttcttccaattcgtccatattggaaaacat<br>taatgagtatgctagaagacatcgcaatgattcgctttcccaagaatgtgataatgaagatgagaacgaaaatctcaattatactgataact<br>tggccaagttttcaaagtctggagtatcaagaaagagctgtatgctaatatttggtatttgctttgttatctggctgtttctctttgacctt |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gtatgcgagggacaatcgattttccaatttgaacgagtacgttccagattcaaacagccacggaactgcttctgccaccacgtctaatcgtt<br>gaaccaaaacagactgaattacctgaaagcaaagattctaacactgattatcaaaaaggagctaaattgagccttagcggctggagatcagg<br>tctgtacaatgtctatccaaaactgatctctcgtggtgaagatgacatatactatgaacacagttttcatcgtatagatgaaaagaggatta<br>cagactctcaacacggtcgaactgtatttaactatgagaaaattgaagtaaatggaatcacgtatacagtgtcatttgtcaccatttctcct<br>tacgattctgccaaattcttagtcgcatgcgactatgaaaaacactggagacattctacgtttgcaaaatatttcatatatgataaggaaag<br>cgaccaagaggatagctttgtacctgtctacgatgacaaggcattgagcttcgttgaatggtcgccctcaggtgatcatgtagtattcgttt<br>ttgaaaacaatgtatacctcaaacaactctcaactttagaggttaagcaggtaacttttgatggtgatgagagtatttacaatggtaagcct<br>gactggatctatgaagaggaagttttaagtagcgacagagccatatggtggaatgacgatggatcgtactttacgttcttgagacttgatga<br>cagcaatgtcccaaccttcaacttgcagcatttttttgaagaaacaggctctgtgtcgaaatatccggtcattgatcgattgaaatatccaa<br>aaccaggatttgacaacccccctggtttctttgtttagttacaacgttgccaagcaaaagttagaaaagctaaatattggagcagcagtttct<br>ttgggagaagacttcgtgctttacagtttaaaatggatagacaattctttttttcttgtcgaagttcacagaccgcacttcgaaaaaaatgga<br>agttactctagtggacattgaagccaattctgcttcggtggtgagaaaacatgatgcaactgagtataacggctggttcactggagaatttt<br>ctgtttatcctgtcgttggagataccattggttacattgatgtaatctattatgaggactacgatcacttggcttattatccagactgcaca<br>tccgataagtatattgtgcttacagatggttcatggaatgttgttggacctggagttttagaagtgcttgaagatagagtctactttatcgg<br>caccaaagaatcatcaatggaacatcacttgtattatacatcattaacgggacccaaggttaaggctgttatggatatcaaagaacctgggt<br>actttgatgtaaacattaagggaaaatatgctttactatcttacagaggccccaaactcccataccagaaatttattgatctttctgaccct<br>agtacaacaagtcttgatgacattttatcgtctaatagaggaattgtcgaggttagtttagcaactcacagcgttcctgtttctacctatac<br>taatgtaacacttgaggacggcgtcacactgaacatgattgaagtgttgcctgccaattttaatcctagcaagaagtacccactgttggtca<br>acatttatggtggaccgggctcccagaagttagatgtgcagttcaacattgggtttgagcatattatttcttcgtcactggatgcaatagtg<br>ctttacatagatccgagaggtactggaggtaaaagctgggcttttaaatcttacgctacagagaaaataggctactgggaaccacgagacat<br>cactgcagtagtttccaagtggatttcagatcactcatttgtgaatcctgacaaaactgcgatatggggggtggtcttacggtgggttcacta<br>cgcttaagacattggaatatgattctggagaggttttcaaatatggtatggctgttgctccagtaactaattggcttttgtatgactccatc<br>tacactgaaagatacatgaaccttccaaaggacaatgttgaaggctacagtgaacacagcgtcattaagaaggtttccaattttaagaatgt<br>aaaccgattcttggtttgtcacgggactactgatgataacgtgcattttcagaacacactaaccttactggaccagttcaatattaatggtg<br>ttgtgaattacgatcttcaggtgtatcccgacagtgaacatagcattgcccatcacaacgcaaataaagtgatctacgagaggttattcaag<br>tggttagagcgggcatttaacgatagattttgtaa |
| PAS_chr1-3_0261 | 48 | atgacctgccaaagtgtagaagagctggatgctattgttgaatcaaagcttagggaggttgataataaagtttcgaacggaaatgttgactt<br>catcaaacaatatctgattcaggcgatgaactattatgacaagtatagatctgaaatcaaaaaaattggacccacagaaaagaaccctaaat<br>actattgttttcaagaggcagcgtatgttaactacaaagcttcccaagctttactaagagagagaatacccaagctgcctggctttggagga<br>tataaatctgcgtattcaaaaatctatcgtgaactgatagaaatggtagaggggcaagaacatgagattgcccagataaaaagcggcttaag<br>gaaaaactttgtgatgatacattagttcttcgactgagaagtttaaaatcaccatctgctactcagcccaaaagtttaccggattctacac<br>ccacttcacaatttaaaccaaaaccttcaaagccttttagtatcacaatcaatgaggaatacatttcggttgaccaattgtcacgccttctt<br>aaaacgaacccgaatgacatactcctcattgatctacggtctcgtcaagagtacgacgtgtatcacattgaagatggctccggggtggacat<br>gtcaatatgtatagaaccaatgagtatcagaaacggatacacagcagaggatctttatcaactttcaatggccgtcaatccagattatgaaa<br>ggagattgttcaagaatcggtctcagtatgaactgttggtatgttatggtaattatgacaacgaggctactgttcaaatgttcatgactatc<br>atgaataaagatacttccctcaagaggcggagcgtctatttgaaatccggaattaagggctggaatcaggatctgagttttcaagattcgaa<br>accgaatgggtacttaactagtacgactgactacttcagtaacactccgaaacacacaattacgcccaaatcatcaaaatcaagttcaaaac<br>ctactttaaaaactactgtcaactctgggcctgcccacactgttgggatcaataatctaggaaatacatgttacatgaattgcatacttcaa<br>tgcctattagaaagtgataagtttgtttcatttttttacaaggcgattataagaaacatatcaatattaatagccgattaggctcgagagg<br>tatattggctacaggatttcatttgttagtgctattaatatccagatcatctggtaaaacagtgactccttcttcatttgccaaagatgttt<br>caacagtgaataagaattttaagttaggagagcaacaggattgttttgaatttttagatttctcctggatagtttacatgaagacctgaat<br>gaatgtgggaatgaaccaccaatcgcagaactcacacctgaagaggaaaagcttagggaagctttacctatcaggattgcttcgaccattga<br>atgggaaaggtatttaaaaaacaattttagcatagtagaagatgtgtttcaagggcagtacttctccagattggaatgtacagtctgtaaaa<br>gcacttcaactacttataactcattcagttcactgtccttgccaatcccattagatcgacaaaatgtcacactagatgactgtttccaggct<br>ttttgttctgtagaagaattgaacggagatgacagatggcattgtccaagctgtaaaaaaaagcaggtcgcttttaagaaacttggtatctc |

TABLE 5-continued

| Protease Gene Symbol/ Locus tag | SEQ ID NO: | Open reading frame nucleotide sequence (5' to 3') |
|---|---|---|
| | | Open reading frame nucleotide sequence for proteases targeted for deletion in *P. pastoris* |
| | | tagactaccaagtgttctgatcgttcactttaaaaggtttcaggtcaagtgggaaacaggtcatataatcaagatagacaagtttatcagtt atccgttcaagctatcaatggacaaatattggcccaaagctcaatcagaagaagaactaagaaacttggagaagctaccatcgagaaatcag aatccccctttcaattatcgattgacaggggtggctaatcattttgggaccagaacatcatctggtcactacacatcatatgttcaaaaagg tggccaatggtattactttgacgatagtgctgtgactagcaatgttgatcgtcataaaatcgtaaatgggaacgcctatgttttattttatc gacgtagttag |
| PAS_chr2-1_0546 | 49 | atggaagccgtgaatttacaaattgaatggattagacaggtgcctccagttactgtggctcttgtagcatccatgtcaatgacctatttttt gcaacgcatagatgtattatcctcaaatatgttcgtgtttgaaagacatcgtgtgtttaatgagatggcctattctcgtttgatactaagtt tcttcttcagcgcccattcgtttgttggattcttttggacattgtacacattatttcagaattcacaggcactcgagctgacctatgaaaac tcaatcgattacctctactcattggtgataatagcaggtttgatcgtggcatgggcctcatacttggggggtccgttcatgctgggatgggt tctagctgacgtcttgagaaccatatggtgcaaacagaatcccaacgaaagaatgtctattttggggctagtttccttcaaggcaggatact ttccatttgtaatacttgccatttcatggctagaaggaagttcaagaaatcttctattaatgctaattagccaaactgtcagtcaggcttat atttttggacaccatatgatgcccgaactacacgggatcgatctgtttctgcctatatggaaattccagtgtttcagacgtcagagacaacc accaattcatcagcatcaagactaa |
| PAS_chr2-2_0398 | 50 | atgtcaaaggtggtggtattcctaaatggattattggcaataacctttacgtttgaacttctctctgttttaagcgtgccaatcaccaagca tatccaactttgttcttatcaaggatataagtttggcgtgtttggatattgcaccgagaataatatctgcacaacgataggaatcggttatc atcgaaattcaatagacgaattgagaggcttttcattaccaagtaatgcaagaagctctatatcaagcttgttggtggttcatttgattggc tgtgtttgcacctttattttatgggttctaagtctcatgttgaatatggatagatttcacagatcattatggttcttattaacgtgtctagt atggacttgtgctttcttttttttttacattattctccttcctggtagacgtgttactatttgtgccacacgttgcgtttggaggttggttga tgttggtaagtactgtattttttggcatttacaggaaccatttttttgcatcatgcgaagaactgtcagctcaagaaaaactcatttgaagaac tacaacgggggaagtacaagtttgatgcggctgcagacgtatatctccaatagctctagaggaagctctgtaaccaatgatgaatacgtctg gtttcaagaaactccattacaagacctctacccccccagacaatcccaattacgacgacatctacggaacgactgaacacgaactaacccgct tggacacaatatctcttgaaaggccaagaataggccttatcacaaacgaaaatgccagcggcgatggtggggtagtttccccaccacagaat gacagtacacttctggaatcttcgggcagaattaggaatgggccactgggagaccgaagtgaatttcccaacggatcaacaagcgaactttc tgcataa |
| PAS_chr4_0835 | 51 | atgaaatacagtgaccaattaatagaagagtacaaagaattatggttaacagcgacatctaatgagcttactagagaatggtgccagggaac tctccacctgagcaaattatacgtttacttgacacaagacttaaagtattttggggatggatttcgacttttaggcaaaaccatttcgttat gtcgccgtaggcaatcgcttgtgtcattaggcaaacatgtggggatgctcagtaatagtgagaacacgtacttcgtggattgtattaacgat cttactgaacagttattaagagatgggatgtacaatgctgaagaattagaagaaatcagtggtttaacgttacctgccgtggaaaggtacct tttattcatgagatcgatggtagagtcttctacaataacttatgcagaaatgattactgtgatgtttgtaatggaacaagtctatctggatt ggtcaaataatggactgagaagtaaacctgacaacttgcattggtggttcaatgaatggattgatatacatagtggggagaactttgaaagc tggtgccagtttttaaaggatgaggtagaccgctgtatacaggagttgaaggatgctaatagagatgatctcgtggcgagggttgaggagat ttttagagaaacattagaacttgaagtcgaattctttaaaagttgttacgatatcacggacgatgaatga |
| PAS_chr1-1_0491 | 52 | atgcactcgaaatttaggtgggtatgtgtcgatactcaattctgcacacaccaccaaaatctgtcgcctttctcttatatctccaacccgag tccaatgtcattttcttaccttgaaggcaacatcgattttaaaggacaggaacttgcaaacaggatcactaaaaaactaatcacatttggtg caattattagttttctggtaggatttttgagtgacaacatcttatacactgtatacactttcgcagcttttggtttattgactgcttctttg gttattccccctttttagcttctacaaaaagaaccctgtaacatggttaccaaagaaatccaaaatagagattcagcattga |
| PAS_chr2-1_0447 | 53 | atgacagactctgttaactctgatgattctgatctggaaatcatagaggtgactgagcctactccaaaagtggaccttttggcccccaatcc agcatttaattttactgcccccataagcaacagtaacggcacaactccaataaggagaaaacttgatgaccaatccaactccaattcttttg ccagactggaatcgttacgggaatcatcagtgaaaccacaagctagtacgttcaatagtagtaggttcatcccccaagccgaccaattttcc aataatcagaataatgaacttgataacaacaatggattcgccgactggatttctaagtcccaacctgaatttccctttccacttaatgatgg accaaaaaaagtccagcaatcaacctacaaactcaaattttgaagagatcatcgatttaactgaagatatcgagataaatacatctgtccccg |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | catctacatcatcttctaccccagttccctccagcacacagaatcagagccatcatatagccaacaacaacacagcacaagatgcgcatatc ttccaagggaaacgacctctccaatcatattcagatgatgaagacgaagatttgcaaattgtaggatccaatattgttcagcagcctctagg aattatgccaggaactttcaacgcccctgcaaacatactccattttgacggttcaaaccagaatgaacaagccagatggctggacttgcgga taaaagatttgttagataatcttcacaatcttcgagttcatgctcagtcgaatattatggagatcaataggttcatttccactttggggcat ttaaacagagaagtttcagagctcaatctaagatatcaatctatcgtgaacaatcctcaggcgaccgctaataatcaaggatacctcactca gcttttgaacaggattcaggagcttactaatgaaaaagcgcacatatttagagagatggatacatccaagataaaacagcaggagattcaca gaagaatccatgctctctcgtcaacaattgacaaactgaaaaaagatcgtgaacttatctttcgaaatgctcaaaatgcttttcacggtgat atgaagaatgaagttttggaaggccagtctttcatggatgcaattcatagggcaaatagcttgggttatgcttcaaatatttattctcgttc tgatgaagacgctggaagcttacaacggcttcttgaaaatatccagcccgatatggaggacaaagacgatgatgaattggctaaaactccga aggagttcaatattcaactgctgaagcatcagagagttgggttagattggctacttcggatggagaagtcaaccaacaaaggaggcatttta gcagatgccatgggcctgggaaaaaccatccaggctattagtattatttacgcaaacaaatggaaaacacaagaagaagccgaagaggaggc aaaacttgaagagaaggttagatccgaaaagtctacatcagaaacgaatggagaggtcagcaaaacgtcaacggcaaagtcggaaaagaaac ccatccaaggagacgaaggatatttcaaaactacgttaataatagcaccagtttctcttctacatcagtgggagtctgaaatcttgttaaag acgaaaccagaatacaggctaaaagttttcatttatcacaagcaaaaaatgtcctcgtttgaagagctccaacagtatgatatagtattaac atcgtatggaactctgtcttctcaaatgaagaagcattttgaagaggcaattaaggaggcagacctacagcccaactcttcatccataccag cagaagactctggaggcatatctttcaagtcaccatttttgcaaaagaaacaaagtttcttcgagtcattctagacgaagcccataagatc aaaggaaaaaatacaatcacttcgaaggcagtcgctttggtgaagtctaaatacagatggtgtttaacgggcacaccgctacaaaataaaat tgaagaactatggcctctacttcgattcttgagaattaagccatattatgatgaaaagcgatttagaactggcatagtattacctataaaga gttccatgtcaggcaaatatgattccacagacaagaagattgctatgaggaaacttcatgccctacttaaagcaatcttgttgaaacgaaac aaagattcgaagattgatggagagcccattctcaagttacccaagaagcatatcattgacacattcatagaaatggaagcaaaagagttaga cttttacaaggatctggaaggacagacagccaaaaaagccgaaaagatgctaaacgctggaaagggacaaggaaatcattattctggtattc ttatcttgctattgagactgagacaaacttgttgccaccatttcctcgtgaagttatctgagatgaagcaagaagccaaattgaaacaggaa gttgctaccaagatgccacaattggccacacaactatctcctgctgtggtaaggagaattaacattgaagcagaggccggatttacgtgtcc tatatgtttggataacatcataaatgagaatgcttgtatattatacaaatgtggacatgttgtttgtcaagattgcaaagacgatttcttca ccaattatcaagagaatgaaactgatgacggtcttagagtgtccaaatgtgtgacctgtcgtttgcctgtcaacgaaagcaatgtaatcagt ttcccagtctacgacaagattgtgaaccagcatatttcagtgatggatatagttaaaagtgagtctccagtgttgtcaaaaattgaaatgat tcaacaactgatccgggagaacaaaggcgtcttcgaatcgtctgccaagatcgataaagcagtggaaatgatacaagagttactgagagaca atccaggggagaagatcatagtttttagtcaattcacaactctcttcgatgtcatagaggtaatactcaaagagaacaacattaaattcatt agatatgacgggtcaatgtctcttagcaatagagatgctgccattcaagagttttatgagagtacggagaaaaacgtaatgcttctttcttt gaaagcagggaacgtggggttgacattgacttgcgcctcccgtgtcataataatggacccatttggaacccatatgtggaagaccaggcca tggatagagcccatagaattggccagttaagagaagttttcgtctatcgaatgttgatcaagaacaccgtcgaagatagaattttgaccatt caaaatacgaaaagagaaatagttgaaaacgctctggataaccagagtttgaatacgatatccaagcttggcaggaacgagttggctttctt atttggtatcggcaattga |
| PAS_chr1-3_0053 | 54 | atggagtgtaaaaaagtcaaagatcgcctagtcacggaatacttaaagattgaatgtagtcgacttaaccgaaggatacgctccctgaaaaa tccaaaagttgagcaagccctactgcaattcaagaactcacgtttggctcacatgagaaaggctcatctggatggaataagaaacccacagt atacggatgacgccatctttcaggcattggaaaccatggatttggaccacatatttgagaaggcaggtagtctttacaactcacagcaacaa gatgaatcaaaaaaagattccctggatgaaacagatttcaccgtggtggcgttgctagattggttcaagaatgacttcttcaaatgggtaaa caagccaccttgtcctgtttgccatagtgaagatgaaagccgcataagaatggtcggatctgcaaggcccactagtgaagaattgtcgtacg gagcaggggtcgtagaggtgtttaattgtgaccattgtagctgtgcaatcagatttccaagatataacgaccctaagaagctcctgagaact agagctggacgatgtggggaatggaataactgttttctgttgtgtctaaaagccttgggtctgaaagctagatgtgtgaggaatgtggaaga tcatgtatggagtgaatactactcggaacatctcaagcggtgggtccatctggatagttgcgagaatgcctttgatcaaccagaactatact gcaaaggttgggggaaaaagatgagctattgttttgcttttgatgacactctcatagaagatgtgagtgccaagtacattactcaaggtaga ctgcctaaaatgctagacgacgaaaccatcagaatatgcttgtatttttttcaaccaggaagctcttaagatggtgagtgaaaatccagaggc attctactccgctttggttaagtatcacagatgtctgtctgcgaatagaaaagagagcgggtcaaaatcacgagccgtgaatgctagtttga cttcattgttaccacgacaatctggtagcgcatcctggacgtctgagagaggcgaaaacggactttag |

TABLE 5-continued

| Open reading frame nucleotide sequence for proteases targeted for deletion in *P. pastoris* | | |
|---|---|---|
| Protease Gene Symbol/ Locus tag | SEQ ID NO: | Open reading frame nucleotide sequence (5' to 3') |
| PAS_chr3_ 0200 | 55 | atgcctataaaggggcggttcaccaaaaagaagccaaaaaggaaagatgagccaaatcgaccgtcccccacccagttcatcaaaaaaatagc ctcattgaaaaagcagaccaggagagatgaggccctggatgtgctacacgaactagcagttgttgtgtcacctttgatgaaagagaacggtt tcactgttggattattatgcgaaatgttcccgaagaatgcctctttattggggctgaatgtgaatatgggttcaaagatcatgatccgattg agacctagccacaacatgaacttgtttttgccaaaaagagagatcatcggtacaatgctccatgagttaacccataatcgcttttcggccca tgatgtaaggttttatgactttcttgagggtctcaagagcaggtttttttgagattcaggtgaaaggatctttacaaactacagggtatgtta actttagtgaagttctatctggtaatgcggcgagagggcaactgattcaaaaggaaaaagagaaaggacaaagattgggtggtaataagcat gcaaaacctatgagagtcctaatcttggaggcggccgagaagagaatgatagactctaaatggtgcggaggagctagcaatgaagtaggcct tccaaaaattgaagatctaatggacgatgaagaagctcaacactctgaactaaaggaagagaatacaaagaaggtcagaaaaattgttcaac ctagcaaaaagaaaattgtagatttggaaaacctaccgaatggcaagtccattattattgatctaactaatgacgatgactaa |
| PAS_chr1- 3_0105 | 56 | atggaacacaattgtctgaaagtcaatgaattggcgctccagttggctcaatcactgcagaacagcaaagtcagcacagctgatcctctaaa gaagaggacaagcagctacagaggcctgagtagcgagcctataatcacagaggaagaaccaacaatcaagggcgactataatagattttaca gtcagtcttcagataagcaagtattggacaataaaccatggttgcaggatggaaactatttcaagactgtatacatttcaacgatagcacta ctgaagatgatgtctcatgcccggtccggtggttcaattgagattatgggcatgctgacaggtaaggtgtttgccaacacattagtcgtaat ggattgctacttacttccggttgaaggtacagagacacgagtgaatgctcaagcggaaggatatgagttcatggtctcttatttggataact taaaggaaatcaagcataacgagaatatcataggatggtatcactctcatcctggttatgggtgctggttgagtggaattgatgttgccact cagaatttaaaccaaaagtttcaagatccctacctggcgatagtgattgatcctgaaagatcagtcagacaaggatttgttgagattggagc attcagaacgtttgctgagccagccgttggaagatcgtcgtcgtcagtttcctctgcaagtggtgcaggaattagtgatgttgcgttttctt ccggtagaaacagtgcatctggaatgtcctcagttctgagtgcaagtaatattagcattgccgaagagctaagcaaacaatcgatcacccaa aatgtttttgacagaactactacaaagattcccaagggcaaaatgactgattttggagctcattcaggaaaatattactcgctagaggttaa ggttttcagatctccactggaggagaaactactggatacgtttggttctaaaacctggattaaaggtttaacgaactactccaacgttgtta atgccgaggaaactcaagtggagttaatgcataaaataatggaagccacggagaacttacggaaggaatctccttctaaattgccatctttg gtgatggggaacctgatttattcaggtgcctctcaaggaacaacagggaaccgcaagcgctcaatgtccaaatcttctatttattcgggttt acaagcttcatcgggtatacccagttctaggtatcctacgaagggaaaaaatatgagtggatctcaattcaatgatgacccgctagcaagat cactggataaaataccgccagatagtccagatcaacagtacgatggcgcattatccattcaacaaccgaaaagagcatataatacacatact tctagagcaggtgggttggccagcgttctgtcctctgggagtatggatcctcaaagttactccatggtaggacgaatgagtctaactaatca atcgccggggacagctctgagaggcctaaatacacctcccaacaaacgaccgcagagaaaccctggtcatacaagctcaggtcaaggaggaa cgcctggaggagtcagtcggtccaaagagaaaattaacaagccaataggtataagcatgattagcaaggatttcaaggttgtcatctcacaa caggtcaaccagatgctacgtcgtcacgtccagaatgacctttttggatccaatagtccctaa |
| PAS_chr3_ 0635 | 57 | atggatcatgcccaacgattgctagaactaagtttttacaatcaaagtctgggcaaatcagtgatagcaaagaaatacagaatagaatcctc tcgatatttgaatgaacaactggacaagtccttgacaagagataatgatctgattggattatgccgtatagcattagacaacaagttgacca tatcagataagattatatggatgagctctcaagttgaagacaacttctttccgccagtttttcaaggcttgaagacgtatattgatagcgac gagatttatcaagagaaacttttaagcgtaccagcggattttgaaccaatagttgaatggaagagttgcacagagttgcccaatgaatggtc aaacaatggtgtggacaatttatttcaggattctttagatgactgttcgtttgtagcttcatttctatcctgcaacaatattggtatccctc tcatggataaagtcattccccacaaaaactcgttcaaatatgcggttagactgactttcaatggttgcgaaaggttggtgtttattgatagc cgtttgcctttgcttaggaatacttccaagactttacgagtgtcaagtttttctaacaaagatctcttatggcctagcatcatcgaaaaagc tttcctgaaaatgtgtgatgatgggtacaagttttcaggatcaaattcagccattgcaaactatgctttgactggctggatccctgaagtca ttaaaacttcttcatgtacaatagcagatattagccgattgcatgaggattttcggaacggaaacgtagtactatgcttgggaacgggcaat ctgaccgagcgagaatgcaaacagtatggattgatccccaatcatgactatgctgtcactaaactatcatttacgaatgattcagaatacaa gtttgacattcgtaatccgtggactaaagggcagaaagcagtgacaattacagatctttcaacctttgaagttatctacgcaaacagaaatc ctataatgttttcgcacatgaaccagctaagcggtatctgtcaaagtcaggttaatgaagagttcatagatctaattcttaaccattcgcag tataccctaggcaatgacggtaattctacaattgatgtgattcttttctttgaaagacattcgttaagaaagaaaatcagtgcagagtctcg tattgagattttccaatcagaaggcgaaagactaatctccagaagaaataaagcaagcaaggaatgtgtttctaataataccaactttcatt tcataacaatcgaactgaaaccgttagaaaaggtaactgtggtaatagatatcggcgagtcttcgattcgaagccatccatttactctaaag |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | gcttttgccaatgattcaactataactttgaacaaagcactttctagacctggttgtttcaagcaaatggacctagagctaacgcccttaaa<br>ctctggtgggaattgggataattatgcttattacaaaaatccacaactcatagtcactcttcacggagattcaacggatgaagctccatttg<br>aatctgctgttttcagcaaaagtgataagaccctatttacgtatacagtgttttggaaaagtgacgatccagactttcctttcatcactgac<br>gcaagcaagaacaagctcgtaagcacagacaataagtataaatacagatcatgtacaagatcaagagttgtttcttgcgacaaaagctattt<br>gttcgtgctgagctcctacgaacctgatgcaattgagtctttcaaagtattttttcaatgttcccacgatttttctatagagtgggctgaga<br>cgtcgcttgggcttttcacaaaggaagaaactttctcctggaaggaccaattagtcaaggagttcattattcaagtctataacccttcaaag<br>ttgaaagttcacgcagtaaacaccaacaacaaacgcagatcaaaactaaattgctctctctcattccaaaacacattaatcagctctttgca<br>agactacacagacaatctctatggatgctttattagcgggaacttggagattcccggcaagtatctattacaagttcataaaaacattatat<br>ctaacgaagaatgtttggtcgaaattggatctagttcgtcatttgagttatgggaacatcattaa |
| PAS_chr4_ 0503 | 58 | atgttgaaaactcgatttcattccagaaagggttttgtaatctacagtggagatgatgaagagagtgacgaagagagtaaacaatggatgtt<br>tcccgagtcgacctttgtaaccaatgggtttgaccaattgttcaaggtgagaaatgtcaataccattaatgacgacgatgacggctaccaat<br>cgttcgatcaaccggattgggcgcaagatttaaccgcagatactcagtatcttgctttaggtgacgaaggggagaatcatcgttcacaacaa<br>gagataggcaacaggaaaagagccaacaaaaagcaaaagaagccaactaaagcaaagacaaaacgtcaacaaagacgcacagccaaaaatga<br>tcaatccacggaacgatctgccatttcacaaccttctaacttaagtacactgaactccttactcaaatctgttcggtctgaactttccaatt<br>ctgatgggagtccccacacattctacgatgtatctctctatgaagaagatctgaacaacctagctgatgacgaatggttgaacgataataac<br>gtctcgtttatctacgagtacattgaaagattttacattacccgttgtttgagcgacaagcttcaattttcatcaaagaagatggtcaattc<br>tcaaataatactcctccgaccttctatggtttttttgctggcacattcaactccaaaagatatccaggattttctcccaccgttggataagt<br>ctggctttatattccttcctctgaacgacaatgatgatctggaaatggctgaaggtggatcccattggtgtcttttagttgtagctgttcac<br>gataacaaatgtttcctctatgactcattagagaatgccaatctcacagagtctgttgcgcttgtgtctaagctgtccactctgctaaacag<br>gcgaatacaactcgttgaaaatacacattgtcctcaacaactcaatggcagtgattgtggagtaatcacaacccaaattacagcactactgg<br>tatcccgactgctttgtgttttgccgggacatcctataaatttggatcttcaaaatgtagctatcaacgcaataagcgggagaatcttcatg<br>ttaaaactcctccaacatgttctgaacaattaa |
| PAS_chr2-1_0569 | 59 | atggcaccaccagtccctgtatatacgagagatgaagtcaagatgcaatttccacagtacatgatgaaatttttgccttcaaactgtgagct<br>gtactccatcatccagaaccaatgtaccttctctgctgacgagataatatgtgtgcccttcaagagggtgtttgccaaatgccggaggggaa<br>accaagaagccaagaggaacataataccagagaatggaggactgaatttaactggaaagaaactaatcccaagagaatacacagtcattgaa<br>gttacggactccctaacgaacaagtacgacaatagtagcctcatggacagatttttttgaggcagaaagagatttaatgataaggtttcaaga<br>atatgaggaacggaacagtaaggaaggagaaataaagtag |
| PAS_chr3_ 1223 | 60 | atgctcagacagtttgctggaagggagttcaagcgtcggttttctacgggaatcaagacgatgccaacaaagcttaccaaactgccaaatgg<br>tattcgtgtcgtaacggacgaagctccgggccattttagtgccatgggcattttcgttgatgctggttcaagatatgagagccagtttccag<br>aattaaccggccactctcacatcatcgatagacttgcattcaaatcaacatccaaattcgatgggaaatctatggtagaaaacaccaatcat<br>ttaggtggcaactttatgtgtgcctcttcaagagagtcattgatataccaggcttcagtgttcaacaaagatgtggacaagatggctgaaat<br>cctcagttctacagtcaaagaacctttatttactgaggaggaagtttctaatcagatagcaacagcagattatgagttggatgagttatggc<br>tgcaacctgacctaattcttcccgaattgtctcaacaggtagcttatggatcaaaaaaatttgggttccccgctgctctgtccgaaggagtct<br>ttagcaaacatctcaagagaatccctttgaagtatcgtgaaatatttttttagacctgagaacttggtcgttgctatgttgggagttcccca<br>cgagaaggccttggaacttgttgataaaaatttaggcgatatgaaatctgtcggttccagtccagtggtcaaagaacctgctaaatatacag<br>gaggagaactttctttgcctccagttcctcctatgggtgggcttcccgagtttcatcacatatatcttacatttgaaggtgtccccgtggac<br>tctgacgatgtctactcactggctactttgcagatgctcgtcggtggtggtggatctttctctgctggtggtccaggaaaaggaatgtatgc<br>cagagcatacacgcgagttctgaatcagtacggttttattgaaagttgcaattcatatatacacaatttctcagactcggggctgtttggtc<br>tctcaatttcaagcattccgcaggcaaataaagttgttgcagaactcttaggtcatgaactgagctgcttgttttctgaaaatccgggcaaa<br>ggtgctcttaccaatgccgaagtaaaccgtgccaaaaatcagctacggtcttctttgttgatgaacttggagagcaagatggttcaattaga<br>agaactaggaagacacattcaagtttatggcagaaaagttgatgtcacagagatgtgtgataaaatcagcaaagttacaaaggaagatctag<br>ttgcaattgcaaagaaagtcttgaccggaagcaacccgactatagttgttcaaggtgacagagaatcttatggagacattgagggtactttg<br>gcatcttttggagttggtttagatgccgcttccaaagcttcaaagaaaaaaacgagaggttggttctaa |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| PAS_chr2-1_0597 | 61 | atggcaattatcaagttcaacgcaggcaaagtcaagattgacgaggaaaccaagctttgtacacccttggcaacaagaggagaaataatcgt ccaattgtcggctgagggcgaagagttttatgatttcaaatgggtccctactgagaacacagctggtgaaggtaaccagtcagagacattct tggtcattccgggcgatgtgacgtggaaacacgtcaaaagttgtaaagatggtagagttttcaaattgacatttttgagtagtggggcaaag agtttgttctggatgcaagatgataatggaaacgaggatgacccatcagagttgacaaccaaagataaggaaattagtgaaaaaattaccaa gttgttcgacgaagaagagtga |
| PAS_chr1-1_0327 | 62 | atgaaacacttggctgtccataagtacaaggtaggagccatcgcagctggcttggttgtctcctataaaatctttgcctaccgcgctgcgtc ttcctcctcctcaaacgtcatcaacttgaccaatatggcaaaaactccaatcactttaaaacccccctcaggctccactccgctgggaccata ctccagagcagatccttgccgaaactgataagtatatatctaccagtcaagaggttgacgattgggtggcaaacagctttgccactgccaat gtggacaccatcaagaaaatagccgccgctgagaatgaacaatacttgccactgtgtcaattgagtttttatcaacatatctcggataacca ggacgttcgtaatgccagtactgttagtgaggagaaaattgataagttctccatcgaatccaaccttagagaagatgtgttcaaaacagtga acaaagtgttcaaacaggttcaagaagattcggaactccaaaagaccttggacccagaatttaggcgtttactagaaaaattgaacctaggt tacgtgagatctggtttagatttatcccaggagaagagagaccaagtcaagagtttgaaacaagaactatcaaccatttcaatcaagtttaa taagaacttgggagaggaaactgaacacatttggttcaccactgaggagttaaaaggtgttccagaatcagttgttgagcagtttgaaacta agaatgagaatgatgttacttaccacaagatgacatacaagtatcctgacctgttcccggtactaaaatatgccgttaatccagctacgaga caaagagcttttgtcggggatcaaaacaagatacctgaaaattcaggattacttgtgaaagccgtcaatttgagaaacgaacttgcaaaagt tttgggttatgatacctatgctgactatatcctggaagtgaagatggccaagaactccaagaatgtttttgaatttcttgatgatgtaaggg aaaaactcagacctctcggagagaaggaactgcaaagaatgttgactctcaaggctaacgacccaaatgctgttgataaggaaaattactac gtctgggatcatcgttactatgataacaagcttcttgaatctgaatacaaagtggatgagcaaaagctggctgaatactttccaatggagtc caccattgaaaaaatgcttgccatttacgagcacttgttcaatttgcagtttcaacaagttgacgattcggagaaacaagtttggcatccag atgtaaaacaattctccgtttggaaaatcgataaccctgattctcctgaatttgtgggctggatctatttgatttgcatccaagagaagga aaatacggtcacgctgctaattttggaatcggtcctagttacatcaaagaagatgggagtaaaaattatcctgtcactgctttggtttgcaa cttttctaaaccatcaaaggataagccatccctattgaagcacaatgaagtcactacattcttccatgagctaggacatggtatccatgatt taattgggcaaactaggtatgctcgtttccatggtacttcagttgctcgtgatttcgttgaatgtccttcacagattctagagtactggacc tggactagagatcaactcaagtctctttcccaacattacaagacaggagaagccctctccgatgaactcattgattcgctagtcaagtccaa gcatgtcaatggcgccattttcaatcttaggcagttacactttggtctctttgacatgaaactacatactgccaaagagcctgaatctttag atgtgacaaggttgtggaacgaattacgtgaggaagtcgctctggttaagaatggtgaccaaattacgaaaggatacggttcatttggacac ctaatgggcggttatgctgctggttactacggatacctgtattctcaagtgtttgccagtgacatttattacacctttttcaaagctgatcc aatgagtacagctcaaggtatcaagtaccgtgatatcattcttgccagaggtggatcaagagaggagctagataatctcaaggaattacttg gaagagagcctacatctgatgcctttatgactgagcttggagtagaaaatggtgcgtccaagttgtaa |
| PAS_chr2-2_0380 | 63 | atgcgtttttggtctcatcctttcggcccttcagacatacaatttcgtcgcatatctcaatgggccaggctctgtctgccattcgtgtatt tcataaaaattctcactcacgtacccaaggtttaaggcgccactctcactactgttgccaccgcaagatagatatgagtacttctactaaac ttccagagcgtcaattgctaccagccaatgttaggcctaccaaatatgatttgacattggagcccttattttctaccttcaagtttaacgga gaagagactatacatttagatgttcaggaggactccagttctattacgctacacgctctagacatcgatctccaagattcactattgataac ttcaaacaagtctaagactcccccgcttcatgtgacaagcaatgatgatgaccaatcgctcacttttcaattcaaagagggtactctagtaa agggagataaggtgcagctgcagttgaaatttgttggtgaattgaatgataagatggccggtttttaccgctcttcatatgaagagaatgga gaaactaaatatttggcaactacccagatggagccaacagattgtcgtcgtgctttcccttcctttgatgagccatcgctaaaagccgtatt caacattgccctcattgctgatcagaaacttacttgtctctcaaacatggacgtgaaagaggaacaatctctcggagatagaaggaagaagg tgatattcaatcccactccactaatttctacttacctaattgcttttattgttggtgatttaaaatatattgaagccgactataactatcgc attcctgtcagagtttatgccacccctggtttagagaagcagggtcgtttttctgtcgagcttgctgctaaaacattagaattctttgagca acagtttgatattgattatcctcttccaaagatggacatggtggcgattcatgatttcagtgcaggagctatggaaaactttggcttgtta cctatagagttgttgatttgctgtacgatgaaaaaaattcaaatttggctactaagcaacgtgttgcagaagttgtccaacacgaattggcg catcagtggtttggtaatcttgtcacaatggagtggtgggagggcctttggctgaatgaaggctttgctacatggatgtcttggtactcttg tgacaagtttttccctgattggaaagtatgggaacaatatgttacagattctttacaacaggctctggctctggacgctctacgtgcttctc |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | accctattgaagttcctgtgaaaagggccgacgagatcaatcaaatttttgacgcaatttcctattctaaaggatcctccttgctaaaatg atctccaaatggctcggagaggatgtgttcattaagggagtctccagttatttaaaaaagcacaggtatggtaatacgaaaaccaccgattt gtgggaatcgctttctgaggtgtctggaaaagatgtggtcaaagttatgagtatctggactggtaaaattggatttccaatcatctcagtaa ctgaaaatgcaaaccgtatcacttttactcagaacagatatttaactactggtgatgtaactcctgaagaggatacgacgatttatcctgtt tttttgggactcaaaacagaaagctcaactgatgagtcgctggtccttgactcaaggtcaatgtcagtagatatccagaattctgactttttt caaagttaatgctgaacaagccggtatttacaggaccaattatgcaccagagagatggatcaaacttggaaagcaacctcaccttctaagtg tagaagaccgtgctggtttggttgcggatgcgggcgctctggctagttctggtcactcatctacaaggaacttttttgaaccttgtaaattca tggaaagatgagtctagctttgttgtctgggacgaaataacttcccgtgttgcagctttaaaagcagcttggttatttgaatcccaatctga cattgacgccctgaatgctttcgtaagagaccttatttctacgaagatcaaaagtatcggatggtcattcaatgataatgaaccattccttg aacaaagactaaagagccttctatatgctactgctgctggtgcaaaagtaccaggagtagttaaatcagcattgataaactttcaaaaatac gttgctggtgataagactgccattcaccctaacataaaggcagttacgtttcaaactgttgcggcccaaggatctgaaaaggaatgggatca gttactcgacatctacaagaaccctgtatctattgatgagaaaattattgctcttaggtctctcggaaggtttgaagatcccatcttgatcg caaagaccctggcactgttatttgatggttccgtaaggtcacaagatatttacgtaccaatgcaaggccttcgtgcgactaagataggagta gagtcacttttcaagtggttgactcttaattgggacaagatttataaattgcttccacctggtctgtcaatgcttggttctgtggttactat cagtacttctgggttcacttccttggatgatcaaaagcgtgtcaaagatttctttgcatcaaaggataccaaaggcttcgaccagggtttgg cccaggcgttagacaccatccaatccaaggcaagttgggtacaacgtgactctaggaatgtatccgattggctacgtgagcagggatacaaa aaatag |
| PAS_chr3_ 0928 | 64 | atgataaggatatccttgctgaaaagagcactgtttccctacgggcgactaccaatgcataatggtaggtggtattcagacataggtggcgg aaattcaaggaatcggaacgaacagaaaccaaaattgcctgtaccaactagtaatgaagttaaggacaatgagtcaaacccggacttcttta ttaaaaacggctttagatcagctgatattgcagagacatcctttgtgaaagacaagggtgctacagtcgaagaggaacgtaatacatcggac agttcacacgaatctcctcaacttaattttaaggaaaccaacgacgaaacgaattcaacgatccaaccaccagtggcaaaattacccacccc aaagcaattgaaacaatacctggataggttcatcgtgggacaagagaagtgcaagaagataatgtcggtcgcagtttacactcattatgttc gaataaataaccaggctcagaaacggaatcagaaggtcgattcctctgaagaaaatgttgagaatgggtttccaaatgttactaaagaattt gaggacgaaaatgacccagattatgttccggatttggagaaatcaaatgttcttttgctgggaccgtctggatcaggcaagaccctgattgc taagactctcgctaaatgtctgcaggttccatttataattcaagattgtacctccttgacccaggctggttatgttggcgaggatattgaga gctgtattgaaaagttgctaattgattcagactacgatattgaaaggtgtgaaaagggaattattgtgctggatgaaatagacaagttggcc aagccctctgtctatacaggaaccaaagatattgcaggagagggtgttcaacaaggccttttaaaactggttgaaggtactacagttacggt tcaatgcaagaggagcaatgctcctgatcataatcagttcggattgaatggcaaagctacaaatcaggacaaggaaaattatatcgttgaca ctacaaatatcttattttaaccctgggagcgtttgtgaacctagataagattgttgcttataggctgaagcagaactctattggattcgat actgatgagtcgaaagatatttctgaaacagactcagtttccgacaaatctacattagaatatgttacacttccagatggatcaaaagtttc agctctggaacttgtgtcttctacggatctacagaattatgggttgattccagaactgatcggcaggcttccgattgtatcttcactttctc ctttaacagttgatgatcttgtggctgtcctgactgagcccaggaactcgatactaaagcaatatgtgcatttctttgacactgtcaatgtc aaacttgctatcacttccaaggcaatcagaaggatagccgagatctcgatcaagaatggtacaggtgcaagaggtctcagagccattttgga gaaactgctactcaatgccaagtatgattgccctggtagtagtatttcatttgtgttagttgatacagatgttataagtaagtctatcgatg agaataaggaaacgggggaattcgtcttcaaagatggtgagccaaagtattactcgcgtggagaattattttcctttttcaatgagttatca aaagaagacgaaaaactcaagacatcaattgaaaagatgtgccaaataccactttccaagaatcgcatagtttactccgaagaggagcaggc aaggttggattcttctaaacctctcgccgtgaagcactatgaacctttcatttga |
| PAS_chr1-3_0184 | 65 | atgagcttcaacctgctaagtgttcctttacgaacgtcaaagccgataccgttaggcgaaagcctaaaagagcttatcaacaatcagtacta ccagacatctgctgcgttcaaatcggatatcgaagagatcgaccaactaagaaatgatgtcctatcaatagaaccaaacaatgatggacttg cattgctcaagagatactatgtacagttagccagcattagccaaaaactccctgattattttatggagtatccctggtttggaacattagga taccaagtaactggccccgtagctctaaaatccctctatttcgaaagaatcaatatagcgtacaacatcgcagcgacgtattcaatcatagg tttaaacgagcccagagctacaggagaaggcttgaaaaaatcatgcatttattttcagtatagtagtggggcattcgaaagtgtactgaagc tagtggagcaaaaaccgaaagagctgacacttcccattgatcttagtgttaacattatgaaaaccctggctaaactcatgctggctcaggcc caggaatgtttttggcaaaaggctgtttctaacactttaaaagataacgttattgcaaggttggcctttcaagtatctcaattttacgatga |

TABLE 5-continued

Open reading frame nucleotide sequence for proteases targeted for deletion in *P. pastoris*

| Protease Gene Symbol/ Locus tag | SEQ ID NO: | Open reading frame nucleotide sequence (5' to 3') |
|---|---|---|
| | | agctctgtctatggcttacaagtgcgatattttaaagtctgaatggatagaacatatgagttgcaagaagctgcattttaaggctgcggccc aatttagacttgcttgtgtggcagtcgctgcttctagacatggagaggaaatagcaagattaaggattgcaaataccatttgcgaaacagca tctagagaagccaagtatcaccttccctctgtatcttccgatttggagagtctttcgaagataatcaaagactctttaagaagaagtgaacg tgataatgatctaatatatctgcaggaagttcctaatgaatcagatcttcctccaattgttgcagcatctatggttgaacctaagccaatag ttgagttaaattcagctgaatgtgcgaaagatacaaagaaatacggcaaaatccttttccatgatcttatgccatacttagtgattgaaatt gcacaggcatttagagagaggcaggattcttatgttgtaaagcatatcaaggagcccatggagatgctgacaaagattcttcacacaatcct tgctgaaaatggacttccggcgttgatagataccatacaaaggcctcaaagattgccaaccaacatccttgaacattgtcaaatactcaatg aaaggggtggcatggacaaacttaaggtatttttcgaagatatcagcaagctaagacacaaaagtgagcaagttctccaaaactgtgtcgaa ttgctacaaatggaagagtccgaaaatgaggaaatgagaaggaagcatggatcacagaggtggaattttgctgactctagggaggcatcagc agatgtcaggaaaagtgtacaggcactagagggctatttgaaacaggcccatgatggtgatcaagtgatctggaatgacttcgaacaattga agccactactaagcatgatgagtgctcctaattcaactaaattactggaagaatttgtaccaaattcaaaattcgtcagacttcctccagaa ttgaaccgaatcgttaacgaattaagagctgatgttaatcaggtcaaaaagctcgcatcgcaaagggaaacttttattaatacagttaaagt aaaaagcaccgacctgtccatattgcccttggtagtttcccattataagaaattacaacaaaacaacattaatacgatcacgacggaattgt tcgaagaagtgttcagacgacaggttagcaacttcgattctgatatcagatttgttcaaaaacacagggacaaccaaatcgagttagagaag catattaaatctttggtccaacaattcaatcagcttagagggaatatagatgcctcgcaagaacgccaaaatgcacttcagttgttggacga tgcctataacggataccttgatttggtaaacaacctcacacagggacttagtttttacaatgatttcactggaaaggcaaatgatgtctatt tgagatgtcaagaattctacaactttcgtaaacaagaagccatgaagctggagcaggaaatatatgctgtatttgaacaaggtaaatctcct cagaaaaaacaactagaagatcaggtttcagatcaaccaaaaagtgaagtcaagtcttcaaagggttattctaatgagctgtggaaccccga cgttggaattaaatttggctag |
| PAS_chr1-4_0286 | 66 | atggtggcctctcttcacattgtcaatccgaatttggcctccgctttcagtttgcctcccaggtcaaacactttgagcgtttccatacacgc ttcggctttgttacagatcctggaatcaagttacttcgaccagaataagaatggtcgtatcataggaaccctcctaggttctaggtctgaag agacaacggaggttcaagtcaaagactctttcatagtttcccacacggaggacggagacgagtttaccattgattcttctcaacgtgaattt gtcgccatccacaagaagtctagcccaagagactcagtcgtaggatggttttccattaactctaaggtcgacagctttatcggactggtcca tgactttttctcaaagggtccagatagcacacacccgtaccctgccatatatttgagtatccagttatgtgacgagagcggatccttcgtag agccagttttcaaggcgtacgttgcctccccagtgggatgttatggagctctggcaagtcacttagaccttgaaaaagctggctcttttgtc ttctctgaagtcccaaccaaggtcatatactctgctaacgaaaaaagtctgctggctcatttcaagaacaacgttgtggaacccaaagttcc aataccacaaaacgacacaaatcaactaatttcacaactcaacaaactcgacgtttccattgaccagttaatagactacgttgacaaagtca tttcaggatctctggatagaaatgatgtgaagaatgatgagattggccgtttcctgttgaccaacttagtttcccttccaacttctccttca aaggaagagctttcatcttccataagctctcatatccaggactcactgatgatcgactacttggcctccgccgtgaaaactcaattagatgt tagctccaaattaatgaacctggtacaagatgataaatag |

TABLE 6

| Polypeptide sequences of targeted proteases | | |
|---|---|---|
| Protease Gene Symbol/Locus tag | SEQ ID NO: | Polypeptide sequence |
| PAS_chr4_0584 | 67 | 1 MLKDQFLLWV ALIASVPVSG VMAAPSESGH NTVEKRDAKN VVGVQQLDFS VLRGDSFESA<br>61 SSENVPRLVR RDDTLEAELI NQQSFYLSRL KVGSHQADIG ILVDTGSSDL WVMDSVNPYC<br>121 SSRSRVKRDI HDEKIAEWDP INLKKNETSQ NKNFWDWLVG TSTSSPSTAT ATGSGSGSGS<br>181 GSGSGSAATA VSVSSAQATL DCSTYGTFDH ADSSTFHDNN TDFFISYADT TFASGIWGYD<br>241 DVIIDGIEVK ELSFAVADMT NSSIGVLGIG LKGLESTYAS ASSVSEMYQY DNLPAKMVTD<br>301 GLINKNAYSL YLNSKDASSG SILFGGVDHE KYSGQLLTVP VINTLASSGY REAIRLQITL<br>361 NGIDVKKGSD QGTLLQGRFA ALLDSGATLT YAPSSVLNSI GRNLGGSYDS SRQAYTIRCV<br>421 SASDTTSLVF NFGGATVEVS LYDLQIATYY TGGSATQCLI GIFSSGSDEF VLGDTFLRSA<br>481 YVVYDLDGLE VSLAQANFNE TDSDVEAITS SVPSATRASG YSSTWSGSAS GTVYTSVQME<br>541 SGAASSSNSS GSNMGSSSSS SSSSSSTSSG DEEGGSSANR VPFSYLSLCL VVILGVCIV |
| PAS_chr3_1157 | 68 | 1 MIINHLVLTA LSIALANDYE SLDLRHIGVL YTAEIQIGSD ETEIEVIVDT GSADLWVIDS<br>61 DAAVCELSYD EIEANSFSSA SAKFMDKIAP PSQELLDGLS EFGFALDGEI SQYLADKSGR<br>121 VSKREENQQD FNINRDEPVC EQFGSFDSSS SDTFQSNNSA FGIAYLDGTT ANGTWVRDTV<br>181 RIGDFAISQQ SFALVNITDN YMGILGLGPA TQQTTNSNPI AANRFTYDGV VDSLRSQGFI<br>241 NSASFSVYLS PDEDNEHDEF SDGEILFGAI DRAKIDGPFR LFPYVNPYKP VYPDQYTSYV<br>301 TVSTIAVSSS DETLIIERRP RLALIDTGAT FSYLPTYPLI RLAFSIHGGF EYVSQLGLFV<br>361 IRTSSLSVAR NKVIEFKFGE DVVIQSPVSD HLLDVSGLFT DGQQYSALTV RESLDGLSIL<br>421 GDTFIKSAYL FFDNENSQLG IGQINVTDDE DIEVVGDFTI ERDPAYSSTW SSDLPHETPT<br>481 RALSTASGGG LGTGINTATS RASSRSTSGS TSRTSSTSGS ASGTSSGASS ATQNDETSTD<br>541 LGAPAASLSA TPCLFAILLL ML |
| PAS_chr1-4_0289 | 69 | 1 MVASHVNNAS ASRSNTSVSH ASASSYDNKN GRGTGSRSTT VVKDSVSHTD GDTDSSRVAH<br>61 KKSSRDSVVG WSNSKVDSGV HDSKGDSTHY AYSCDSGSVV KAYVASVGCY GAASHDKAGS<br>121 VSVTKVYSAN KSAHKNNVVK VNDTNSNKDV SDDYVDKVSG SDRNDVKNDG RTNVSTSSKS<br>181 SSSSHDSMDY ASAVKTDVSS KMNVDDK |

TABLE 7

| Forward (F) and Reverse (R) Primers for 5' and 3' homology arms (HA) targeting protease ORF | | |
|---|---|---|
| Description | SEQ ID NO: | 5' to 3' Sequence |
| PAS_chr1-1_0174 5' HA F | 70 | ACCTATTGTTTACCTTCCTG |
| PAS_chr1-1_0174 5' HA R | 71 | GAATTCTCTCACTTAATCTTTAGCTCCCATGCTCATCTTG |
| PAS_chr1-1_0174 3' HA F | 72 | GCGGCCGCaagaagttgattGTTTATTTGTAGGCGGTGCC |
| PAS_chr1-1_0174 3' HA R | 73 | GGGCTATCCGCCTTATCTTG |
| PAS_chr1-1_0226 5' HA F | 74 | AATAACTTCATGACTGCATT |
| PAS_chr1-1_0226 5' HA R | 75 | GAATTCTCTCACTTAATCTTAGTTTAAATAATATGGAGAT |
| PAS_chr1-1_0226 3' HA F | 76 | GCGGCCGCaagaagttgattATTGGAGAAAAGGAATACAC |
| PAS_chr1-1_0226 3' HA R | 77 | GGCATCTCCGTCTGGTGCAG |
| KO_PAS_chr3_1087 5' HA F | 78 | CAAGGTTCGAAACTGCAGCT |
| KO_PAS_chr3_1087 5' HA R | 79 | CTCACTTAATCTTCTGTACTCTGAAGAGAGAGCAAACCAATGGCAA |
| KO_PAS_chr3_1087 3' HA F | 80 | AGAAGTTGATTGAGACTTTCAACGAGGGTCCTTTGGCAATCATTGGT |
| KO_PAS_chr3_1087 3' HA R | 81 | ACCCCAGGACCAGGTATTTC |
| KO_PAS_chr4_0584 5' HA F | 82 | TACTACAGGCTGGCTGTTCC |
| KO_PAS_chr4_0584 5' HA R | 83 | CTCACTTAATCTTCTGTACTCTGAAGAAGTCCAACTGTTGAACGCC |
| KO_PAS_chr4_0584 3' HA F | 84 | AGAAGTTGATTGAGACTTTCAACGAGGGTCCCCTTCAGCTACCTTT |
| KO_PAS_chr4_0584 3' HA R | 85 | TCCCTGCTAAGCCCTAATCG |
| KO_PAS_chr3_0076 5' HA F | 86 | AAGTTGTATGGCCGTCCTCA |
| KO_PAS_chr3_0076 5' HA R | 87 | CTCACTTAATCTTCTGTACTCTGAAGTGAGTCTTGGTTGTGTCGGT |
| KO_PAS_chr3_0076 3' HA F | 88 | AGAAGTTGATTGAGACTTTCAACGAGGCCTCCTGTTTGATCGGTTC |

TABLE 7-continued

Forward (F) and Reverse (R) Primers for 5' and 3' homology arms (HA) targeting protease ORF

| Description | SEQ ID NO: | 5' to 3' Sequence |
|---|---|---|
| KO_PAS_chr3_0076 3' HA R | 89 | GTGCCATGGTGACGTTACAG |
| KO_PAS_chr3_0691 5' HA F | 90 | CGGAGTTATAGGGGACGCTT |
| KO_PAS_chr3_0691 5' HA R | 91 | CTCACTTAATCTTCTGTACTCTGAAGCGTCACATCATAGCCGTTCTC |
| KO_PAS_chr3_0691 3' HA F | 92 | AGAAGTTGATTGAGACTTTCAACGAGCGTCAAAAGTGGTCGTGGAC |
| KO_PAS_chr3_0691 3' HA R | 93 | TGGCCCAGTTACACGGAATA |
| KO_PAS_chr3_0303 5 HA F | 94 | GTCGATCGTTGGTGTGTGAC |
| KO_PAS_chr3_0303 5' HA R | 95 | CTCACTTAATCTTCTGTACTCTGAAGGAGCCGACTTTGACATCGAC |
| KO_PAS_chr3_0303 3' HA F | 96 | AGAAGTTGATTGAGACTTTCAACGAGAGCGAAGAGACTGGTTCCAA |
| KO_PAS_chr3_0303 3' HA R | 97 | AGCTGTTCTAACCGTCCTCA |
| KO_PAS_chr3_0815 5' HA F | 98 | CTTGGAATATCTGTGGGCGC |
| KO_PAS_chr3_0815 5' HA R | 99 | CTCACTTAATCTTCTGTACTCTGAAGTCATGACCAGCAGTTGTTCA |
| KO_PAS_chr3_0815 3' HA F | 100 | AGAAGTTGATTGAGACTTTCAACGAGATGCTGCAGGAAGGAACACT |
| KO_PAS_chr3_0815 3' HA R | 101 | CAAACTCTGCACCTCCAAGC |
| KO_PAS_chr3_1157 5' HA F | 102 | CTCTGATTGCACGAGAAGGC |
| KO_PAS_chr3_1157 5' HA R | 103 | CTCACTTAATCTTCTGTACTCTGAAGTGAAAGGCGATTGGAGTTGC |
| KO_PAS_chr3_1157 3' HA F | 104 | AGAAGTTGATTGAGACTTTCAACGAGCTGGCTCTGCTTCTGGTACT |
| KO_PAS_chr3_1157 3' HA R | 105 | GATGTTGAGGCGGGCATAAG |
| KO_PAS_chr1-4_0164 5' HA F | 106 | TTTCAACGGGGTTCTACGGA |
| KO_PAS_chr1-4_0164 5' HA R | 107 | CTCACTTAATCTTCTGTACTCTGAAGGTGGTAGTATGTGTGTTGGTGT |
| KO_PAS_chr1-4_0164 3' HA F | 108 | AGAAGTTGATTGAGACTTTCAACGAGCTGCGCTTTCAAGTACTGCA |
| KO_PAS_chr1-4_0164 3' HA R | 109 | TGTCTTCCTCGTCTTCCTCG |
| KO_PAS_chr3_0979 5' HA F | 110 | CGGGCAATAATCAGTGGAGC |
| KO_PAS_chr3_0979 5' HA R | 111 | CTCACTTAATCTTCTGTACTCTGAAGCGTTGGAGGTAATGCATGGG |
| KO_PAS_chr3_0979 3' HA F | 112 | AGAAGTTGATTGAGACTTTCAACGAGGGCGGACCGTGTATTAGAGA |
| KO_PAS_chr3_0979 3' HA R | 113 | TCAGAGAAGCCAGTGGAAGG |
| KO_PAS_chr3_0803 5' HA F | 114 | TTCCTCGGCCTCTTTATGCT |
| KO_PAS_chr3_0803 5' HA R | 115 | CTCACTTAATCTTCTGTACTCTGAAGCAACGTGGCTAACTCCTTGG |
| KO_PAS_chr3_0803 3' HA F | 116 | AGAAGTTGATTGAGACTTTCAACGAGGTTGTCGACGGCATTGAAGA |
| KO_PAS_chr3_0803 3' HA R | 117 | TCGGTTCAAAGCCCCTAAGT |
| KO_PAS_chr3_0394 5' HA F | 118 | AGGTGTGAAATGCGCTGATC |
| KO_PAS_chr3_0394 5' HA R | 119 | CTCACTTAATCTTCTGTACTCTGAAGAAACCAACAACGCCTGGTAC |
| KO_PAS_chr3_0394 3' HA F | 120 | AGAAGTTGATTGAGACTTTCAACGAGTCACAGGCTGAAGGATCGAA |
| KO_PAS_chr3_0394 3 HA R | 121 | CCATGGTGTGTTTTCCGGTT |
| KO_PAS_chr2-1_0366 5' HA F | 122 | TGAGGGACAAAGTAATGGGGT |
| KO_PAS_chr2-1_0366 5' HA R | 123 | CTCACTTAATCTTCTGTACTCTGAAGACCGAAGTCATGGTTGGAAA |
| KO_PAS_chr2-1_0366 3' HA F | 124 | AGAAGTTGATTGAGACTTTCAACGAGCTACCGCAGACAACCCATTC |
| KO_PAS_chr2-1_0366 3' HA R | 125 | CGCTCCCTCATCGAGTACTT |

TABLE 7-continued

| Forward (F) and Reverse (R) Primers for 5' and 3' homology arms (HA) targeting protease ORF | | |
|---|---|---|
| Description | SEQ ID NO: | 5' to 3' Sequence |
| KO_PAS_chr3_0842 5' HA F | 126 | CAGACATCGTGGAAACTGCC |
| KO_PAS_chr3_0842 5' HA R | 127 | CTCACTTAATCTTCTGTACTCTGAAGTATCTGCTTCGATCCCTGCA |
| KO_PAS_chr3_0842 3' HA F | 128 | AGAAGTTGATTGAGACTTTCAACGAGTTCTCCCGTCCAGTTAGCAG |
| KO_PAS_chr3_0842 3' HA R | 129 | ATTTCAGAAGCTCCGCATCC |
| KO_PAS_chr1-3_0195 5' HA F | 130 | ACAAAAGCACGCGATTGAGA |
| KO_PAS_chr1-3_0195 5' HA R | 131 | CTCACTTAATCTTCTGTACTCTGAAGACACTCACGGTTGTTTGCAA |
| KO_PAS_chr1-3_0195 3' HA F | 132 | AGAAGTTGATTGAGACTTTCAACGAGAACCCCAACAAGCGGCTATA |
| KO_PAS_chr1-3_0195 3' HA R | 133 | ACCCGGATCTGCTAGTGAAG |
| KO_PAS_chr1-4_0052 5' HA F | 134 | CGTATGCTCGTGTGACTGTG |
| KO_PAS_chr1-4_0052 5' HA R | 135 | CTCACTTAATCTTCTGTACTCTGAAGTTCCTATGCCTGGCGATGAT |
| KO_PAS_chr1-4_0052 3' HA F | 136 | AGAAGTTGATTGAGACTTTCAACGAGAGGGAGTCTTGTATAGTTGAGCA |
| KO_PAS_chr1-4_0052 3' HA R | 137 | AGCAGGGGTATTTTCACGGA |
| KO_PAS_chr2-2_0057 5' HA F | 138 | AGCATGATTGTGTTGGGTGG |
| KO_PAS_chr2-2_0057 5' HA R | 139 | CTCACTTAATCTTCTGTACTCTGAAGAATCCGATACTGTAGCCCCG |
| KO_PAS_chr2-2_0057 3' HA F | 140 | AGAAGTTGATTGAGACTTTCAACGAGGCAAAGAAAACTGGCCACAC |
| KO_PAS_chr2-2_0057 3' HA R | 141 | GGAAGGCCCTATTCACGACT |
| KO_PAS_chr1-3_0150 5' HA F | 142 | CACCATTTCCCTGCTGTGTC |
| KO_PAS_chr1-3_0150 5' HA R | 143 | CTCACTTAATCTTCTGTACTCTGAAGTCAATACCGAAGACTCCGCA |
| KO_PAS_chr1-3_0150 3' HA F | 144 | AGAAGTTGATTGAGACTTTCAACGAGGGGAGGTATTCAGGAGGCAT |
| KO_PAS_chr1-3_0150 3' HA R | 145 | GCTCGATCAGATATTGTCCGC |
| KO_PAS_chr1-3_0221 5' HA F | 146 | AGCAGCTCTCCAATCAGTGT |
| KO_PAS_chr1-3_0221 5' HA R | 147 | CTCACTTAATCTTCTGTACTCTGAAGCTGGAATTGTGATCCCGCTG |
| KO_PAS_chr1-3_0221 3 HA F | 148 | AGAAGTTGATTGAGACTTTCAACGAGTTTTGAAGCAAGCCTACCCC |
| KO_PAS_chr1-3_0221 3' HA R | 149 | CAGGATCCAGCCGCTAAAAC |
| KO_PAS_FragD_0022 5' HA F | 150 | TGAACAAGCAGCCACATCAC |
| KO_PAS_FragD_0022 5' HA R | 151 | CTCACTTAATCTTCTGTACTCTGAAGTGAGGGCCATTCTGACATACT |
| KO_PAS_FragD_0022 3' HA F | 152 | AGAAGTTGATTGAGACTTTCAACGAGGTGAGGTATTTAACTGCACGAG |
| KO_PAS_FragD_0022 3' HA R | 153 | TCGCCTACATAGTCTGCACA |
| KO_PAS_chr2-1_0159 5' HA F | 154 | ACCTCATGCCATGTCTGTCA |
| KO_PAS_chr2-1_0159 5' HA R | 155 | CTCACTTAATCTTCTGTACTCTGAAGTTGACTGCCGCTTCAAAGTC |
| KO_PAS_chr2-1_0159 3' HA F | 156 | AGAAGTTGATTGAGACTTTCAACGAGCCGCCAGAGAATTTGTGCTT |
| KO_PAS_chr2-1_0159 3' HA R | 157 | TAGAGGTGAACGTTTGGCCT |
| KO_PAS_chr2-1_0326 5' HA F | 158 | AATCCATCACCTCCACCCAG |
| KO_PAS_chr2-1_0326 5' HA R | 159 | CTCACTTAATCTTCTGTACTCTGAAGGCTGCTGGAGTAAAAGGTCC |
| KO_PAS_chr2-1_0326 3' HA F | 160 | AGAAGTTGATTGAGACTTTCAACGAGCAAGCAGCAACCATCTACGG |
| KO_PAS_chr2-1_0326 3' HA R | 161 | AACCTCATCCACTGTCAGCA |
| KO_PAS_chr2-2_0056 5' HA F | 162 | GGAAGACAAAGTTCGCTCCG |

TABLE 7-continued

Forward (F) and Reverse (R) Primers for 5' and 3' homology arms (HA) targeting protease ORF

| Description | SEQ ID NO: | 5' to 3' Sequence |
|---|---|---|
| KO_PAS_chr2-2_0056 5' HA R | 163 | CTCACTTAATCTTCTGTACTCTGAAGTCATAGTTGAGAGCCTCCTTGT |
| KO_PAS_chr2-2_0056 3' HA F | 164 | AGAAGTTGATTGAGACTTTCAACGAGACAATGCACTAGGACGGGAT |
| KO_PAS_chr2-2_0056 3' HA R | 165 | CTTGAATCAGGCGACGTACC |
| KO_PAS_chr1-4 0611 5' HA F | 166 | CCCAGCTCTCTTTCACTCCA |
| KO_PAS_chr1-4 0611 5' HA R | 167 | CTCACTTAATCTTCTGTACTCTGAAGTTGAAGAGCAGCAGAGTCGA |
| KO_PAS_chr1-4 0611 3' HA F | 168 | AGAAGTTGATTGAGACTTTCAACGAGTTAATTGCCCACAGTGTCGC |
| KO_PAS_chr1-4 0611 3' HA R | 169 | ACCTTCCACAGTCGACGAAT |
| KO_PAS_chr1-1_0274 5' HA F | 170 | ACAAACAGTCAAATGCACGGA |
| KO_PAS_chr1-1_0274 5' HA R | 171 | CTCACTTAATCTTCTGTACTCTGAAGTCCTTCCACCTTTCCAACGT |
| KO_PAS_chr1-1_0274 3' HA F | 172 | AGAAGTTGATTGAGACTTTCAACGAGGGGGTAGAGAAGTTAGGGAGG |
| KO_PAS_chr1-1_0274 3' HA R | 173 | GGAACTACAACTGGAGGCCT |
| KO_PAS_chr4_0834 5' HA F | 174 | TAGTGCCGGTTCCATGGATT |
| KO_PAS_chr4_0834 5 HA R | 175 | CTCACTTAATCTTCTGTACTCTGAAGGGTCTATGGGTTGATGCGGA |
| KO_PAS_chr4_0834 3' HA F | 176 | AGAAGTTGATTGAGACTTTCAACGAGATGTGTTGCTCGCTCTAGGT |
| KO_PAS_chr4_0834 3' HA R | 177 | CGACAAACACACCAAGGTCC |
| KO_PAS_chr3_0896 5' HA F | 178 | GTTGTTGGAGTGAGCGATGG |
| KO_PAS_chr3_0896 5' HA R | 179 | CTCACTTAATCTTCTGTACTCTGAAGCCTCCGTTGATACTCCCGAT |
| KO_PAS_chr3_0896 3' HA F | 180 | AGAAGTTGATTGAGACTTTCAACGAGTGCATTCAAGGCTGGCAAAT |
| KO_PAS_chr3_0896 3' HA R | 181 | GCATATGGAGTGGTGTGCAG |
| KO_PAS_chr3_0561 5' HA F | 182 | CGGGTAGCATTGAACGTACG |
| KO_PAS_chr3_0561 5' HA R | 183 | CTCACTTAATCTTCTGTACTCTGAAGATGCTACGGTAAACACCCCA |
| KO_PAS_chr3_0561 3' HA F | 184 | AGAAGTTGATTGAGACTTTCAACGAGACTGGAGAAAGCTTGGTCGA |
| KO_PAS_chr3_0561 3' HA R | 185 | AGGCACCAGAAGAAAGAGCT |
| KO_PAS_chr3_0633 5' HA F | 186 | GGACACGTTTGGAGCTTCTT |
| KO_PAS_chr3_0633 5' HA R | 187 | CTCACTTAATCTTCTGTACTCTGAAGGCCCACCAATTCAGCAACTT |
| KO_PAS_chr3_0633 3' HA F | 188 | AGAAGTTGATTGAGACTTTCAACGAGGATGCTGGTCACATGGTTCC |
| KO_PAS_chr3_0633 3' HA R | 189 | AACCGCCAATAGTTTCAGCC |
| KO_PAS_chr4_0013 5' HA F | 190 | GGATGAGAAAGCGGCTTCTG |
| KO_PAS_chr4_0013 5' HA R | 191 | CTCACTTAATCTTCTGTACTCTGAAGGTGCCAAAAGTCTGATCCGG |
| KO_PAS_chr4_0013 3' HA F | 192 | AGAAGTTGATTGAGACTTTCAACGAGTGCCACTTCGTTCTTTGACG |
| KO_PAS_chr4_0013 3' HA R | 193 | ACGGATCAGTGATGGCGTAT |
| KO_PAS_chr1-1_0379 5' HA F | 194 | ATGGGATCTGGACGACGTTT |
| KO_PAS_chr1-1_0379 5' HA R | 195 | CTCACTTAATCTTCTGTACTCTGAAGAGCTGGATCACAAACATTCGG |
| KO_PAS_chr1-1_0379 3' HA F | 196 | AGAAGTTGATTGAGACTTTCAACGAGCTTTGAGTGTTGGTCCCTGC |
| KO_PAS_chr1-1_0379 3' HA R | 197 | CGGCTACCAAGTCAGACCTT |
| KO_PAS_chr2-1_0172 5' HA F | 198 | GTTGCCCATTACGTCCTGTG |
| KO_PAS_chr2-1_0172 5' HA R | 199 | CTCACTTAATCTTCTGTACTCTGAAGCCTTTGATCTTTGGTGCATCTTG |

TABLE 7-continued

Forward (F) and Reverse (R) Primers for 5' and 3' homology arms (HA) targeting protease ORF

| Description | SEQ ID NO: | 5' to 3' Sequence |
|---|---|---|
| KO_PAS_chr2-1_0172 3' HA F | 200 | AGAAGTTGATTGAGACTTTCAACGAGCACTACAGCTGGGAACGAGA |
| KO_PAS_chr2-1_0172 3' HA R | 201 | ACGGGTTGGAAAAGTTGAGC |
| KO_PAS_chr3_0866 5 HA F | 202 | AGTGGGGTTGGAGATTGGAG |
| KO_PAS_chr3_0866 5' HA R | 203 | CTCACTTAATCTTCTGTACTCTGAAGACGATTCCAGCATAGCCTGT |
| KO_PAS_chr3_0866 3' HA F | 204 | AGAAGTTGATTGAGACTTTCAACGAGCTGGTAGCCGCAAAACTTCA |
| KO_PAS_chr3_0866 3' HA R | 205 | GCGTTGAATCCTCCTCGTTC |
| KO_PAS_chr3_0299 5' HA F | 206 | CTGTGGGGTCTGAACATCCT |
| KO_PAS_chr3_0299 5' HA R | 207 | CTCACTTAATCTTCTGTACTCTGAAGAGCTGCTAGGGTTCATTGAGT |
| KO_PAS_chr3_0299 3' HA F | 208 | AGAAGTTGATTGAGACTTTCAACGAGCTCCCTTGGGTACGTCAACT |
| KO_PAS_chr3_0299 3' HA R | 209 | TGGCAGTCTTCACATGTCCT |
| KO_PAS_chr1-4_0251 5' HA F | 210 | AGCTGGTCAAGTCTGGTACC |
| KO_PAS_chr1-4_0251 5' HA R | 211 | CTCACTTAATCTTCTGTACTCTGAAGGAGGTCTAGTGTGTGAGGCT |
| KO_PAS_chr1-4_0251 3' HA F | 212 | AGAAGTTGATTGAGACTTTCAACGAGAGAAGGTATAGGGAATATGCGGT |
| KO_PAS_chr1-4_0251 3' HA R | 213 | TAGCCACAACCCTGATGACG |
| KO_PAS_chr4_0874 5' HA F | 214 | TACACTGGGACGCAGATGTT |
| KO_PAS_chr4_0874 5' HA R | 215 | CTCACTTAATCTTCTGTACTCTGAAGTGCTCAAACTCTGTATCCGTTG |
| KO_PAS_chr4_0874 3' HA F | 216 | AGAAGTTGATTGAGACTTTCAACGAGCTTTCAAGGCCGCAATGCTA |
| KO_PAS_chr4_0874 3' HA R | 217 | CTTCCTTTGCAGTTGGTGGT |
| KO_PAS_chr3_0513 5' HA F | 218 | GGGTCTTTGGCTTTGGTGAG |
| KO_PAS_chr3_0513 5' HA R | 219 | CTCACTTAATCTTCTGTACTCTGAAGCGTCTCTGGAACTCGTCGAT |
| KO_PAS_chr3_0513 3' HA F | 220 | AGAAGTTGATTGAGACTTTCAACGAGCCCCAAGTCAAGGAGGAGTT |
| KO_PAS_chr3_0513 3' HA R | 221 | GAGTCCAATCACGGCCAATC |
| KO_PAS_chr1-1_0127 5' HA F | 222 | TGCTTCTTCGGACAGATCGT |
| KO_PAS_chr1-1_0127 5' HA R | 223 | CTCACTTAATCTTCTGTACTCTGAAGTACTGATTGAAGGGTCGGCA |
| KO_PAS_chr1-1_0127 3' HA F | 224 | AGAAGTTGATTGAGACTTTCAACGAGTTGTACGGACCAGGAAGCAT |
| KO_PAS_chr1-1_0127 3' HA R | 225 | TTCCTCTGCCTCTTCCTTGG |
| KO_PAS_chr4_0686 5' HA F | 226 | AGCATGCAAACACGAGGTAC |
| KO_PAS_chr4_0686 5' HA R | 227 | CTCACTTAATCTTCTGTACTCTGAAGAGAGGAAAACGAGCTTGGGT |
| KO_PAS_chr4_0686 3' HA F | 228 | AGAAGTTGATTGAGACTTTCAACGAGATCAAGGTTGCCAGCGAATG |
| KO_PAS_chr4_0686 3 HA R | 229 | ACCCTACAGAACCGCAATGA |
| KO_PAS_chr2-2_0159 5' HA F | 230 | ACAGCCCAAATAGAGACGCA |
| KO_PAS_chr2-2_0159 5' HA R | 231 | CTCACTTAATCTTCTGTACTCTGAAGAGGAGCCCAGTTTTACGTCA |
| KO_PAS_chr2-2_0159 3' HA F | 232 | AGAAGTTGATTGAGACTTTCAACGAGTATCCCGCGGTGAAGACTAC |
| KO_PAS_chr2-2_0159 3' HA R | 233 | GTGTTGCTAAGCCTGTGGAC |
| KO_PAS_chr3_0388 5' HA F | 234 | TCCTCCTTTCGACGCTTCTT |
| KO_PAS_chr3_0388 5' HA R | 235 | CTCACTTAATCTTCTGTACTCTGAAGACAGCTGTGAATCATGAAGTTTT |
| KO_PAS_chr3_0388 3' HA F | 236 | AGAAGTTGATTGAGACTTTCAACGAGATTCTCACTGGCAGAACGGA |

TABLE 7-continued

Forward (F) and Reverse (R) Primers for 5' and 3' homology arms (HA) targeting protease ORF

| Description | SEQ ID NO: | 5' to 3' Sequence |
|---|---|---|
| KO_PAS_chr3_0388 3' HA R | 237 | TTTTCACGTTGAGGCCACTG |
| KO_PAS_chr3_0419 5' HA F | 238 | AGCTCCGCAGTAACAGGAAT |
| KO_PAS_chr3_0419 5' HA R | 239 | CTCACTTAATCTTCTGTACTCTGAAGTCAAAGCAACTTATGGCGGT |
| KO_PAS_chr3_0419 3' HA F | 240 | AGAAGTTGATTGAGACTTTCAACGAGCTCTTCGCAGCACCAGAAAG |
| KO_PAS_chr3_0419 3' HA R | 241 | TCGTTGTTGCTGGTGTTCTG |
| KO_PAS_chr1-3_0258 5' HA F | 242 | AGTTTGAAGGCACGTTGGTC |
| KO_PAS_chr1-3_0258 5' HA R | 243 | CTCACTTAATCTTCTGTACTCTGAAGACTCCAACAGGACTTTGAGGT |
| KO_PAS_chr1-3_0258 3' HA F | 244 | AGAAGTTGATTGAGACTTTCAACGAGAAATGTGGAAGTTGCAGCGG |
| KO_PAS_chr1-3_0258 3' HA R | 245 | AGGTTGATCGCCGTCTTGTA |
| KO_PAS_chr4_0913 5' HA F | 246 | TCTTCATGAGGTGGTAGGCG |
| KO_PAS_chr4_0913 5' HA R | 247 | CTCACTTAATCTTCTGTACTCTGAAGAGAGGGCAGATGACATACCG |
| KO_PAS_chr4_0913 3' HA F | 248 | AGAAGTTGATTGAGACTTTCAACGAGGAGAAACTGGAGGTGCTCGT |
| KO_PAS_chr4_0913 3' HA R | 249 | CAAGGCATTCAGTTGACCGT |
| KO_PAS_chr1-1_0066 5' HA F | 250 | ACCAACGAGCCTTACAGACA |
| KO_PAS_chr1-1_0066 5' HA R | 251 | CTCACTTAATCTTCTGTACTCTGAAGTTTTGACCGTCAGTGCATGG |
| KO_PAS_chr1-1_0066 3' HA F | 252 | AGAAGTTGATTGAGACTTTCAACGAGGTCGGAGGTGTGAGAATTGA |
| KO_PAS_chr1-1_0066 3' HA R | 253 | TGGGAACTATGTGGCTCCTC |
| KO_PAS_chr2-2_0310 5' HA F | 254 | CGAGCTATCAGTACTCCCGG |
| KO_PAS_chr2-2_0310 5' HA R | 255 | CTCACTTAATCTTCTGTACTCTGAAGGGTTCTCAGCTGTCCGAGAT |
| KO_PAS_chr2-2_0310 3 HA F | 256 | AGAAGTTGATTGAGACTTTCAACGAGTAGCATTGCCCATCACAACG |
| KO_PAS_chr2-2_0310 3' HA R | 257 | GTGGGAAGACTATTGATGCGA |
| KO_PAS_chr1-3_0261 5' HA F | 258 | GGGAAATCGCTGAGGTGTAC |
| KO_PAS_chr1-3_0261 5' HA R | 259 | CTCACTTAATCTTCTGTACTCTGAAGAGGTCATCTGGAAGCTTTGC |
| KO_PAS_chr1-3_0261 3' HA F | 260 | AGAAGTTGATTGAGACTTTCAACGAGGGTGGCCAATGGTATTACTTTGA |
| KO_PAS_chr1-3_0261 3' HA R | 261 | ATAAGAGCCCCGATACAGGC |
| KO_PAS_chr2-1_0546 5' HA F | 262 | CTTGACACACTTTGCTCCTGA |
| KO_PAS_chr2-1_0546 5' HA R | 263 | CTCACTTAATCTTCTGTACTCTGAAGAGTAGCTGACCTGTTGTGCC |
| KO_PAS_chr2-1_0546 3' HA F | 264 | AGAAGTTGATTGAGACTTTCAACGAGGGACACCATATGATGCCCGA |
| KO_PAS_chr2-1_0546 3' HA R | 265 | CAGATCAAGTCCAAGTCCGC |
| KO_PAS_chr2-2_0398 5' HA F | 266 | AGAGACTTTGCGAGAGTCCC |
| KO_PAS_chr2-2_0398 5' HA R | 267 | CTCACTTAATCTTCTGTACTCTGAAGTGCAATATCCAAACACGCCA |
| KO_PAS_chr2-2_0398 3' HA F | 268 | AGAAGTTGATTGAGACTTTCAACGAGACTTCTGGAATCTTCGGGCA |
| KO_PAS_chr2-2_0398 3' HA R | 269 | GGATGTTTGGGCCATTGTGA |
| KO_PAS_chr4_0835 5' HA F | 270 | CAATCTCTCGCTTCATCACG |
| KO_PAS_chr4_0835 5' HA R | 271 | CTCACTTAATCTTCTGTACTCTGAAGTCGCTGTTAACCATAATTCTTTG |
| KO_PAS_chr4_0835 3' HA F | 272 | AGAAGTTGATTGAGACTTTCAACGAGGCGAGGGTTGAGGAGATTTT |
| KO_PAS_chr4_0835 3' HA R | 273 | GGCCATGGCACTATTTTGTT |

TABLE 7-continued

Forward (F) and Reverse (R) Primers for 5' and 3' homology arms (HA) targeting protease ORF

| Description | SEQ ID NO: | 5' to 3' Sequence |
|---|---|---|
| KO_PAS_chr1-1_0491 5' HA F | 274 | ACGTACTTCCCGCCCAATAA |
| KO_PAS_chr1-1_0491 5' HA R | 275 | CTCACTTAATCTTCTGTACTCTGAAGCCCACCTAAATTTCGAGTGCA |
| KO_PAS_chr1-1_0491 3' HA F | 276 | AGAAGTTGATTGAGACTTTCAACGAGACACTTTCGCAGCTTTTGGT |
| KO_PAS_chr1-1_0491 3' HA R | 277 | TCCTCCTTGCCATGAAGAGG |
| KO_PAS_chr2-1_0447 5' HA F | 278 | GCCTGATGAAGATGATGCCG |
| KO_PAS_chr2-1_0447 5' HA R | 279 | CTCACTTAATCTTCTGTACTCTGAAGAGGCTCAGTCACCTCTATGA |
| KO_PAS_chr2-1_0447 3' HA F | 280 | AGAAGTTGATTGAGACTTTCAACGAGTGATCAAGAACACCGTCGAAG |
| KO_PAS_chr2-1_0447 3' HA R | 281 | TCCCTTTGTTGGTCGTACGA |
| KO_PAS_chr1-3_0053 5' HA F | 282 | TGGTTCAACTTGTAGCGCAT |
| KO_PAS_chr1-3_0053 5 HA R | 283 | CTCACTTAATCTTCTGTACTCTGAAGGGGCTTGCTCAACTTTTGGA |
| KO_PAS_chr1-3_0053 3' HA F | 284 | AGAAGTTGATTGAGACTTTCAACGAGCGACAATCTGGTAGCGCATC |
| KO_PAS_chr1-3_0053 3' HA R | 285 | ATGCTCGTACAAAGACCCCA |
| KO_PAS_chr3_0200 5' HA F | 286 | TGAGATCTCCAAGTGCAGCA |
| KO_PAS_chr3_0200 5' HA R | 287 | CTCACTTAATCTTCTGTACTCTGAAGGACGGTCGATTTGGCTCATC |
| KO_PAS_chr3_0200 3' HA F | 288 | AGAAGTTGATTGAGACTTTCAACGAGTGAAGAAGCTCAACACTCTGAAC |
| KO_PAS_chr3_0200 3' HA R | 289 | TGATTGACGGCACCCTGTAT |
| KO_PAS_chr1-3_0105 5' HA F | 290 | CAATAATTCAGCTGCGCCCT |
| KO_PAS_chr1-3_0105 5' HA R | 291 | CTCACTTAATCTTCTGTACTCTGAAGCCTCTGTAGCTGCTTGTCCT |
| KO_PAS_chr1-3_0105 3' HA F | 292 | AGAAGTTGATTGAGACTTTCAACGAGAGGAGTCAGTCGGTCCAAAG |
| KO_PAS_chr1-3_0105 3' HA R | 293 | TGTGGGCTGGGATGTGTAAT |
| KO_PAS_chr3_0635 5' HA F | 294 | AGCACGGTCAAGTAAATCGC |
| KO_PAS_chr3_0635 5' HA R | 295 | CTCACTTAATCTTCTGTACTCTGAAGTGCTATCACTGATTTGCCCA |
| KO_PAS_chr3_0635 3' HA F | 296 | AGAAGTTGATTGAGACTTTCAACGAGGGAGATTCCCGGCAAGTATC |
| KO_PAS_chr3_0635 3' HA R | 297 | GGCTTTCTGACTACCTGGGT |
| KO_PAS_chr4_0503 5' HA F | 298 | AAAGGGAAGAAGGGTGCAGT |
| KO_PAS_chr4_0503 5' HA R | 299 | CTCACTTAATCTTCTGTACTCTGAAGAAGGTCGACTCGGGAAACAT |
| KO_PAS_chr4_0503 3' HA F | 300 | AGAAGTTGATTGAGACTTTCAACGAGTGGTATCCCGACTGCTTTGT |
| KO_PAS_chr4_0503 3' HA R | 301 | TGGAATGGCTCGAGAATGGT |
| KO_PAS_chr2-1_0569 5' HA F | 302 | ACCAACAGGCTGAACACTAGA |
| KO_PAS_chr2-1_0569 5' HA R | 303 | CTCACTTAATCTTCTGTACTCTGAAGTCGTCAGCAGAGAAGGTACA |
| KO_PAS_chr2-1_0569 3' HA F | 304 | AGAAGTTGATTGAGACTTTCAACGAGACGGACTCCCTAACGAACAA |
| KO_PAS_chr2-1_0569 3' HA R | 305 | TCTGATGGTTGGCTTTGCTT |
| KO_PAS_chr3_1223 5' HA F | 306 | CGGTTTGTGGCCCATCTATG |
| KO_PAS_chr3_1223 5' HA R | 307 | CTCACTTAATCTTCTGTACTCTGAAGAAAACCGACGCTTGAACTCC |
| KO_PAS_chr3_1223 3' HA F | 308 | AGAAGTTGATTGAGACTTTCAACGAGAAGTCTTGACCGGAAGCAAC |
| KO_PAS_chr3_1223 3' HA R | 309 | GGGCCTTAACAAACACCACA |
| KO_PAS_chr2-1_0597 5 HA F | 310 | TAGAGGCGGAAAGGAACGAG |

TABLE 7-continued

Forward (F) and Reverse (R) Primers for 5' and 3' homology arms (HA) targeting protease ORF

| Description | SEQ ID NO: | 5' to 3' Sequence |
|---|---|---|
| KO_PAS_chr2-1_0597 5' HA R | 311 | CTCACTTAATCTTCTGTACTCTGAAGTTGCCAAGGGTGTACAAAGC |
| KO_PAS_chr2-1_0597 3' HA F | 312 | AGAAGTTGATTGAGACTTTCAACGAGACCAAGTTGTTCGACGAAGA |
| KO_PAS_chr2-1_0597 3' HA R | 313 | CAACACATACCAGGCGAAGG |
| KO_PAS_chr1-1_0327 5' HA F | 314 | CCCTCCTCCGCCATCATTAT |
| KO_PAS_chr1-1_0327 5' HA R | 315 | CTCACTTAATCTTCTGTACTCTGAAGTAGGAGACAACCAAGCCAGC |
| KO_PAS_chr1-1_0327 3' HA F | 316 | AGAAGTTGATTGAGACTTTCAACGAGGGAGTAGAAAATGGTGCGTCC |
| KO_PAS_chr1-1_0327 3' HA R | 317 | AATGGCTCCAAATCACAGGC |
| KO_PAS_chr2-2_0380 5' HA F | 318 | GCTTTGAGGAATGCGTGAAGA |
| KO_PAS_chr2-2_0380 5' HA R | 319 | CTCACTTAATCTTCTGTACTCTGAAGGTAGTGAGAGTGGCGCCTTA |
| KO_PAS_chr2-2_0380 3' HA F | 320 | AGAAGTTGATTGAGACTTTCAACGAGTGGGTACAACGTGACTCTAGG |
| KO_PAS_chr2-2_0380 3' HA R | 321 | ACACTCTTAAGGCTCGTCGT |
| KO_PAS_chr3_0928 5' HA F | 322 | CTCCTCCACTTCAGTATCCGT |
| KO_PAS_chr3_0928 5' HA R | 323 | CTCACTTAATCTTCTGTACTCTGAAGTTCCTTGAATTTCCGCCACC |
| KO_PAS_chr3_0928 3' HA F | 324 | AGAAGTTGATTGAGACTTTCAACGAGGAGCAGGCAAGGTTGGATTC |
| KO_PAS_chr3_0928 3' HA R | 325 | CTGGGCAGCAAATAACGGTT |
| PAS_chr1-3_0184 5' HA F | 326 | CCAAAGTTGGCTCCGAGTAG |
| PAS_chr1-3_0184 5' HA R | 327 | CTCACTTAATCTTCTGTACTCTGAAGCCTAACGGTATCGGCTTTGA |
| PAS_chr1-3_0184 3' HA F | 328 | AGAAGTTGATTGAGACTTTCAACGAGGGCAAAATCCTTTTCCATGA |
| PAS_chr1-3_0184 3' HA R | 329 | GAAGAAGGCCAAGTGTGATA |
| KO_PAS_chr1-4_0289 5' HA F | 330 | GACGAGACGCTGTTCCTTTC |
| KO_PAS_chr1-4_0289 5' HA R | 331 | CTCACTTAATCTTCTGTACTCTGAAGTGTGAAGAGAGGCCACCATT |
| KO_PAS_chr1-4_0289 3' HA F | 332 | AGAAGTTGATTGAGACTTTCAACGAGTGATCGACTACTTGGCCTCC |
| KO_PAS_chr1-4_0289 3' HA R | 333 | AACAACATTCAAGCTGCCGT |

TABLE 8

Forward and reverse primers for amplifying modified sequences

| Description | SEQ ID NO: | Sequence (5' to 3') |
|---|---|---|
| KO_PAS_chr3_1087 Verification F | 334 | ATCGGCAAAGATGAAGCGAC |
| KO_PAS_chr3_1087 Verification R | 335 | GCTGGACACTTCTGAGCTCA |
| KO_PAS_chr4_0584 Verification F | 336 | ACTTGTCAGGACGATACGGA |
| KO_PAS_chr4_0584 Verification R | 337 | CCGGTCTCCCTGGAAATAGA |
| KO_PAS_chr3_0076 Verification F | 338 | GCGAGGTCCTTGTCAATGAG |
| KO_PAS_chr3_0076 Verification R | 339 | ACAAGAACTCGGGCTCCTTT |
| KO_PAS_chr3_0691 Verification F | 340 | TTGCAGCGCTCCATAATGTC |
| KO_PAS_chr3_0691 Verification R | 341 | GCTGATTCTGAGAACGCTGG |
| KO_PAS_chr3_0303 Verification F | 342 | GCCATTCTTCGGTGCAGTAG |

TABLE 8-continued

Forward and reverse primers for amplifying modified sequences

| Description | SEQ ID NO: | Sequence (5' to 3') |
|---|---|---|
| KO_PAS_chr3_0303 Verification R | 343 | TAGAGTTGTCCCAAACGGCA |
| KO_PAS_chr3_0815 Verification F | 344 | CGTGGTTCTCGAGGCTCTAT |
| KO_PAS_chr3_0815 Verification R | 345 | GGAGTTGGAACGTCGTAGGA |
| KO_PAS_chr3_1157 Verification F | 346 | AGTTGTCCGTCATTAGCCCT |
| KO_PAS_chr3_1157 Verification R | 347 | TGTTCCCTTTCGGCTAGACA |
| KO_PAS_chr1-4_0164 Verification F | 348 | ACGGTTGAGGGCATTACGTA |
| KO_PAS_chr1-4_0164 Verification R | 349 | TTGTCTTCCACCCCTTCGTT |
| KO_PAS_chr3_0979 Verification F | 350 | GGTTGGCCTTGGACATTGTT |
| KO_PAS_chr3_0979 Verification R | 351 | TGCTCTTCGGTACTCATGCT |
| KO_PAS_chr3_0803 Verification F | 352 | TTTGGCCATGCTGAGCTTTT |
| KO_PAS_chr3_0803 Verification R | 353 | AAGCCCGATCACTTGCATTT |
| KO_PAS_chr3_0394 Verification F | 354 | CACCTAATGTTTGGCACCCC |
| KO_PAS_chr3_0394 Verification R | 355 | ATCCCAGACTGACATCGCAA |
| KO_PAS_chr2-1_0366 Verification F | 356 | CCGCCAGAAATTCATGCCAT |
| KO_PAS_chr2-1_0366 Verification R | 357 | TCGTTTCACTGTACCATGCA |
| KO_PAS_chr3_0842 Verification F | 358 | ACCAGTCCGCATTTTCACTG |
| KO_PAS_chr3_0842 Verification R | 359 | GTGGACAGCTGCAATCGTAG |
| KO_PAS_chr1-3_0195 Verification F | 360 | CAACTGGGAAGCCTGCATTT |
| KO_PAS_chr1-3_0195 Verification R | 361 | CCTTGCATATCCGTTTGCCA |
| KO_PAS_chr1-4_0052 Verification F | 362 | GGAGGTTCAGGAGCAGGAAT |
| KO_PAS_chr1-4_0052 Verification R | 363 | CGGTTTCATCTGTTGCCTCC |
| KO_PAS_chr2-2_0057 Verification F | 364 | GTCGCCCATGTTCTTTCGAT |
| KO_PAS_chr2-2_0057 Verification R | 365 | CAAACAGGCTGGAAACCACA |
| KO_PAS_chr1-3_0150 Verification F | 366 | AATCTCCACGTTCAGTTGCG |
| KO_PAS_chr1-3_0150 Verification R | 367 | TCATCCCTTGAAAACCCCGA |
| KO_PAS_chr1-3_0221 Verification F | 368 | TTGTGGAGGGAGATTCAGGC |
| KO_PAS_chr1-3_0221 Verification R | 369 | AAGGTAAGGAACGTGCTTGC |
| KO_PAS_FragD_0022 Verification F | 370 | GTTCTACTGTTCACGTGCTCT |
| KO_PAS_FragD_0022 Verification R | 371 | ACCGGTTAGAATACATGCTGC |
| KO_PAS_chr2-1_0159 Verification F | 372 | CGAAAAGAAGCTGGACTCCG |
| KO_PAS_chr2-1_0159 Verification R | 373 | TTCCATCGTACGACCAGTGT |
| KO_PAS_chr2-1_0326 Verification F | 374 | AGCGATGAGGCCAACAGTAT |
| KO_PAS_chr2-1_0326 Verification R | 375 | TGTCCAGCCCAAAAGACTGA |
| KO_PAS_chr2-2_0056 Verification F | 376 | CTCCTGGGGCTCGTACTAAG |
| KO_PAS_chr2-2_0056 Verification R | 377 | CCTCAATAACGACGGCCTTG |
| KO_PAS_chr1-4_0611 Verification F | 378 | CCTTTTCCTGATCAGTGGGG |
| KO_PAS_chr1-4_0611 Verification R | 379 | TGTTGGGGAATGAAACACGA |
| KO_PAS_chr1-1_0274 Verification F | 380 | GAAGGACGAGTAGGGTTGCT |

TABLE 8-continued

Forward and reverse primers for amplifying modified sequences

| Description | SEQ ID NO: | Sequence (5' to 3') |
|---|---|---|
| KO_PAS_chr1-1_0274 Verification R | 381 | TCCTGATCTGGCTCGTTTGT |
| KO_PAS_chr4_0834 Verification F | 382 | ACCTCCAACTCCTGAAAGCA |
| KO_PAS_chr4_0834 Verification R | 383 | CCTCGAGTCTGGGCTTTACA |
| KO_PAS_chr3_0896 Verification F | 384 | GGAGAGATGCCAGACCAAGT |
| KO_PAS_chr3_0896 Verification R | 385 | AGCCTGTTCTACTGCATACGT |
| KO_PAS_chr3_0561 Verification F | 386 | CCATTTCTTGTACCCTGGGC |
| KO_PAS_chr3_0561 Verification R | 387 | GCAGAAAAGGCGCGAATTTC |
| KO_PAS_chr3_0633 Verification F | 388 | GGGAAAGGATGTGGACCAAC |
| KO_PAS_chr3_0633 Verification R | 389 | TGGCCAAGAGTGTCCAATTG |
| KO_PAS_chr4_0013 Verification F | 390 | TAACAGATGGCGCACGTAGA |
| KO_PAS_chr4_0013 Verification R | 391 | CCTTGCGTTCCCAGGTAAAG |
| KO_PAS_chr1-1_0379 Verification F | 392 | TGTGGTATGGTTTGGGGCTA |
| KO_PAS_chr1-1_0379 Verification R | 393 | ACTCCCGTTCCTCCATGTTC |
| KO_PAS_chr2-1_0172 Verification F | 394 | ACGGTACAAAAGGCGTTTCA |
| KO_PAS_chr2-1_0172 Verification R | 395 | AGTCAAACTCGGTGGTAGGT |
| KO_PAS_chr3_0866 Verification F | 396 | CGGTTATCATGTGCCTGCTC |
| KO_PAS_chr3_0866 Verification R | 397 | ATGTTGCTGCTCCGAAATCC |
| KO_PAS_chr3_0299 Verification F | 398 | GATCTGCTGGCCTTGAGAGT |
| KO_PAS_chr3_0299 Verification R | 399 | CTATGTCCTGGTGTTTGCCG |
| KO_PAS_chr1-4 0251 Verification F | 400 | GCCAATGATGATCTCGCAGG |
| KO_PAS_chr1-4 0251 Verification R | 401 | GCCTTTGATATGCCGTCGTT |
| KO_PAS_chr4_0874 Verification F | 402 | TCGAGTAATGCTTCCCACCA |
| KO_PAS_chr4_0874 Verification R | 403 | AGCTTTCACAACAGCGATCG |
| KO_PAS_chr3_0513 Verification F | 404 | TGATTGCTTCTGGGTTGCTG |
| KO_PAS_chr3_0513 Verification R | 405 | CAAAACCGGCGTAAAATGGC |
| KO_PAS_chr1-1_0127 Verification F | 406 | TTGTGCTGCATCTGTGTGAG |
| KO_PAS_chr1-1_0127 Verification R | 407 | AGCCTACAAGTGGTTACAGGT |
| KO_PAS_chr4_0686 Verification F | 408 | GGAAACCGACCAGCCTAAAG |
| KO_PAS_chr4_0686 Verification R | 409 | AGTCGCACCAGGTTATCACA |
| KO_PAS_chr2-2_0159 Verification F | 410 | GGAAAGCTGCCCAGAAACTC |
| KO_PAS_chr2-2_0159 Verification R | 411 | TGAGAGGATTCGTTGTGGCT |
| KO_PAS_chr3_0388 Verification F | 412 | CTATGTCGAAGTAGCGGTGC |
| KO_PAS_chr3_0388 Verification R | 413 | AGAGTGGCACTGCTATCGAA |
| KO_PAS_chr3_0419 Verification F | 414 | CGTACAAACTTGGCAGCTGT |
| KO_PAS_chr3_0419 Verification R | 415 | GCTGTGTTGTAAATTCCGGC |
| KO_PAS_chr1-3_0258 Verification F | 416 | ACAACCCGGAAGACAACTCT |
| KO_PAS_chr1-3_0258 Verification R | 417 | TGTCGTTGCCTTCCCGATAT |
| KO_PAS_chr4_0913 Verification F | 418 | GAAGATGGGAGAGGGTGCTT |

TABLE 8-continued

Forward and reverse primers for amplifying modified sequences

| Description | SEQ ID NO: | Sequence (5' to 3') |
|---|---|---|
| KO_PAS_chr4_0913 Verification R | 419 | CTTGTTGACGACGGTAGCAG |
| KO_PAS_chr1-1_0066 Verification F | 420 | CCCTAGTCTCGTTCGAAGGG |
| KO_PAS_chr1-1_0066 Verification R | 421 | GGCACAGCAGGTTTTCGTAT |
| KO_PAS_chr2-2_0310 Verification F | 422 | GGAGATTCTGATGCTACCCCA |
| KO_PAS_chr2-2_0310 Verification R | 423 | TGGAGCCATCAGATCAGGAC |
| KO_PAS_chr1-3_0261 Verification F | 424 | CCTGTTCTTGCAAGCCTTCA |
| KO_PAS_chr1-3_0261 Verification R | 425 | TAAGACATGCGACCACCAGA |
| KO_PAS_chr2-1_0546 Verification F | 426 | CATGGCCAATGTCGAACTGT |
| KO_PAS_chr2-1_0546 Verification R | 427 | AGCTGGCTGAAAAGGTGTTG |
| KO_PAS_chr2-2_0398 Verification F | 428 | CTCAGTGTTGGAAAGCACCC |
| KO_PAS_chr2-2_0398 Verification R | 429 | TAGGGAATCTTTGGTGGCGT |
| KO_PAS_chr4_0835 Verification F | 430 | GGAACCTAGAGCGAGCAACA |
| KO_PAS_chr4_0835 Verification R | 431 | CAGGCTCTATTGTCGACGTG |
| KO_PAS_chr1-1_0491 Verification F | 432 | GGAGGTGATGACAATGCCAC |
| KO_PAS_chr1-1_0491 Verification R | 433 | CTGTGAAGCTCCTCCTACGT |
| KO_PAS_chr2-1_0447 Verification F | 434 | GGACACTGCTGGACAAGAGA |
| KO_PAS_chr2-1_0447 Verification R | 435 | TACTGACGCCGAAGAGCTAG |
| KO_PAS_chr1-3_0053 Verification F | 436 | CCGATCGCAAAATAGTGGCA |
| KO_PAS_chr1-3_0053 Verification R | 437 | GTTGTGGTTGTATGCGGTCA |
| KO_PAS_chr3_0200 Verification F | 438 | CAATAACTCCACTGGTGCCG |
| KO_PAS_chr3_0200 Verification R | 439 | TCGTTATACTCCAGCGTGCT |
| KO_PAS_chr1-3_0105 Verification F | 440 | GGGCTCAAAATCTGGAACCA |
| KO_PAS_chr1-3_0105 Verification R | 441 | CAATGCAGTACTCACCGGTG |
| KO_PAS_chr3_0635 Verification F | 442 | AAGCTGACGACCCCTTAGAC |
| KO_PAS_chr3_0635 Verification R | 443 | CTATCGTGTCTGGGCTGCTA |
| KO_PAS_chr4_0503 Verification F | 444 | AAGGAGATTGCCGCAACTCT |
| KO_PAS_chr4_0503 Verification R | 445 | GTGGAGTCAGAGTCGAGAGG |
| KO_PAS_chr2-1_0569 Verification F | 446 | CCCAGCTTTTATACGGCTTGG |
| KO_PAS_chr2-1_0569 Verification R | 447 | CAGCAAAAGCTCGTGATCCA |
| KO_PAS_chr3_1223 Verification F | 448 | TGCGGGTAGTCGATTGATGT |
| KO_PAS_chr3_1223 Verification R | 449 | TCACGTATCTCAGCAACAGGA |
| KO_PAS_chr2-1_0597 Verification F | 450 | GGACCTAGGAAATACGCCCA |
| KO_PAS_chr2-1_0597 Verification R | 451 | ACTCCAGTTCCACAAGTCCA |
| KO_PAS_chr1-1_0327 Verification F | 452 | ACTGCCAACCGTTTACTCCA |
| KO_PAS_chr1-1_0327 Verification R | 453 | GCGCGGAAGATTAAAGTCGT |
| KO_PAS_chr2-2_0380 Verification F | 454 | TTGGACTCGATCGATGAGGG |
| KO_PAS_chr2-2_0380 Verification R | 455 | TGATGACTTCCAAGATGCGC |
| KO_PAS_chr3_0928 Verification F | 456 | TCACCTGGAGCAACTGATGT |

TABLE 8-continued

| Forward and reverse primers for amplifying modified sequences | | |
|---|---|---|
| Description | SEQ ID NO: | Sequence (5' to 3') |
| KO_PAS_chr3_0928 Verification R | 457 | GTTTGGTACGCTTGTAGGCC |
| PAS_chr1-3_0184 Verification F | 458 | GATGAGCAAGCATCCATTCA |
| PAS_chr1-3_0184 Verification R | 459 | AAAGACAGGAGCGTGAGCAT |
| KO_PAS_chr1-4 0289 Verification F | 460 | CTCAACTTCGCTTGCCCTTT |
| KO_PAS_chr1-4 0289 Verification R | 461 | TGGGAAACAGAACGATGAACT |

TABLE 9

| 18B Vector | | |
|---|---|---|
| Description | SEQ ID NO: | 5' to 3' Sequence |
| 18B silk-like polypeptide encoding sequence | 462 | ggtggttacg gtccaggcgc tggtcaacaa ggtccaggaa gtggtggtca acaaggacct 60<br>ggcggtcaag gaccctacgg tagtggccaa caaggtccag gtggagcagg acagcagggt 120<br>ccgggaggcc aaggacctta cggaccaggt gctgctgctg ccgccgctgc cgctgccgga 180<br>ggttacggtc caggagccgg acaacagggt ccaggtggag ctggacaaca aggtccagga 240<br>tcacaaggtc ctggtggaca aggtccatac ggtcctggtg ctggtcaaca gggaccaggt 300<br>agtcaaggac ctggttcagg tggtcagcag ggtccaggag gacagggtcc ttacggccct 360<br>tctgccgctg cagcagcagc cgctgccgca ggaggatacg gacctggtgc tggacaacga 420<br>tctcaaggac caggaggaca aggtccttat ggacctggcg ctggccaaca aggacctggt 480<br>tctcagggtc caggttcagg aggccaacaa ggcccaggag gtcaaggacc atacggacca 540<br>tccgctgcgg cagctgcagc tgctgcaggt ggatatggcc caggagccgg acaacagggt 600<br>cctggttcac aaggtccagg atctggtggt caacagggac caggcggcca gggaccttat 660<br>ggtccaggag ccgctgcagc agcagcagct gttggaggtt acggccctgg tgccggtcaa 720<br>caaggcccag gatctcaggg tcctggatct ggaggacaac aaggtcctgg aggtcagggt 780<br>ccatacggac cttcagcagc agctgctgct gcagccgctg gtggttatgg acctggtgct 840<br>ggtcaacaag gaccgggttc tcagggtccg ggttcaggag gtcagcaggg ccctggtgga 900<br>caaggacctt atggacctag tgcggctgca gcagctgccg ccgcaggtgg ttacggtcca 960<br>ggcgctggtc aacaaggtcc aggaagtggt ggtcaacaag gacctggcgg tcaaggaccc 1020<br>tacggtagtg gccaacaagg tccaggtgga gcaggacagc agggtccggg aggccaagga 1080<br>ccttacggac caggtgctgc tgctgccgcc gctgccgctg ccggaggtta cggtccagga 1140<br>gccggacaac agggtccagg tggagctgga caacaaggtc caggatcaca aggtcctggt 1200<br>ggacaaggtc catacggtcc tggtgctggt caacagggac caggtagtca aggacctggt 1260<br>tcaggtggtc agcagggtcc aggaggacag ggtccttacg gcccttctgc cgctgcagca 1320<br>gcagccgctg ccgcaggagg atacggacct ggtgctggac aacgatctca aggaccagga 1380<br>ggacaaggtc cttatggacc tggcgctggc caacaaggac ctggttctca gggtccaggt 1440<br>tcaggaggcc aacaaggccc aggaggtcaa ggaccatacg gaccatccgc tgcggcagct 1500<br>gcagctgctg caggtggata tggcccagga gccggacaac agggtcctgg ttcacaaggt 1560<br>ccaggatctg gtggtcaaca gggaccaggc ggccagggac cttatggtcc aggagccgct 1620<br>gcagcagcag cagctgttgg aggttacggc cctggtgccg gtcaacaagg cccaggatct 1680<br>cagggtcctg gatctggagg acaacaaggt cctggaggtc agggtccata cggaccttca 1740<br>gcagcagctg ctgctgcagc cgctggtggt tatggacctg gtgctggtca acaaggaccg 1800<br>ggttctcagg gtccgggttc aggaggtcag cagggccctg gtggacaagg accttatgga 1860<br>cctagtgcgg ctgcagcagc tgccgccgca ggtggttacg gtccaggcgc tggtcaacaa 1920<br>ggtccaggaa gtggtggtca acaaggacct ggcggtcaag gaccctacgg tagtggccaa 1980<br>caaggtccag gtggagcagg acagcagggt ccgggaggcc aaggacctta cggaccaggt 2040<br>gctgctgctg ccgccgctgc cgctgccgga ggttacggtc caggagccgg acaacagggt 2100<br>ccaggtggag ctggacaaca aggtccagga tcacaaggtc ctggtggaca aggtccatac 2160<br>ggtcctggtg ctggtcaaca gggaccaggt agtcaaggac ctggttcagg tggtcagcag 2220<br>ggtccaggag gacagggtcc ttacggccct tctgccgctg cagcagcagc cgctgccgca 2280<br>ggaggatacg gacctggtgc tggacaacga tctcaaggac caggaggaca aggtccttat 2340<br>ggacctggcg ctggccaaca aggacctggt tctcagggtc caggttcagg aggccaacaa 2400<br>ggcccaggag gtcaaggacc atacggacca tccgctgcgg cagctgcagc tgctgcaggt 2460<br>ggatatggcc caggagccgg acaacagggt cctggttcac aaggtccagg atctggtggt 2520<br>caacagggac caggcggcca gggaccttat ggtccaggag ccgctgcagc agcagcagct 2580<br>gttggaggtt acggccctgg tgccggtcaa caaggcccag gatctcaggg tcctggatct 2640<br>ggaggacaac aaggtcctgg aggtcagggt ccatacggac cttcagcagc agctgctgct 2700<br>gcagccgctg gtggttatgg acctggtgct ggtcaacaag gaccgggttc tcagggtccg 2760<br>ggttcaggag gtcagcaggg ccctggtgga caaggacctt atggacctag tgcggctgca 2820<br>gcagctgccg ccgca 2835 |
| 18B polypeptide sequence | 463 | GGYGPGAGQQGPGSGGQQGPGGQGPYGSGQQGPGGAGQQGPGGQGPYGPGAAAAAAAAAGGYGPGAGQQG<br>PGGAGQQGPGSQGPGGQGPYGPGAGQQGPGSQGPGSGGQQGPGGQGPYGPSAAAAAAAAAGGYGPGAGQR<br>SQGPGGQGPYGPGAGQQGPGSQGPGSGGQQGPGGQGPYGPSAAAAAAAAGGYGPGAGQQGPGSQGPGSGG<br>QQGPGGQGPYGPGAAAAAAAVGGYGPGAGQQGPGSQGPGSGGQQGPGGQGPYGPSAAAAAAAAGGYGPGA<br>GQQGPGSQGPGSGGQQGPGGQGPYGPSAAAAAAAAGGYGPGAGQQGPGSGGQQGPGGQGPYGSGQQGPGG<br>AGQQGPGGQGPYGPGAAAAAAAAAGGYGPGAGQQGPGGAGQQGPGSQGPGGQGPYGPGAGQQGPGSQGPG<br>SGGQQGPGGQGPYGPSAAAAAAAAAGGYGPGAGQRSQGPGGQGPYGPGAGQQGPGSQGPGSGGQQGPGGQ |

TABLE 9-continued

18B Vector

| Description | SEQ ID NO: | 5' to 3' Sequence |
|---|---|---|
| | | GPYGPSAAAAAAAAGGYGPGAGQQGPGSQGPGSGGQQGPGGQGPYGPGAAAAAAAVGGYGPGAGQQGPGS<br>QGPGSGGQQGPGGQGPYGPSAAAAAAAAGGYGPGAGQQGPGSQGPGSGGQQGPGGQGPYGPSAAAAAAAA<br>GGYGPGAGQQGPGSGGQQGPGGQGPYGSGQQGPGGAGQQGPGGQGPYGPGAAAAAAAAAGGYGPGAGQQG<br>PGGAGQQGPGSQGPGGQGPYGPGAGQQGPGSQGPGSGGQQGPGGQGPYGPSAAAAAAAAAGGYGPGAGQR<br>SQGPGGQGPYGPGAGQQGPGSQGPGSGGQQGPGGQGPYGPSAAAAAAAAGGYGPGAGQQGPGSQGPGSGG<br>QQGPGGQGPYGPGAAAAAAAVGGYGPGAGQQGPGSQGPGSGGQQGPGGQGPYGPSAAAAAAAAGGYGPGA<br>GQQGPGSQGPGSGGQQGPGGQGPYGPSAAAAAAAA |
| Repeat sequence of a silk-like polypeptide | 464 | GGYGPGAGQQGPGSGGQQGPGGQGPYGSGQQGPGGAGQQGPGGQGPYGPGAAAAAAAAAGGYGPGAGQQG<br>GYGPGAGQQGPGGAGQQGPGSQGPGGQGPYGPGAGQQGPGSQGPGSGGQQGPGGQGPYGPSAAAAAAAAA<br>GGYGPGAGQRSQGPGGQGPYGPGAGQQGPGSQGPGSGGQQGPGGQGPYGPSAAAAAAAAGGYGPGAGQQG<br>PGSQGPGSGGQQGPGGQGPYGPGAAAAAAAVGGYGPGAGQQGPGSQGPGSGGQQGPGGQGPYGPSAAAAA<br>AAAGGYGPGAGQQGPGSQGPGSGGQQGPGGQGPYGPSAAAAAAAA |

TABLE 10

Zeocin Cassette with HA arms for KU70 deletion in *P. pastoris*

| Description | SEQ ID NO: | 5' to 3' Sequence |
|---|---|---|
| Plasmid sequence | 465 | ggagttgaatcacatcttactggatagcgagctttttgacgaagtgaaaatttctaattttaaacaagaggaaggggtca<br>aaaacggagatatcttatacttggaaaaagagatgacaatcagtgatttcatcaattttgtatctagttggccttctgtg<br>ttttcgtggaagcagcaacgaggaaaggagggtatcctagatgatttttacaacgaactgaacgactgctttgagggggg<br>taacatgaaagtaatatggaactccgtcctagtatttgccaggaggaagcaaagggttgtataggctttagtacttatag<br>aggaaacggggttacgtgcaagcgcgcatgcctgagctttgagggggggggactttcacatctcttcttctcacacttagc<br>cctaacacagagaataataaaaagcattgcaagatgagtgttgtcagcaagcaatacgacatccacgaaggcattatctt<br>tgtaattgaattgaccccggagcttcacgcgccggcttcagaagggaaatctcagctccagatcatcttagagaatgtca<br>gtgaggttatttctgagctaatcattaccttgcccggtacaggaatagggtgttaccttattaattacgacggtggtcaa<br>aacgacgaaatttaccccattttttgagttacaagacctgaatttggaaatgatgaaacaattgtaccaagtcttggagga<br>ccatgtaagtgggcttaatcctctcgagaagcaattcccaattgaacacagtaaaccgttatcagccactctgttctttc<br>acttaaggtctctttttttacatggcgaagactcataagcgtactggaagacattacaacttgaaaaagattttcttgttc<br>actaataacgataaaccttacaatggaaactctcagctgagagttcccttgaagaaaaccctggctgattacaatgacgt<br>agacattactttgattccgtttcttctgaacaagccttcaggtgtcaagtttgacaagacggaatactcagaaattttgt<br>tctatgataaagatgcttgttcgatgtcaattgaggagatccgccaacgaatttctagacataaggagatcaagcgggtt<br>tacttcacctgtcctttgaaaatcgcaaataacttgtgcatttctgtgaaaggttattctatgttttatcatgaaactcc<br>aaggaagatcaaatttgtcgtcaatgagggttcaactttcaaagatgtggagacaaaatctcagtttgtcgatccaacat<br>ccggaaaagagttttccagtgaacagctgatcaaagcatatcctctaggtgccgatgcttacattcctttaaactcagag<br>caagtcaaaacaataaatcgatttaatgatatcatcaatatcccctctttggaaattctaggtttcagggatatatctaa<br>ttggttgccacagtatcagtttggcaaagcatcgtttttatcccctaataactatggtgattttacacattcgcagagaa<br>catttagttgtcttcagtaatgtcttgtttcttttgttgcagtggtgagccattttgacttcgtgaaagtttctttagaa<br>tagttgtttccagaggccaaacattccacccgtagtaaagtgcaagcgtaggaagaccaagactggcataaatcaggtat<br>aagtgtcgagcactggcaggtgatcttctgaaagtttctactagcagataagatccagtagtcatgcatatggcaacaat<br>gtaccgtgtggatctaagaacgcgtcctactaaccttcgcattcgttggtccagtttgttgttatcgatcaacgtgacaa<br>ggttgtcgattccgcgtaagcatgcatacccaaggacgcctgttgcaattccaagtgagccagttccaacaatctttgta<br>atattagagcacttcattgtgttgcgcttgaaagtaaaatgcgaacaaattaagagataatctcgaaaccgcgacttcaa<br>acgccaatatgatgtgcggcacacaataagcgttcatatccgctgggtgactttctcgctttaaaaaattatccgaaaaa<br>atttttgacggctagctcagtcctaggtacgctagcattaaagaggagaaaatggctaaactgacctctgctgttccggt<br>tctgaccgctcgtgacgttgctggtgctgttgagttctggaccgaccgtctgggtttctctcgtgacttcgttgaagacg<br>acttcgctggtgttgttcgtgacgacgttaccctgttcatctctgctgttcaggaccaggttgttccggacaacaccctg<br>gcttgggtttgggttcgtggtctggacgaactgtacgctgaatggtctgaagttgtttctaccaacttccgtgacgcttc<br>tggtccggctatgaccgaaatcggtgaacagccgtggggtcgtgagttcgctctgcgtgacccggctggtaactgcgttc<br>acttcgttgctgaagaacaggactaacacgtccgacggcggcccacgggtcccaggcctcggagatccgtcccccttttc<br>ctttgtcgatatcatgtaattagttatgtcacgcttacattcacgccctccccccacatccgctctaaccgaaaaggaag<br>gagttagacaacctgaagtctaggtccctatttatttttttatagttatgttagtattaagaacgttatttatatttcaa<br>atttttcttttttttctgtacagacgcgtgtacgcatgtaacattatactgaaaaccttgcttgagaaggttttgggacg<br>ctcgaaggctttaatttgcaagctgtattagtttcacttttcagcaacctggtcggaaagatccacatcaagaatggata<br>ccaaccccaagagtatgaaaatccttccctacaatggcacttcaaaatgttacgtgacgattaccttcaattggaacacg<br>atatcgacatcagtgaccccccttgagaaacaaaagtacataaacagcctcgatgagacaaaaaccaagatcatgaaacta<br>cgggactatgtcaaggaaactgccgatgatgacgacccttcacggcttgccaacactctcaaagagctcaaccaagagct<br>gaacaaaatttccaactttgatatcatcgccaataagaagccaaagacccccacgacagtagaccctgttcctactgatg<br>atgacatcatcaacgcctggaaggcaggaactctgaacggtttcaaggtggatcaattacgaaaatacgtaaggtcacga<br>aacaactttctggagacggcctccaaaaaggcagatctcatcgccaacattgacaagtactttcagcagaagttcaaaga<br>gactaaggcctgattcgtgttccttactttttcctcgcaacgtgtttttttcccaccacattgcctatgttgtaatgcaa<br>tgcagatgctggcccagtttttgacgattctcgaaaattggcattttcgtcgatgccattggccaaactgaaaattcaag<br>acaaaatagattggattttatctgcaacgtcttccacctacacaaccactctacaaacttcagacaaacatgtttataaa<br>agcagctactagatccaaaatgacaagttcgttattctctactacgtttgttgtggcatttggattggtggctagcaaca<br>acctcttgccatgtcctgttgaccactctatgaataacgagactccgcaagaattgaaaccattgcaggctgaatcttct<br>actagaaagttgaactcttccgcttaagtcaaataaaactactgacacagatgatgcacagaaacaacggatcacgctct<br>tgactgattagtcccgtcattttggttctcattttcttcacagtcacctatcaatgtatgatcacctggaaggatttccc<br>tacgatacttcaaatcttttacttgataatattactcattatggctcaggaatgcagactgcctgattcaagacgctgct |

TABLE 10-continued

Zeocin Cassette with HA arms for KU70 deletion in *P. pastoris*

| Description | SEQ ID NO: | 5' to 3' Sequence |
|---|---|---|
| | | cttcttatttaacacttgtacactaaccccatggaagccagggaagggaataaccatctctctggtaataaatcggtctttatttatgcatagaaaaggaatctattatatttcgttcatttggcactctgctaactgtagattaacgggtctcgtaaattcaaaatcttcttccgatcaaaccggggtgaaatattacttctcgtgcatagctaattttcaaataaccgtcctaaaatgaacggtcatttacctggactctcttgccaaatgggcaacaaaacataaagctgatcagaacgtaactagtctctcggaatccat |
| HA F | 466 | ggagttgaatcacatcttactg |
| KU70 HA 1 | 467 | gacaactaaatgttctctgcgaatgtgtaaaatcaccatagttattaggggataaaaacgatgctttgccaaactgatactgtggcaaccaattagatatatccctgaaacctagaatttccaaagaggggatattgatgatatcattaaatcgatttattgttttgacttgctctgagtttaaaggaatgtaagcatcggcacctagaggatatgctttgatcagctgttcactggaaaactcttttccggatgttggatcgacaaactgagattttgtctccacatctttgaaagttgaaccctcattgacgacaaatttgatcttccttggagtttcatgataaaacatagaataacctttcacagaaatgcacaagttatttgcgattttcaaaggacaggtgaagtaaacccgcttgatctccttatgtctagaaattcgttggcggatctcctcaattgacatcgaacaagcatctttatcatagaacaaaatttctgagtattccgtcttgtcaaacttgacacctgaaggcttgttcagaagaaacggaatcaaagtaatgtctacgtcattgtaatcagccagggttttcttcaagggaactctcagctgagagtttccattgtaaggtttatcgttattagtgaacaagaaaatctttttcaagttgtaatgtcttccagtacgcttatgagtcttcgccatgtaaaaaagagaccttaagtgaaagaacagagtggctgataacggtttactgtgttcaattgggaattgcttctcgagaggattaagcccacttacatggtcctccaagacttggtacaattgtttcatcatttccaaattcaggtcttgtaactcaaaaatggggtaaatttcgtcgttttgaccaccgtcgtaattaataaggtaacaccctattcctgtaccgggcaaggtaatgattagctcagaaataacctcactgacattctctaagatgatctggagctgagatttcccttctgaagccggcgcgtgaagctccggggtcaattcaattacaaagataatgccttcgtggatgtcgtattgcttgctgacaacactcat |
| KU70 HA 2 | 468 | tcaggccttagtctctttgaacttctgctgaaagtacttgtcaatgttggcgatgagatctgcctttttggaggccgtctccagaaagttgtttcgtgaccttacgtattttcgtaattgatccaccttgaaaccgttcagagttcctgccttccaggcgttgatgatgtcatcatcagtaggaacagggtctactgtcgtgggggtctttggcttcttattggcgatgatatcaaagttggaaattttgttcagctcttggttgagctctttgagagtgttggcaagccgtgaagggtcgtcatcatcggcagtttccttgacatagtcccgtagtttcatgatcttggtttttgtctcatcgaggctgtttatgtacttttgtttctcaaggggtcactgatgtcgatatcgtgttccaattgaaggtaatcgtcacgtaacatttgaagtgccattgtagggaaggattttcatactcttggggttggtatccattcttgatgtggatctttccgaccaggttgctgaaaagtgaaactaatac |
| pILV5 | 469 | ttcagtaatgtcttgtttcttttgttgcagtggtgagccatttgacttcgtgaaagtttctttagaatagttgtttccagaggccaaacattccacccgtagtaaagtgcaagcgtaggaagaccaagactggcataaatcaggtataagtgtcgagcactggcaggtgatcttctgaaagtttctactagcagataagatccagtagtcatgcatatggcaacaatgtaccgtgtggatctaagaacgcgtcctactaaccttcgcattcgttggtccagtttgttgttatcgatcaacgtgacaaggttgtcgattccgcgtaagcatgcatacccaaggacgcctgttgcaattccaagtgagccagttccaacaatctttgtaatattagagcacttcattgtgttgcgcttgaaagtaaaatgcgaacaaattaagagataatctcgaaaccgcgacttcaaacgccaatatgatgtgcggcacacaataagcgttcatatccgctgggtgactttctcgctttaaaaaattatccgaaaaaattt |
| RM2734; testR | 470 | cagaggccaaacattccacc |
| pproRBS | 471 | ttaaagaggagaaa |
| Sh ble (codon optimized) | 472 | atggctaaactgacctctgctgttccggttctgaccgctcgtgacgttgctggtgctgttgagttctggaccgaccgtctgggtttctctcgtgacttcgttgaagacgacttcgctggtgttgttcgtgacgacgttaccctgttcatctctgctgttcaggaccaggttgttccggacaacaccctggcttgggtttgggttcgtggtctggacgaactgtacgctgaatggtctgaagttgtttctaccaacttccgtgacgcttctggtccggctatgaccgaaatcggtgaacagccgtggggtcgtgagttcgctctgcgtgacccggctggtaactgcgttcacttcgttgctgaagaacaggactaa |
| CYC1 terminator | 473 | cacgtccgacggcggcccacgggtcccaggcctcggagatccgtcccccttttcctttgtcgatatcatgtaattagttatgtcacgcttacattcacgccctccccccacatccgctctaaccgaaaaggaaggagttagacaacctgaagtctaggtccctatttatttttttatagttatgttagtattaagaacgttatttatatttcaaatttttcttttttttctgtacagacgcgtgtacgcatgtaacattatactgaaaaccttgcttgagaaggttttgggacgctcgaaggctttaatttgcaagct |
| Rm3386; F test oligo | 474 | aggagttagacaacctgaag |
| HA R | 475 | gtaactagtctctcggaatccat |

TABLE 11

Nourseothricin Cassette for protease deletion in *P. pastoris*

| Description | SEQ ID NO: | 5' to 3' Sequence |
|---|---|---|
| Plasmid sequence | 476 | cttcagagtacagaagattaagtgagagaattctaccgttcgtatagcatacattatacgaagttatttcagtaatgtcttgtttcttttgttgcagtggtgagccatttgacttcgtgaaagtttctttagaatagttgtttccagaggccaaacattccacccgtagtaaagtgcaagcgtaggaagaccaagactggcataaatcaggtataagtgtcgagcactggcaggtgatc |

TABLE 11-continued

Nourseothricin Cassette for protease deletion in *P. pastoris*

| Description | SEQ ID NO: | 5' to 3' Sequence |
|---|---|---|
| | | ttctgaaagtttctactagcagataagatccagtagtcatgcatatggcaacaatgtaccgtgtggatctaagaacgcgt cctactaaccttcgcattcgttggtccagtttgttgttatcgatcaacgtgacaaggttgtcgattccgcgtaagcatgc atacccaaggacgcctgttgcaattccaagtgagccagttccaacaatctttgtaatattagagcacttcattgtgttgc gcttgaaagtaaaatgcgaacaaattaagagataatctcgaaaccgcgacttcaaacgccaatatgatgtgcggcacaca ataagcgttcatatccgctgggtgactttctcgctttaaaaaattatccgaaaaaattttttgacggctagctcagtccta ggtacgctagcattaaagaggagaaaatgactactcttgatgacacagcctacagatataggacatcagttccgggtgac gcagaggctatcgaagccttggacggttcattcactactgatacggtgtttagagtcaccgctacaggtgatggcttcac cttgagagaggttcctgtagacccacccttaacgaaagttttccctgatgacgaatcggatgacgagtctgatgctggtg aggacggtgaccctgattccagaacatttgtcgcatacggagatgatggtgacctggctggctttgttgtggtgtcctac agcggatggaatcgtagactcacagttgaggacatcgaagttgcacctgaacatcgtggtcacggtgttggtcgtgcact gatgggactggcaacagagtttgctagagaaagaggagccggacatttgtggttagaagtgaccaatgtcaacgctcctg ctattcacgcatataggcgaatgggtttcactttgtgcggtcttgatactgctttgtatgacggaactgcttctgatggt gaacaagctctttacatgagtatgccatgtccatagcacgtccgacggcggcccacgggtcccaggcctcggagatccgt ccccctttcctttgtcgatatcatgtaattagttatgtcacgcttacattcacgccctccccccacatccgctctaacc gaaaaggaaggagttagacaacctgaagtctaggtccctatttatttttttatagttatgttagtattaagaacgttatt tatatttcaaatttttctttttttctgtacagacgcgtgtacgcatgtaacattatactgaaaccttgcttgagaagg ttttgggacgctcgaaggctttaatttgcaagctataacttcgtatagcatacattataccttgttatgcggccgcaaga agttgattgagactttcaacgag |
| AOX1 pA | 477 | cttcagagtacagaagattaagtgaga |
| terminator Lox71 F | 478 | taccgttcgtatagcatacattatacgaagttat |
| pILV5 | 479 | ttcagtaatgtcttgtttcttttgttgcagtggtgagccattttgacttcgtgaaagtttctttagaatagttgtttcca gaggccaaacattccacccgtagtaaagtgcaagcgtaggaagaccaagactggcataaatcaggtataagtgtcgagca ctggcaggtgatcttctgaaagtttctactagcagataagatccagtagtcatgcatatggcaacaatgtaccgtgtgga tctaagaacgcgtcctactaaccttcgcattcgttggtccagtttgttgttatcgatcaacgtgacaaggttgtcgattc cgcgtaagcatgcatacccaaggacgcctgttgcaattccaagtgagccagttccaacaatctttgtaatattagagcac ttcattgtgttgcgcttgaaagtaaaatgcgaacaaattaagagataatctcgaaaccgcgacttcaaacgccaatatga tgtgcggcacacaataagcgttcatatccgctgggtgactttctcgctttaaaaaattatccgaaaaaattt |
| pproRBS | 480 | ttaaagaggagaaa |
| nat (Nourseo-thricin resistance) | 481 | atgactactcttgatgacacagcctacagatataggacatcagttccgggtgacgcagaggctatcgaagccttggacgg ttcattcactactgatacggtgtttagagtcaccgctacaggtgatggcttcaccttgagagaggttcctgtagacccac ccttaacgaaagttttccctgatgacgaatcggatgacgagtctgatgctggtgaggacggtgaccctgattccagaaca tttgtcgcatacggagatgatggtgacctggctggctttgttgtggtgtcctacagcggatggaatcgtagactcacagt tgaggacatcgaagttgcacctgaacatcgtggtcacggtgttggtcgtgcactgatgggactggcaacagagtttgcta gagaaagaggagccggacatttgtggttagaagtgaccaatgtcaacgctcctgctattcacgcatataggcgaatgggt ttcactttgtgcggtcttgatactgctttgtatgacggaactgcttctgatggtgaacaagctctttacatgagtatgcc atgtccatag |
| CYC1 terminator | 482 | cacgtccgacggcggcccacgggtcccaggcctcggagatccgtccccctttcctttgtcgatatcatgtaattagtta tgtcacgcttacattcacgccctccccccacatccgctctaaccgaaaaggaaggagttagacaacctgaagtctaggtc cctatttatttttttatagttatgttagtattaagaacgttatttatatttcaaatttttctttttttctgtacagacg cgtgtacgcatgtaacattatactgaaaccttgcttgagaaggttttgggacgctcgaaggctttaatttgcaagct |
| LoxKR3 F | 483 | ataacttcgtatagcatacattataccttgttat |
| HSP82 | 484 | gcggccgcaagaagttgattgagactttcaacgag |

TABLE 12

Exemplary nourseothricin cassettes with HA arms for protease deletion in *P. pastoris*

| Description | SEQ ID NO: | 5' to 3' Sequence |
|---|---|---|
| Nourseothricin cassette with homology arms targeting PAS_chr4_0584 | 485 | tactacaggctggctgttcctcgcatggtgtttaatgtcctgactgggttttcgtttatcggtattaccggag ccaccttgactgtaagggaacgatactggactaagagagtaatgcgaaaggcaacagcgtttctggcgaacct aatcaatgacggttacgagtttactactcctaaagccagtcttattttgctagagcgagtcaacgcttactta aagggccagggacctaattatgacatcgattttgacgagcaggaggcgttcattaaagaaatggaggagttga ggacctctggtggatatgagaacagatactcatattcaggaaccgatgaaacacccagagatccgggttgcct gtttcttcccattgctttaaataaatggcactttgatgtgctagactgcctgaggatatacggtactcaggaa gatctggaatctaaattattaagtgttcagcaattggtgttacaatgttgcatgaagcacagtggcatgactc cagacatggtctttgcaacggaagtagctcagaagccgaccttcgaagacgacatagtttgtgatgatattga cgcttatgcccagggggtgattgtctagattattgttacacgccaagcaattactccagaactttagaaatt catggcaagattgctaccttacaacgagagctggggctatgctataatattctcggaattttggaccgtttttt ccgattaaggtttttagctccattgcgccaacccccgctctccagactccttcgttatccagcattcagcatg |

TABLE 12-continued

Exemplary nourseothricin cassettes with HA arms for protease deletion in *P. pastoris*

| Description | SEQ ID NO: | 5' to 3' Sequence |
|---|---|---|
| | | gacaggttcaaaaaataaaatttcttgatatgggtccacttcaaacatgcgcctacctgtaggaaaaaaaaag agaacataaatatgccgcgaacagaaaacgtaatgtactgttctatatataaactgttcagatcaatcataaa ttctcagtttcaaactttccgctcagccagattttattcgtaaagaacgcatcattggctctatgttgaagga tcagttcttgttatgggttgctttgatagcgagcgtaccggtttccggcgtgatggcagctcctagcgagtcc gggcataacacggttgaaaaacgagatgccaaaaacgttgttggcgttcaacagttggacttcttcagagtac agaagattaagtgagagaattctaccgttcgtatagcatacattatacgaagttatttcagtaatgtcttgtt tcttttgttgcagtggtgagccattttgacttcgtgaaagtttctttagaatagttgtttccagaggccaaac attccacccgtagtaaagtgcaagcgtaggaagaccaagactggcataaatcaggtataagtgtcgagcactg gcaggtgatcttctgaaagtttctactagcagataagatccagtagtcatgcatatggcaacaatgtaccgtg tggatctaagaacgcgtcctactaaccttcgcattcgttggtccagtttgttgttatcgatcaacgtgacaag gttgtcgattccgcgtaagcatgcatacccaaggacgcctgttgcaattccaagtgagccagttccaacaatc tttgtaatattagagcacttcattgtgttgcgcttgaaagtaaaatgcgaacaaattaagagataatctcgaa accgcgacttcaaacgccaatatgatgtgcggcacacaataagcgttcatatccgctgggtgactttctcgct ttaaaaaattatccgaaaaaatttttgacggctagctcagtcctaggtacgctagcattaaagaggagaaaat gactactcttgatgacacagcctacagatataggacatcagttccgggtgacgcagaggctatcgaagccttg gacggttcattcactactgatacggtgtttagagtcaccgctacaggtgatggcttcaccttgagagaggttc ctgtagacccacccttaacgaaagttttccctgatgacgaatcggatgacgagtctgatgctggtgaggacgg tgaccctgattccagaacatttgtcgcatacggagatgatggtgacctggctggctttgttgtggtgtcctac agcggatggaatcgtagactcacagttgaggacatcgaagttgcacctgaacatcgtggtcacggtgttggtc gtgcactgatgggactggcaacagagtttgctagagaaagaggagccggacatttgtggttagaagtgaccaa tgtcaacgctcctgctattcacgcatataggcgaatgggtttcactttgtgcggtcttgatactgctttgtat gacggaactgcttctgatggtgaacaagctctttacatgagtatgccatgtccatagcacgtccgacggcggc ccacgggtcccaggcctcggagatccgtcccccttttcctttgtcgatatcatgtaattagttatgtcacgct tacattcacgccctcccccacatccgctctaaccgaaaaggaaggagttagacaacctgaagtctaggtccc tatttatttttttatagttatgttagtattaagaacgttatttatatttcaaatttttcttttttttctgtac agacgcgtgtacgcatgtaacattatactgaaaaccttgcttgagaaggttttgggacgctcgaaggctttaa tttgcaagctataacttcgtatagcatacattatacgaagttatgcggccgcaagaagttgattgagactttc aacgagggtccccttcagctacctttctctctgtttggtagttattctcggcgtgtgtatagtatagtataaa agggcctacattggataggcttcaacattcctcaataaacaaacatccaacatcgcgcattccgcatttcgca tttcacatttcgcgcctgccttcctttaggttctttgaatcatcatcaatcgtcgccgtctacatcagagcag gacttatctttgccttccccaaaaattgccactccgtcaaatagattcttttgaatccttgactatttttgcc taaataggtttttgttagtttttcttcaaagcccaaaagaaactctatttagattcatccagaaacaatcttt ttctcaccccatttcgaagtgccgtggagcacagacataaaaagatgactaccgttcaacctacagggccaga caggctcaccctgccgcatattctactggaattcaacgatggctcctcgcagcatgcagtgatcgagctaagc atgaacgaggggattaatatatccacccatgagtggaatccatccactaatgagcaatcgccacgggaagaga gagcaccaccccaacaatccaatccatcgcatcatccagaatcatcgaacatagctactcaaagtcccgctca ggaaaccgagactcagcccggcattccaggactagataggcctgcctttgatacctcggcaacggggtcgtca gaacaggttgacccagtacagggaaggatcctggatgatattataggccaatcattaaggacttccgaagaag acgataccgaatcccgccagagaccacgagaccagaagaacattatgatcaccgtgaattacttgtacgcaga cgacacaaattccagaagtgctaatacaaacaaccagacgcccaataacacttctagaacttccgacagtgaa cgtgtgggctccttatcgttgcacgttccggatctaccagataatgccgacgattactatatcgatgtactca ttaaactaaccacaagcattgccctcagcgtcatcacgtccatgatcaagaaacgattagggcttagcaggga |
| PAS_chr4_0584 Homology Arm 1 | 486 | tactacaggctggctgttcctcgcatggtgtttaatgtcctgactgggttttcgtttatcggtattaccggag ccaccttgactgtaagggaacgatactggactaagagagtaatgcgaaaggcaacagcgtttctggcgaacct aatcaatgacggttacgagtttactactcctaaagccagtcttattttgctagagcgagtcaacgcttactta aagggccagggacctaattatgacatcgattttgacgagcaggaggcgttcattaaagaaatggaggagttga ggacctctggtggatatgagaacagatactcatattcaggaaccgatgaaacacccagagatccgggttgcct gtttcttcccattgctttaaataaatggcactttgatgtgctagactgcctgaggatatacggtactcaggaa gatctggaatctaaattattaagtgttcagcaattggtgttacaatgttgcatgaagcacagtggcatgactc cagacatggtctttgcaacggaagtagctcagaagccgaccttcgaagacgacatagtttgtgatgatattga cgcttatgcccagggggggtgattgtctagattattgttacacgccaagcaattactccagaactttagaaatt catggcaagattgctaccttacaacgagagctggggctatgctataatattctcggaattttggaccgttttt ccgattaaggtttttagctccattgcgccaaccccgctctccagactccttcgttatccagcattcagcatg gacaggttcaaaaaataaaatttcttgatatgggtccacttcaaacatgcgcctacctgtaggaaaaaaaaag agaacataaatatgccgcgaacagaaaacgtaatgtactgttctatatataaactgttcagatcaatcataaa ttctcagtttcaaactttccgctcagccagattttattcgtaaagaacgcatcattggctctatgttgaagga tcagttcttgttatgggttgctttgatagcgagcgtaccggtttccggcgtgatggcagctcctagcgagtcc gggcataacacggttgaaaaacgagatgccaaaaacgttgttggcgttcaacagttggactt |
| PAS_chr4_0584 Homology Arm 2 | 487 | ggtccccttcagctacctttctctctgtttggtagttattctcggcgtgtgtatagtatagtataaaagggcc tacattggataggcttcaacattcctcaataaacaaacatccaacatcgcgcattccgcatttcgcatttcac atttcgcgcctgccttcctttaggttctttgaatcatcatcaatcgtcgccgtctacatcagagcaggactta tctttgccttccccaaaaattgccactccgtcaaatagattcttttgaatccttgactatttttgcctaaata ggtttttgttagtttttcttcaaagcccaaaagaaactctatttagattcatccagaaacaatctttttctca ccccatttcgaagtgccgtggagcacagacataaaaagatgactaccgttcaacctacagggccagacaggct caccctgccgcatattctactggaattcaacgatggctcctcgcagcatgcagtgatcgagctaagcatgaac gaggggattaatatatccacccatgagtggaatccatccactaatgagcaatcgccacgggaagagagagcac |

TABLE 12-continued

Exemplary nourseothricin cassettes with HA arms for protease deletion in *P. pastoris*

| Description | SEQ ID NO: | 5' to 3' Sequence |
|---|---|---|
| | | caccccaacaatccaatccatcgcatcatccagaatcatcgaacatagctactcaaagtcccgctcaggaaac<br>cgagactcagcccggcattccaggactagataggcctgcctttgatacctcggcaacggggtcgtcagaacag<br>gttgacccagtacagggaaggatcctggatgatattataggccaatcattaaggacttccgaagaagacgata<br>ccgaatcccgccagagaccacgagaccagaagaacattatgatcaccgtgaattacttgtacgcagacgacac<br>aaattccagaagtgctaatacaaacaaccagacgcccaataacacttctagaacttccgacagtgaacgtgtg<br>ggctccttatcgttgcacgttccggatctaccagataatgccgacgattactatatcgatgtactcattaaac<br>taaccacaagcattgccctcagcgtcatcacgtccatgatcaagaaacgattagggcttagcaggga |
| Nourseothricin cassette with homology arms targeting PAS_chr3_1157 | 488 | gccttctcgtgcaatcagagctgttgaaagagagaagagggcacacggaagctgctgttcaattgtgtgaatt<br>gaccggattacaacctgctggagtgataggagagctggttcgtgacgaggacggctctatgatgcgattagac<br>gactgtgttcagtttggtctccgccacaacgtaaaaattatcaaccttgaccagatcattgaatacatggatt<br>ccaagaacagctagatacgatggataggaatacagagatatcatgattgaggaacgtaagagcttttttcgaaa<br>gtgtgagtttgtggtgagggccaggcggtggggaggtggtggggagcctccttggtcgaatgtagatatagta<br>agcaagacacaagagcgcgcgaagtcttcaacgaggcggcgttgggtcttgtacgcaacgtaatgactacaca<br>gttgagcttgtcgcgaaccggtcgacattttgatcatgcatactatgttgagacaccatctcgtactattgcg<br>gcaaccagctgtaaatttgactaattaaagctgatgaaggatgcagggcgtcgtcaatttttttgattgattgc<br>atttaattgtttgagccattcaaggctgaatgcccggcaccctagacccttcttgtgagtactataaacccgc<br>aggcagggtacccttggccttctgcgagactaccagtcataacgtatatccacaatgtactagtaatagcccc<br>ggaaaactctaatcccacagaacgtctaacgcctcctatgtcatcgatacccattcgcactactgccatggcc<br>ccccttacgtgatcatttcacttactcccgcctaagcttcgcccacatgcctgcgttttgccaagatttactg<br>acgagtttggtttactcatcctctatttataactactagactttcaccattcttcaccaccctcgtgccaatg<br>atcatcaaccacttggtattgacagccctcagcattgcactagcaagtgcgcaactccaatcgcctttcactt<br>cagagtacagaagattaagtgagagaattctaccgttcgtatagcatacattatacgaagttatttcagtaat<br>gtcttgtttcttttgttgcagtggtgagccattttgacttcgtgaaagtttctttagaatagttgtttccaga<br>ggccaaacattccacccgtagtaaagtgcaagcgtaggaagaccaagactggcataaatcaggtataagtgtc<br>gagcactggcaggtgatcttctgaaagtttctactagcagataagatccagtagtcatgcatatggcaacaat<br>gtaccgtgtggatctaagaacgcgtcctactaaccttcgcattcgttggtccagtttgttgttatcgatcaac<br>gtgacaaggttgtcgattccgcgtaagcatgcatacccaaggacgcctgttgcaattccaagtgagccagttc<br>caacaatctttgtaatattagagcacttcattgtgttgcgcttgaaagtaaaatgcgaacaaattaagagata<br>atctcgaaaccgcgacttcaaacgccaatatgatgtgcggcacacaataagcgttcatatccgctgggtgact<br>ttctcgctttaaaaaattatccgaaaaaatttttgacggctagctcagtcctaggtacgctagcattaaagag<br>gagaaaatgactactcttgatgacacagcctacagatataggacatcagttccgggtgacgcagaggctatcg<br>aagccttggacggttcattcactactgatacggtgtttagagtcaccgctacaggtgatggcttcaccttgag<br>agaggttcctgtagacccacccttaacgaaagttttccctgatgacgaatcggatgacgagtctgatgctggt<br>gaggacggtgaccctgattccagaacatttgtcgcatacggagatgatggtgacctggctggctttgttgtgg<br>tgtcctacagcggatggaatcgtagactcacagttgaggacatcgaagttgcacctgaacatcgtggtcacgg<br>tgttggtcgtgcactgatgggactggcaacagagtttgctagagaaagaggagccggacatttgtggttagaa<br>gtgaccaatgtcaacgctcctgctattcacgcatataggcgaatgggtttcactttgtgcggtcttgatactg<br>ctttgtatgacggaactgcttctgatggtgaacaagctctttacatgagtatgccatgtccatagcacgtccg<br>acggcggcccacgggtcccaggcctcggagatccgtcccccttttcctttgtcgatatcatgtaattagttat<br>gtcacgcttacattcacgccctcccccacatccgctctaaccgaaaaggaaggagttagacaacctgaagtc<br>taggtccctatttatttttttatagttatgttagtattaagaacgttatttatatttcaaatttttcttttttt<br>ttctgtacagacgcgtgtacgcatgtaacattatactgaaaaccttgcttgagaaggttttgggacgctcgaa<br>ggctttaatttgcaagctataacttcgtatagcatacattataccttgttatgcggccgcaagaagttgattg<br>agactttcaacgagctggctctgcttctggtacttcttcaggtgcatcttctgctactcaaaatgacgaaaca<br>tccactgatcttggagctccagctgcatctttaagtgcaacgccatgtctttttgccatcttgctgctcatgt<br>tgtagtagactttttttttcactgagtttttatgtactactgattacattgtgtaggtgtaatgatgtgcact<br>ataatactaatatagtcaaaatgctacagaggaaagtgcaggttgcctgtggtggtttttcttattagcaccc<br>tctgaacactctttacctctaacatcctcagccatgctaatcgcgcataaaataaatcttcgaactttttttcc<br>attttatgctcataaagcttccttactgtcaccttatcaaaagagcttttgccactaaagtagtcacacccag<br>aattgctcccgaatatcgtccaacaatgctaggatctgtggaaagtttgacaaataatttgaacaccttgagc<br>ttgaagcttcctgaagttaatatccaaggctcctttccagaaagtaacccagtggaccttttgagaaactaca<br>tcactcaagaacttagtaaaatttctggagttgacaaagaattgattttcccagccttggaatggggtaccac<br>actggaaaaaggtgatcttttgatcccagttcctcgtctgagaataaagggtgctaatcctaaagatttagcc<br>gaacaatgggctgctgcattcccaaagggtggatatcttaaagacgttattgcgcaaggacctttcttgcagt<br>tctttttttaacacatcggttctgtacaagttggtgatatctgatgctctggagagaggcgatgactttggtgc<br>acttcctctaggaaagggacaaaaagttatagtggagttttcttctccaaatattgccaaacctttccacgct<br>ggccatcttagaagtacaatcatcggtggttttatttccaatctgtatgaaaagctgggtcatgaagttatga<br>ggatgaattatttgggagactggggaaaacaatttggtgttcttgcagtaggatttgagcgttacggtgatga<br>ggcaaaattaaagactgatccaatcaaccatttgtttgaggtctatgttaaaatcaaccaagatattaaggct<br>caatcagagtctactgaggagattgcagaagggcaatcattagatgaccaggcaagagcttttttcaagaaaa<br>tggaaaatggcgacgaatcggctgtaagcttgtggaaaagattccgtgagttatccattgagaagtacattga<br>tacttatgcccgcctcaacatc |
| PAS_chr3_1157 Homology Arm 1 | 489 | gccttctcgtgcaatcagagctgttgaaagagagaagagggcacacggaagctgctgttcaattgtgtgaatt<br>gaccggattacaacctgctggagtgataggagagctggttcgtgacgaggacggctctatgatgcgattagac<br>gactgtgttcagtttggtctccgccacaacgtaaaaattatcaaccttgaccagatcattgaatacatggatt<br>ccaagaacagctagatacgatggataggaatacagagatatcatgattgaggaacgtaagagcttttttcgaaa<br>gtgtgagtttgtggtgagggccaggcggtggggaggtggtggggagcctccttggtcgaatgtagatatagta<br>agcaagacacaagagcgcgcgaagtcttcaacgaggcggcgttgggtcttgtacgcaacgtaatgactacaca<br>gttgagcttgtcgcgaaccggtcgacattttgatcatgcatactatgttgagacaccatctcgtactattgcg<br>gcaaccagctgtaaatttgactaattaaagctgatgaaggatgcagggcgtcgtcaatttttttgattgattgc<br>atttaattgtttgagccattcaaggctgaatgcccggcaccctagacccttcttgtgagtactataaacccgc<br>aggcagggtacccttggccttctgcgagactaccagtcataacgtatatccacaatgtactagtaatagcccc |

TABLE 12-continued

| Description | SEQ ID NO: | 5' to 3' Sequence |
|---|---|---|
| Exemplary nourseothricin cassettes with HA arms for protease deletion in *P. pastoris* | | |
| | | ggaaaactctaatcccacagaacgtctaacgcctcctatgtcatcgatacccattcgcactactgccatggcc<br>ccccttacgtgatcatttcacttactcccgcctaagcttcgcccacatgcctgcgttttgccaagatttactg<br>acgagtttggtttactcatcctctatttataactactagactttcaccattcttcaccaccctcgtgccaatg<br>atcatcaaccacttggtattgacagccctcagcattgcactagcaagtgcgcaactccaatcgcctttca |
| PAS_chr3_1157 Homology Arm 2 | 490 | ctggctctgcttctggtacttcttcaggtgcatcttctgctactcaaaatgacgaaacatccactgatcttgg<br>agctccagctgcatctttaagtgcaacgccatgtctttttgccatcttgctgctcatgttgtagtagactttt<br>tttttcactgagtttttatgtactactgattacattgtgtaggtgtaatgatgtgcactataatactaatata<br>gtcaaaatgctacagaggaaagtgcaggttgcctgtggtggtttttcttattagcaccctctgaacactcttt<br>acctctaacatcctcagccatgctaatcgcgcataaaataaatcttcgaactttttttccattttatgctcata<br>aagcttccttactgtcaccttatcaaaagagcttttgccactaaagtagtcacacccagaattgctcccgaat<br>atcgtccaacaatgctaggatctgtggaaagtttgacaaataatttgaacaccttgagcttgaagcttcctga<br>agttaatatccaaggctcctttccagaaagtaacccagtggaccttttgagaaactacatcactcaagaactt<br>agtaaaatttctggagttgacaaagaattgattttcccagccttggaatggggtaccacactggaaaaaggtg<br>atcttttgatcccagttcctcgtctgagaataaagggtgctaatcctaaagatttagccgaacaatgggctgc<br>tgcattcccaaagggtggatatcttaaagacgttattgcgcaaggacctttcttgcagttctttttttaacaca<br>tcggttctgtacaagttggtgatatctgatgctctggagagaggcgatgactttggtgcacttcctctaggaa<br>agggacaaaaagttatagtggagttttcttctccaaatattgccaaacctttccacgctggccatcttagaag<br>tacaatcatcggtggtttatttccaatctgtatgaaaagctgggtcatgaagttatgaggatgaattatttg<br>ggagactggggaaaacaatttggtgttcttgcagtaggatttgagcgttacggtgatgaggcaaaattaaaga<br>ctgatccaatcaaccatttgtttgaggtctatgttaaaatcaaccaagatattaaggctcaatcagagtctac<br>tgaggagattgcagaagggcaatcattagatgaccaggcaagagctttttttcaagaaaatggaaaatggcgac<br>gaatcggctgtaagcttgtggaaaagattccgtgagttatccattgagaagtacattgatacttatgcccgcc<br>tcaacatc |
| Nourseothricin cassette with homology arms targeting PAS_chr1-4_0289 | 491 | gacgagacgctgttcctttcaacttgtccacttggactgacaagtcaacacctgttactaattcttttgtcat<br>ctctcagtatgaagacacgcgtgttcctcaatcagccaccagttctacacatccaaacatacctaaacacgcc<br>aaagagtatccgttagcaaatgggccacctgggtggtgttggaattcccattccagtatgtcgacagaccaac<br>caatatatccaggacaccaatatccaccaccgcttcagcagcactaccactttgcttcacccaggcaactatc<br>aaactctagctctgggacgtcatccgttcctttccaaccacccccctgctggtcaattacaaccacaaggtaat<br>tctatgttcatacacatgccattttcgctaaatggcccaccagctgctggacagcaattgataccaccccaag<br>gactagcctcaatacctgtcggccccggcaacaacagttccctattggttagccaaggtgcacctggcggcta<br>ttctttagcttcaccagcgttgtcaccggtagatgcgaccttcgaagatcccgtcaagagactgcccaaaaag<br>cggacaaaaactggatgtctcacttgccgtaagagacgaatcaaatgtgacgaacgcaagccgttctgtttca<br>actgtgaaaaaagcaaaaaggtgtgtactggttttacgcatctattcaaagatccccctagcaaatcctaccc<br>tcccagttcagatggtgcctcccctgttgccaatgaccaccctgtcccccaaggcaaaactttggtgaattg<br>aggggcagtctgaattacatcatcaactagaagaatgcttattccttttctctactgtataatcacgacgtta<br>tgtcctttaatataagaaacgacaattaaaccactttaggtggacataatccatttctggatgctgttcgatg<br>tgtagtgtctaaaccgatactgagatttctctttctctttctctttttttttttttttcctaccatttccttca<br>agaaaatacacctttcgacagatcatcataaatggtggcctctcttcacacttcagagtacagaagattaagt<br>gagagaattctaccgttcgtatagcatacattatacgaagttatttcagtaatgtcttgtttcttttgttgca<br>gtggtgagccatttgacttcgtgaaagtttctttagaatagttgtttccagaggccaaacattccacccgta<br>gtaaagtgcaagcgtaggaagaccaagactggcataaatcaggtataagtgtcgagcactggcaggtgatctt<br>ctgaaagtttctactagcagataagatccagtagtcatgcatatggcaacaatgtaccgtgtggatctaagaa<br>cgcgtcctactaaccttcgcattcgttggtccagtttgttgttatcgatcaacgtgacaaggttgtcgattcc<br>gcgtaagcatgcatacccaaggacgcctgttgcaattccaagtgagccagttccaacaatctttgtaatatta<br>gagcacttcattgtgttgcgcttgaaagtaaaatgcgaacaaattaagagataatctcgaaaccgcgacttca<br>aacgccaatatgatgtgcggcacacaataagcgttcatatccgctgggtgactttctcgctttaaaaaattat<br>ccgaaaaaatttttgacggctagctcagtcctaggtacgctagcattaaagaggagaaaatgactactcttga<br>tgacacagcctacagatataggacatcagttccgggtgacgcagaggctatcgaagccttggacggttcattc<br>actactgatacggtgtttagagtcaccgctacaggtgatggcttcaccttgagagaggttcctgtagacccac<br>ccttaacgaaagttttccctgatgacgaatcggatgacgagtctgatgctggtgaggacggtgaccctgattc<br>cagaacatttgtcgcatacggagatgatggtgacctggctggctttgttgtggtgtcctacagcggatggaat<br>cgtagactcacagttgaggacatcgaagttgcacctgaacatcgtggtcacggtgttggtcgtgcactgatgg<br>gactggcaacagagtttgctagagaaagaggagccggacatttgtggttagaagtgaccaatgtcaacgctcc<br>tgctattcacgcatataggcgaatgggtttcactttgtgcggtcttgatactgctttgtatgacggaactgct<br>tctgatggtgaacaagctctttacatgagtatgccatgtccatagcacgtccgacggcggcccacgggtccca<br>ggcctcggagatccgtcccccttttcctttgtcgatatcatgtaattagttatgtcacgcttacattcacgcc<br>ctccccccacatccgctctaaccgaaaaggaaggagttagacaacctgaagtctaggtccctatttattttttt<br>tatagttatgttagtattaagaacgttatttatatttcaaatttttcttttttttctgtacagacgcgtgtac<br>gcatgtaacattatactgaaaaccttgcttgagaaggttttgggacgctcgaaggctttaatttgcaagctat<br>aacttcgtatagcatacattataccttgttatgcggccgcaagaagttgattgagactttcaacgagtgatcg<br>actacttggcctccgccgtgaaaactcaattagatgttagctccaaattaatgaacctggtacaagatgataa<br>ataggaactcaaatacaaagcctaccattaatgactgttttatttttatactaaagtagctaaagggtgatta<br>tcaaggagtggttaacgatctattcctagcagggcactcagctcatcgatctttccaatatcggcgtataacg<br>cttccacttctatcaacgtatcttcgttaaaaagaccacctctggtgggaactaatccttctgctgccgcctc<br>tgctaaactctgtcttcgaatccgtttcttactaacatcagcttcgacagataagccactcttctttatcttt<br>ttcttagatcctgttttgaatctcagggactttactggtgccataacaacttcctgttccagtaccttgttct<br>tcttactctttttttggtattaaagaatgtcccgccttgagtcctcgatcatccttggccatactcaatcgtct<br>agtagtgctgttgaaatgctgtaaagaagaggaatatcttcttaaatggttggtatctttttcagcaaccaca<br>cctttgtttcggaaagcggataatggcacattgcttggattgatagaagaagctataaaagcccatcctgcgt<br>ttggagcagtttgattgctctgagttactatgttcaactgtgtattggcaaaagccttagagtcgctgtctga<br>ttcgcttatattgagtaaatcatccaggtccaatagaggaacagaaccagtctgcttcccttttggttttgta<br>cgatccctaattgcacccttcacagaaagttctacccgtttggactttatactgtctttgttctctgatactg |

TABLE 12-continued

Exemplary nourseothricin cassettes with HA arms for protease deletion in *P. pastoris*

| Description | SEQ ID NO: | 5' to 3' Sequence |
|---|---|---|
| | | atcgcattgaaaacccatcaataatctcaaagggtttgccacagtccgaggtggtccaaattccaatcactgg<br>agggataggatccactttggaagatgccagaacttcttttgcaattttggtaccaatttttttattggatgtt<br>ttgggaagagcttcatcttcatcagtggagttgctgctttcgttgtcatctacttttggtcatcttctagtt<br>cgtcgtcgtctgaagcaatagcatctgaggaggacgcatctccttcacctttgaaaaagtaattaaataggta<br>ggagtcatcatcagaatcttgttcttggtctgatcccctttcgacggcagcttgaatgttgtt |
| PAS_chr1-4_0289 Homology Arm 1 | 492 | gacgagacgctgttcctttcaacttgtccacttggactgacaagtcaacacctgttactaattcttttgtcat<br>ctctcagtatgaagacacgcgtgttcctcaatcagccaccagttctacacatccaaacatacctaaacacgcc<br>aaagagtatccgttagcaaatgggccacctgggtggtgttggaattcccattccagtatgtcgacagaccaac<br>caatatatccaggacaccaatatccaccaccgcttcagcagcactaccactttgcttcacccaggcaactatc<br>aaactctagctctgggacgtcatccgttcctttccaaccacccccctgctggtcaattacaaccacaaggtaat<br>tctatgttcatacacatgccattttcgctaaatggcccaccagctgctggacagcaattgataccaccccaag<br>gactagcctcaatacctgtcggccccggcaacaacagttccctattggttagccaaggtgcacctggcggcta<br>ttctttagcttcaccagcgttgtcaccggtagatgcgaccttcgaagatcccgtcaagagactgcccaaaaag<br>cggacaaaaactggatgtctcacttgccgtaagagacgaatcaaatgtgacgaacgcaagccgttctgtttca<br>actgtgaaaaaagcaaaaaggtgtgtactggttttacgcatctattcaaagatcccccctagcaaatcctaccc<br>tcccagttcagatggtgcctcccctgttgccaatgaccaccctgtcccccccaaggcaaaactttggtgaattg<br>aggggcagtctgaattacatcatcaactagaagaatgcttattccttttctctactgtataatcacgacgtta<br>tgtcctttaatataagaaacgacaattaaaccactttaggtggacataatccatttctggatgctgttcgatg<br>tgtagtgtctaaaccgatactgagatttctctttctctttctcttttttttttttttcctaccatttccttca<br>agaaaatacacctttcgacagatcatcataaatggtggcctctcttcaca |
| PAS_chr1-4_0289 Homology Arm 2 | 493 | tgatcgactacttggcctccgccgtgaaaactcaattagatgttagctccaaattaatgaacctggtacaaga<br>tgataaataggaactcaaatacaaagcctaccattaatgactgttttatttttatactaaagtagctaaaggg<br>tgattatcaaggagtggttaacgatctattcctagcagggcactcagctcatcgatctttccaatatcggcgt<br>ataacgcttccacttctatcaacgtatcttcgttaaaaagaccacctctggtgggaactaatccttctgctgc<br>cgcctctgctaaactctgtcttcgaatccgtttcttactaacatcagcttcgacagataagccactcttcttt<br>atctttttcttagatcctgttttgaatctcagggactttactggtgccataacaacttcctgttccagtacct<br>tgttcttcttactctttttttggtattaaagaatgtcccgccttgagtcctcgatcatccttggccatactcaa<br>tcgtctagtagtgctgttgaaatgctgtaaagaagaggaatatcttcttaaatggttggtatctttttcagca<br>accacacctttgtttcggaaagcggataatggcacattgcttggattgatagaagaagctataaaagcccatc<br>ctgcgtttggagcagtttgattgctctgagttactatgttcaactgtgtattggcaaaagccttagagtcgct<br>gtctgattcgcttatattgagtaaatcatccaggtccaatagaggaacagaaccagtctgcttccctttggt<br>tttgtacgatccctaattgcacccttcacagaaagttctacccgtttggactttatactgtctttgttctctg<br>atactgatcgcattgaaaacccatcaataatctcaaagggtttgccacagtccgaggtggtccaaattccaat<br>cactggagggataggatccactttggaagatgccagaacttcttttgcaattttggtaccaatttttttattg<br>gatgttttgggaagagcttcatcttcatcagtggagttgctgctttcgttgtcatctacttttggtcatctt<br>ctagttcgtcgtcgtctgaagcaatagcatctgaggaggacgcatctccttcacctttgaaaaagtaattaaa<br>taggtaggagtcatcatcagaatcttgttcttggtctgatcccctttcgacggcagcttgaatgttgtt |

The invention claimed is:

1. A *Pichia pastoris* microorganism, in which the activity of a YPS1-1 protease comprising a polypeptide sequence at least 95% identical to SEQ ID NO: 67, a YPS1-2 protease comprising a polypeptide sequence at least 95% identical to SEQ ID NO: 68, and a YPS 1-5 protease comprising a polypeptide sequence at least 95% identical to the polypeptide sequence encoded by the YPS1-5 gene set forth by SEQ ID NO: 5 have been attenuated or eliminated, wherein each of said polypeptide sequences has a protease activity before said attenuation or elimination, and wherein said microorganism expresses a recombinant protein.

2. The microorganism of claim 1, wherein said YPS1-1 protease comprises SEQ ID NO: 67.

3. The microorganism of claim 1, wherein said YPS1-1 protease is encoded by a YPS1-1 gene comprising a polynucleotide sequence at least 95% identical to SEQ ID NO: 1 and encoding a polypeptide having protease activity.

4. The microorganism of claim 3, wherein said YPS1-1 gene comprises SEQ ID NO: 1.

5. The microorganism of claim 1, wherein said YPS1-2 protease comprises SEQ ID NO: 68.

6. The microorganism of claim 1, wherein said YPS1-2 protease is encoded by a YPS1-2 gene comprising a polynucleotide sequence at least 95% identical to SEQ ID NO: 2 and encoding a polypeptide having protease activity.

7. The microorganism of claim 6, wherein said YPS1-2 gene comprises SEQ ID NO: 2.

8. The microorganism of claim 1, wherein said YPS1-5 protease is encoded by a YPS1-5 gene comprising a polynucleotide sequence at least 95% identical to SEQ ID NO: 5 and encoding a polypeptide having protease activity.

9. The microorganism of claim 8, wherein said YPS1-5 gene comprises SEQ ID NO: 5.

10. The microorganism of claim 1, wherein said YPS1-1 protease is encoded by a YPS1-1 gene, wherein said YPS1-2 protease is encoded by a YPS1-2 gene, and wherein said YPS1-5 protease is encoded by a YPS1-5 gene, and wherein said YPS1-1 gene, said YPS1-2 gene, said YPS1-5 gene have been mutated or knocked out.

11. The microorganism of claim 1, wherein said recombinant protein comprises one or more repeat sequences $\{GGY-[GPG-X_1]_{n1}-GPS-(A)_{n2}\}_{n3}$, wherein each X1 in each $[GPG-X_1]_{n1}$ is separately one of SGGQQ (SEQ ID NO: 515), GAGQQ (SEQ ID NO: 516), GQGPY (SEQ ID NO: 517), AGQQ (SEQ ID NO: 518), or SQ;

n1 is from 4 to 8;

n2 is from 6 to 20; and n3 is from 2 to 20.

12. The microorganism of claim 11, wherein said recombinant protein comprises SEQ ID NO: 463.

13. A *Pichia Pastoris* engineered microorganism comprising YPS1-1, YPS1-2, and YPS1-5 activity reduced by a mutation or deletion of the YPS1-1 gene comprising SEQ ID NO: 1, the YPS1-2 gene comprising SEQ ID NO: 2, and the YPS1-5 gene comprising SEQ ID NO: 5, wherein said microorganism further comprises a recombinantly expressed protein comprising a polypeptide sequence comprising SEQ ID NO: 463.

14. A cell culture comprising the microorganism of claim 1.

15. The cell culture of claim 14, wherein said recombinantly expressed protein is less degraded than in a cell culture comprising an otherwise identical *Pichia pastoris* microorganism whose YPS1-1, YPS1-2, and YPS1-5 activities have not been attenuated or eliminated.

16. A *Pichia pastoris* microorganism, in which the activity of a YPS1-1 protease comprising a polypeptide sequence at least 95% identical to SEQ ID NO: 67, a YPS1-2 protease comprising a polypeptide sequence at least 95% identical to SEQ ID NO: 68, and a YPS1-5 protease comprising a polypeptide sequence at least 95% identical to the polypeptide sequence encoded by the YPS1-5 gene set forth by SEQ ID NO: 5 have been attenuated or eliminated, wherein each of said polypeptide sequences has a protease activity before said attenuation or elimination.

17. The microorganism of claim 1, wherein said YPS1-5 protease comprises an amino acid sequence encoded by SEQ ID NO: 5.

* * * * *